(12) United States Patent
Dunn et al.

(10) Patent No.: US 10,704,084 B2
(45) Date of Patent: Jul. 7, 2020

(54) METHODS AND KITS FOR THERANOSTIC APPLICATIONS

(71) Applicant: TriBiotica LLC, Madison, WA (US)

(72) Inventors: Ian Dunn, Sydney (AU); Matthew Lawler, Madison, WI (US)

(73) Assignee: TriBiotica LLC, Madison, WI (US)

( * ) Notice: Subject to any disclaimer, the term of this patent is extended or adjusted under 35 U.S.C. 154(b) by 0 days.

(21) Appl. No.: 15/529,807

(22) PCT Filed: Dec. 2, 2015

(86) PCT No.: PCT/US2015/063368
§ 371 (c)(1),
(2) Date: May 25, 2017

(87) PCT Pub. No.: WO2016/089958
PCT Pub. Date: Jun. 9, 2016

(65) Prior Publication Data
US 2018/0023123 A1    Jan. 25, 2018

Related U.S. Application Data

(60) Provisional application No. 62/086,658, filed on Dec. 2, 2014, provisional application No. 62/086,661, filed on Dec. 2, 2014.

(51) Int. Cl.
| | | |
|---|---|---|
| C12Q 1/68 | (2018.01) | |
| C12Q 1/6816 | (2018.01) | |
| C12N 15/10 | (2006.01) | |
| C40B 20/00 | (2006.01) | |
| C40B 40/00 | (2006.01) | |

(52) U.S. Cl.
CPC ....... C12Q 1/6816 (2013.01); C12N 15/1093 (2013.01); *C12Q 2533/107* (2013.01); *C12Q 2563/107* (2013.01); *C40B 20/00* (2013.01); *C40B 40/00* (2013.01)

(58) Field of Classification Search
None
See application file for complete search history.

(56) References Cited

U.S. PATENT DOCUMENTS

| | | | |
|---|---|---|---|
| 5,514,546 A | 5/1996 | Kool | |
| 5,858,731 A * | 1/1999 | Sorge | .......... B01J 19/0046 435/91.1 |
| 2002/0172965 A1 | 11/2002 | Kamb et al. | |
| 2005/0026178 A1 | 2/2005 | Nilsen-Hamilton | |
| 2005/0048192 A1 | 3/2005 | Raines et al. | |
| 2005/0089890 A1 | 4/2005 | Cubicciotti | |
| 2005/0287548 A1 | 12/2005 | Bao | |
| 2006/0099592 A1 | 5/2006 | Freskgard | |
| 2006/0147963 A1 | 7/2006 | Barone et al. | |
| 2007/0099222 A1 | 5/2007 | Gee et al. | |
| 2007/0190597 A1 | 8/2007 | Agnew et al. | |
| 2008/0044834 A1 | 2/2008 | Heyduk et al. | |
| 2008/0050731 A1 | 2/2008 | Agnew et al. | |
| 2008/0071074 A1 | 3/2008 | Skrzypczynski et al. | |
| 2009/0124571 A1 | 5/2009 | Morvan et al. | |
| 2010/0048866 A1 | 2/2010 | Raines et al. | |
| 2010/0055728 A1 | 3/2010 | Yang | |
| 2012/0009566 A1 | 1/2012 | Soukka | |
| 2015/0203841 A1 | 7/2015 | Rasmussen | |
| 2016/0025726 A1 | 1/2016 | Altin et al. | |
| 2016/0106854 A1 | 4/2016 | Dunn et al. | |

FOREIGN PATENT DOCUMENTS

| | | |
|---|---|---|
| JP | H10512446 | 12/1998 |
| JP | 2009528988 | 8/2009 |
| JP | 2014055167 | 3/2014 |
| WO | 0061775 A1 | 10/2000 |
| WO | 2004011486 | 2/2004 |
| WO | 2006058496 | 6/2006 |
| WO | 2011089393 A1 | 7/2011 |
| WO | 2012057689 | 5/2012 |
| WO | 2014197547 A1 | 11/2014 |
| WO | 2015122835 | 8/2015 |
| WO | 2016089958 | 6/2016 |
| WO | 2017049094 | 3/2017 |

OTHER PUBLICATIONS

Wu et al, Genomics 4, 560 (1989).*
Pai et al., "Using RNA aptamers and the proximity ligation assay for the detection of cell surface antigens", Methods Mol Biol, 2009, 504, pp. 385-398.
Monroy-Contreras et al., "Molecular Beacons: Powerful Tools for Imaging RNA in Living Cells", Journal of Nucleic Acids, 2011, 2011, pp. 1-15.
Ponomarenko et al., "Recent advacnes in self-assembled fluorescent DNA structures and probes" Curr Top Med Chem, 2015, 15(13), pp. 1162-1178.
Office Action dated Aug. 6, 2018 in U.S. Appl. No. 14/895,398.
Restriction Requirement dated Mar. 28, 2017, issued in related U.S. Appl. No. 14/895,398.

(Continued)

*Primary Examiner* — James Martinell
(74) *Attorney, Agent, or Firm* — Stradley Ronon Stevens & Young, LLP

(57) ABSTRACT

The present disclosure is directed to methods and kits for identifying, enriching, and evaluating templated assembly reactants. Some embodiments disclose methods for identifying templated assembly targets by synthesizing templated assembly reactants, hybridizing the templated assembly reactants to target nucleic acids, performing a templated assembly reaction, and identifying the target nucleic acids that hybridized to the templated assembly reactants. Libraries of templated assembly reactants, a kit for identifying templated assembly targets, and a pair of templated assembly targets enriched from a library of chemically-ligated oligonucleotides spatially elicited (CLOSE) products are also disclosed.

10 Claims, 67 Drawing Sheets

Specification includes a Sequence Listing.

(56) References Cited

OTHER PUBLICATIONS

Imoto et al., "DNA-templated click chemistry for creation of novel DNA binding molecules" Bioorganic & Medicinal Chem Lett, 2008, 18(20), p. 5660-5663.
Walder et al., "Complementary carrier peptide synthesis: general strategy and implications for prebiotic origin of peptide synthesis", PNAS, 1979, 76(1), p. 51-55.
Blanco-Canosa and Dawson, "An efficient Fmoc-SPPS approach for the generation of thioester peptide precursors for use in native chemical ligation", Angew Chem Int Ed Engl, 2008, 47(36), p. 6851-6855.
Le Gall et al., "Protable flanking sequences modulate CTL epitope processing", J Clin Invest 2007, 117(11), p. 3563-3575.
Roosild et al., "Structure of anti-FLAG M2 Fab domain and its use in the stabilization of engineered membrane proteins", Acta Crystallogr Sect F Struct Biol Cryst Commun, 2006, 62(9), p. 835-839.
Sletten et al., "From mechanism to mouse: a tale of two bioorthogonal reactions", Acc Chem Res, 2011, 44(9), p. 666-676.
Tam and Raines, "Coulombic effects on the traceless Staudinger ligation in water" Bioorg Med Chem, 2009, 17(3), p. 1055-1063.
Tam et al., "Water-souble phosphinothiols for traceless Staudinger ligation and integration with expressed protein ligation", J Am Chem Soc, 2007, 129(37), p. 11421-11430.
International Search Report and Written opinion for PCT/US2015/063368. (2016).
Office Action dated Nov. 15, 2017 in related U.S. Appl. No. 14/895,398.
Bendifallah et al., "Evaluation of Cell-Penetrating Peptides (CPPs) as Vehicles for Intracellular Delivery of Antisense Peptide Nucleic Acid (PNA)", Bioconjugate Chem, 2006, 17, pp. 750-758.
Kazane, et al., "Self-Assembled Antibody Multimers Through Peptide Nucleic Acid Conjugation", JACS, 2012, 135, pp. 340-346.
Zhao et al, "Solid-phase synthesis and evaluation of TAR RNA targeted beta-carboline-nucleoside conjugates", Organic and Biomolecular Chemistry, 2008, 6(20), pp. 3741-3750.
Clackson et al., "Redesigning an FKBP-ligand interface to generate chemical dimerizers with novel specificity", PNAS USA, 1998, 95(18):10437-10442.
Kalia et al., "Reactivity of Intein Thioesters: Appending a Functional Group to a Protein", ChemBioChem, 2006, 7:1375-1383.
Knecht et al., "Oligohis-tags: mechanisms of binding to Ni2+ surfaces", J Mol Recognit, 2009, 22:270-279.
Official Action dated Jun. 11, 2019 in related U.S. Appl. No. 14/895,398.
Overkamp et al., "Benchmarking various green fluorescent protein variants in Bacillus subtilis, *Streptococcus pneumoniae*, and Lactococcus lactis for live cell imaging", Appl Environ Microbiol, 2013, 79(20):6481-6490.
Paulmurugan et al., "Monitoring protein-protein interactions using split synthetic renilla luciferase protein-fragment-assisted complementation", Anal Chem, 2003, 75(7):1584-1589.
Weisbrod et al., "Synthesis of Water-Soluble Phosphinophenol for Traceless Staudinger Ligation", Synlett, 2010, 5:787-789.
Official Action dated Aug. 6, 2018 in related U.S. Appl. No. 14/895,398.
Niwayama et al., "A Pyrene Maleimide with a Flexible Linker for Sampling of Longer Inter-Thiol Distances by Excimer Formation", PLoS One, 2011, 6(10), e26691.
Notice of Allowance dated Nov. 21, 2019 related U.S. Appl. No. 14/895,398.
Office Action dated Dec. 11, 2019 related U.S. Appl. No. 15/601,449.

* cited by examiner

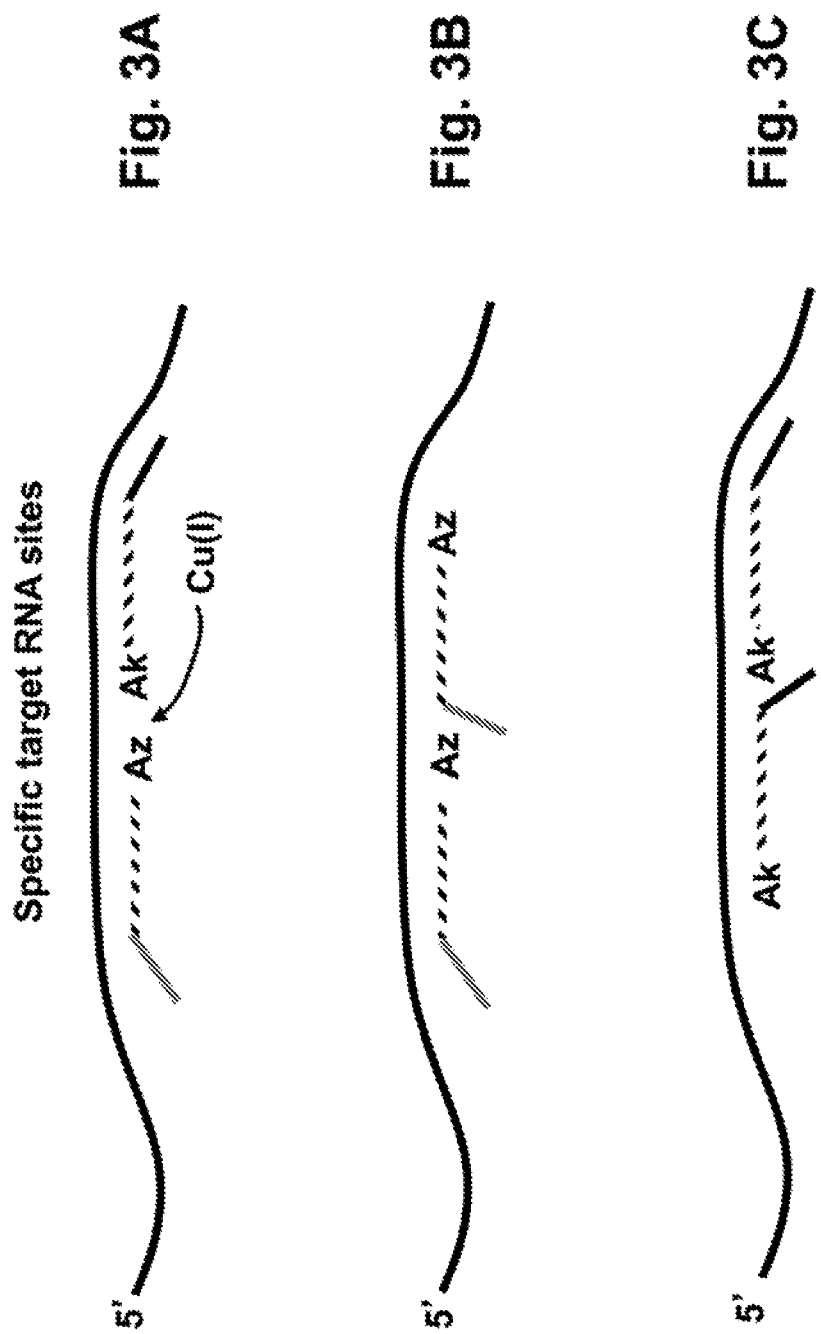

| Sequence Name | L | R |
|---|---|---|
| CL1 | TGGATCTCTGC | TTAAAGTGACC |
| CL2 | TCAGTGTGTGC | TGCGGCACACTC |
| CL3 | ACGGGCCCGGC | TTCGCGTCCAG |
| CL4 | TCTTTTACCCC | TCTGCCCAGGC |
| CL5 | ACACCCTCGCC | TACCTTCTCCC |
| CL6 | TCACATTCACC | TTGTGGATGTG |
| CL8 | GGCCCTTCTAC | TCGTCTCCGGC |
| CL9 | TTCAATGGGCC | TTACCCAGTGC |
| CL10 | ATCAACCCTGC | TGTATTCGCCA |
| CL11 | ACCCCGATTGC | TGGCAGTCGGC |
| CL12 | ACCTAACAGGC | TTCATCCGTTC |
| CL13 | TTCGAACGATCC | TAGGTCGTTCA |
| CL14 | ATAGAAGGGGC | TTAGGCCAACA |
| CL15 | CCAACTGTAGC | TAGGCGGTTGG |
| CL16 | CCCGGCCTCCC | TTCCTAGCTGC |
| CL17 | AAACCGACAGC | TATGCTGTCGG |
| CL19 | ATTCGCCCCCC | TCCGGCTTCGGT |
| Rnd1 | ACATAAGCAAC | TTATCGTAGTC |
| Rnd2 | CGTCAAATTCC | TAGCCCTCTTA |
| Rnd3 | TATGTGTCAAC | TATGGCGTAGA |
| Rnd4 | ACTGGATTGAC | TCTGTTTGACG |
| Rnd5 | GTACCTGCTGC | TATCGGTACGG |
| Rnd6 | TGACCGAGAAC | TTCTGTCGGGC |
| Rnd7 | ATACTTTCCAC | TAACGCCCCGT |
| Rnd8 | ATCGATGCTGC | TAACGAATCGA |
| Rnd9 | TGCACGCTCCC | TCGTCTTTGAA |
| Rnd10 | AACGCATAAAC | TCATACAAGTG |
| Rnd11 | GACAGATGATC | TGGGTACGGGC |
| Rnd12 | CTCTAATACAC | TTCCAACACTC |
| Rnd13 | TACGCCCTCTC | TTCAAGAGCTA |
| Rnd14 | GAAGGGCACCC | TCTGCAGTTGG |
| Rnd15 | AAAGGGAATTC | TATTTCGTAAG |
| Rnd16 | GCGAGCCCATC | TACCGTCATTC |
| Rnd17 | ATGCGGAAGAC | TGTTAACACGA |

| | CLOSE Clones | Random Seqs | Expected Random |
|---|---|---|---|
| L: %GC 10mer | 56.5 | 45.9 | 50.0 |
| R: % GC 10-mer | 61.8 | 50.0 | 50.0 |

| | | | |
|---|---|---|---|
| L: GC% half3' | 64.7 | 42.4 | 50.0 |
| R: GC% half5' | 57.6 | 47.1 | 50.0 |

High % GC content may reflect a selection for more stable CLOSE sites with current Cu(I)-catalyzed protocol.

Fig. 4

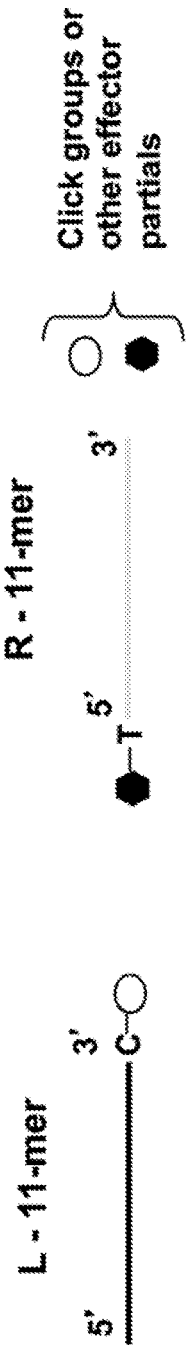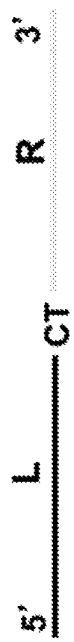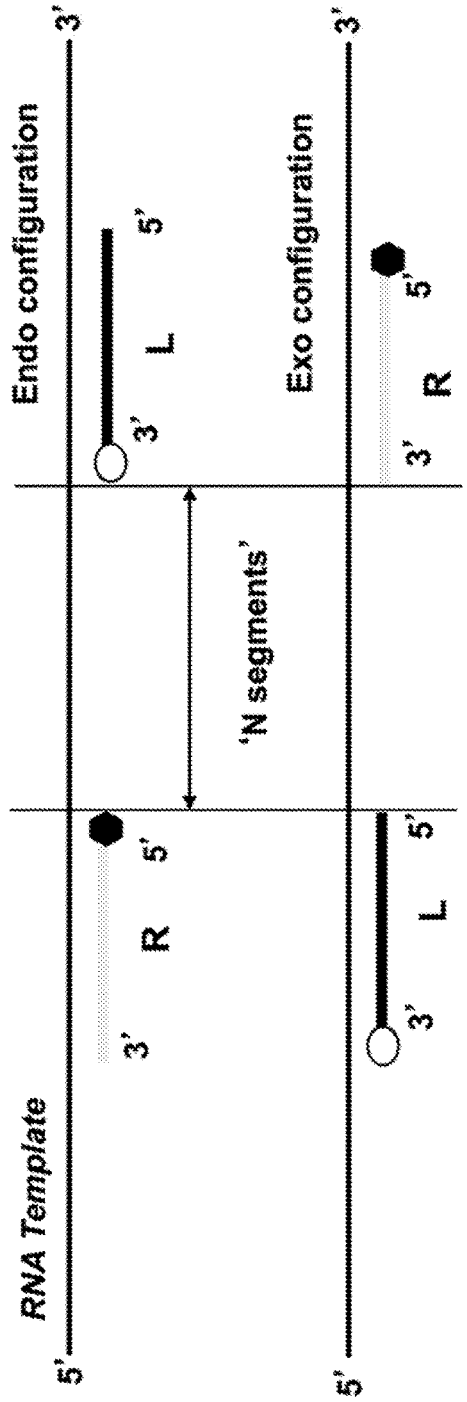
Fig. 14

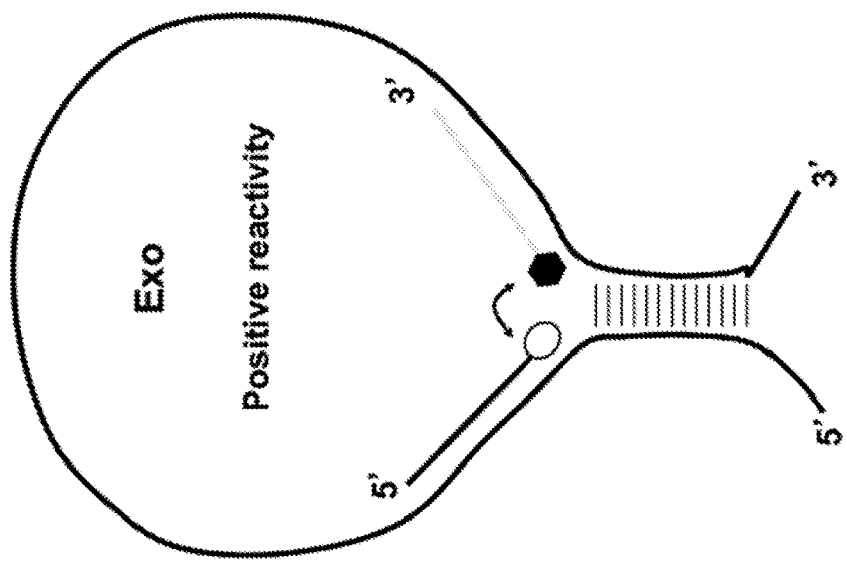
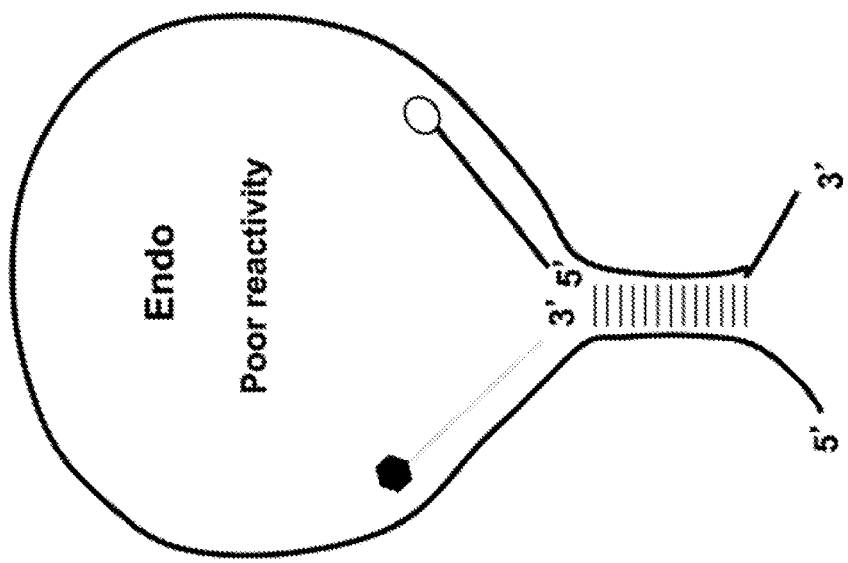
Fig. 15

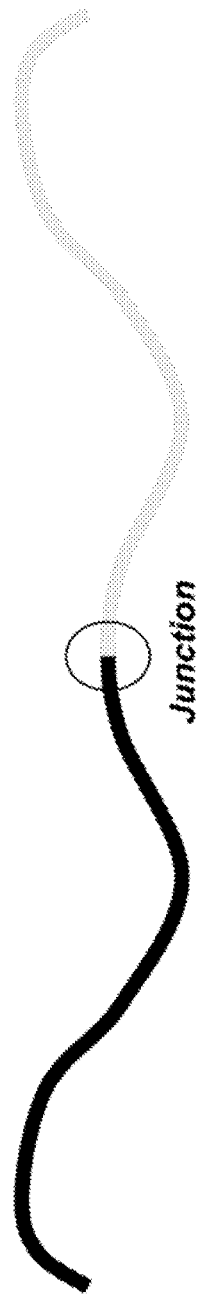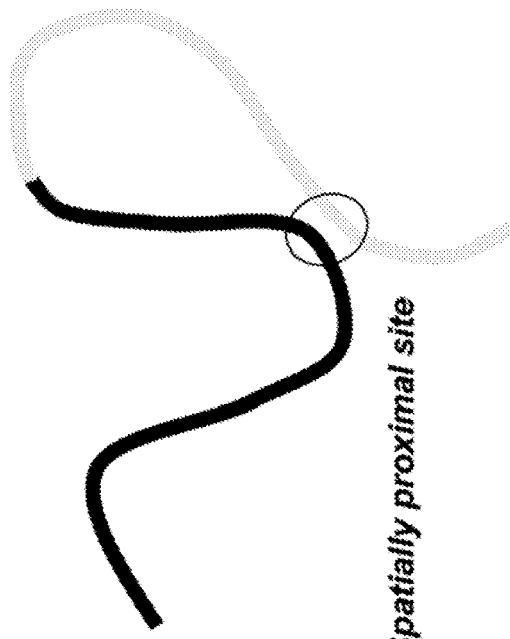
Aberrant transcript from translocation
Junction
(Sequences on either side of the junction correspond to normal transcripts; but the entire fusion transcript is aberrant).
Thus, for tumor-specific transcripts of this type, only the junction sequence or *discontinuous sites* can unambiguously flag tumor identity.
*Spatially proximal site*
Fig. 28

Fig. 31

CLOSE clones from BCR-ABL hybridization probe dBBc2-01 clone sequence
ATAAGCACCTCTCAAGGTCTG
Reverse complement
CAGACCTTGAA | GAGGTGCTTAT
ABL match    BCR match
4111-4119    3071-3079

N = 1032 dBBc2-08 clone sequence
TGACCTGCTCCCACCCCTCCT
Reverse complement
AGGAGGGGTGA | GGAGCAGGTCA
ABL match    BCR match
7567-7575    3053-3060

N = 4507

Purification method
in agarose gels

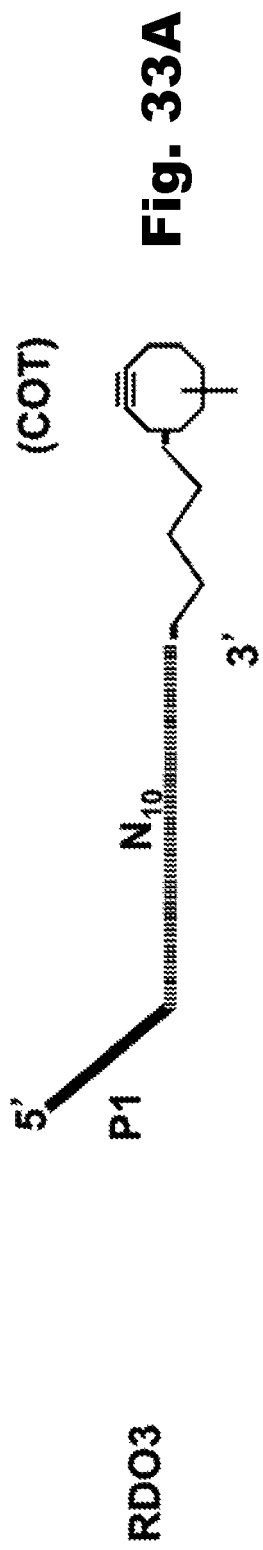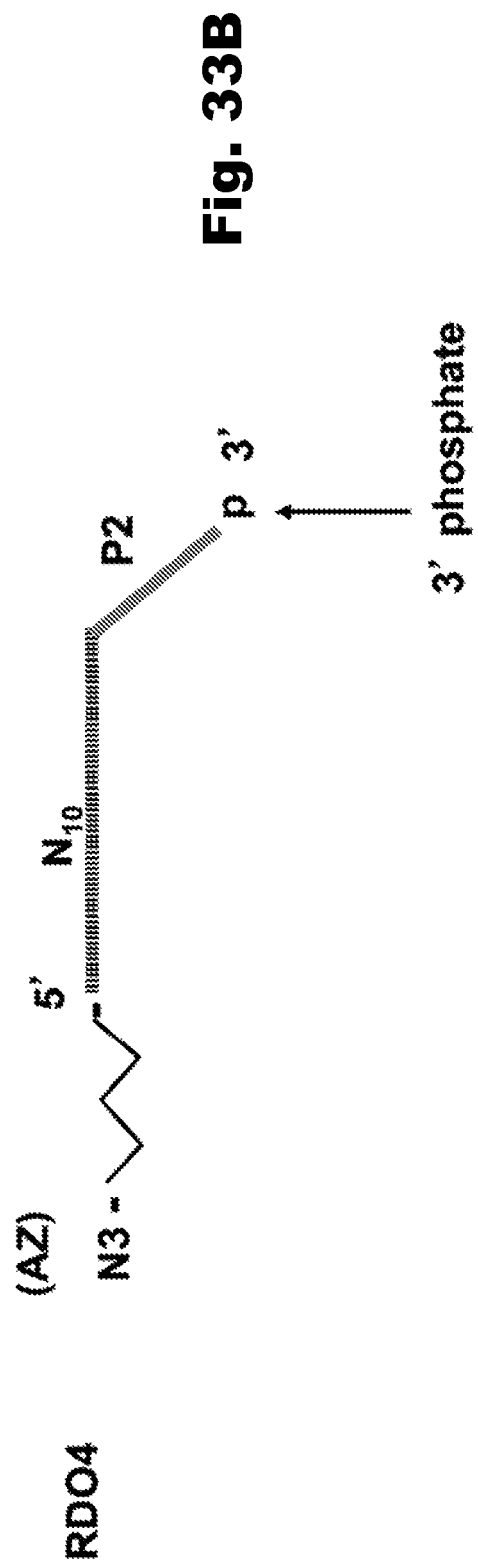

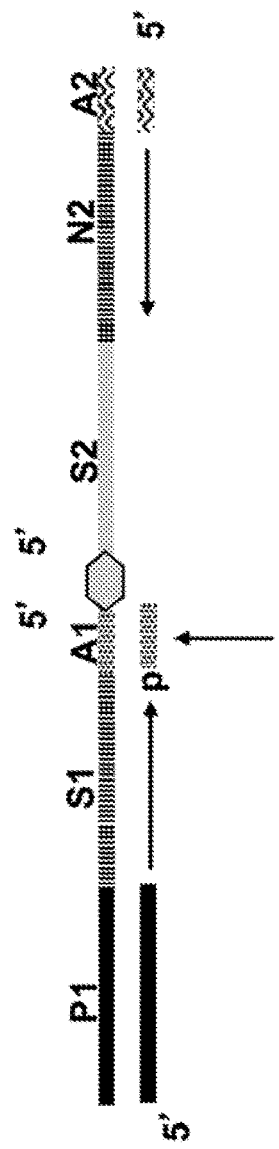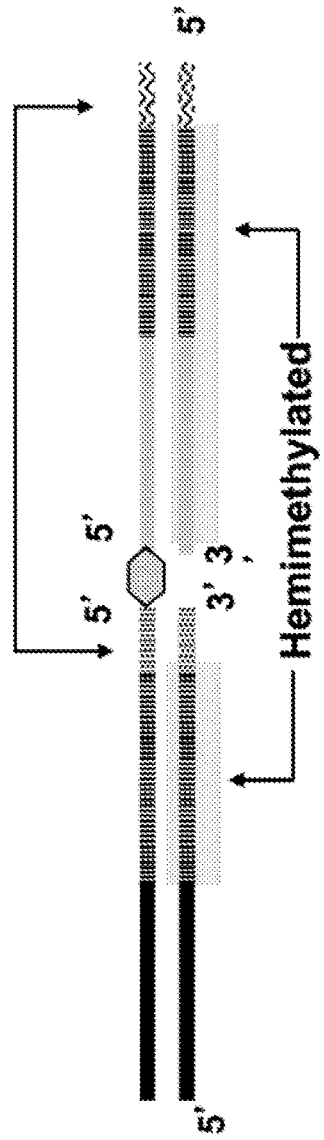
Fig. 38

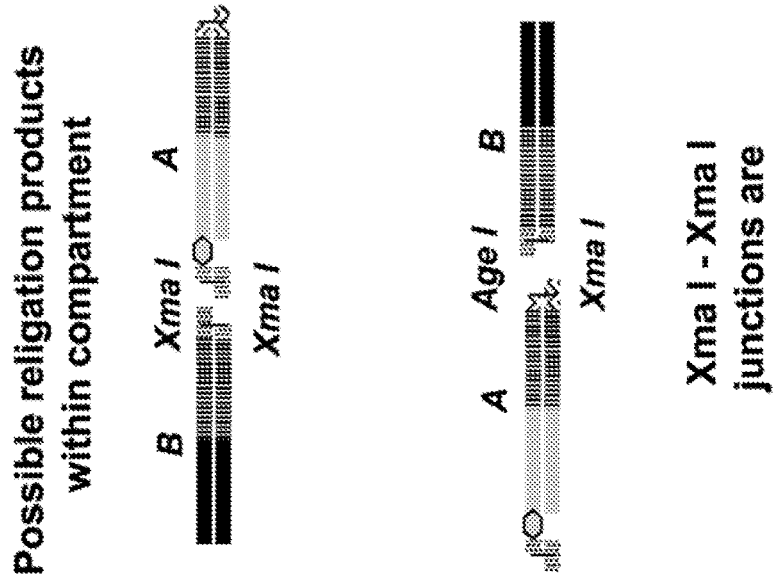
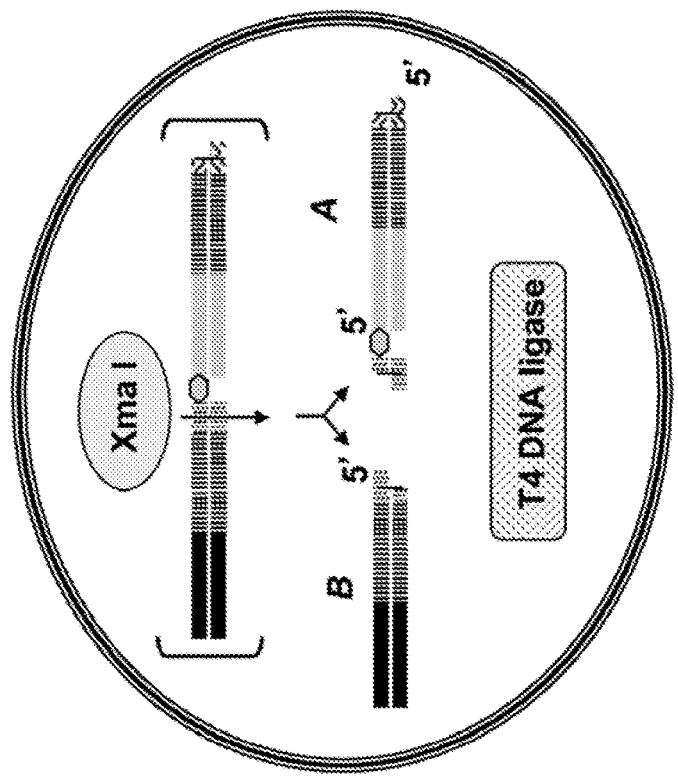
Fig. 41

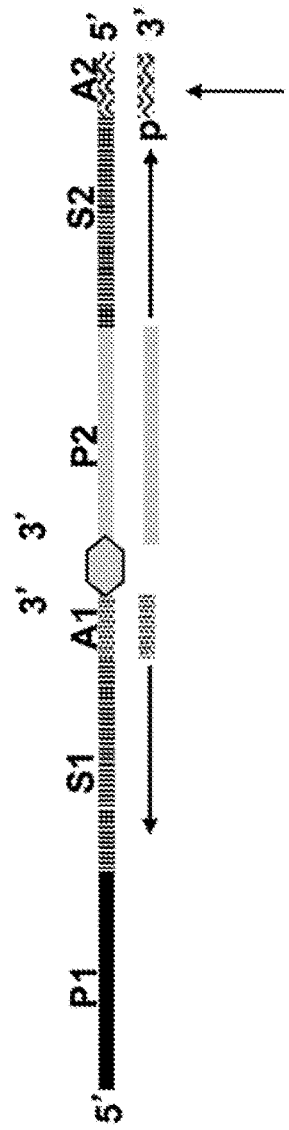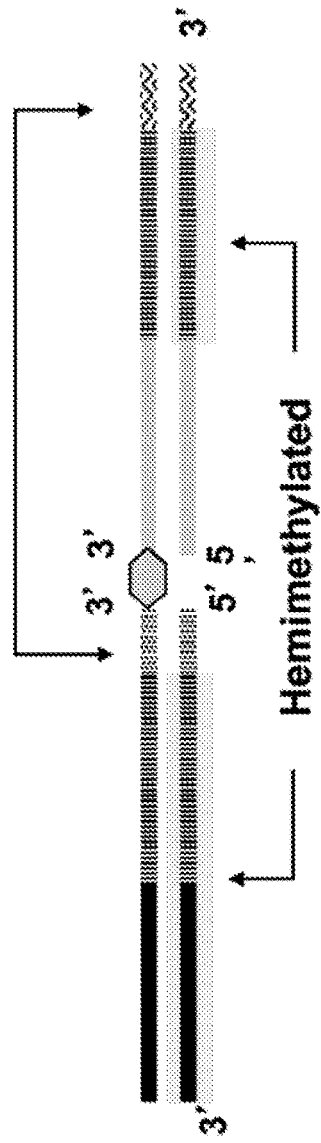
Fig. 46

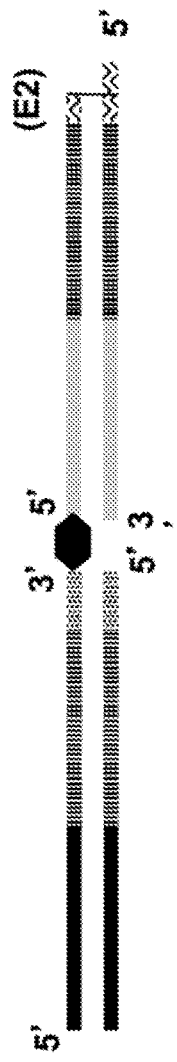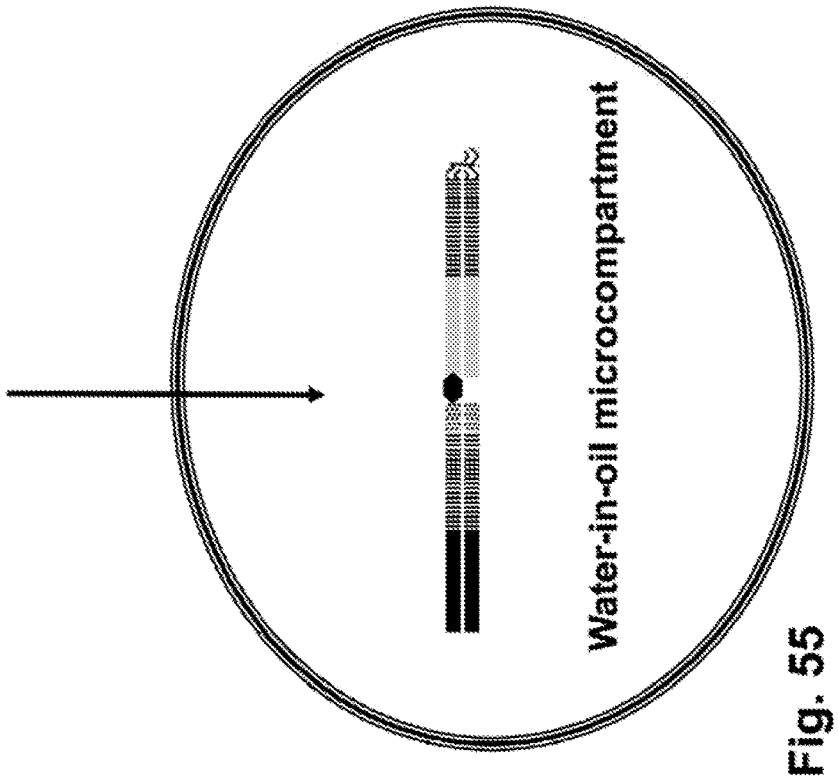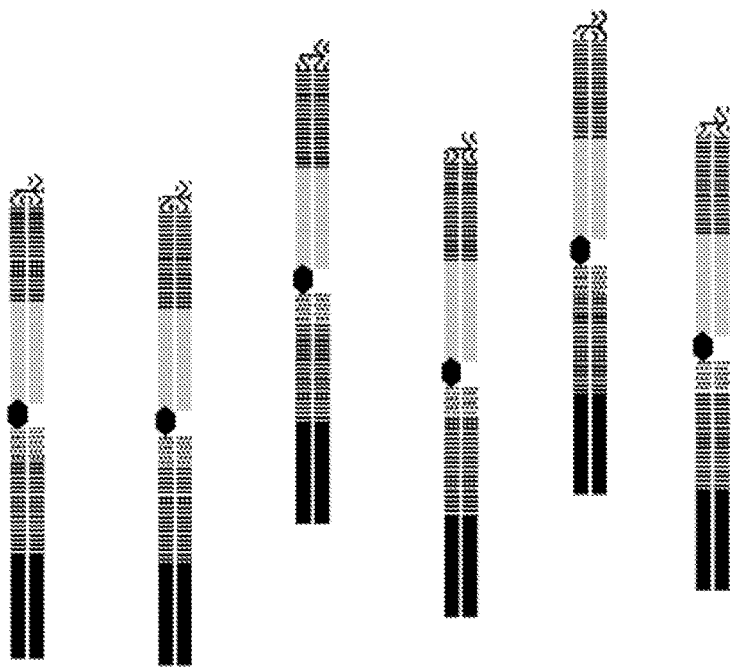
Fig. 55

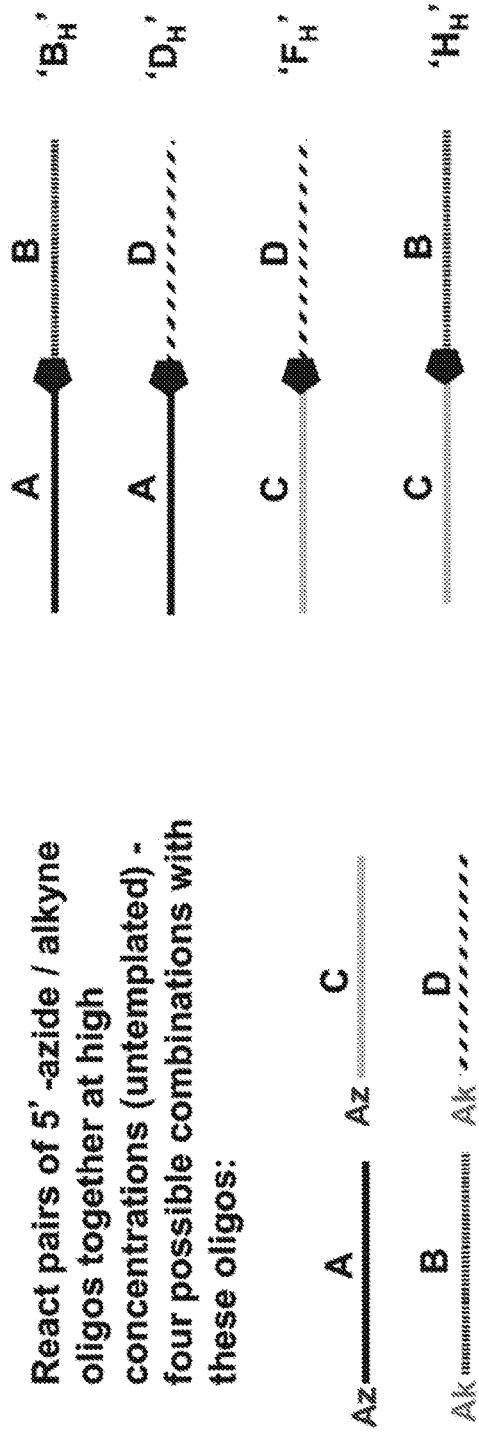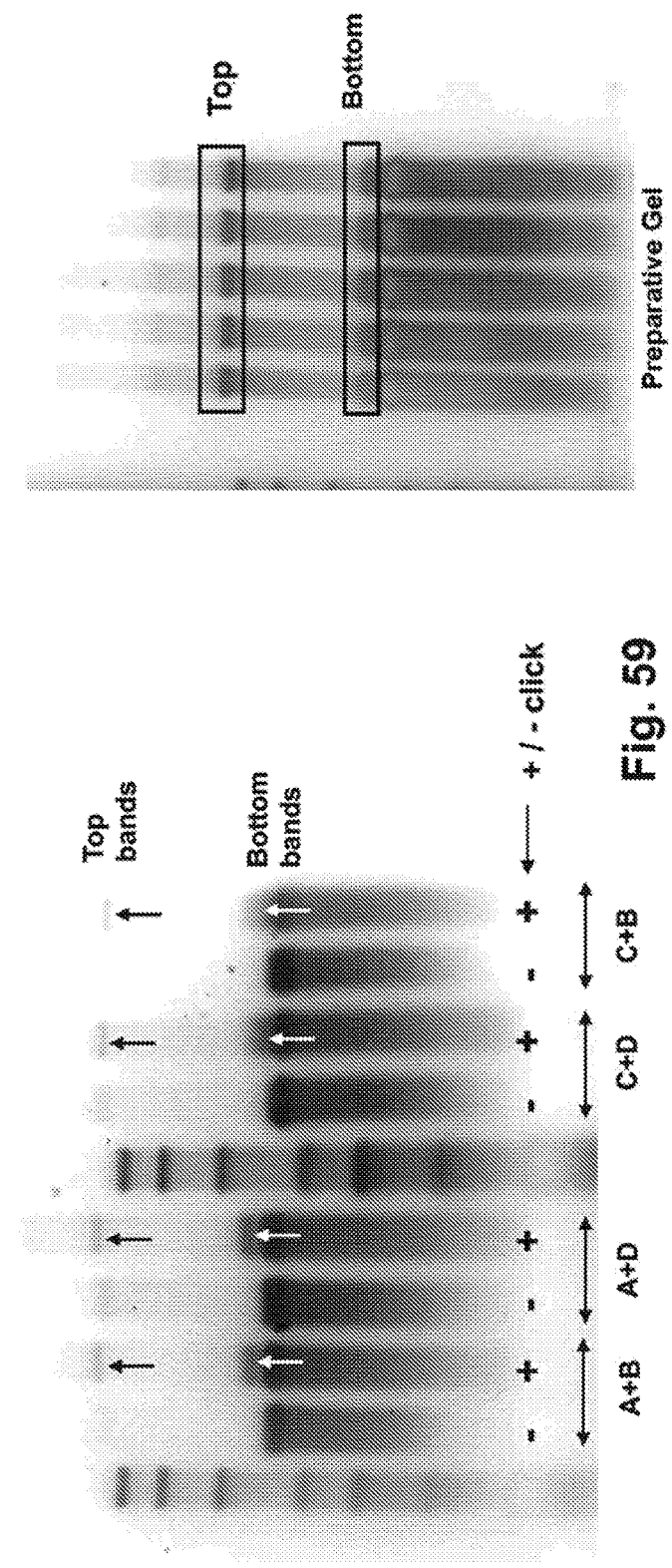
Fig. 59

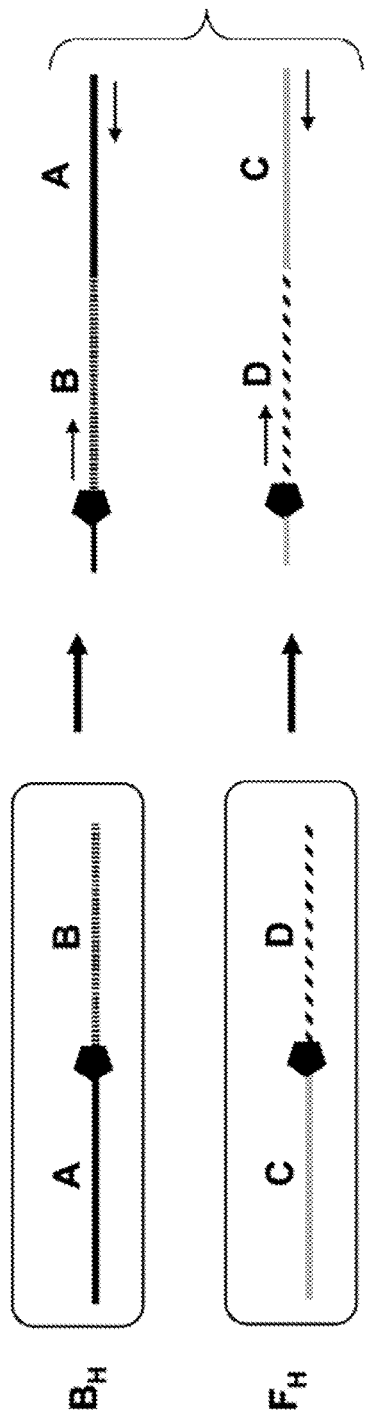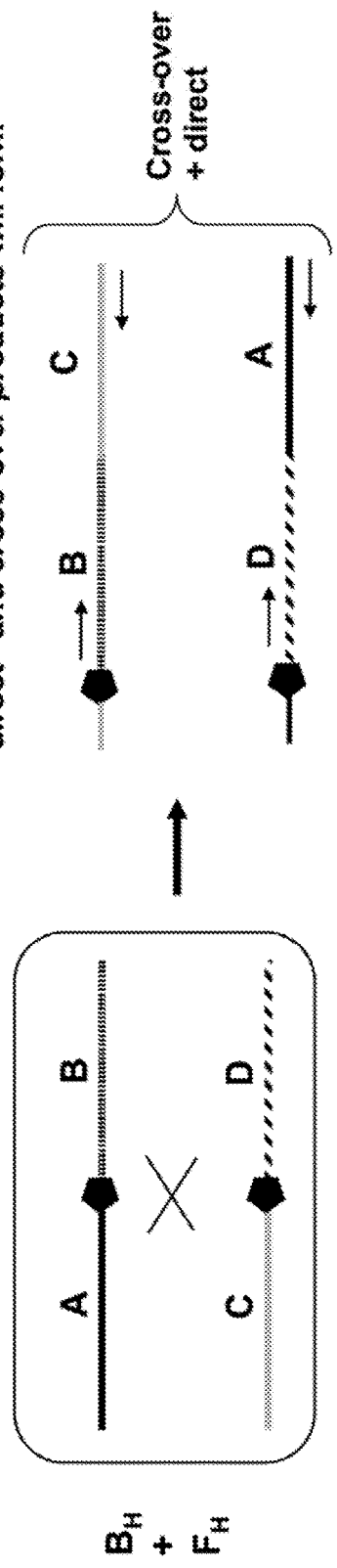
Fig. 63

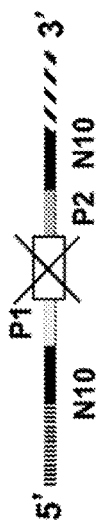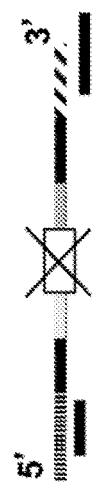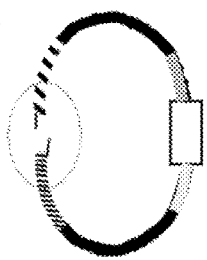
Fig. 67

SEQUENCE LISTING

<160> NUMBER OF SEQ ID NOS: 126

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic

```
<400> SEQUENCE: 1
tggatctctg c                                                              11

<210> SEQ ID NO 2
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 2
ttaaagtgac c                                                              11

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 3
tgagtgtgtg c                                                              11

<210> SEQ ID NO 4
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 4
tgcgcacact c                                                              11

<210> SEQ ID NO 5
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 5
acgggcccgg c                                                              11

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 6
ttcgcgtcca g                                                              11

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 7
tcttttacgc c                                                              11

<210> SEQ ID NO 8
<211> LENGTH: 11
```

```
<212> TYPE: DNA
<213> ORGANISM: Artificial Sequence
<220> FEATURE:
<223> OTHER INFORMATION: Description of Artificial Sequence: Synthetic

<400> SEQUENCE: 8
tctgcccagg c                                                          11

<210> SEQ ID NO 9
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 9
acaccctcgc c                                                          11

<210> SEQ ID NO 10
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 10
taccttctcc c                                                          11

<210> SEQ ID NO 11
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 11
tcacattcac c                                                          11

<210> SEQ ID NO 12
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 12
ttgtggatgt g                                                          11

<210> SEQ ID NO 13
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 13
ggcccttcta c                                                          11

<210> SEQ ID NO 14
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 14
```

```
tcgtctgcgg c                                                           11

<210> SEQ ID NO 15
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 15
ttcaatgggc c                                                           11

<210> SEQ ID NO 16
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 16
ttacccagtg c                                                           11

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 17
atcaaccctg c                                                           11

<210> SEQ ID NO 18
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 18
tgtattcgcc a                                                           11

<210> SEQ ID NO 19
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 19
acgccgattg c                                                           11

<210> SEQ ID NO 20
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 20
tggcagtcgg c                                                           11

<210> SEQ ID NO 21
<211> LENGTH: 11
<212> TYPE: DNA
<213> ORGANISM: Artificial Sequence
```

-continued

```
<220> FEATURE:
<223> OTHER INFORMATION: Description of Artificial Sequence: Synthetic

<400> SEQUENCE: 21
acctaacagc c                                                              11

<210> SEQ ID NO 22
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 22
ttcatccgtt c                                                              11

<210> SEQ ID NO 23
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 23
ttgaacgatc c                                                              11

<210> SEQ ID NO 24
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 24
taggtcgttc a                                                              11

<210> SEQ ID NO 25
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 25
atagaagggg c                                                              11

<210> SEQ ID NO 26
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 26
ttaggccaac a                                                              11

<210> SEQ ID NO 27
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 27
ccaactgtag c                                                              11
```

<210> SEQ ID NO 28
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 28
taggcggttg g                                                          11

<210> SEQ ID NO 29
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 29
cccggcctcc c                                                          11

<210> SEQ ID NO 30
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 30
ttcctagctg c                                                          11

<210> SEQ ID NO 31
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 31
aaaccgacag c                                                          11

<210> SEQ ID NO 32
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 32
tatgctgtcg g                                                          11

<210> SEQ ID NO 33
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 33
attcgccccc c                                                          11

<210> SEQ ID NO 34
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 34
tccgcttcgg t					11

<210> SEQ ID NO 35
<211> LENGTH: 56
<212> TYPE: DNA
<213> ORGANISM: Artificial Sequence
<220> FEATURE:
<223> OTHER INFORMATION: Description of Artificial Sequence: Synthetic

<400> SEQUENCE: 35
taactgtcaa aagccactgt gtcctgaaga aaagcaaaga catctggaca aaaagc					56

<210> SEQ ID NO 36
<211> LENGTH: 15
<212> TYPE: RNA
<213> ORGANISM: Artificial Sequence
<220> FEATURE:
<223> OTHER INFORMATION: Description of Artificial Sequence: Synthetic

<400> SEQUENCE: 36
uccagauguc uuugc					15

<210> SEQ ID NO 37
<211> LENGTH: 30
<212> TYPE: RNA
<213> ORGANISM: Artificial Sequence
<220> FEATURE:
<223> OTHER INFORMATION: Description of Artificial Sequence: Synthetic

<400> SEQUENCE: 37
gaaauagaug guccagcugg acaagcagaa					30

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 38
cttgtccagc tggaccatct					20

<210> SEQ ID NO 39
<211> LENGTH: 1338
<212> TYPE: DNA
<213> ORGANISM: Artificial Sequence
<220> FEATURE:
<223> OTHER INFORMATION: Description of Artificial Sequence: Synthetic

<400> SEQUENCE: 39
aagctgcgcc acgtcttcct gttcaccgac ctgcttctct gcaccaagct					50 caagaagcag agcggaggca aaacgcagca gtatgactgc aaatggtaca					100 ttccgctcac ggatctcagc ttccagatgg tggatgaact ggaggcagtg					150 cccaacatcc ccctggtgcc cgatgaggag ctggacgctt tgaagatcaa					200 gatctcccag atcaagaatg acatccagag agagaagagg gcgaacaagg					250 gcagcaaggc tacggagagg ctgaagaaga agctgtcgga gcaggagtca					300 ctgctgctgc ttatgtctcc cagcatggcc ttcagggtgc acagccgcaa					350 cggcaagagt tacacgttcc tgatctccct tgactatgag cgtgcagagt					400

```
ggagggagaa catccgggag cagcagaaga agtgtttcag aagcttctcc        450
ctgacatccg tggagctgca gatgctgacc aactcgtgtg tgaaactcca        500
gactgtccac agcattccgc tgaccatcaa taaggaagat gatgagtctc        550
cggggctcta tgggtttctg aatgtcatcg tccactcagc cactggattt        600
aagcagagtt caaaagccct tcagcggcca gtagcatctg actttgagcc        650
tcagggtctg agtgaagccg ctcgttggaa ctccaaggaa aaccttctcg        700
ctggacccag tgaaaatgac cccaaccttt tcgttgcact gtatgatttt        750
gtggccagtg gagataacac tctaagcata actaaaggtg aaaagctccg        800
ggtcttaggc tataatcaca tggggaatg tgtgaagcc caaaccaaaa          850 atggccaagg ctgggtccca agcaactaca tcacgccagt caacagtctg        900
gagaaacact cctggtacca tgggcctgtg tcccgcaatg ccgctgagta        950
tctgctgagc agcgggatca atggcagctt cttggtgcgt gagagtgaga       1000
gcagtcctgg ccagaggtcc atctcgctga gatacgaagg gagggtgtac       1050
cattacagga tcaacactgc ttctgatggc aagctctacg tctcctccga       1100
gagccgcttc aacaccctgg ccgagttggt tcatcatcat tcaacggtgg       1150
ccgacgggct catcaccacg ctccattatc cagccccaaa gcgcaacaag       1200
cccactgtct atggtgtgtc ccccaactac gacaagtggg agatggaacg       1250
cacggacatc accatgaagc acaagctggg cggggggccag tacggggagg      1300 tgtacgaggg cgtgtggaag aaatacagcc tgacggtg                    1338
```

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 40
ataagcacct cttcaaggtc tg                                        22

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 41
tgacctgctc ctcaccctc ct                                         22

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 42
cagaccttga agaggtgctt at                                        22

<210> SEQ ID NO 43
<211> LENGTH: 22
<212> TYPE: DNA
<213> ORGANISM: Artificial Sequence

```
<220> FEATURE:
<223> OTHER INFORMATION: Description of Artificial Sequence: Synthetic

<400> SEQUENCE: 43 aggagggtg aggagcaggt ca                                              22

<210> SEQ ID NO 44
<211> LENGTH: 16
<212> TYPE: DNA
<213> ORGANISM: Artificial Sequence
<220> FEATURE:
<223> OTHER INFORMATION: Description of Artificial Sequence: Synthetic

<400> SEQUENCE: 44
gagttcaaaa gccctt                                                    16

<210> SEQ ID NO 45
<211> LENGTH: 32
<212> TYPE: DNA
<213> ORGANISM: Artificial Sequence
<220> FEATURE:
<223> OTHER INFORMATION: Description of Artificial Sequence: Synthetic
<220> FEATURE:
<221> NAME/KEY: misc_feature
<222> LOCATION: (22)..(31)
<223> OTHER INFORMATION: n is any nucleotide

<400> SEQUENCE: 45
catctccacc tccataaccc annnnnnnnn nc                                  32

<210> SEQ ID NO 46
<211> LENGTH: 31
<212> TYPE: DNA
<213> ORGANISM: Artificial Sequence
<220> FEATURE:
<223> OTHER INFORMATION: Description of Artificial Sequence: Synthetic
<220> FEATURE:
<221> NAME/KEY: misc_feature
<222> LOCATION: (1)..(10)
<223> OTHER INFORMATION: n is any nucleotide

<400> SEQUENCE: 46
nnnnnnnnnn aggtgatagg tggaggtggt a                                   31

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic

<400> SEQUENCE: 47
catctccacc tccataac                                                  18

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 48
taccacctcc acctatcacc t                                              21

<210> SEQ ID NO 49
<211> LENGTH: 21
<212> TYPE: RNA
```

<213> ORGANISM: Artificial Sequence
<220> FEATURE:
<223> OTHER INFORMATION: Description of Artificial Sequence: Synthetic

<400> SEQUENCE: 49
uggguuaugg agguggagau g     21

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic

<400> SEQUENCE: 50
uaccaccucc accaucacc u     21

<210> SEQ ID NO 51
<211> LENGTH: 10
<212> TYPE: DNA
<213> ORGANISM: Artificial Sequence
<220> FEATURE:
<223> OTHER INFORMATION: Description of Artificial Sequence: Synthetic

<400> SEQUENCE: 51
tggaccatct     10

<210> SEQ ID NO 52
<211> LENGTH: 10
<212> TYPE: DNA
<213> ORGANISM: Artificial Sequence
<220> FEATURE:
<223> OTHER INFORMATION: Description of Artificial Sequence: Synthetic

<400> SEQUENCE: 52
cttgtccagc     10

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 53
gaaatagatg gtccagctgg acaagcagaa     30

<210> SEQ ID NO 54
<211> LENGTH: 62
<212> TYPE: DNA
<213> ORGANISM: Artificial Sequence
<220> FEATURE:
<223> OTHER INFORMATION: Description of Artificial Sequence: Synthetic

<400> SEQUENCE: 54
gcgcgcgcgc tgctggacaa gtccttttttt ccttttttttcc tagatggtcc     50 atgcgcgcgc gc     62

<210> SEQ ID NO 55
<211> LENGTH: 62
<212> TYPE: DNA
<213> ORGANISM: Artificial Sequence
<220> FEATURE:
<223> OTHER INFORMATION: Description of Artificial Sequence: Synthetic

<400> SEQUENCE: 55

```
gcgcgcgcgc tagatggtcc atcctttttt ccttttttcc tgctggacaa        50
gtgcgcgcgc gc                                                 62
```

<210> SEQ ID NO 56
<211> LENGTH: 60
<212> TYPE: DNA
<213> ORGANISM: Artificial Sequence
<220> FEATURE:
<223> OTHER INFORMATION: Description of Artificial Sequence: Synthetic

<400> SEQUENCE: 56

```
gcgcgcgcgc tccttgctgg acaagttttc cttttagatg gtccattcct        50
gcgcgcgcgc                                                    60
```

<210> SEQ ID NO 57
<211> LENGTH: 60
<212> TYPE: DNA
<213> ORGANISM: Artificial Sequence
<220> FEATURE:
<223> OTHER INFORMATION: Description of Artificial Sequence: Synthetic

<400> SEQUENCE: 57

```
acggactgct tccttgctgg acaagttttc cttttagatg gtccattcct        50
tcatcaaacc                                                    60
```

<210> SEQ ID NO 58
<211> LENGTH: 10
<212> TYPE: DNA
<213> ORGANISM: Artificial Sequence
<220> FEATURE:
<223> OTHER INFORMATION: Description of Artificial Sequence: Synthetic

<400> SEQUENCE: 58

```
agatggtcca                                                    10
```

<210> SEQ ID NO 59
<211> LENGTH: 10
<212> TYPE: DNA
<213> ORGANISM: Artificial Sequence
<220> FEATURE:
<223> OTHER INFORMATION: Description of Artificial Sequence: Synthetic

<400> SEQUENCE: 59

```
gctggacaag                                                    10
```

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 60

```
gaaatagatg gtccagctgg acaagcagaa                              30
```

<210> SEQ ID NO 61
<211> LENGTH: 52
<212> TYPE: DNA
<213> ORGANISM: Artificial Sequence
<220> FEATURE:
<223> OTHER INFORMATION: Description of Artificial Sequence: Synthetic

<400> SEQUENCE: 61

```
agatggtcca gtcggcgcgc ctcgaaaacg aggcgcgccg acgctggaca        50
ag                                                            52
```

<210> SEQ ID NO 62
<211> LENGTH: 54
<212> TYPE: DNA
<213> ORGANISM: Artificial Sequence
<220> FEATURE:
<223> OTHER INFORMATION: Description of Artificial Sequence: Synthetic

<400> SEQUENCE: 62
agatggtcca tgtcggcgcg cctcgaaaac gaggcgcgcc gactgctgga      50
caag                                                       54

<210> SEQ ID NO 63
<211> LENGTH: 52
<212> TYPE: DNA
<213> ORGANISM: Artificial Sequence
<220> FEATURE:
<223> OTHER INFORMATION: Description of Artificial Sequence: Synthetic

<400> SEQUENCE: 63
agatggtcca gcccccaggc cgcatacgac ggctagggag cggctggaca      50
ag                                                         52

<210> SEQ ID NO 64
<211> LENGTH: 16
<212> TYPE: RNA
<213> ORGANISM: Artificial Sequence
<220> FEATURE:
<223> OTHER INFORMATION: Description of Artificial Sequence: Synthetic

<400> SEQUENCE: 64
uuucuucagg acacag                                          16

<210> SEQ ID NO 65
<211> LENGTH: 15
<212> TYPE: RNA
<213> ORGANISM: Artificial Sequence
<220> FEATURE:
<223> OTHER INFORMATION: Description of Artificial Sequence: Synthetic

<400> SEQUENCE: 65
uccagauguc uuugc                                           15

<210> SEQ ID NO 66
<211> LENGTH: 54
<212> TYPE: DNA
<213> ORGANISM: Artificial Sequence
<220> FEATURE:
<223> OTHER INFORMATION: Description of Artificial Sequence: Synthetic

<400> SEQUENCE: 66
ttctggctgg acaagtcaag aacccgcagt tcgtgttcga gatggtccag      50
aaca                                                       54

<210> SEQ ID NO 67
<211> LENGTH: 54
<212> TYPE: DNA
<213> ORGANISM: Artificial Sequence
<220> FEATURE:
<223> OTHER INFORMATION: Description of Artificial Sequence: Synthetic

<400> SEQUENCE: 67
ttctgagatg gtccatcaag aacccgcagt tcgtgttcgg ctggacaagg      50

```
aaca                                                             54

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 68
gaaauagaug guccagcugg acaagcagaa                                 30

<210> SEQ ID NO 69
<211> LENGTH: 10
<212> TYPE: DNA
<213> ORGANISM: Artificial Sequence
<220> FEATURE:
<223> OTHER INFORMATION: Description of Artificial Sequence: Synthetic

<400> SEQUENCE: 69
agauggucca                                                       10

<210> SEQ ID NO 70
<211> LENGTH: 10
<212> TYPE: DNA
<213> ORGANISM: Artificial Sequence
<220> FEATURE:
<223> OTHER INFORMATION: Description of Artificial Sequence: Synthetic

<400> SEQUENCE: 70
gcuggacaag                                                       10

<210> SEQ ID NO 71
<211> LENGTH: 32
<212> TYPE: DNA
<213> ORGANISM: Artificial Sequence
<220> FEATURE:
<223> OTHER INFORMATION: Description of Artificial Sequence: Synthetic

<400> SEQUENCE: 71
ctccataacc catggacatg taccggtgat cc                              32

<210> SEQ ID NO 72
<211> LENGTH: 32
<212> TYPE: DNA
<213> ORGANISM: Artificial Sequence
<220> FEATURE:
<223> OTHER INFORMATION: Description of Artificial Sequence: Synthetic

<400> SEQUENCE: 72
gatccccggg ctatgtctag aggagaagga ga                              32

<210> SEQ ID NO 73
<211> LENGTH: 32
<212> TYPE: DNA
<213> ORGANISM: Artificial Sequence
<220> FEATURE:
<223> OTHER INFORMATION: Description of Artificial Sequence: Synthetic

<400> SEQUENCE: 73
ctccataacc caaggatcct caccggtgat cc                              32

<210> SEQ ID NO 74
<211> LENGTH: 32
<212> TYPE: DNA
<213> ORGANISM: Artificial Sequence
```

```
<220> FEATURE:
<223> OTHER INFORMATION: Description of Artificial Sequence: Synthetic

<400> SEQUENCE: 74
gatccccggg taccgagcat aggagaagga ga                                   32

<210> SEQ ID NO 75
<211> LENGTH: 12
<212> TYPE: DNA
<213> ORGANISM: Artificial Sequence
<220> FEATURE:
<223> OTHER INFORMATION: Description of Artificial Sequence: Synthetic

<400> SEQUENCE: 75
ctccataacc ca                                                         12

<210> SEQ ID NO 76
<211> LENGTH: 12
<212> TYPE: DNA
<213> ORGANISM: Artificial Sequence
<220> FEATURE:
<223> OTHER INFORMATION: Description of Artificial Sequence: Synthetic

<400> SEQUENCE: 76
aggagaagga ga                                                         12

<210> SEQ ID NO 77
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 77
ggatcaccgg t                                                          11

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 78
gcctctaagt ctccttctcc t                                               21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 79
catctccacc tccataaccc a                                               21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 80
cacctccata acccatggac a                                               21
```

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 81
ctaagtctcc ttctcctcta gaca                                              24

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 82
ccacctccat aacccaagga t                                                 21

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 83
tctaagtctc cttctcctat gct                                               23

<210> SEQ ID NO 84
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 84
catctccacc tccataaccc at                                                22

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 85
gcctctaagt ctccttctcc tc                                                22

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 86
catctccacc tccataaccc aa                                                22

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 87
gcctctaagt ctccttctcc ta                                        22

<210> SEQ ID NO 88
<211> LENGTH: 16
<212> TYPE: DNA
<213> ORGANISM: Artificial Sequence
<220> FEATURE:
<223> OTHER INFORMATION: Description of Artificial Sequence: Synthetic

<400> SEQUENCE: 88
uuucuucagg acacag                                               16

<210> SEQ ID NO 89
<211> LENGTH: 55
<212> TYPE: DNA
<213> ORGANISM: Artificial Sequence
<220> FEATURE:
<223> OTHER INFORMATION: Description of Artificial Sequence: Synthetic

<400> SEQUENCE: 89
taactgtcaa aagccactgt gtcctgaaga aagcaaagac atctggacaa           50
aaagc                                                           55

<210> SEQ ID NO 90
<211> LENGTH: 57
<212> TYPE: DNA
<213> ORGANISM: Artificial Sequence
<220> FEATURE:
<223> OTHER INFORMATION: Description of Artificial Sequence: Synthetic

<400> SEQUENCE: 90
taactgtcaa aagccactgt gtcctgaaga aaagcaaag acatctggac            50 aaaaagc                                                         57

<210> SEQ ID NO 91
<211> LENGTH: 58
<212> TYPE: DNA
<213> ORGANISM: Artificial Sequence
<220> FEATURE:
<223> OTHER INFORMATION: Description of Artificial Sequence: Synthetic

<400> SEQUENCE: 91
taactgtcaa aagccactgt gtcctgaaga aaaagcaaa gacatctgga            50 caaaaagc                                                        58

<210> SEQ ID NO 92
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 92
acataagcaa c                                                    11

<210> SEQ ID NO 93
<211> LENGTH: 11
<212> TYPE: DNA
<213> ORGANISM: Artificial Sequence
<220> FEATURE:
<223> OTHER INFORMATION: Description of Artificial Sequence: Synthetic

```
<400> SEQUENCE: 93
ttatcgtagt c                                                              11

<210> SEQ ID NO 94
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 94
cgtcaaattc c                                                              11

<210> SEQ ID NO 95
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 95
tagccctgtt a                                                              11

<210> SEQ ID NO 96
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 96
tatgtgtcaa c                                                              11

<210> SEQ ID NO 97
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 97
tatggcgtag a                                                              11

<210> SEQ ID NO 98
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 98
actggattga c                                                              11

<210> SEQ ID NO 99
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 99
tctgtttgac g                                                              11

<210> SEQ ID NO 100
<211> LENGTH: 11
```

```
<212> TYPE: DNA
<213> ORGANISM: Artificial Sequence
<220> FEATURE:
<223> OTHER INFORMATION: Description of Artificial Sequence: Synthetic

<400> SEQUENCE: 100
gtacctgctg c                                                          11

<210> SEQ ID NO 101
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 101
tatcggtacg g                                                          11

<210> SEQ ID NO 102
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 102
tgaccgagaa c                                                          11

<210> SEQ ID NO 103
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 103
ttctgtcggg c                                                          11

<210> SEQ ID NO 104
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 104
atactttcca c                                                          11

<210> SEQ ID NO 105
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 105
taacgccccg t                                                          11

<210> SEQ ID NO 106
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 106
```
atcgatgctg c    11

<210> SEQ ID NO 107
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 107
taacgaatcg a    11

<210> SEQ ID NO 108
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 108
tgcacgctcc c    11

<210> SEQ ID NO 109
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 109
tcgtctttga a    11

<210> SEQ ID NO 110
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 110
aacgcataaa c    11

<210> SEQ ID NO 111
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 111
tcatacaagt g    11

<210> SEQ ID NO 112
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 112
gacagatgat c    11

<210> SEQ ID NO 113
<211> LENGTH: 11
<212> TYPE: DNA
<213> ORGANISM: Artificial Sequence

```
<220> FEATURE:
<223> OTHER INFORMATION: Description of Artificial Sequence: Synthetic

<400> SEQUENCE: 113
tgggtacggg c                                                          11

<210> SEQ ID NO 114
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 114
ctctaataca c                                                          11

<210> SEQ ID NO 115
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 115
ttccaacact c                                                          11

<210> SEQ ID NO 116
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 116
tacgccctct c                                                          11

<210> SEQ ID NO 117
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 117
ttcaagagct a                                                          11

<210> SEQ ID NO 118
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 118
gaagggcacc c                                                          11

<210> SEQ ID NO 119
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 119
tctgcagttg g                                                          11
```

```
<210> SEQ ID NO 120
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 120
aaagggaatt c                                                          11

<210> SEQ ID NO 121
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 121
tatttcgtaa g                                                          11

<210> SEQ ID NO 122
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 122
gcgagcccat c                                                          11

<210> SEQ ID NO 123
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 123
taccgtcatt c                                                          11

<210> SEQ ID NO 124
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 124
atgcggaaga c                                                          11

<210> SEQ ID NO 125
<211> LENGTH: 11
<212> TYPE: DNA
<213> ORGANISM: Artificial Sequence
<220> FEATURE:
<223> OTHER INFORMATION: Description of Artificial Sequence: Synthetic

<400> SEQUENCE: 125
tgttaacacg a                                                          11

<210> SEQ ID NO 126
<211> LENGTH: 69
<212> TYPE: DNA
<213> ORGANISM: Artificial Sequence
<220> FEATURE:
<223> OTHER INFORMATION: Description of Artificial Sequence: Synthetic
```

```
<400> SEQUENCE: 126
tgcgcttctg ggtgaatgtg atcaagaacc cgcagttcgt gttcgacatc cacaagaaca        60
gcatcacgg                                                                 69
```

METHODS AND KITS FOR THERANOSTIC APPLICATIONS

CROSS-REFERENCE TO RELATED APPLICATIONS

This application is a 35 U.S.C. § 371 national phase application of PCT Application No. PCT/US15/63368 filed Dec. 2, 2015, which claims priority to U.S. Provisional Application Nos. 62/086,661 filed Dec. 2, 2014, and 62/086,658 filed Dec. 2, 2014, each of which is incorporated herein by reference in its entirety.

FIELD

The present disclosure provides for the identification, enrichment, and evaluation of templated assembly targets.

BACKGROUND

A goal of drug development is delivering potent bio-therapeutic interventions that are specific for pathogenic cells, such as virus infected cells, neoplastic cells, cells producing an autoimmune response, and other dysregulated or dysfunctional cells without risk of toxicity to adjacent normal cells or the overall health of the patient. Unfortunately, developing these agents is extremely difficult.

A method that has emerged to allow delivery of potent interventions to pathogenic cells while mitigating toxicity to normal cells is targeting therapeutics against molecular markers specific for pathogenic cells. Targeted therapeutics have shown extraordinary clinical results in restricted cases, but are currently limited in their applicability due to a lack of accessible markers for targeted therapy. It is extremely difficult, and often impossible, to discover protein markers for many pathogenic cell types.

Existing nucleic acid-targeted therapies, such as siRNA, are able to down-modulate expression of potentially dangerous genes, but do not deliver potent cytotoxic or cytostatic interventions and thus are not particularly efficient at eliminating the dangerous cells themselves.

Hence, there exists a need to develop highly targeted therapeutics without the poor efficacy and/or severe side effects of existing interventions.

SUMMARY

The present disclosure is directed to methods and kits for identifying, enriching, and evaluating templated assembly targets.

Some embodiments are directed to methods for identifying templated assembly targets including synthesizing a first population of templated assembly reactants and a second population of corresponding templated assembly reactants, wherein the first and second populations of templated assembly reactants comprise oligonucleotide sequences; hybridizing both populations of templated assembly reactants to target nucleic acids; performing a templated assembly reaction, wherein the hybridized first population of templated assembly reactants and the hybridized second population of corresponding templated assembly reactants undergo templated assembly; and identifying the target nucleic acids that hybridized to either the first or second population of templated assembly reactants that underwent templated assembly, wherein the hybridized target nucleic acids are the templated assembly targets.

In some embodiments, synthesizing the first and second population of templated assembly reactants can include synthesizing random or gene-specific oligonucleotides sequences of about 5 to about 100 nucleotides long or about 7 to about 30 nucleotides long. The templated assembly reactants can also include nuclease-resistant phosphodiester backbones or nuclease-resistant sugar moieties. The templated assembly reactants can include a 5' or a 3'priming site adjacent to the oligonucleotide sequences. The populations of templated assembly reactants can also include modifications, such as a 5'-azide and a 3'-alkyne group; a 5'-alkyne and a 3'-azide group; and an N-hydroxysuccinimide and a cyclooctyne on corresponding populations. The modification can be specific for a traceless Staudinger ligation selected from either a traceless phosphinophenol Staudinger ligation or a traceless phosphinomethanethiol Staudinger ligation. The templated assembly reactants can also include a spacer or linker, such as at least 6 carbon atoms.

In some embodiments, the method can include obtaining the target nucleic acids prior to hybridizing the populations of templated assembly reactants to the target nucleic acids. Isolating nucleic acids from a target sample can also be included in the methods.

In some embodiments, the target sample can be at least one of a cell population, a tumor, a tissue, or an organ. The target nucleic acids can also maintain their native secondary structures. The target nucleic acids can also include cellular nucleic acid templates, such as genomic or expressed genes for known oncogenes or tumor suppressors, cell cycle regulators and mediators, transcriptonal regulators and mediators, translational regulators and mediators, telomerases, cytoskeletal components, and kinases.

In some embodiments, hybridizing both populations of templated assembly reactants to the target nucleic acids can include removing unbound templated assembly reactants. Removing unbound templated assembly reactants can also include removing the unbound reactants by at least one of an enzymatic digestion, an ultrafiltration, or a gel size-exclusion chromatography, or any combination thereof.

In some embodiments, the templated assembly reaction can be at least one of a click chemical reaction, a Staudinger reduction, a non-traceless Staudinger ligation, a traceless Staudinger ligation, a traceless phosphinophenol Staudinger ligation, a traceless phosphinomethanethiol Staudinger ligation, a native chemical ligation, and a bio-orthogonal chemical reaction, or any combination thereof.

In some embodiments, identifying the target nucleic acids can include removing the hybridized first population of templated assembly reactants and the hybridized second population of corresponding templated assembly reactants that failed to undergo templated assembly. Microcompartmentalizing the reacted templated assembly reactants from the unreacted templated assembly reactants and/or amplifying the hybridized target nucleic acids, may also be included in the identification. Additionally, sequencing the hybridized target nucleic acids can be used to identify the target nucleic acids.

The present disclosure is also directed to libraries of templated assembly reactants for identifying templated assembly targets including at least a first and second population of templated assembly reactants, where the templated assembly reactants include an oligonucleotide sequence and a modification for reaction in a templated assembly reaction. Kits for identifying templated assembly targets including a library of oligonucleotides for identifying templated assembly targets having oligonucleotide sequences modified as corresponding templated assembly reactants and reagents are also disclosed. Additionally, a pair of templated assembly targets enriched from a library of chemically-ligated oligonucleotides spatially elicited (CLOSE) products having oligonucleotides chemically ligated due to their spatial proximity through hybridization to cellular nucleic acid templates is included.

The present disclosure is also directed to methods for enrichment of a pair of templated assembly targets from a library of chemically-ligated oligonucleotides spatially elicited (CLOSE) products including obtaining a library of oligonucleotides chemically ligated through templated assembly due to spatial proximity to cellular nucleic acid targets, amplifying the library of ligated oligonucleotide-cellular nucleic acid targets and selectively enriching for ligated oligonucleotide-cellular nucleic acid targets, wherein the ligated targets are selected for relevance to a pathology of an aberrant cell of interest or to a discontinuous hybridization to the cellular nucleic acid targets are disclosed. The methods can also include removing ligated targets derived from matched normal cells of interest.

Pairs of templated assembly targets enriched from a library of chemically-ligated oligonucleotides spatially elicited (CLOSE) products comprising oligonucleotides chemically ligated due to their spatial proximity through hybridization to cellular nucleic acid templates are also included. The CLOSE library can be made of short PCR product duplexes of the chemically ligated oligonucleotides, such as from amplified library of chemically ligated products or an amplified library of rearranged chemically ligated products. The oligonucleotides can be differentially enriched in a CLOSE library derived from aberrant target cells as compared to a CLOSE library derived from normal cells. The oligonucleotides can also be selectively enriched for ligated targets differentially derived from aberrant target cells and not matched normal cells of interest.

The present disclosure is also directed to methods of evaluating a pair of chemically-ligated oligonucleotides spatially elicited (CLOSE) products for templated assembly including modifying the pair of CLOSE products as templated assembly reactants, transfecting the pair of modified CLOSE products into a target aberrant cell of interest, and screening for templated assembly of the pair of modified CLOSE products. The CLOSE products can also be modified by adding a pyrene group, such as pyrene maleimide, and/or including a spacer arm between the pyrene and maleimide.

BRIEF DESCRIPTION OF DRAWINGS

The appended drawings have been included herein so that the above-recited features, advantages and objects of the disclosure will become clear and can be understood in detail. These drawings form a part of the specification. It is to be noted, however, that the appended drawings illustrate some embodiments of the disclosure and should not be considered to limit the scope of the claims.

FIGS. 3A, 3B, and 3C are representative diagrams showing productive and non-productive hybridizations between specific oligonucleotides from separately 5'- and 3'-labeled random decamer populations; 3A) productive, from both 5'-azide and 3'-alkyne modified populations; 3B) non-productive, from 5'-azide modified populations only; and 3C) non-productive, from 3-alkyne-modified population only.

FIG. 4 shows representative examples of CLOSE clones (C1-C19) in comparison to an equal number of random oligonucleotides of the same pattern (Rnd1-Rnd17); CL1=TGGATCTCTGC (SEQ ID NO:1), TTAAAGTGACC (SEQ ID NO:2); CL2=TGAGTGTGTGC (SEQ ID NO:3), TGCGCACACTC (SEQ ID NO:4); CL3=ACGGGCCCGGC (SEQ ID NO:5), TTCGCGTC-CAG (SEQ ID NO:6); CL4=TCTTTTACGCC (SEQ ID NO:7); TCTGCCCAGGC (SEQ ID NO:8); CL5 =ACAC-CCTCGCC (SEQ ID NO:9); TACCTTCTCCC (SEQ ID NO: 10); CL6 =TCACATTCACC (SEQ ID NO:11); TTGTGGATGTG (SEQ ID NO:12); CL8 =GGCCCTTC-TAC (SEQ ID NO:13); TCGTCTGCGGC (SEQ ID NO:14); CL9 =TTCAATGGGCC (SEQ ID NO:15); TTACCCA-GTGC (SEQ ID NO:16); CL10 =ATCAACCCTGC (SEQ ID NO:17); TGTATTCGCCA (SEQ ID NO:18); CL11 =ACGCCGATTGC (SEQ ID NO:19); TGGCA-GTCGGC (SEQ ID NO:20); CL12 =ACCTAACAGCC (SEQ ID NO:21); TTCATCCGTTC (SEQ ID NO:22); CL13 =TTGAACGATCC (SEQ ID NO:23); TAGGTCGT-TCA (SEQ ID NO:24); CL14 =ATAGAAGGGGC (SEQ ID NO:25); TTAGGCCAACA (SEQ ID NO:26); CL15 =CCAACTGTAGC (SEQ ID NO:27); TAGGCGGT-TGG (SEQ ID NO:28); CL16 =CCCGGCCTCCC (SEQ ID NO:29); TTCCTAGCTGC (SEQ ID NO:30); CL17 = AAACCGACAGC (SEQ ID NO:31); TATGCTGTCGG (SEQ ID NO:32); CL19 =ATTCGCCCCCC (SEQ ID NO:33); TCCGCTTCGGT (SEQ ID NO:34); Rnd1 = ACATAAGCAAC (SEQ ID NO:92); TTATCGTAGTC (SEQ ID NO:93); Rnd2 =CGTCAAATTCC (SEQ ID NO:94); TAGCCCTGTTA (SEQ ID NO:95); Rnd3 =TAT-GTGTCAAC (SEQ ID NO:96); TATGGCGTAG a (SEQ ID NO:97); Rnd4 =ACTGGATTGAC (SEQ ID NO:98); TCT-GTTTGACG (SEQ ID NO:99); Rnd5 =GTACCTGCTGC (SEQ ID NO:100); TATCGGTACGG (SEQ ID NO:101); Rnd6 =TGACCGAGAAC (SEQ ID NO:102); TTCT-GTCGGGC (SEQ ID NO:103); Rnd7 =ATACTTTCCAC (SEQ ID NO:104); TAACGCCCCGT (SEQ ID NO:105); Rnd8 =ATCGATGCTGC (SEQ ID NO:106); TAAC-GAATCGA (SEQ ID NO:107); Rnd9 =TGCACGCTCCC (SEQ ID NO:108); TCGTCTTTGAA (SEQ ID NO:109); Rnd10 =AACGCATAAAC (SEQ ID NO:110), TCATA-CAAGTG (SEQ ID NO:111); Rnd11 =GACAGATGATC (SEQ ID NO:112), TGGGTACGGGC (SEQ ID NO:113); Rnd2 =CTCTAATACAC (SEQ ID NO:114), TTC-CAACACTC (SEQ ID NO:115); Rnd13 =TACGCCCTCTC (SEQ ID NO:116), TTCAAGAGCT a (SEQ ID NO:117); Rnd14 =GAAGGGCACCC (SEQ ID NO:118), TCTGCA-GTTGG (SEQ ID NO:119); Rnd15 =AAAGGGAATTC (SEQ ID NO:120), TATTTCGTAAG (SEQ ID NO:121); Rnd16 =GCGAGCCCATC (SEQ ID NO:122), TACCGT-CATTC (SEQ ID NO:123); Rnd17 =ATGCGGAAGAC (SEQ ID NO:124), TGTTAACACGA (SEQ ID NO:125).

FIG. 14 depicts representative CLOSE site nomenclature conventions; L- and R-CLOSE oligonucleotides hybridizing to discontinuous sites on a template can either have their chemically modified ends linearly directed towards each other ("endo" configuration) or opposed to each other ("exo" configuration); some configurations may accelerate effector partial reactivity, depending on: 1) distance between L and R sites (N sequences as above), 2) flexibility of N and flanking sequences; and 3) secondary structures promoting spatial proximity.

FIG. 15 depicts representative discontinuous "endo" vs. "exo" sites within secondary structural loops; if hybridization sites are within a loop, the ends of an exo configuration can be spatially brought together, while the conventional endo orientation is poorly active.

FIG. 28 depicts representative target-directed CLOSE; a schematic example of an expressed translocation, where two normal transcripts are effectively fused together; while there is only one possible junction sequence that can be targeted as a linear contiguous sequence, there are many potential CLOSE sites formed through spatial proximity mediated by higher-order RNA folding and secondary structures.

FIG. 31 depicts a representative BCR-ABL segment used as a probe for target-directed CLOSE (1338 bases; SEQ ID NO:39); black text: BCR sequence; gray text: ABL sequence (junction at GAGTTCAA/AAGCCCTT; SEQ ID NO:44); priming sites for the relevant amplification primers are underlined.

FIGS. 33A and 33B depict representative schematic configurations of RDOs with terminal azide and cyclooctyne groups; P1, P2: primer sites 1 and 2 respectively; N10: random decamer tracts; COT: 3'-terminal modified cycloalkyne; Az: 5'-terminal azide group.

FIG. 38 illustrates representative extensions incorporating 5'-methyl-dCTP and using complementary segment to region A1; hemimethylated regions of resulting extended duplexes are indicated by gray background shading; S1 and S2 denote selected subpopulations of decamers from the original random decamer total populations.

FIG. 41 shows representative Xma I cutting (in the specified embodiment) and re-ligation of 5'-5' linkages within microcompartments.

FIG. 46 shows representative extensions incorporating 5'-methyl-dCTP and using complementary segment to region A2; hemimethylated regions of resulting extended duplexes are indicated by gray background shading; S1 and S2 denote selected subpopulations of decamers from the original random decamer total populations.

FIG. 55 shows representative partitioning of 5'-3' chemically ligated duplex products into in vitro microcompartments; here each fragment has been initially cleaved with restriction enzyme E2 (Age I in the specified embodiment).

FIG. 59 depicts representative testing of the ability of in vitro compartmentalization to enable molecule-specific rearrangements, for amplification and identification of specific sequences; step 1. validation model: make 4× oligonucleotides, two with 5'-azides, and two with 5' linear alkynes (joinable by Cu(I) mediated click chemistry); each designed with specific marker sequences, and to enable differential amplifications.

product of the expected size is only formed when both cutting and religation are applied; closely similar rearrangements enable amplification of 3'-3' or "unreadable" 5'-3' joins.

Figure 61:
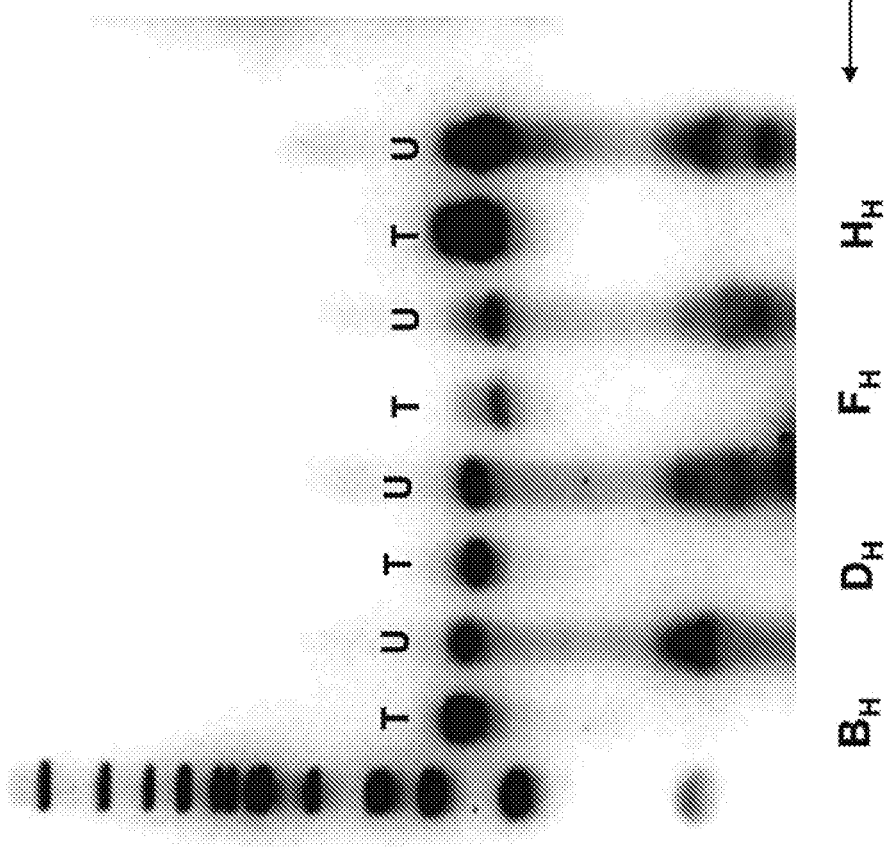

FIG. 61 depicts representative testing of purified Top band 5'-5' chemical ligation adducts (from excised gel bands), run side-by-side with samples of corresponding unpurified material.

Figure 62:
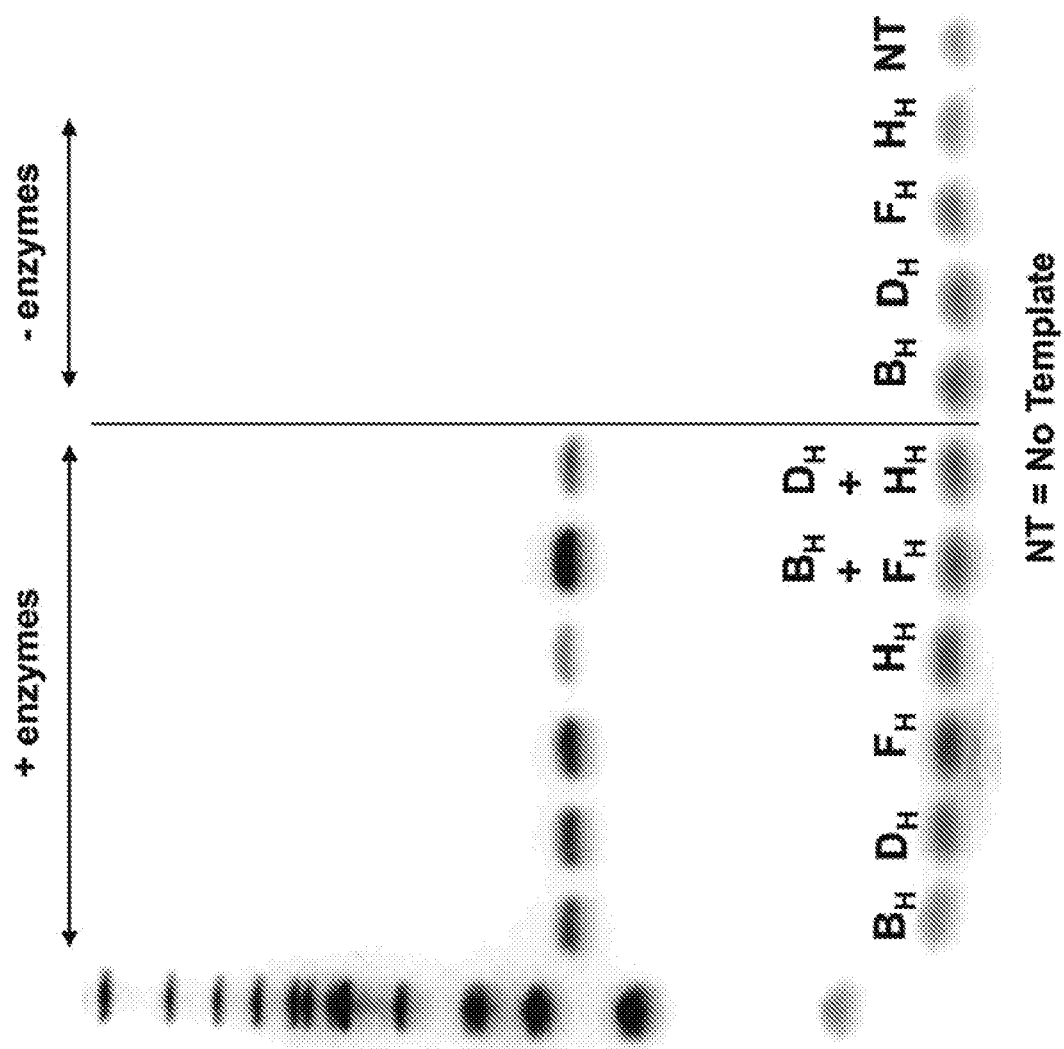

FIG. 62 depicts representative testing use of enzymes (Age I, Xma I, T4 DNA ligase) designed to enable amplifiable products with all model Top band 5'-5' adduct products.

FIG. 63 depicts representative principle of the model oligonucleotide detection system for successful IVC; in this case, duplexed 5'-5' adducts are precut Age I for testing in IVC, such that only Xma I and ligase are needed to complete the rearrangements.

Figure 64:
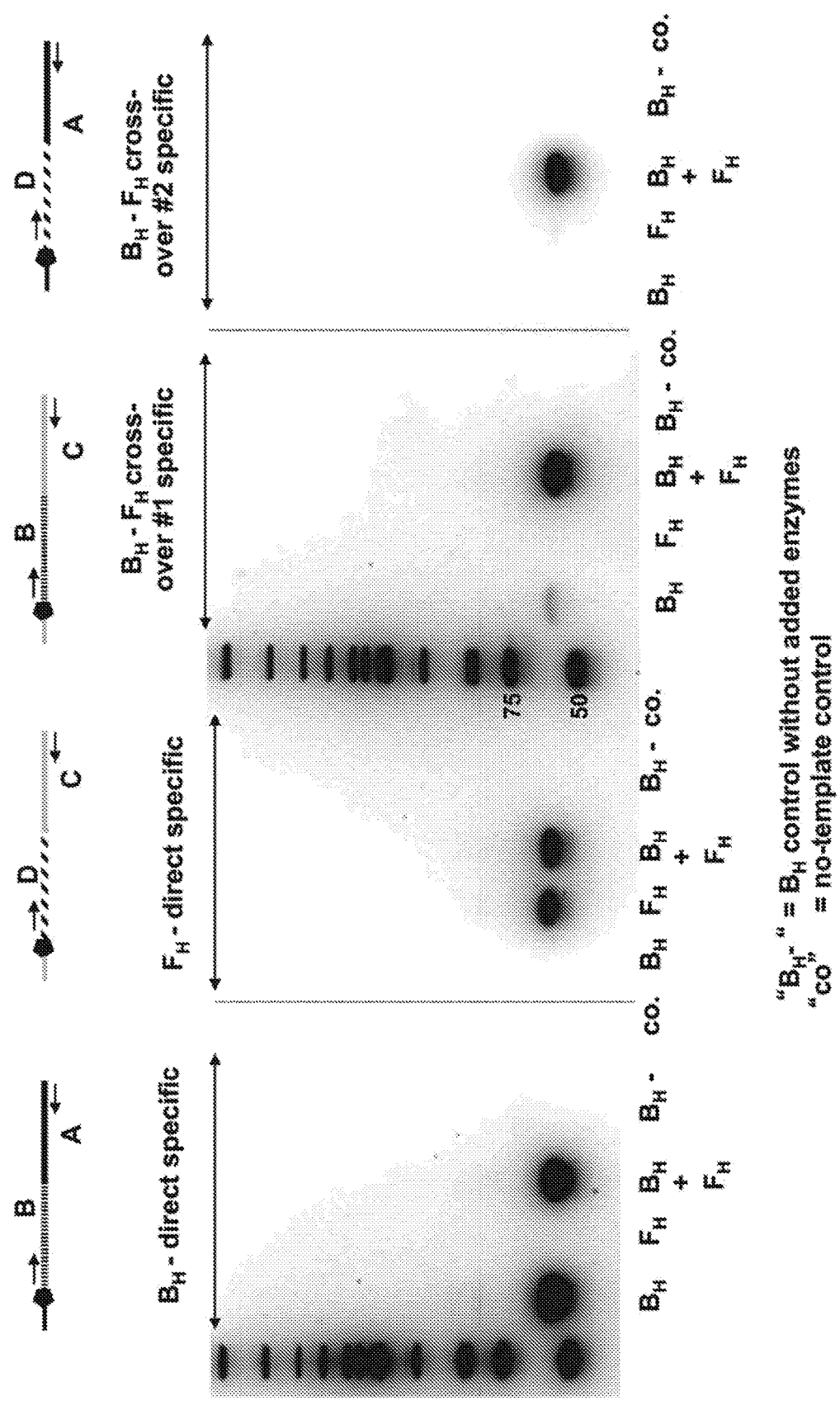

FIG. 64 depicts representative testing primers designed to detect specific rearrangements, whether direct (single-molecule) or specific cross-overs; for mixtures of two different 5'-5' products undergoing the enzymatic rearrangements, specific primer pairs must be able to identify only each direct product, or a specific cross-over product.

Figure 65:
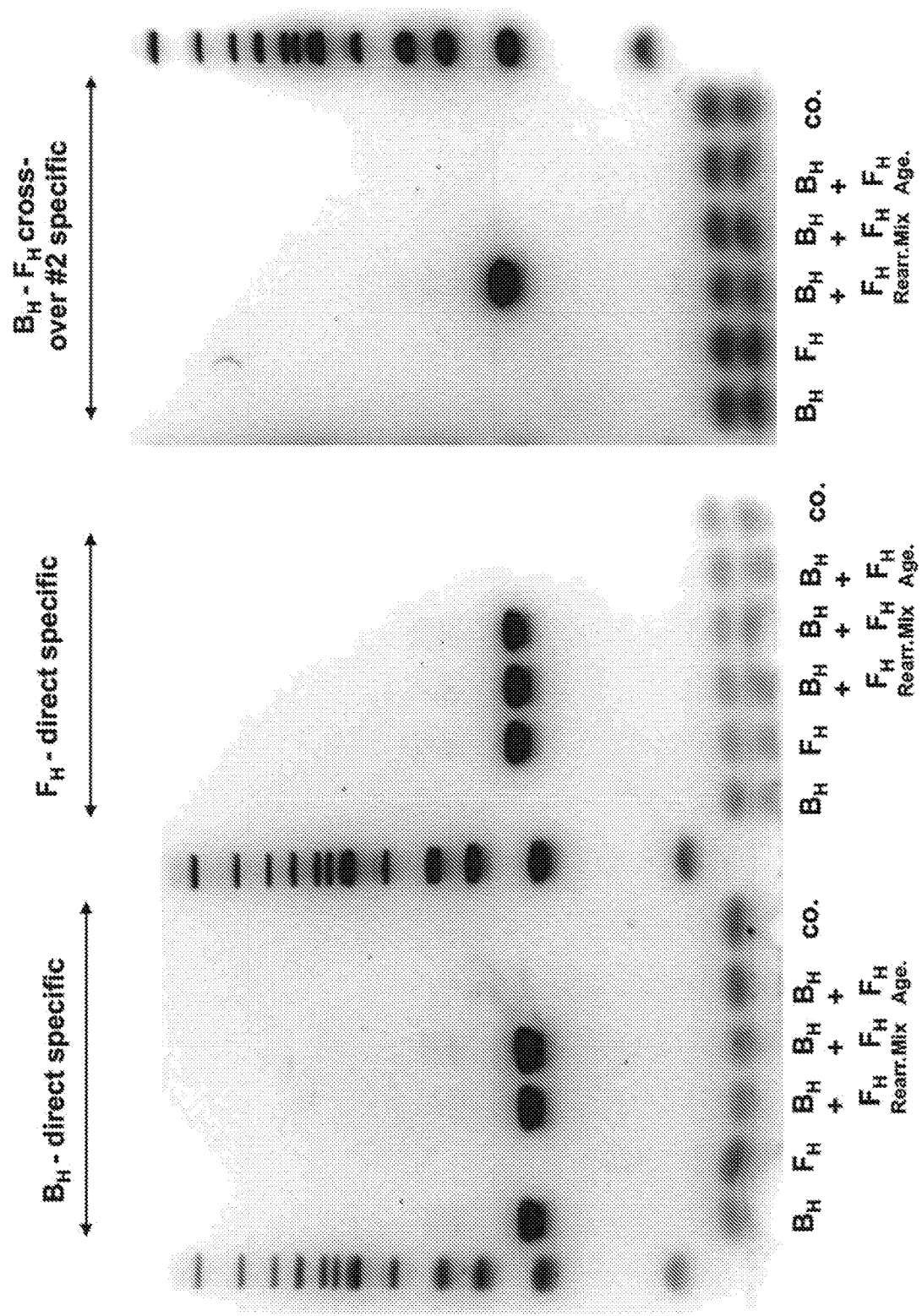

FIG. 65 depicts representative testing specificity of rearrangement-directed primers with pre formed rearrangements without PCR-induced artefactual crossing-over; BH, FH=direct rearrangements BH and FH adducts respectively; BH+FH rearr=rearrangement process performed with BH and FH products simultaneously present (thus allowing cross-over rearrangements); BH+FH Mix=BH and FH adduct rearrangements performed separately, and then mixed together prior to PCR; BH+FH Age=BH and FH adducts cut with Age I only and mixed prior to PCR; co=no-template control.

Figure 66:
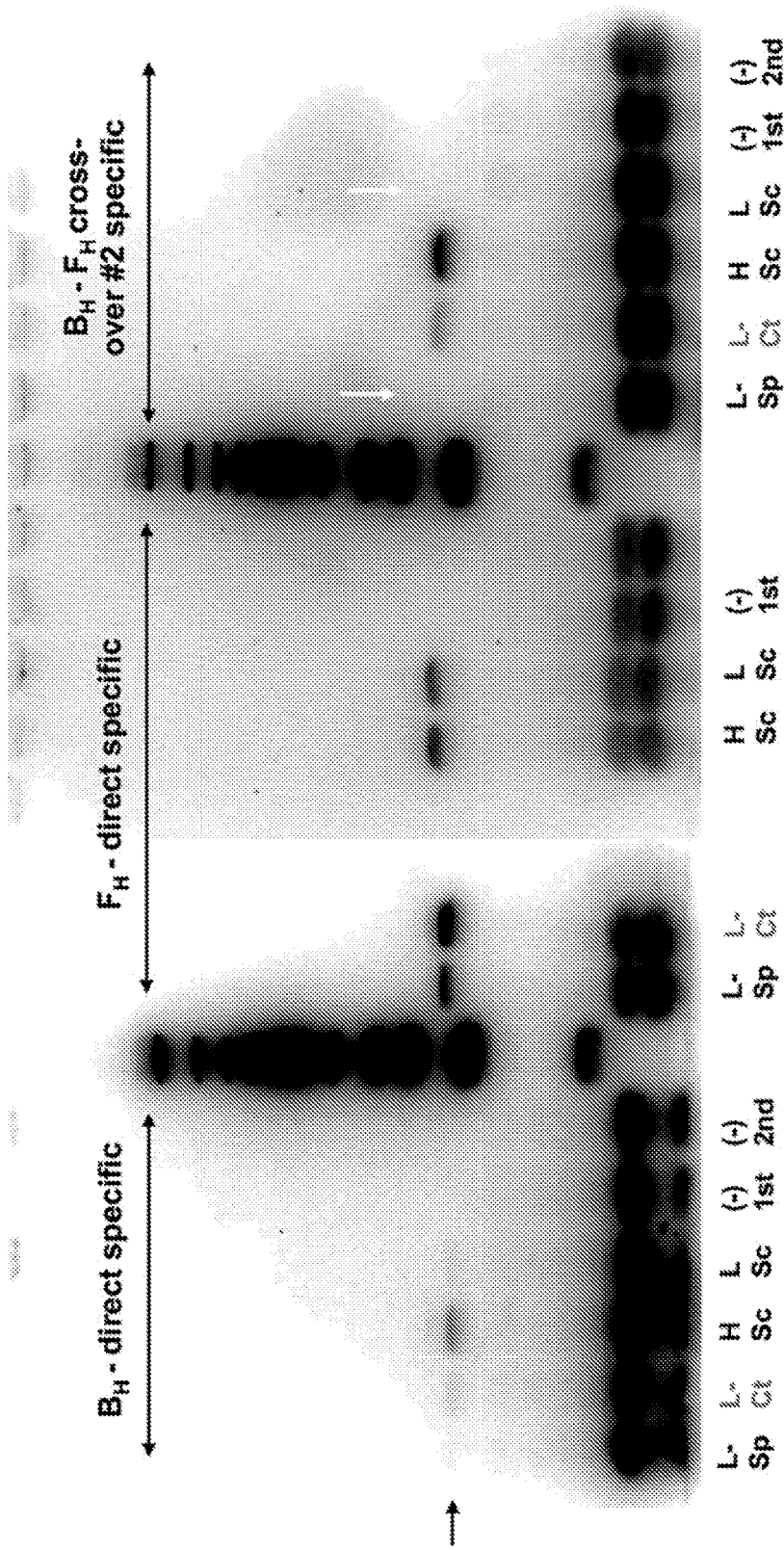

FIG. 66 depicts representative nested PCR results of in vitro compartmentalization test; no detectable cross-over products were observed (vertical white arrows).

FIG. 67 depicts representative CLOSE amplification of 5'-3' joins, by means of circularization and inverse PCR; this applies direct read-through is not possible owing to the formation of bulky non-traceless products; a potential problem with this approach is cross-ligation between separate molecules (rather than circularization), which would scramble the correct information; this can be minimized by performing the religation step at low concentrations.

DESCRIPTION

The present disclosure is directed to methods and kits for identifying, enriching, and evaluating templated assembly reactants.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of any other embodiments. Such modifications and variations are intended to be included within the scope of the present disclosure.

All publications, patents and patent applications cited herein, whether supra or infra, are hereby incorporated by reference in their entirety. As used in this specification and the appended claims, the singular forms "a," "an," and "the" include plural references unless the content clearly dictates otherwise. The terms used in this disclosure adhere to standard definitions generally accepted by those having ordinary skill in the art. In case any further explanation might be needed, some terms have been further elucidated below.

The term "about," as used herein, refers to variations in a numerical quantity that can occur, for example, through measuring or handling procedures in the real world; through inadvertent error in these procedures; through differences in the manufacture, source, or purity of compositions or reagents, and the like. Typically, the term "about" as used herein means greater or lesser than the value or range of values stated by 1/10 of the stated values, e.g., ±10%. For instance, a concentration value of about 30% can mean a concentration from 27% to 33%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the claims include equivalents to the recited values, e.g., variations in the numerical quantity of such values that can occur, but would be recognized to be equivalents by a person skilled in the art.

The phrases "active effector structure" and "effector structure" are used interchangeably herein and refer to the active portion of a templated assembly product that triggers a desired effect.

The term "base," as used herein, refers to a molecule containing a purine or pyrimidine group, or an artificial analogue, that forms a binding pair with another corresponding base via Watson-Crick or Hoogsteen bonding interactions. Bases further contain groups that facilitate covalently joining multiple bases together in a polymer, such as an oligomer. Non-limiting examples include nucleotides, nucleosides, peptide nucleic acid residues, or morpholino residues.

The terms "bind," "binds," "binding," and "bound," as used herein, refer to a stable interaction between two molecules that are close to one another. The terms include physical interactions, such as chemical bonds (either directly linked or through intermediate structures), as well as non-physical interactions and attractive forces, such as electrostatic attraction, hydrogen bonding, and van der Waals/dispersion forces.

The phrase "bioconjugation chemistry," as used herein, refers to the chemical synthesis strategies and reagents that ligate common functional groups together under mild conditions, facilitating the modular construction of multi-moiety compounds.

As used herein, "chemically-ligated oligonucleotides spatially elicited" refers to pairs of oligonucleotides that have been chemically ligated as a consequence of their spatial proximity through hybridization to target nucleic acid templates.

The phrase "effector partial moiety," as used herein, refers to a portion of a templated assembly reactant that contributes to the chemical structure of the effector structure in a product formed by nucleic acid templated assembly. An effector partial moiety may be a distinct portion of the reactant, or may include or be comprised of part or all of the nucleic acid recognition moiety and/or the selectively-reactive moiety.

The terms "linker" and "spacer" are used interchangeable herein and refer to a molecule adjacent to the oligonucleotide sequence in the templated assembly reactant. A linker can be an additional oligonucleotide sequence, a peptide, a non-active portion of a peptidomimetic structure, a non-active portion of a drug, or other bioactive compound that is less than 20 kDa. A linker may be comprised of branched or unbranched covalently bonded molecular chain.

The phrase "non-traceless bio-orthogonal chemistry," as used herein, refers to a reaction involving selectively-reactive moieties in which part or all of the structure of the selectively-reactive moieties is retained in the product structure.

The phrase "nucleic acid recognition moiety" as used herein refers to an oligonucleotide that facilitates sequence-specific binding to a target nucleic acid. An example of a nucleic acid recognition moiety is an oligonucleotide sequence that binds to a target nucleic acid.

The terms "oligonucleotide sequences" and "oligomer," are used interchangeably herein and refer to a molecule comprised of multiple units where some or all of the units are bases capable of forming Watson-Crick or Hoogsteen base-pairing interactions, allowing sequence-specific binding to nucleic acids in a duplex or multiplex structure. Non-limiting examples include oligonucleotides, peptide nucleic acid oligomers, and morpholino oligomers.

The phrase "pathogenic cell" as used herein can refer to a cell that is capable of causing or promoting a diseased or an abnormal condition, such as a cell infected with a virus, a tumor cell, and a cell infected with a microbe, or a cell that produces a molecule that induces or mediates diseases that include, but are not limited to allergy, anaphylaxis, inflammation and autoimmunity.

The phrase "pharmaceutically acceptable" when used herein refers to a material that is not biologically or otherwise unacceptable that can be incorporated into a composition and administered to a patient without causing unacceptable biological effects or interacting in an unacceptable manner with other components of the composition.

The phrase "pharmaceutically acceptable salt" means a salt prepared from a base or an acid which is acceptable for administration to a patient, such as a mammal (e.g., salts having acceptable mammalian safety for a given dosage regime).

The term "salt" as used herein can include salts derived from pharmaceutically acceptable inorganic acids and bases and salts derived from pharmaceutically acceptable organic acids and bases and their derivatives and variants thereof.

The term "sample," as used herein, refers to any system that templated assembly reactants can be administered into, where nucleic acid templated assembly may occur. Non-limiting examples may include living cells, fixed or pre-served cells, whole organisms, tissues, tumors, lysates, or in vitro assay systems.

The phrase "selectively-reactive moiety" refers to the portion of a templated assembly reactant that enables formation of product, such as through a chemical reaction with a corresponding templated assembly reactant. For example, a selectively-reactive moiety can react readily with a corresponding selectively-reactive moiety, but does not readily react with natural biomolecules.

The phrases "set of corresponding reactants" or "corresponding templated assembly reactants" are referred to herein as templated assembly reactants that come together on a single target template to take part in a templated assembly reaction.

In any embodiment herein, a "subject" can be a cell, in vitro, such as a cell in culture, or in vivo within a living organism. In some embodiments, the subject can be a microorganism. In some embodiments, the subject can be a cell derived from or comprised in a sample obtained from a larger organism. For example, the subject can be a cell comprised in a sample obtained from an organism by a biopsy procedure, and the method can be performed on it. In some embodiments, the subject can be a progeny (by cell division) of a progenitor cell obtained from an organism. A subject can also be a mammal. Examples of subjects can include but are not limited to, humans, horses, monkeys, dogs, cats, mice, rates, cows, pigs, goats and sheep. In some embodiments, "subjects" are generally human patients.

The term "superantigen," as used herein, refers to an antigen that binds to a broad subset of T cells that express a particular variable (V) region.

The phrase "traceless bio-orthogonal chemistry," as used herein, refers to a reaction involving selectively-reactive moieties in which a naturally occurring bond, for example an amide, is formed by elimination of part or all of the selectively-reactive moieties from the product structure.

The phrase "target compartment" as used herein refers to a cell, virus, tissue, tumor, lysate, other biological structure, spatial region, or sample that contains target nucleic acid, or a different amount of target nucleic acids than a non-target compartment.

The phrases "target nucleic acid sequence" and "target nucleic acid" are used interchangeably and refer to a sequence of units or nucleic acids which are intended to act as a template for nucleic acid templated assembly.

The phrases "templated assembly," "templated assembly reaction" and "nucleic acid templated assembly" are used interchangeably herein and refer to the synthesis of a product structure or structures on a target nucleic acid, such that product formation can be facilitated by templated assembly reactants being assembled in proximity when bound to the target nucleic acid.

The phrase "templated assembly ligation product," as used herein, refers to the product structure or structures formed by interaction, binding or reaction of one or more nucleic acid templated assembly reactants.

The phrase "templated assembly reactant" as used herein refers to an oligonucleotide sequence that binds to a target nucleic acid in a sequence-specific manner and participates in product formation during a templated assembly reaction.

Also included herein are "derivatives" or "analogs" such as salts, hydrates, solvates thereof, or other molecules that have been subjected to chemical modification and maintain the same biological activity or lack of biological activity, and/or ability to act as a templated assembly reactant, or function in a manner consistent with a templated assembly reactant.

Targeted template assembly produces desired chemical structures when in the presence of one or more targets, such as specific nucleic acid sequences. The disclosed methods and kits allow identification, analysis, or discovery of specific genetic templates. The disclosed methods and kits also identify the specific nucleic acid sequences targeted by templated assembly to avoid off-target toxicity and enhance specific reactivity. The disclosed methods and kits further enrich and evaluate specific nucleic acid sequences for template assembly. By identifying unique nucleic acid sequences for target cells, directed intervention can be focused on these specific cells, such as by self-destruction or immunotherapeutic destruction by other cells, without inducing toxicity against non-target cells, such as normal cells, that lack the template target.

The identification of templated assembly targets can include methods and kits for synthesizing templated assembly reactants, hybridizing the templated assembly reactants to target nucleic acids, performing a templated assembly reaction, and identifying the target nucleic acids that hybridized with the templated assembly reactants.

The phrase "templated assembly reactant" as used herein refers to an oligonucleotide sequence that binds to a target nucleic acid in a sequence-specific manner and participates in product formation during a templated assembly reaction. The templated assembly reactants can include a nucleic acid recognition moiety, such as an oligonucleotide sequence. U.S. Application No. 61/831,133, which is incorporated herein by reference in its entirety, discloses targeted templated assembly reactants that include a nucleic acid recognition moiety, a selectively-reactive moiety, and a effector partial moiety to produce a targeted therapeutic. In the present disclosure, the templated assembly reactants do not require, but may still include, an effector partial moiety. The identification, analysis, or discovery of target nucleic acids does not require the production of an effector function, such as disclosed in U.S. Application No. 61/831,133, so the presence of at least a nucleic acid recognition moiety and a selectively-reactive moiety are included in the templated assembly reactant. In some embodiments, a first population of templated assembly reactants and a second population of corresponding templated assembly reactants are disclosed, where the first population includes different oligonucleotide sequences or different libraries of oligonucleotide sequences than the second population. In some embodiments, a first population of templated assembly reactants and a second population of corresponding templated assembly reactants are disclosed, where the first population includes specific oligonucleotide sequences and chemical modifications differing from the second population.

Oligonucleotide sequences may be synthesized by several methods known in the art. Nucleotide-based oligonucleotide sequences may be synthesized in solution or on a solid-phase using phosphoramidite chemistry. Peptide nucleic acids may also be synthesized in solution or on a solid phase using methods known in the art. Various methods of morpholino synthesis could also be used. Any of the aforementioned types of oligonucleotide sequences may also be obtained fully synthesized from various commercial sources.

The oligonucleotide sequences may include sequences of base-pair forming units, such as nucleic acids or nucleic acid analogues. The oligonucleotide sequences may be made of multiple units where some or all of the units are bases capable of forming Watson-Crick or Hoogsteen base-pairing interactions, allowing sequence-specific binding to target nucleic acids in a duplex or multiplex structure.

The phrase "nucleic acid" is well known in the art. A "nucleic acid" as used herein will generally refer to a molecule (i.e., a strand) of DNA, RNA or a derivative or analog thereof, comprising a nucleotide. A nucleotide includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The phrase "nucleic acid" or "RNA molecule" encompasses the terms "oligonucleotide" and "polynucleotide," each as a subgenus of "nucleic acid."

The oligonucleotide sequences may be DNA nucleotides, RNA nucleotides, phosphorothioate-modified nucleotides, 2'-O-alkylated RNA nucleotides, halogenated nucleotides, locked nucleic acid nucleotides (LNA), peptide nucleic acids (PNA), morpholino nucleic acid analogues (morpholinos), pseudouridine nucleotides, xanthine nucleotides, hypoxanthine nucleotides, 2'-deoxyinosine nucleotides, other nucleic acid analogues capable of base-pair formation, or combinations thereof. In some embodiments, the oligonucleotide sequences includes nucleic acids and hybridizes to mRNA targets.

Commercially available derivatized bases may be incorporated to introduce functional groups including but not limited to amines, hydrazides, thiols, carboxylic acids, isocyanates, aldehydes which may then be conjugated with active functional groups on other moieties using standard techniques of bioconjugation chemistry to facilitate synthesis of the complete templated assembly reactant.

The oligonucleotide sequences may also incorporate, interact with or be bound to specialized units. For example, when using the templated assembly reactants, including an oligonucleotide sequence, in the presence of nucleases that may degrade standard DNA or RNA, such as in live cells or lysates, it may be desirable to incorporate nuclease-resistant bases into the oligonucleotide sequences. Some non-limiting examples can include phosphorothioate bases, 2'-O-alkylated or 2'-halogenated RNA bases, locked nucleic acids, peptide nucleic acids, morpholinos or a chimera including at least one of these. Unlike antisense probes that depend on RNase H activity, internal bases of the oligomer need not induce RNase H hydrolysis of a target RNA transcript. Thus, there is no requirement for RNase H-inducing bases at any position in the oligonucleotide sequence.

The templated assembly reactants can be synthesized to include oligonucleotide sequences that are random sequences or gene specific sequences. In some embodiments, the templated assembly reactants can bind to a target nucleic acid through a gene specific oligonucleotide sequence. The oligonucleotide sequences can be contiguous or non-contiguous sequences complementary to one or more target nucleic acids. The phrases "target nucleic acid sequence" and "target nucleic acid" are used interchangeably and refer to a sequence of units or nucleic acids which are intended to act as a target or template for nucleic acid templated assembly.

The oligonucleotide sequences can be gene specific by being complementary to a hybridization site on a target nucleic acid, allowing sequence-specific binding to the target nucleic acid. In some embodiments, the oligonucleotide sequence is a contiguous sequence that is complementary to a target nucleic acid. In some embodiments, the oligonucleotide sequence is selected such that its sequence is not similar to sequences known to be present in non-target nucleic acids. In some embodiments, the oligonucleotide sequence includes one or more mutations found within the target nucleic acid, allowing specific binding of the templated assembly reactants to the target nucleic acids but not to non-target nucleic acids that do not contain the mutation. In some embodiments, the oligonucleotide sequence may be synthesized with a stem-loop structure, with possible improvement in the desired binding interaction with target nucleic acids.

The oligonucleotide sequences can also be random sequences. The random oligonucleotide sequences can include any of the above base-pair forming units or specialized units in a random sequence.

The oligonucleotide sequences can be from about 5 to about 100 nucleotides long. In some embodiments, the random or gene specific sequence can be about 5 to about 100 nucleotides long. The oligonucleotides sequences can be any of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides long. In some embodiments, the oligonucleotides sequences can be from about 5 to about 30 nucleotides long, from about 7 to about 25 nucleotides long, or from about 7 to about 15 nucleotides long.

The oligonucleotide sequences, whether random or gene specific, can be complementary to a target nucleic acid with a length of the oligonucleotide sequence anywhere from about 5 to about 100 bases in length. In some embodiments, the oligonucleotide sequences can be complementary to the target nucleic acid with an oligonucleotide sequence length in the range of about 5 to about 50 bases in length, about 5 to about 40 bases in length, or about 10 to about 30 bases in length.

The oligonucleotide sequences can also be optimized to provide chemical properties. The length of oligonucleotide sequences can be selected based on chemical properties, such as melting and annealing temperatures of the complementary sequence. The melting temperature, $T_m$, is defined as the temperature in degrees Celsius, at which 50% of all molecules of a given oligonucleotide sequences are hybridized into a double strand, and 50% are present as single strands. The annealing temperature is generally 5 C lower than the melting temperature.

The $T_m$ of the oligonucleotide sequences can be in a range from about 10 C below to about 40 C above the temperature of the conditions in which the templated assembly reactant will be used. For example, if templated assembly reactants are to be used at 37 C, the oligonucleotide may be designed with an expected $T_m$ from 27 C to 77 C. In some embodiments, the template assembly reactants can be used at approximately 37 C, and the $T_m$ of the oligonucleotide sequences can be designed to be in the range of about 37 C to about 52 C.

In some embodiments, oligonucleotide sequences can be designed such that the $T_m$ to bind the target nucleic acid is substantially different from the $T_m$ to bind a similar non-target nucleic acid. For example, the oligonucleotide sequences may be designed such that the hybridization site it binds to on a target nucleic acid includes the site of a mutation. In some embodiments, the $T_m$ of the oligonucleotide sequences binding to the target nucleic acid is at or above the temperature at which the templated assembly reactant will be used, while the $T_m$ of the oligonucleotide sequences binding to the non-target nucleic acid is below the temperature at which the templated assembly reactant will be used. The oligonucleotide sequences will then bind to the mutant target sequence, but not to the non-target, non-mutant sequence.

The $T_m$ of the oligonucleotide sequences can be in a range from about 10 C below to about 40 C above the temperature of the conditions in which the templated assembly reactant will be used. For example, if templated assembly reactants are to be used at 37 C, the oligonucleotide sequences may be designed with an expected $T_m$ from 27 C to 77 C. In some embodiments, the template assembly reactants can be used at approximately 37 C, and the $T_m$ of the oligonucleotide sequences can be designed to be in the range of about 37 C to about 52 C.

The templated assembly reactant can also include a 5' and/or a 3' priming site adjacent to the oligonucleotide sequences. The priming site can be directly flanking the oligonucleotide sequence or can be separated from the oligonucleotide sequence by a linker sequence. Primer sequences commonly used in the art can be included. Such examples may include, but are not limited to, M13, T3, T7, SP6, VF2, VR, modified versions thereof, complementary sequences thereof, and reverse sequences thereof. In addition, custom primer sequences are also included.

The templated assembly reactants can also include an intermediate, such as a linker or spacer. The linker can be an additional oligonucleotide sequence ranging from 1 to about 50 nucleotides long. The linker can also be a peptide, a non-active portion of a peptidomimetic structure, a non-active portion of a drug, or other bioactive compound that is less than 20 kDa. A linker may be comprised of branched or unbranched covalently bonded molecular chain. In some embodiments, the linker is a spacer of at least 6 carbon atoms.

The templated assembly reactants can also include a modification adjacent to the oligonucleotide sequences to be reactive in a templated assembly reaction, such as a selectively-reactive moiety. Such modifications for templated assembly reactions are disclosed in U.S. Application No. 61/831,133, which is incorporated herein by reference in its entirety. In some embodiments, the modification is flanking the oligonucleotide sequence. As used herein, the "flanking sequence" can refer to a region immediately, e.g. within 1 to 5 basepairs, or within close proximity to, e.g. within 5 to 20 basepairs, the oligonucleotide sequence.

The modification can be biologically inert. In particular, the modification on one oligonucleotide sequence can interact readily with a corresponding modification on another oligonucleotide sequence, but will not readily interact with natural biomolecules. This is to ensure that the templated assembly reaction is formed when corresponding templated assembly reactants are assembled. It also safeguards against non-specific reactions occurring in the environment and prevents the formation of unintended products.

Examples of selectively-reactive moieties, modifications for reactivity in a templated assembly reaction, can include adding a bio-orthogonal reactive moiety. The bio-orthogonal reactive moiety can include those groups that can undergo "click" reactions between azides and alkynes, traceless or non-traceless Staudinger reactions between azides and phosphines, and native chemical ligation reactions between thioesters and thiols. Additionally, the bio-orthogonal moiety can be any of an azide, a cyclooctyne, a nitrone, a norbornene, an oxanorbornadiene, a phosphine, a dialkyl phosphine, a trialkyl phosphine, a phosphinothiol, a phosphinophenol, a cyclooctene, a nitrile oxide, a thioester, a tetrazine, an isonitrile, a tetrazole, a quadricyclane, and derivatives thereof.

In some embodiments, a first population of templated assembly reactants and a second population of corresponding templated assembly reactants are disclosed. The first population can include one modification and the second population can include a corresponding modification. For example, the first population can include azides on the templated assembly reactants and the second population can include alkynes on the templated assembly reactants, such that the first and second populations are capable of reacting in a click reaction to produce ligated products.

Multiple modifications for reactivity in a templated assembly reaction can be used with the methods and kits disclosed herein, some non-limiting examples include:

Azide-alkyne "Click Chemistry": click chemistry is highly selective as neither azides nor alkynes react with common biomolecules under typical conditions. Azides of the form R—N$_3$ and terminal alkynes of the form R—C≡CH or internal alkynes of the form R—C≡C—R react readily with each other to produce Huisgen cycloaddition products in the form of 1,2,3-triazoles

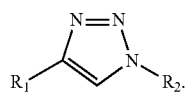

Azide-based templated assembly reactants have the substructure: R—N$_3$ where R is a chemical linker, nucleic acid recognition moiety, or effector partial moiety. Azides and azide derivatives may be readily prepared from commercially available reagents.

Azides can also be introduced to an effector partial moiety during synthesis of the effector partial moiety. In some embodiments, an azide group is introduced into a effector partial moiety comprised of a peptide by incorporation of a commercially available azide-derivatized standard amino acid or amino acid analogue during synthesis of the effector partial moiety peptide using standard peptide synthesis methods. Amino acids may be derivatized with an azide replacing the α-amino group, affording a structure of the form:

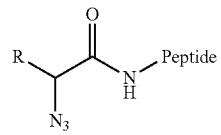

where R is a side chain of a standard amino acid or non-standard amino acid analogue.

Commercially available products can introduce azide functionality as an amino acid side chains, resulting in a structure of the form:

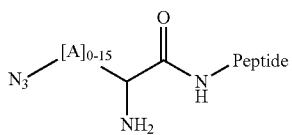

where A is any atom and its substituents in a side chain of a standard amino acid or non-standard amino acid analogue.

An azide may also be introduced into a effector partial moiety peptide after synthesis by conversion of an amine group on the peptide to an azide by diazotransfer methods. Bioconjugate chemistry can also be used to join commercially available derivatized azides to chemical linkers, nucleic acid recognition moieties, or effector partial moieties that contain suitable reactive groups.

Standard alkynes can be incorporated into a templated assembly reactant by methods similar to azide incorporation. Alkyne-functionalized nucleotide analogues are commercially available, allowing alkyne groups to be directly incorporated at the time of nucleic acid recognition moiety synthesis. Similarly, alkyne-derivatized amino acid analogues may be incorporated into a effector partial moiety by standard peptide synthesis methods. Additionally, diverse functionalized alkynes compatible with bioconjugate chemistry approaches may be used to facilitate the incorporation of alkynes to other moieties through suitable functional or side groups.

Azide-activated alkyne "Click Chemistry": Standard azide-alkyne chemistry reactions typically require a catalyst, such as copper(I). Since copper(I) at catalytic concentrations is toxic to many biological systems, standard azide-alkyne chemistry reactions have limited uses in living cells. Copper-free click chemistry systems based on activated alkynes circumvent toxic catalysts.

Activated alkynes often take the form of cyclooctynes, where incorporation into the cyclooctyl group introduces ring strain to the alkyne

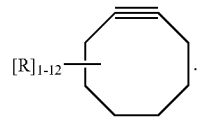

Heteroatoms or substituents may be introduced at various locations in the cyclooctyl ring, which may alter the reactivity of the alkyne or afford other alternative chemical properties in the compound. Various locations on the ring may also serve as attachment points for linking the cyclooctyne to a nucleic acid templated assembly moiety or linker. These locations on the ring or its substituents may optionally be further derivatized with accessory groups.

Multiple cyclooctynes are commercially available, including several derivatized versions suitable for use with standard bioconjugation chemistry protocols. Commercially available cyclooctyne derivatized nucleotides can aid in facilitating convenient incorporation of the selectively-reactive moiety during nucleic acid recognition moiety synthesis

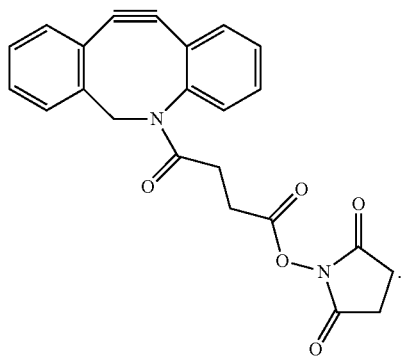 [SMILES: O=C(CCC(=O)N1Cc2ccccc2C#Cc2ccccc21)ON1C(=O)CCC1=O]

Cyclooctyne-azide based bio-orthogonal chemistry may produce templated assembly products of the general structure:

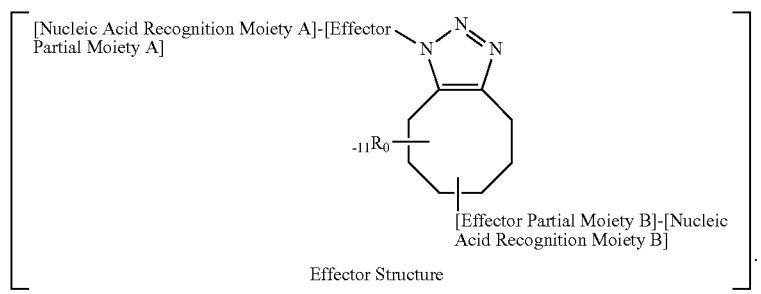

Another Example

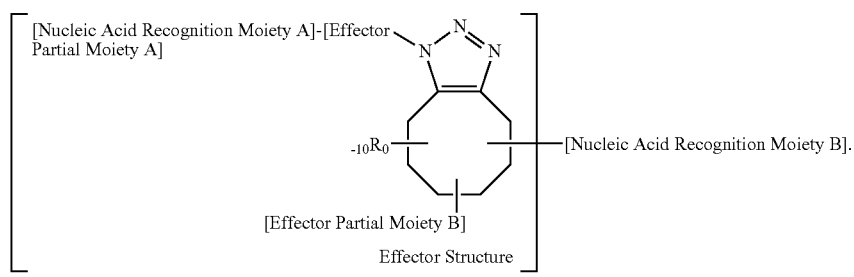

Azide-Phosphine Staudinger Chemistry: The Staudinger reduction, based on the rapid reaction between an azide and a phosphine or phosphite with loss of $N_2$, also represents a bio-orthogonal reaction. The Staudinger ligation, in which covalent links are formed between the reactants in a Staudinger reaction, is suited for use in nucleic acid templated assembly. Both non-traceless and traceless forms of the Staudinger ligation allow for a diversity of options in the chemical structure of products formed in these reactions.

Non-Traceless Staudinger Ligation: The standard Staudinger ligation is a non-traceless reaction between an azide and a phenyl-substituted phosphine such as triphenylphosphine, where an electrophilic trap substituent on the phosphine, such as a methyl ester, rearranges with the aza-ylide intermediate of the reaction to produce a ligation product linked by a phosphine oxide. An example of a Staudinger ligation product formed by templated assembly reactants A and B may have the structure:

are available commercially and suitable for incorporation into templated assembly reactants:

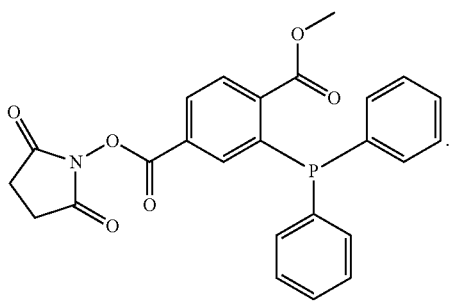

Phenyl-substituted phosphines carrying electrophilic traps can also be readily synthesized. Derivatized versions

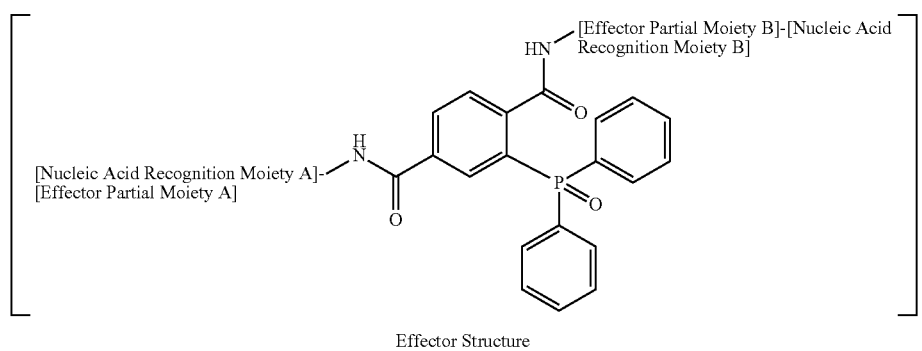

Traceless Staudinger Ligation: In some embodiments, phosphines capable of traceless Staudinger ligations may be utilized as selectively-reactive moieties. In a traceless reaction, the phosphine serves as a leaving group during rearrangement of the aza-ylide intermediate, creating a ligation typically in the form of a native amide bond. Compounds capable of traceless Staudinger ligation generally take the form of a thioester derivatized phosphine or an ester derivatized phosphine:

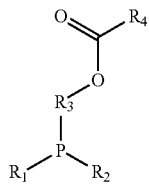

Ester derivatized phosphines for traceless Staudinger ligation.

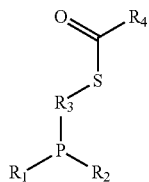

Thioester derivatized phosphines for traceless Staudinger ligations.

Chemical linkers or accessory groups may optionally be appended as substituents to the R groups in the above structures, providing attachment points for nucleic acid recognition moieties or for the introduction of additional functionality to the reactant.

Traceless Phosphinophenol Staudinger Ligation: Compared to the non-traceless Staudinger phenylphosphine compounds, the orientation of the electrophilic trap ester on a traceless phosphinophenol is reversed relative to the phenyl group. This enables traceless Staudinger ligations to occur in reactions with azides, generating a native amide bond in the product without inclusion of the phosphine oxide

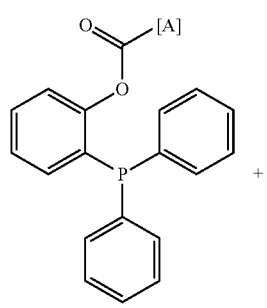

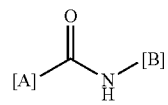

Traceless Ligation
Product Effector
Structure

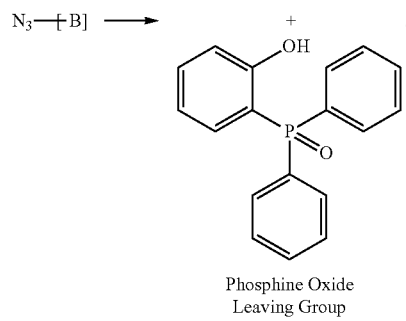

Phosphine Oxide
Leaving Group

The traceless Staudinger ligation may be performed in aqueous media without organic co-solvents if suitable hydrophilic groups, such as tertiary amines, are appended to the phenylphosphine. An article by Weisbord and Marx (2010) describes preparation of water-soluble phosphinophenol, which may be loaded with a desired effector partial moiety containing a carboxylic acid (such as the C-terminus of a peptide) via the mild Steglich esterification using a carbodiimide such as dicyclohexylcarbodiimide (DCC) or N,N'-diisopropylcarbodiimide (DIC) and an ester-activating agent such as 1-hydroxybenzotriazole (HOBT). This approach facilitates synthesis of templated assembly reactants of the form:

Water-soluble phosphinophenol-based traceless templated assembly reactant structure.

Traceless Phosphinomethanethiol Staudinger Ligation: Phosphinomethanethiols represent an alternative to phosphinophenols for mediating traceless Staudinger ligation reactions. In general, phosphinomethanethiols possess favorable reaction kinetics compared with phosphinophenols in mediating traceless Staudinger reaction. U.S. Application 2010/0048866 and an article to Tam et al. (2007) describe preparation of water-soluble phosphinomethanethiols of the form:

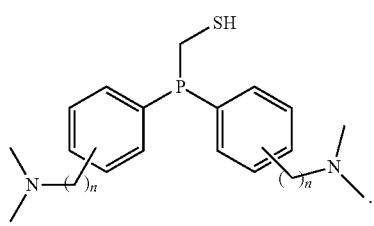

These compounds may be loaded with a peptide or other payload, in the form of an activated ester, to form a thioester suitable for use as a traceless bio-orthogonal reactive group:

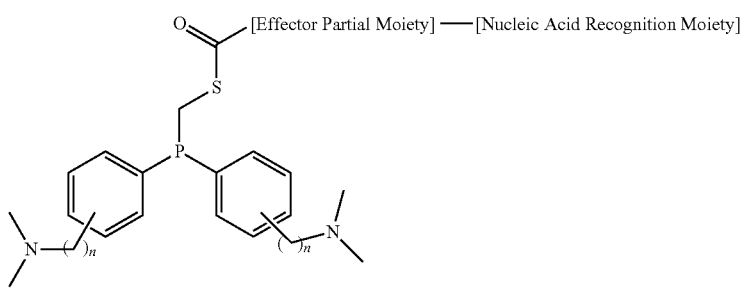

Templated assembly reactant structure based on water-soluble phosphinomethanethiol traceless Staudinger bio-orthogonal chemistry.

Native Chemical Ligation: Native chemical ligation is a bio-orthogonal approach based on the reaction between a thioester and a compound bearing a thiol and an amine. The classic native chemical ligation is between a peptide bearing a C-terminal thioester and another bearing an N-terminal cysteine, as seen below:

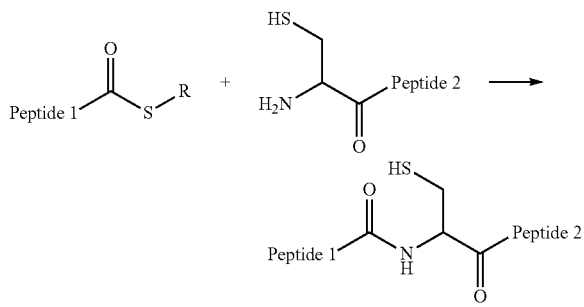

Native chemical ligation may be utilized to mediate traceless reactions producing a peptide or peptidomimetic containing an internal cysteine residue, or other thiol-containing residue if non-standard amino acids are utilized.

N-terminal cysteines may be incorporated by standard amino acid synthesis methods. Terminal thioesters may be generated by several methods known in the art, including condensation of activated esters with thiols using agents such as dicyclohexylcarbodiimide (DCC), or introduction during peptide synthesis via the use of "Safety-Catch" support resins.

Other Templated Assembly Reaction Moieties: Any suitable bio-orthogonal reaction chemistry may be utilized for synthesis of templated assembly reactants, as long as it efficiently mediates a reaction in a highly selective manner in complex biologic environments. A recently developed non-limiting example of an alternative bio-orthogonal chemistry that may be suitable is reaction between tetrazine and various alkenes such as norbornene and trans-cyclooctene, which efficiently mediates bio-orthogonal reactions in aqueous media.

In some embodiments, the templated assembly reactants can also include an effector partial moiety, such that when a set of corresponding templated assembly reactants participates in a templated assembly reaction, an active effector product can be generated. The effector partial moiety can be a portion of an active effector structure, such that when a set of corresponding templated assembly reactants take part in a templated reaction, their effector partial moieties combine to produce the desired active effector structure in the templated assembly ligation product. Thus, the effector partial moiety contributes to the chemical structure of the active effector structure. The effector partial moiety can be a distinct portion of the templated assembly reactant, or may include part or all of the nucleic acid recognition moiety and/or part or all of the selectively-reactive moiety. The phrases "active effector structure" and "effector structure" are used interchangeably herein and refer to the active portion of a templated assembly product that triggers a desired effect.

The effector partial moiety does not possess the targeted activity or the same level of activity associated with the active effector structure. In some embodiments, the effector partial structure is substantially inactive as compared to the active effector structure. In some embodiments, the individual effector partial moieties can possess separate activity, but binding the effector partial moieties together create an activity not possessed by them individually. For example, a bivalent effector structure that binds two different antibodies (each binds to a effector partial structure), making the effector suitable e.g., for detection in a sandwich ELISA for diagnostic evaluation. In some embodiments, the effector partial moieties together create a signal that can be detected upon a templated assembly reaction, such as luminescence.

The identification of templated assembly targets can include hybridizing the templated assembly reactants to target nucleic acids.

Nucleic acids, such as DNA or RNA, from a source of interest can be hybridized with the templated assembly reactants to selectively bind the oligonucleotide sequences. A target nucleic acid "complement(s)" or is "complementary" to the oligonucleotide when it is capable of base-pairing with the oligonucleotide according to the standard Watson-Crick, Hoogsteen or reverse Hoogsteen binding complementarity rules.

As used herein, the terms "complementary" and "complement(s)" refer to an oligonucleotide comprising a sequence of consecutive nucleotides or semi-consecutive nucleotides (e.g., one or more nucleotide moieties are not present in the molecule) capable of hybridizing to a target nucleic acid strand or duplex that may be consecutive, semi-consecutive or non-consecutive nucleotides even if less than all the nucleotides do not base pair with a counterpart nucleotide. In some embodiments, a "complementary" nucleic acid comprises a sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range derivable therein, of the oligonucleotide sequence is capable of base-pairing with a single or double stranded target nucleic acid during hybridization. In some embodiments, the term "complementary" refers to an oligonucleotide that may hybridize to target nucleic acid strand or duplex in stringent conditions, as would be understood by one of ordinary skill in the art.

In some embodiments, a "partly complementary" nucleic acid comprises a sequence that may hybridize in low stringency conditions to a single or double stranded nucleic acid, or contains a sequence in which less than about 70% of the nucleotide sequence is capable of base-pairing with a single or double stranded nucleic acid molecule during hybridization.

Prior to hybridization, the oligonucleotides modified to nucleic acid template reactants are subjected to a transient heat-denaturation step (2 minutes/80° C.). The samples are exposed to conditions conducive for hybridization to accessible tracts of target nucleic acids by complementary oligonucleotides.

Any nucleic acid can be a possible target nucleic acid for nucleic acid templated assembly provided that at least some sequence information is available, sufficient to bind the oligonucleotide either directly or indirectly. Some non-limiting examples of nucleic acid recognition moiety units can include oligonucleotides, peptide nucleic acid oligomers, and morpholino oligomers. Some non-limiting examples of target nucleic acid sequences or oligonucleotides can include mRNA, genomic or organellar DNA, episomal or plasmid DNA, viral DNA or RNA, miRNA, rRNA, snRNA, tRNA, or any other biological or artificial nucleic acid sequence.

In some embodiments, the target nucleic acid can be present in a target compartment but absent in a non-target compartment. An example of this embodiment includes nucleic acid sequences present in a pathogenic or diseased cell, but absent in a healthy cell. The phrase "pathogenic cell" as used herein can refer to a cell that is capable of causing or promoting a diseased or an abnormal condition, such as a cell infected with a virus, a tumor cell, and a cell infected with a microbe.

Any cell, virus, tissues, spatial regions, lysate, or other subcomponent of a sample that contains a target nucleic acid can provide the target nucleic acid. Target compartments that contain the target nucleic acid can include, but are not limited to, pathogenic cells, cancer cells, viruses, host cells infected by a virus or other pathogen, or cells of the immune system that are contributing to autoimmunity such as cells of the adaptive or innate immune systems, transplant rejection, or an allergic response. In some embodiments, a target nucleic acid can be present in a virus or cell infected by a virus, but absent in healthy cells. Some non-limiting examples of virus can include DNA viruses, RNA viruses, or reverse transcribing viruses. In some embodiments, a target nucleic acid can be present in a tumor or cancerous cell, but absent in healthy cells. Some non-limiting examples of cancers can include those caused by oncoviruses, such as the human papilloma viruses, Epstein-Barr virus, hepatitis B virus, hepatitis C virus, human T-lymphotropic viruses, Merkel cell polyoma virus, and Kaposi's sarcoma-associated herpesvirus. In some embodiments, a target nucleic acid can be present in an infectious agent or microbe, or a cell infected by an infectious agent or microbe but is absent in healthy cells. Some non-limiting examples of infectious agents or microbes can include viruses, bacteria, fungi, protists, prions, or eukaryotic parasites.

The target nucleic acid sequence can also be a fragment, portion or part of a gene, such as an oncogene, a mutant gene, an oncoviral gene, a viral nucleic acid sequence, a microbial nucleic acid sequence, a differentially expressed gene, and a nucleic acid gene product thereof.

Some non-limiting examples of virus-specific target nucleic acids can include sequences present in DNA viruses, RNA viruses, or reverse transcribing viruses. Some non-limiting examples of cancer-specific nucleic acids can include sequences derived from oncoviruses, including, but not limited to, human papilloma virus, Epstein-Barr virus, hepatitis B virus, hepatitis C virus, human T-lymphotropic virus, Merkel cell polyoma virus, and Kaposi's sarcoma-associated herpesvirus. Examples of cancer-specific target nucleic acids can include mutant oncogenes, such as mutated ras, HRAS, KRAS, NRAS, BRAF, EGFR, FLT1, FLT4, KDR, PDGFRA, PDGFRB, ABL1, PDGFB, MYC, CCND1, CDK2, CDK4, or SRC genes; mutant tumor suppressor genes, such as TP53, TP63, TP73, MDM1, MDM2, ATM, RB1, RBL1, RBL2, PTEN, APC, DCC, WT1, IRF1, CDK2AP1, CDKN1A, CDKN1B, CDKN2A, TRIM3, BRCA1, or BRCA2 genes; and genes expressed in cancer cells, where the gene may not be mutated or genetically altered, but is not expressed in healthy cells of a sample at the time of administration, such as carcinoembryonic antigen.

The target nucleic acids can be obtained prior to hybridizing the oligonucleotides in the templated assembly reactants to the target nucleic acids. The target nucleic acids can further be isolated from a target sample, such as a cell population, a tumor, a tissue, or an organ. The target nucleic acids can also be present in a whole cell lysate and not separated or isolated other cellular materials. In some embodiments, the native secondary structures of the target nucleic acids is maintained prior to hybridization.

In some embodiments, the target nucleic acid can be present in differential amounts or concentrations in the target compartments as compared to the non-target compartments. Examples can include, but are not limited to, genes expressed at a different level in cancer cells than in healthy cells, such as myc, telomerase, HER2, or cyclin-dependent kinases. In some embodiments, the target nucleic acid sequence can be a gene that is at least 1.5×-fold or 2.0×-fold differentially expressed in the target versus the non-target compartments. Some examples of these can include, but are not limited to, genes related to mediating Type I allergic responses, for which target RNA molecules contain immunoglobulin epsilon heavy chain sequences; genes expressed in T cell subsets, such as specific T cell receptors (TCRs) which recognize self-antigens in the context of particular major histocompatibility (MHC) proteins like proinsulin-derived peptide and clonally-specific mRNAs containing α or β variable-region sequences, derived from diabetogenic CD8+ T cells; and cytokines whose production may have adverse outcomes through exacerbation of inflammatory responses, including but not limited to TNF-alpha, TNF-beta, IL-1, IL-2, IL-4, IL-6, IL-8, IL-10, IL-12, IL-15, IL-17, IL-18, IL-21, IL-22, IL-27, IL-31, IFN-gamma, OSM, and LIF.

In some embodiments, a target nucleic acid is present in target compartments and an acceptable subgroup of non-target compartments, but not in a different or distinct subgroup of non-target compartments. Some non-limiting examples can include genes expressed in cancer cells and limited to classes of healthy cells, such as cancer-testis antigens, survivin, prostate-specific antigen, carcinoembryonic antigen (CEA), alpha-fetoprotein and other onco-fetal proteins. Also, many tissues and organs are not essential to otherwise healthy life in the face of serious disease. For example, melanocyte antigens, such as Melan-A/MART-1 and gp100 are expressed on many malignant melanomas as well as normal melanocytes, and therapies that target these antigens can destroy both tumors and normal melanocytes, resulting in vitiligo, but major tumor reduction. Likewise, the reproductive organs may be surgically removed, such as testis, ovary and uterus, as well as associated organs such as breast and prostate may be targeted when tumors of these tissues arise, and destruction of normal tissues within these organs may be a tolerable consequence of therapy. Furthermore, some cells that produce hormones, such as thyroxine and insulin can be replaced with the relevant peptide or protein, allowing potential targeting of normal cells that may exist in the presence of tumors of these origins.

Target nucleic acids can also include novel sequences, not previously identified. In some embodiments, a sample or samples can be evaluated by sequence analysis, such as next-generation sequencing, whole-transcriptome (RNA-seq) or whole-genome sequencing, microarray profiling, serial analysis of gene expression (SAGE), to determine the genetic makeup of the sample. Target nucleic acid sequences can be identified as those present in target compartments, but not present in non-target compartments, or present in differential amounts or concentrations in target compartments as compared to non-target compartments. Sequences identified by this method can then serve as target nucleic acids.

The oligonucleotide sequence of the templated assembly reactant can hybridize under hybridization conditions with varying stringency. The phrase "hybridization conditions" refers to conditions under which the oligonucleotides will hybridize to its target nucleic acids, typically in a complex mixture of nucleic acids, such as whole cell lysates, but to no other sequences. Hybridization conditions are sequence dependent and will be different in different circumstances. Longer sequences hybridize specifically at higher temperatures. An extensive guide to the hybridization of nucleic acids is found in Tijssen, Techniques in Biochemistry and Molecular Biology—Hybridisation with Nucleic Probes, "Overview of principles of hybridization and the strategy of nucleic acid assays" (1993). Generally, hybridization conditions are selected to be about 5-10 C lower than the thermal melting point (Tm) for the specific sequence at a defined ionic strength pH. The Tm is the temperature (under defined ionic strength, pH, and nucleic concentration) at which 50% of the oligonucleotides complementary to the target hybridize to the target nucleic acids at equilibrium (as the target nucleic acids are present in excess, at Tm, 50% of the probes are occupied at equilibrium).

The templated assembly reactants with oligonucleotide sequences can be present in an excess over the target nucleic acids during hybridization. In some embodiments, the oligonucleotides can be present in about a 10-100 fold excess over the target nucleic acids. The oligonucleotides can be about 5×, 10×, 15×, 20×, 25×, 30×, 35×, 40×, 45×, 50×, 55×, 60×, 65×, 70×, 75×, 80×, 85×, 90×, 95×, 100×, 125×, 150×, 200×, 300×, or any amount in between, excess over the target nucleic acids.

While excess of templated assembly reactants with oligonucleotide sequences (effector partials) over target templates is permissable, the converse situation (excess of target template) may reduce templated assembly efficacy. This "template titration" effect indicates that quantitation of template levels is highly useful, as well as identification of suitable specific sites within an RNA target molecule. Very low levels of an RNA target may also be counter-productive in terms of the application of templated assembly. Thus, an ideal range may exist for a specific template, influenced by steady-state template levels and other factors, including efficiency of target site access.

Hybridization conditions can be those in which the salt concentration is less than about 1.0 M sodium ion, typically about 0.01 to 1.0 M sodium ion concentration (or other salts) at pH 7.0 to 8.3 and the temperature is at least about 30 C for short probes (e.g., 10 to 50 nucleotides) and at least about 60 C for long oligonucleotides (e.g., greater than 50 nucleotides). Hybridization conditions may also be achieved with the addition of destabilizing agents such as formamide. For selective or specific hybridization, a positive signal is at least two times background, optionally 10 times background hybridization. Exemplary hybridization hybridization conditions can be as following: 50% formamide, 5×SSC, and 1% SDS, incubating at 42 C, or, 5×SSC, 1% SDS, incubating at 65 C, with wash in 0.2×SSC, and 0.1% SDS at 65 C. Such hybridizations and wash steps can be carried out for, e.g., 5, 10, 15, 30, 60, 90, or more minutes. In an exemplary embodiment, such hybridizations and wash steps can be carried out for periods of 2-16 hours.

Excess unbound templated assembly reactants can also be removed after hybridization. The unbound templated assembly reactants can be removed by methods commonly used in the art, such as but not limited to, enzymatic digestion, ultrafiltration, or gel size-exclusion chromatography.

Hybridizations can also be performed successively. In some embodiments, a first population of templated assembly reactants is hybridized to the target nucleic acids. Excess unbound templated assembly reactants of the first population can be removed. Then the second population of corresponding templated assembly reactants can be hybridized to the target nucleic acids that have been hybridized to the first population. Excess unbound templated assembly reactants of the second population can also be removed.

Nucleic acid templated assembly brings two or more templated assembly reactants into proximity to generate a templated assembly ligation product. The phrase "templated assembly ligation product," as used herein, refers to the product structure or structures formed by interaction, binding or reaction of one or more nucleic acid templated assembly reactants. A templated assembly ligation product may include an active effector product capable of producing a desired biological activity. Templated assembly ligation product formation is facilitated by the individual templated assembly reactants being assembled in a position- and/or orientation-specific manner through binding interactions, such as hybridization and annealing, with a target nucleic acid. Templated assembly reactants that come together on a single target template to take part in a templated assembly reaction are referred to herein as a "set of corresponding reactants" or "corresponding templated assembly reactants." A set of corresponding templated assembly reactants bind in a sequence-specific manner to spatially proximate parts of a nucleic acid target template, and readily react with each other to produce templated assembly ligation products including an active effector structure.

The templated assembly reaction can be, but is not limited to the following reactions: a click chemical reaction, a Staudinger chemistry, a non-traceless Staudinger ligation, traceless Staudinger ligation, a native chemical ligation, and other template assembly reactions. In some embodiments, the templated assembly reaction can be either a traceless phosphinophenol Staudinger ligation or a traceless phosphinomethanethiol Staudinger ligation. In some embodiments, click reactions can be performed.

Templated assembly reactions are further disclosed in U.S. Application No. 61/831,133, which is incorporated herein by reference in its entirety.

Excess unbound templated assembly reactants can also be removed after templated assembly. The unbound templated assembly reactants can be removed by methods commonly used in the art, such as but not limited to, enzymatic digestion, ultrafiltration, or gel size-exclusion chromatography.

Identifying the target nucleic acids can include any, or a combination of, amplifying the reacted or unreacted templated assembly reactants; selective cleavage of reacted or unreacted templated assembly reactants; microcompartmentalizing the reacted templated assembly reactants from the unreacted templated assembly reactants; and sequencing the oligonucleotides from the reacted templated assembly reactants.

Identification of the target nucleic acids can be performed by amplification of the complementary reacted templated assembly (CLOSE) reactants with primers complementary to the priming sites carried by the specific oligonucleotides. Only templated assembly reactant pairs (one from each separately-modified population) that have chemically joined via specific templated assembly reaction with the formation of triazole product are potentially amplifiable by PCR, by virtue of the specific linkage produced between the reactants.

In addition to effector partial sites for templated assembly that are contiguous within a target RNA sequence, non-contiguous (discontinuous) target sites may be effective, provided that they are brought into spatial proximity by virtue of folded RNA secondary structures, or other higher-order structural arrangements. Non-limiting examples of such secondary structural motifs include stem loops, internal sites within loops, and pseudoknots.

Oligonucleotides from the templated assembly reactants may hybridize to target nucleic acids in a spatially-proximal manner, yet be unable to promote amplifiable templated assembly reaction linkages. This may occur when the hybridizations juxtapose non-biologically amplifiable 5'-5' or 3'-3' ends, or where the templated assembly reaction between 5'- and 3'-modified ends of the template assembly reactants results in products whose size or structure is incompatible with polymerases.

Selective cleavage of the reacted templated assembly reactants, or reacted products, can also be performed. Restriction digestion of reacted products over unreacted products can utilize sites engineered into primer sites or linker sequences adjacent to the oligonucleotide sequences. Reacted and unreacted products can also be differentiated by methylation specific enzymes. In some embodiments, cleavage enzymes that are sensitive to 5-methylcytosine hemimethylation can be used. In some embodiments, the reacted products can be made double stranded through polymerase extension. The resulting duplex can be cleaved with an enzyme that recognizes a restriction site in the primer sites or linker sequences.

The cleaved reacted products can also be enzymatically ligated to preserve the linkage information between proximally-hybridized sequences and enable amplification.

In vitro compartmentalization can also be used to isolate templated assembly reaction linkages relies from unreacted templated assembly reactants by sequestering unreacted strands into individually-isolated compartments, preventing their ligation or reaction with other unreacted strands that may give spurious amplification signals (signals which have not resulted from original templated assembly reactions). These conditions can be achievable by forming emulsions which may be produced from any suitable combination of immiscible liquids. Hydrophilic solvents form "aqueous" droplets of microscopic or colloidal size. "Droplets" are also referred to as "microcompartments" herein. The aqueous droplets in the colloid can be formed from any hydrophilic material suitable for forming an emulsion, containing biochemical components in a stable form; and providing an environment in which the described reactions can occur.

The emulsion may be stabilized by addition of one or more surface-active agents (surfactants). These surfactants are termed emulsifying agents and act at the hydrophilic/hydrophobic interface to prevent (or at least delay) separation of the phases. Many hydrophobic liquids such as oils and many emulsifiers can be used for the generation of biphasic emulsions; a recent compilation listed over 16,000 surfactants, many of which are used as emulsifying agents (Ash, M. and Ash, I. Handbook of industrial surfactants. Gower Publishing Ltd: Aldershot, Hampshire, UK (1993); and Schick, Nonionic surfactants. Marcel Dekker: N.Y. (1996)) such as sorbitan monooleate (SPAN™ 80; ICI)) and polyoxyethylenesorbitan monooleate (TWEEN™ 80; ICI)).

The sequence of the oligonucleotides can be determined and verified using any suitable sequencing method including, but not limited to, chemical degradation (A. M. Maxam and W. Gilbert, Methods of Enzymology, 1980, 65, 499-560), matrix-assisted laser desorption ionization time-of-flight (MALDI-TOF) mass spectrometry (Pieles et al., Nucleic Acids Res., 1993, 21, 3191-3196), mass spectrometry following alkaline phosphatase and exonuclease digestions (Wu et al., Anal. Biochem., 2001, 290, 347-352), and the like.

In some embodiments, the target nucleic acids can be identified by amplifying the reacted or unreacted templated assembly reactants and sequencing the oligonucleotides from the reacted templated assembly reactants.

Methods for enrichment of templated assembly reactants are also disclosed. The enrichment can select for reacted templated assembly reactants with templated assembly targets having relevance to a pathology, diseased state, an aberrant cell of interest, or a particular cellular nucleic acid target.

In some embodiments, enrichment of a pair of templated assembly effectors from a library of chemically-ligated oligonucleotides spatially elicited (CLOSE) products includes obtaining a library of oligonucleotides chemically ligated through templated assembly due to spatial proximity to cellular nucleic acid targets, amplifying the library of ligated oligonucleotide-cellular nucleic acid targets, and selectively enriching for ligated oligonucleotide-cellular nucleic acid targets, wherein the ligated targets are selected for relevance to a pathology of an aberrant cell of interest or to a discontinuous hybridization to the cellular nucleic acid targets.

In some embodiments, templated assembly effectors that have hybridized to a cellular RNA target source can be enriched towards a specific target RNA, where these are known from previous observations. Such a target-directed enrichment may be applied after chemical ligation of spatially proximal CLOSE effectors, and is herein termed "target-directed CLOSE." The required target-directed enrichment is achievable by hybridizations between the subsets of CLOSE libraries which bind total cellular RNA, and a specific nucleic acid probe sequence corresponding to the target of interest. Such hybridizations are most efficient when both the CLOSE sublibrary and probes are rendered as single strands of appropriate complementarity.

As used herein, "chemically-ligated oligonucleotides spatially elicited" refers to pairs of oligonucleotides that have been chemically ligated as a consequence of their spatial proximity through hybridization to target nucleic acid templates.

A large CLOSE collection is referred to as a CLOSE library, which can be in primary, rearranged, or amplified forms. A primary CLOSE library includes chemical products of templated assembly reactions resulting from spatially-enabled reactions. An amplified CLOSE library can be derived directly from PCR of a primary library with a readable chemical ligation point, or indirectly, where PCR was permitted by priming site manipulations as achieved with a rearranged library. In some embodiments, the CLOSE products include short PCR product duplexes of the chemically ligated oligonucleotides. Amplification of the CLOSE products can be performed by amplification of the chemically ligated oligonucleotides with primers complementary to the priming sites carried by the specific oligonucleotides. Only oligonucleotides pairs (one from each separately-modified population) that have chemically joined via the templated assembly reaction are potentially amplifiable by PCR, by virtue of the linkage produced between the oligonucleotides.

Excess unbound templated assembly reactants can also be removed after templated assembly. The unbound templated assembly reactants can be removed by methods commonly used in the art, such as but not limited to, sequential precipitations with polyethylene glycol 8000 (PEG), enzymatic digestion, ultrafiltration, or gel size-exclusion chromatography.

Subtraction can also be used to enrich ligated oligonucleotide pairs of the CLOSE library. The ligated oligonucleotide pairs derived from a target cell or tissue from the CLOSE library can be enriched over ligated oligonucleotide pairs derived from a different cell or tissue. In some embodiments, the ligated oligonucleotide pairs derived from aberrant target cells can be enriched over ligated oligonucleotide pairs derived from a normal cell counterpart. In some embodiments, the ligated targets from an aberrant cell of interest can be enriched by removing ligated targets derived from normal cells of interest. Subtraction may be effected between libraries of ligated oligonucleotide pairs derived from aberrant target cells and normal cells, where biotinylated normal sequences are removed after hybridization by means of solid-phase streptavidin binding. The remaining ligated oligonucleotide pairs after subtraction can be further processed for identification.

A method of valuating a pair of chemically-ligated oligonucleotides spatially elicited (CLOSE) products for templated assembly is also disclosed. The pair of CLOSE products as templated assembly reactants can be modified to interact readily with a corresponding modification on another templated assembly reactant, but will not readily interact with natural biomolecules. The modifications can impart a reactivity in a templated assembly reaction, such as a selectively-reactive moiety reactivity in a templated assembly reaction. Examples of a selectively-reactive moiety can include adding a bio-orthogonal reactive moiety. In some embodiments, a pyrene group, such as pyrene maleimide, can be added on the CLOSE products.

Similar as described above, the CLOSE products can also include 5' and/or 3' priming sites, and/or an intermediate, such as a linker or spacer. The CLOSE products can also be further processed for identification as described herein.

In some embodiments, a library of templated assembly reactants for identifying the templated assembly targets are disclosed. The library can include templated assembly reactants. In some embodiments, the library includes first and second populations of templated assembly reactants, where the templated assembly reactants include an oligonucleotide sequence and a modification for reaction in a templated assembly reaction.

In some embodiments, a library can include chemically-ligated oligonucleotides spatially elicited (CLOSE) products. The library can also include at least one pair of templated assembly targets enriched to include oligonucleotides chemically ligated due to their spatial proximity through hybridization to cellular nucleic acid templates. The CLOSE library can include an amplified library of chemically ligated products, and enriched oligonucleotides derived from aberrant target cells compared to normal cells.

The kits described herein can be used for discovery of novel templating sites in cells of interest. These can be linear sites within a continuous segment of target RNA template, discontinuous (conformationally-enabled) sites in the same target template, or sites within separate templates juxtaposed via higher-order nucleic acid or nucleoprotein complexes that form within specific cells.

A templating site specific to cells of interest can be identified with the kits and methods described herein and used as a diagnostic criterion for identifying the presence of such cells of interest within a large background of other cells. For example, in a sample of blood, urine, ascites, cerebrospinal fluid, bronchial lavage, oral washings and sputum, Pap smears, tissue biopsies or organs, bile, fecal matter, or other bodily fluids or parts.

In embodiments where detection is based on fluorescence, kits can include templated assembly reactants that generate a fluorescent signal upon ligation of the templated assembly reactants, for example pyrene excimers, and fluorescent detection reagents. In some embodiments, kits can include templated assembly reactants that catalyze an enzymatic reaction upon ligation of the templated assembly reactants and detection reagents for the enzymatic read-out, such as, but not limited to, ELISAs.

Diagnostic test evaluations of a set of corresponding templated assembly reactants and the subject may be employed. This evaluation may serve to determine if a particular set of templated assembly reactants can be competent to produce an effector structure in a given subject. This may be useful if the templated assembly reactants have not been utilized previously, or if a current sample is significantly different from previous samples, e.g. the sample contains a lower level of target nucleic acid than previous samples. The kits and diagnostics can also detect the presence or absence of target nucleic acids in a sample, or the abundance of target nucleic acids in a sample. The kits and diagnostics may also be useful in determining if a nucleic acid target is accessible for templated assembly reactions, providing information about secondary structures of a nucleic acid target in a sample. In some embodiments, the competency of the templated assembly reactants to identify target nucleic acids can be determined.

The kits and diagnostics can include contacting the corresponding templated assembly reactants with a sample or multiple samples. Identification of a convenient in vitro readout for the activity produced by a successful templated assembly reaction is also included. Such readouts may include, but are not limited to, enzymatic activity like sandwich enzyme-linked immunosorbent and phosphatase assays, phosphorescence, immunofluorescence, bioluminescence, and the like may be performed.

To perform the in vitro sandwich-style diagnostic evaluation assay, the following steps can be carried out. A sample or samples can be obtained from a subject to assay in vitro. Optionally, a target compartment sample (e.g., tumor biopsy) and non-target compartment negative control (e.g., a sample of healthy tissue) are obtained. Samples may be lysed in a suitable buffer to release nucleic acids, which may facilitate ease of use or increase the sensitivity of the assay. Templated assembly reactants can be administered to the sample or lysate. When target nucleic acid is present, templated assembly ligation products are formed.

Ligated products can then be bound by an immobilized capture molecule. The molecule may be immobilized on a vessel, such as a microtiter plate well, or on a substrate, such as an agarose bead or magnetic bead that is mixed with assay medium. Sample material and non-ligated reactants can be removed and the immobilized complex can be washed. A detector molecule specific for an accessible part of the templated assembly ligation product can be incubated with the immobilized complex, and an appropriate detection readout can be performed. In some embodiments, specificity of the detector molecule, capture molecule, or both, may selectively detect a structure on the templated assembly ligation product that is not present on any templated assembly reactant before the templated assembly reaction occurs, such that the templated assembly ligation products can be captured and/or detected. For example, the specificity of the capture molecule selectively detects an effector product structure that is not present in the starting templated assembly reactants, ensuring that only templated ligation products are captured and detected.

In some embodiments, the specificity of the detector molecule can selectively detect a structure on one templated assembly reactant, and the specificity of the capture molecule can selectively detect a structure on a different templated assembly reactant, such that a templated assembly ligation product would include both structures and thus be detected. Sets of templated assembly reactants contained on a single compound may be incompatible with this embodiment.

In order that the subject matter disclosed herein may be more efficiently understood, examples are provided below. It should be understood that these examples are for illustrative purposes only and are not to be construed as limiting the claimed subject matter in any manner.

EXAMPLES

Example 1: Identification of Templated Assembly Target Sequences or Structures from a Sample, Using a Library of Templated Assembly Reactants Producing Amplifiable Linkages Between Oligonucleotides Bearing Pre-Appended Primer Sites (Actual Example)

Two RDO populations are synthesized. Random regions are constituted of 25:25:25:25 dA:dC:dG:dT ratios during phosphoramidite-based synthesis. One synthetic population has a 5'-iodo-dT modification for subsequent chemical conversion to a 5' azide group, and a 3'-priming site for a PCR primer, capped with a 3'-phosphate group designed to prevent unwanted polymerase extensions from this end. The other bears a 5'-priming site for a PCR primer and a 3'-5-methyl-C alkyne modification (propargyl group). Configurations of these oligonucleotides are depicted in FIGS. 1A, 1B, 1C, and 1D.

RNA from a cellular source of interest is hybridized with the random oligonucleotide populations. One principle relies on hybridization to accessible tracts of cellular RNAs by specific members from each library. Where two oligonucleotides from both libraries anneal to RNA sequences in sufficient spatial proximity, click-reactivity is suitable. The resulting chemical joining of such proximal strands allows their subsequent amplification and identification. Prior to hybridization, the modified oligonucleotides are subjected to a transient heat-denaturation step (2 minutes/80 C), but this is not applicable to the RNA target, owing to the need to preserve native secondary structures. Whole-cell lysates may also be screened in an equivalent manner, where both protease and RNase inhibitors are used in order to protect endogenous native folded RNA or ribonucleoprotein structures.

RNA may be prepared by any standard procedures, including, but not limited to, kits from commercial suppliers such as Qiagen and Norgen.

RNA may be prepared in the form of a whole cytoplasmic lysate, obtained under gentle conditions. Such conditions may be achieved, but are not limited to, the example of osmotic lysis, with a hypotonic buffer of 20 mM Tris pH 7.4, 10 mM NaCl, and 3 mM $MgCl_2$. Lysis of cells should be performed where proteins are protected by protease-inhibitor cocktails with 1 mM phenylmethanesulfonyl fluoride (PMSF), and also in the presence of oxidation-insensitive ribonuclease inhibitors, such as (but not limited to) murine RNase inhibitor (New England Biolabs).

The RNA-oligonucleotide hybridizations are performed with both random chemically-modified populations simultaneously in a 50:50 mixture with respect to each other by molarity, in a 10-100 fold excess over RNA quantities present, calculated by assuming an average molecular weight of the cellular RNA of 1500 bases, and with 1-10 micrograms of starting RNA. Hybridizations may be effected for periods of 2-16 hours. Hybridizations can be performed in 50 mM Tris pH 7.5, 10 mM $MgCl_2$, 100 mM NaCl, 1 mM dithioerythritol, and 2.4 units/ml murine RNase inhibitor (New England Biolabs).

When the hybridization step(s) are finished, unbound oligonucleotides are removed by PEG precipitation, ultrafiltration or gel size-exclusion chromatography. (Random oligonucleotides that have hybridized to the cellular RNA will co-purify with the RNA as long as the conditions favor DNA:RNA duplex persistence).

Figure 1A:
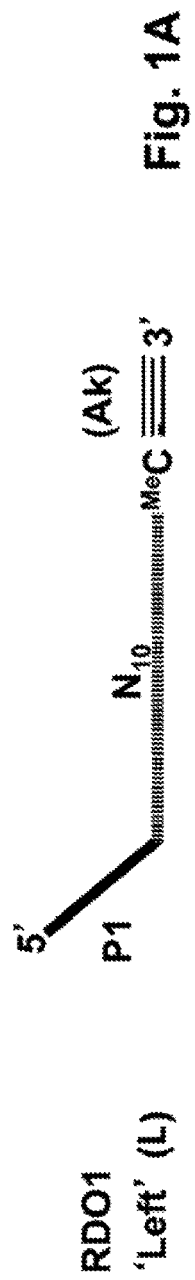
FIGS. 1A, 1B, 1C, and 1D illustrate schematic configurations of: 1A) random decamer oligonucleotide (RDO); P1: Primer site 1; N10: random decamer tracts; Me-C: 5-methyl deoxycytidine residue; Ak: 3'-terminal alkyne, in the form of a 3'-propargyl group; 1B) RDO2; P2: Primer site 2; N10: random decamer tracts; Az: 5'-terminal azide group; 1C) RDO1 hybridized to a 2'-O-methyl oligonucleotide complementary to the primer site (RDO1:P1C); P1: Primer site 1; N10: random decamer tracts; Ak: 3'-terminal alkyne, in the form of a 3'-propargyl group; and 1D) RDO2 hybridized to a 2'-O-methyl oligonucleotide complementary to the primer site (RDO2:P2C); P2: Primer site 1; N10: random decamer tracts; Az: 5'-terminal azide group; RDO1 and RDO2 are, for convenience, referred to as "Left" (L) and "Right" (R) oligonucleotides in the context of CLOSE libraries.
Figure 1B:
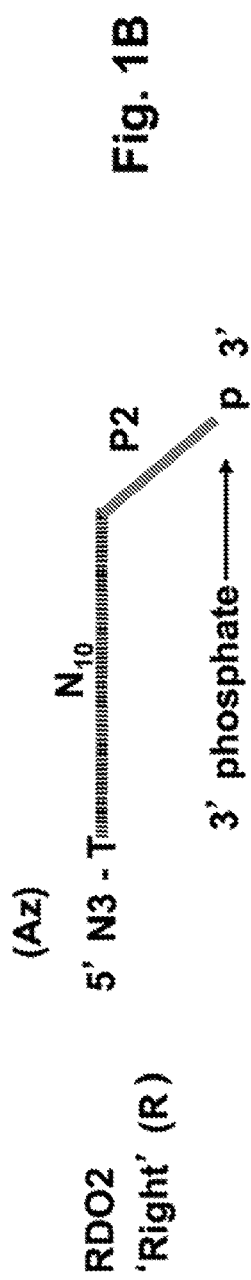
Figure 1C:
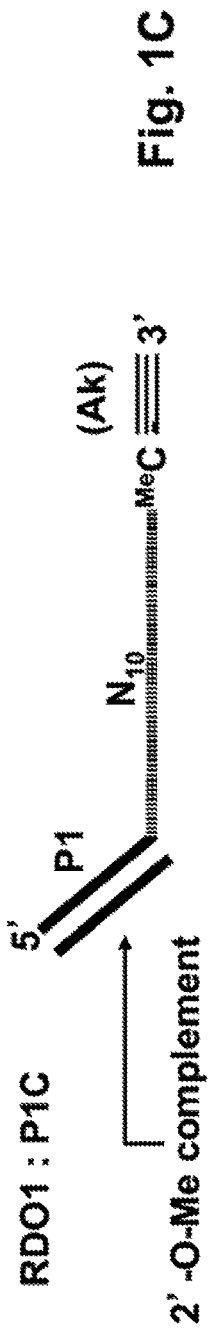
Figure 1D:
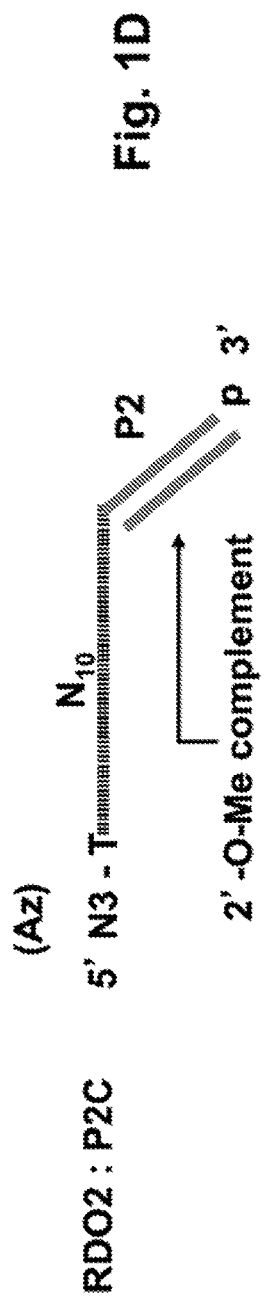

In an alternative procedure, unbound oligonucleotides are depleted by treatment with DNase I, where hybridized RNA:DNA duplexes are insensitive to DNase I action, and unhybridized primer sites P1 and P2 are protected by duplexing with 2'-O-methyl complementary strands (FIG. 1C, FIG. 1D). The DNase I treatment may be used as an alternative to other purification methods, or in conjunction with subsequent PEG precipitation, ultrafiltration or gel size-exclusion chromatography.

Cu(I)-click catalyzed reactions are then performed in 50-100 µl volumes for 30-60 minutes/25 C. Until this step is completed, it is best to preserve the structural integrity of the target cellular RNAs, using stringent RNase-free conditions as much as possible, and suitable RNase inhibitors. Cu(I)-click catalysis may be performed with commercial kits, or with individual components as known in the art. Alternatively, the Cu(I) component can be delivered using specific chelators, including, but not limited to, the compounds TBTA, THPTA, BTTAA and BTTES (Besanceney-Webler et al., Angewandt Chemie International Edition, 2011, 50, 8051-8056).

After completion of the Cu(I)-catalyzed click reactions, the preparations are desalted to remove copper ions, most conveniently using small disposable spin columns (Biorad or Pierce).

Figure 2:
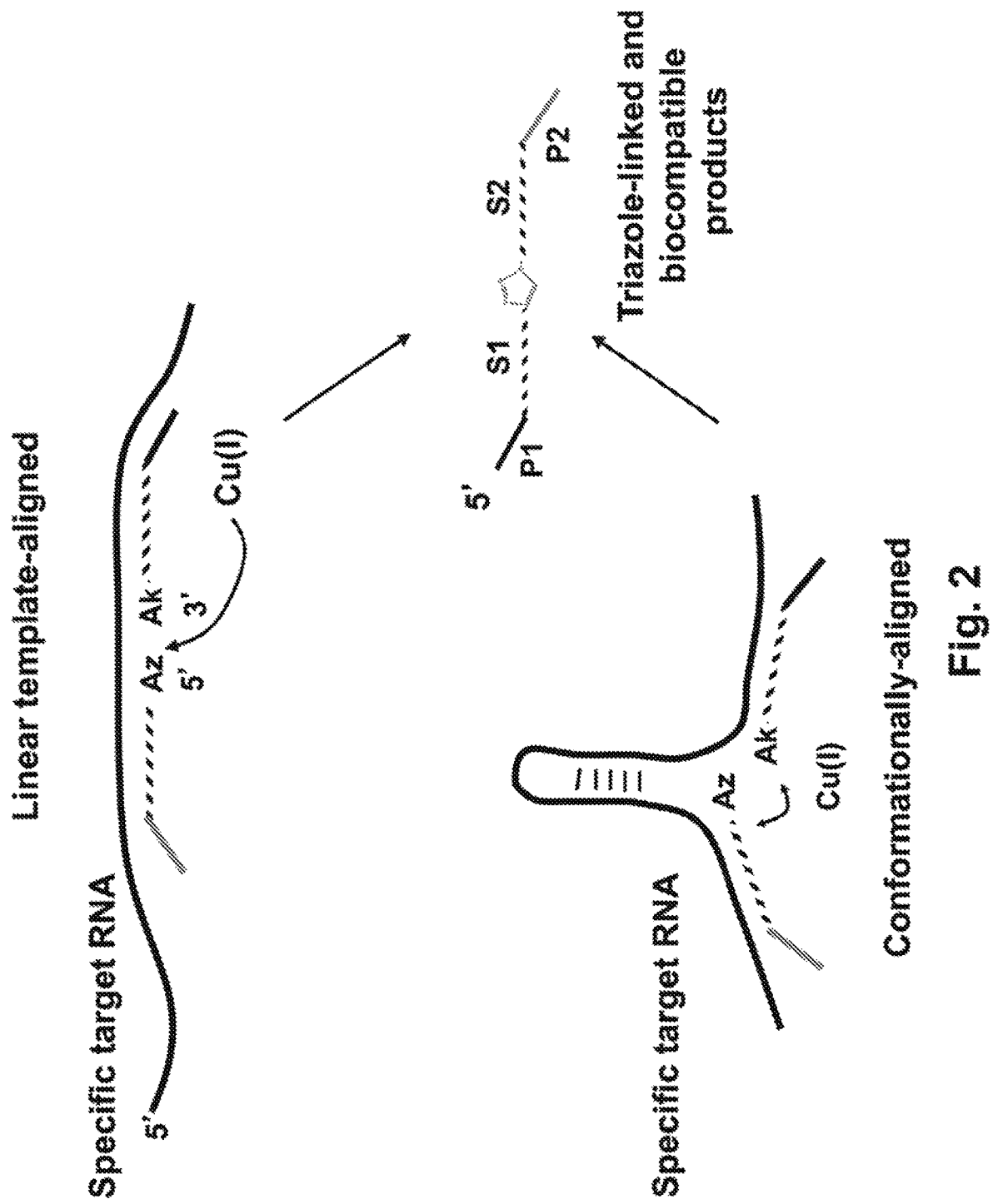
FIG. 2 shows representative hybridization-mediated spatial alignments of labeled 5'- and 3'-ends of specific oligonucleotides from RDO populations, on either linear (contiguous) sites of discontinuous (conformationally-determined) sites; S1 and S2 denote selected subpopulations of decamers from the original random decamer total populations.

PCR is then performed with primers matching the priming sites carried by the specific oligonucleotides selected from the original random populations. Only oligonucleotide pairs (one from each separately-modified population) that have chemically joined are potentially amplifiable by this PCR process, by virtue of the "biocompatible" triazole linkage produced by the specific 5'-azide/3'-alkyne oligonucleotides used (FIG. 2). Such joining can be promoted by either contiguous sites or sites juxtaposed by target RNA folding (FIG. 2). Products can only be formed by CLOSE oligonucleotides that have annealed to target template in the correct orientations (FIGS. 3A, 3B, 3C).

Example 2: High-Volume Sequencing and Differential Bioinformatic Analysis of CLOSE Libraries (Prophetic Example)

Herein any pairs of oligonucleotides that have been chemically ligated as a consequence of their spatial proximity through hybridization to cellular RNA templates are referred to for convenience by the acronym CLOSE, denoting Chemically-Ligated Oligonucleotides, Spatially Elicited. A large CLOSE collection is referred to as a CLOSE library, which can be in primary, rearranged, or amplified forms.

A primary CLOSE library contains the chemical products of click chemical reactions resulting directly from spatially-enabled reactions. An amplified CLOSE library is thus either derived directly from PCR of a primary library with a readable chemical ligation point, or indirectly, where PCR has become permitted by priming site manipulations as achieved with a rearranged library.

Any amplified CLOSE library (whether directly or indirectly) is a large collection of short duplexes of the chemically ligated oligonucleotides defined by the PCR primers and priming sites used and the originally ligated spatially adjacent pair of oligonucleotides.

Amplified CLOSE libraries from aberrant cells of interest vs. their normal counterparts may be directly subjected to sequencing and bioinformatic analyses. More focused approaches employ differential subtractive hybridizations to narrow the field of candidates.

Bands corresponding to the PCR amplification products of primary CLOSE libraries are excised from gels and cloned.

In some embodiments of CLOSE cloning, excised bands are cloned by means of 1-base 5' dA overhangs resulting from amplification with Taq DNA polymerase. Such 5' dA-CLOSE fragments are cloned into plasmid vectors with single base 5' dT overhangs. Large numbers of plasmid clones in suitable E. coli hosts are isolated as mini-scale preparations, and subjected to conventional automated sequencing with primers up and downstream from the CLOSE insert, placed at a sufficient distance such that the read-through of the CLOSE insert is complete.

Sequenced CLOSE clones were uniformly in the expected configuration, where a (+) strand 22-mer dimer (corresponding to the original single-stranded oligonucleotides) (from L- to R-, FIGS. 1A, 1B, 1C, and 1D) is 5' $N_{10}$-CT-$N_{10}$. A series of arbitrarily selected CLOSE clone sequences were compared to a set of randomly generated sequences of the same pattern (FIG. 4). The CLOSE series had significantly higher GC content than would be expected on a purely random basis, suggesting that the hybridization-based selection procedure favored the greater stability conferred by higher GC levels.

In some embodiments of CLOSE cloning, excised bands are prepared for next-generation sequencing according to Illumina protocols. In some embodiments of CLOSE cloning, excised bands are prepared for next-generation sequencing according to other Next-Generation Sequencing protocols, including, but not limited to, protocols for Pyrosequencing, ABI SOLiD sequencing, Helicos, Nanopore sequencing, and Ion Torrent sequencing.

When large numbers of CLOSE clones from aberrant cell sources have been sequenced, it is prudent to compare the accumulated sequence data with corresponding data from normal cells as closely matched to the aberrant cell targets as possible, in terms of their differentiation state and cell expression phenotypes, genotypes, and distribution of polymorphisms. This analysis corresponds to an in silico subtraction method.

Sequence data is obtained from matched normal cells to the sequence CLOSE clones from amplified CLOSE libraries, by correspondence with the Method used for the CLOSE library of interest from aberrant cells.

Sets of CLOSE sequence data from aberrant cells and matched normal cells of interest are subjected to bioinformatic analyses. The (+) strands of each CLOSE sequence are definable as two decamer tracts separated by a CT dinucleotide, corresponding (post-amplification) to the chemical ligation point between the 3'-(5-methyl)-dC-propargyl and 5'-dT-azide groups borne by the original oligonucleotides.

Selection criterion for rejection of candidate CLOSE clones include: failure to find any significant match between either of the decamer tracts and the expressed or genomic sequences of the cells of interest. "Significance" is here defined as at least a 70% match for either tract.

CLOSE sequence pairs from the aberrant cell source of interest will be ranked by their frequency of appearance from random picking of cloned CLOSE libraries (by conventional cloning and sequencing).

Using the frequency-ranking criterion as a procedural guideline, CLOSE pairs from aberrant cell sources will be screened against CLOSE pairs from corresponding normal sources. Where matches with the normal cell source are identified, the matching CLOSE pairs from aberrant cells will be excluded from further analysis.

Other criteria for flagging aberrant CLOSE sequence pairs as being of special interest are: 1) Either or both of the decamer sequences composing a CLOSE pair matching sequences of potential relevance to the pathology of the aberrant cell of interest, or 2) where the CLOSE pair-matches are identified as occurring discontinuously on the same RNA strand, or on separate RNA strands.

Sequences of potential interest noted for tumor cells include, but are not limited to, genomic or expressed genes for known oncogenes or tumor suppressors, cell cycle regulators and mediators, transcriptonal regulators and mediators, translational regulators and mediators, telomerases, cytoskeletal components, and kinases.

Example 3: Utilizing CLOSE Libraries to Identify Sequences or Structures Specific to Cells of Interest Through Physical CLOSE Library Subtraction (Prophetic Example)

Subtraction may be effected between libraries of ligated oligonucleotide pairs derived from aberrant target cells and normal cells, where biotinylated normal sequences are removed after hybridization by means of solid-phase streptavidin binding.

Amplified CLOSE libraries obtained according to the protocols disclosed herein are derived from aberrant cells of interest.

Normal cells as closely matched as possible to the same lineage and differentiation state of the aberrant cells of interest are chosen. Non-limiting examples include: melanoma cells, normal melanocytes, B lymphomas, normal B cells, T lymphomas, and normal T cells.

Figure 5:
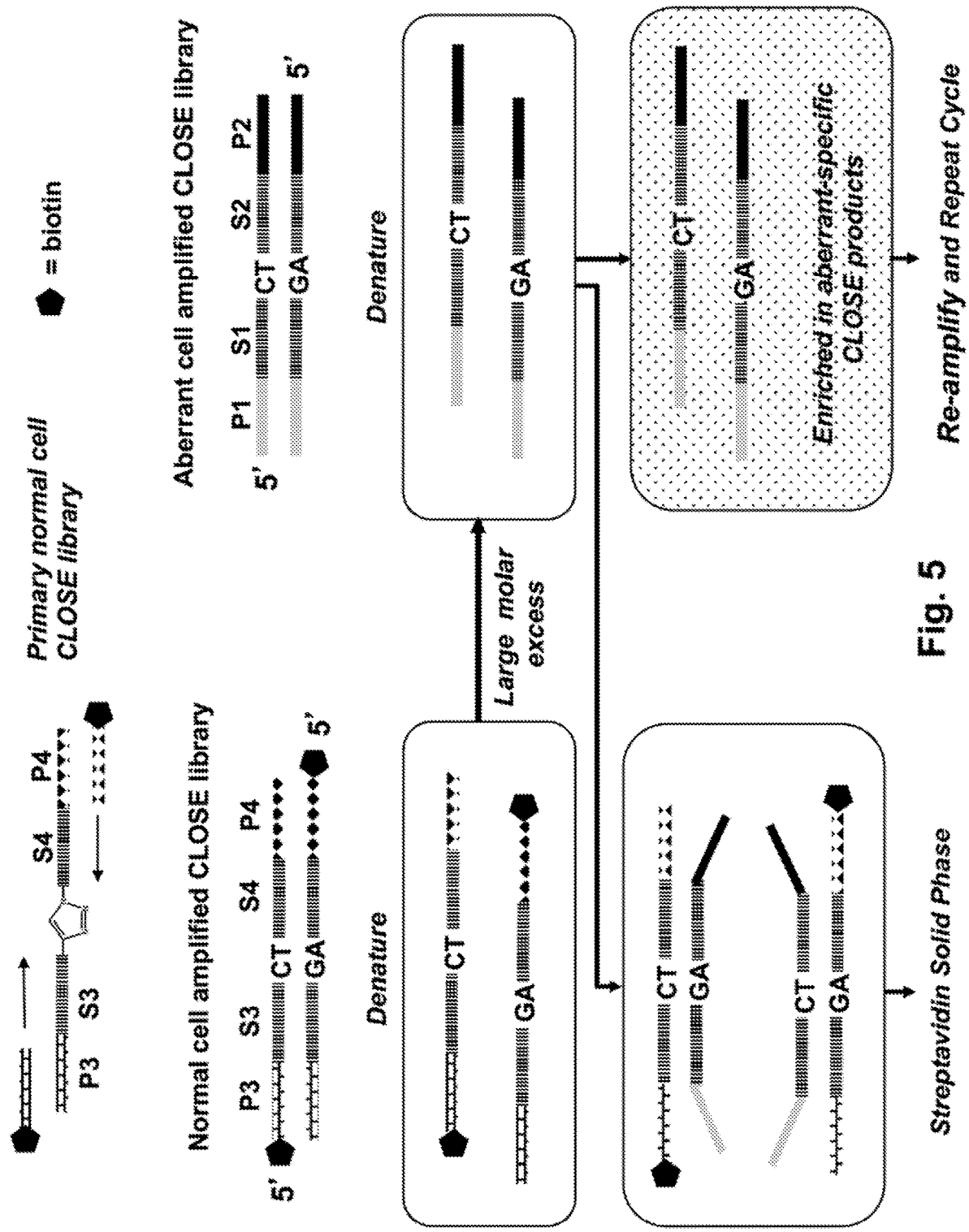
FIG. 5 shows representative subtraction of CLOSE libraries from aberrant cell sources with CLOSE libraries from corresponding normal cells; P1-P4 denote distinct priming sites; S1 and S2 denote selected decamer tracts from aberrant cells, from initially random regions; S3 and S4 denote selected decamer tracts from corresponding normal cells, from initially random regions.

CLOSE libraries are obtained from the matched normal cells of interest. Such libraries should be prepared in an identical manner as for the corresponding aberrant cells, except for the use of distinct priming sites (P3, P4) in the initial oligonucleotides (FIG. 5). Also, primers used in the final amplification step should bear 5'-biotin groups, such that the amplified CLOSE products themselves are biotinylated on both strands (FIG. 5).

When obtained from PCR reactions, both normal and aberrant CLOSE libraries are phenol-extracted and precipitated with 0.3 M sodium acetate and 2.5 volumes of ethanol, washed with 70% ethanol, dried, and redissolved in 20 μl TE. The normal biotinylated amplified CLOSE library is then mixed with its counterpart non-biotinylated library from aberrant cells, in a 10:1 ratio for normal:aberrant CLOSE products. The mixed library is denatured at 95° C. for 10 minutes, and then slowly cooled to room temperature.

The re-hybridized products are then treated with excess solid-phase streptavidin to immobilize and remove all biotinylated strands. In non-limiting embodiments, the solid-phase streptavidin may be magnetic streptavidin beads or streptavidin-agarose. The binding capacity of any solid-phase streptavidin matrix used should be at least 10-fold in excess of the total number of moles of biotinylated oligonucleotides.

The solid-phase streptavidin matrix is then separated from the unbound non-biotinylated remainder, which is constituted by oligonucleotides from the aberrant cell CLOSE library that have not hybridized with biotinylated oligonucleotides from the corresponding normal cell library. In embodiments where magnetic streptavidin beads are used, a magnetic separator accomplishes the pull-down of solid-phase streptavidin. In separation embodiments where streptavidin-agarose is used, the solid-phase streptavidin is separated by centrifugation at 5000 g/10 minutes.

A sample of the soluble-phase material is then amplified using primers specific for the CLOSE library from the aberrant cell source of interest (FIG. 5). The re-amplified enriched CLOSE library is then subjected to a second cycle of subtraction against the original normal cell CLOSE library. The re-amplified enriched CLOSE library is then subjected to a third cycle of subtraction against the original normal cell CLOSE library. The re-amplified enriched CLOSE library is then subjected to sequence analyses Example 4: Utilizing CLOSE Libraries to Identify Sequences or Structures Specific to Cells of Interest Through RNA Selection (Prophetic Example)

Alternatively, oligonucleotide pairs restricted to aberrant cells may be selected through binding of cross-hybridizing pairs (within populations derived from aberrant cells themselves) with normal cellular RNA sources.

Amplified CLOSE libraries obtained according to the protocols herein are derived from aberrant cells of interest.

Figure 6:
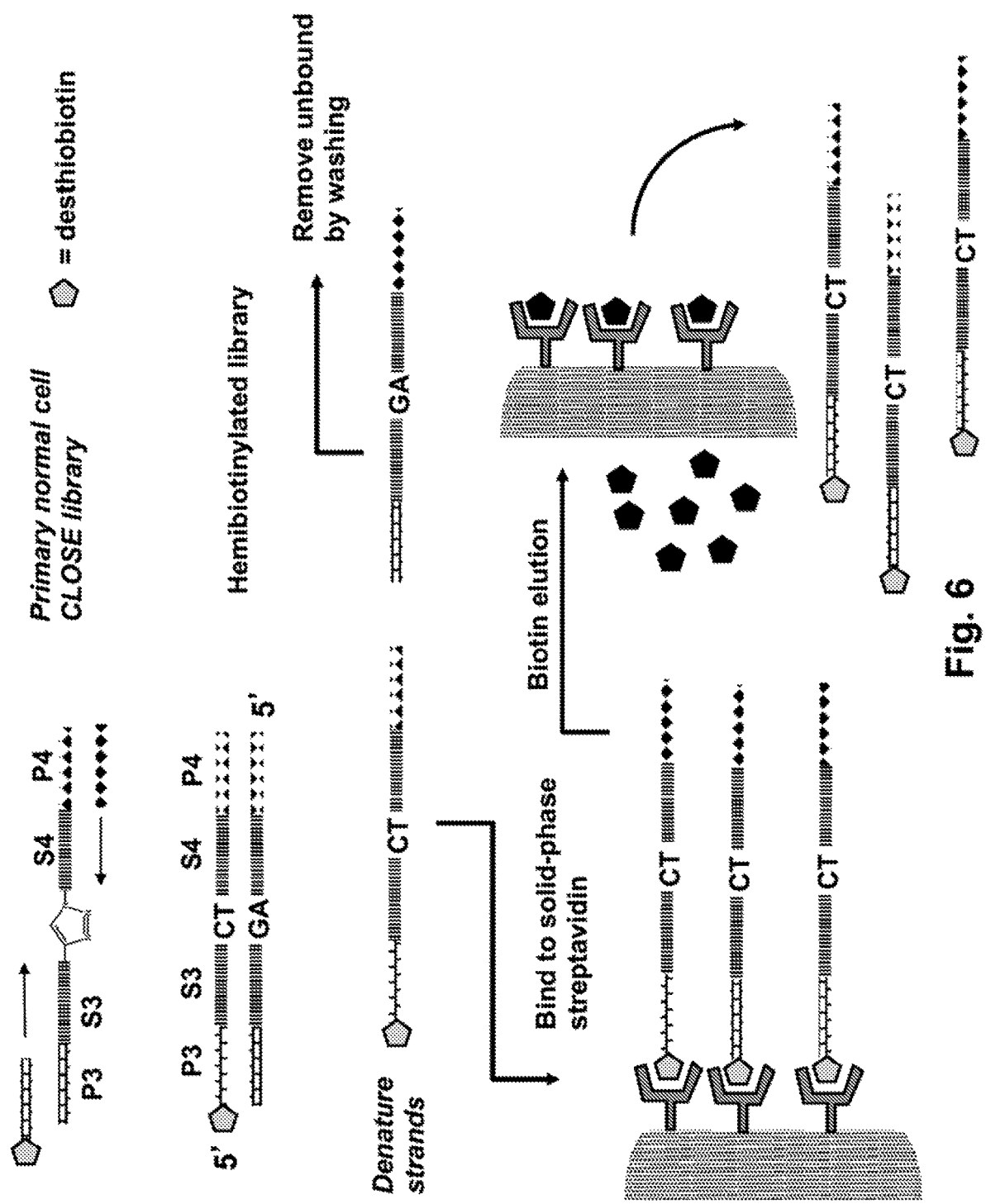
FIG. 6 shows a representative procedure for obtaining purified desthiobiotinylated 'top' strands (corresponding to strands of a primary CLOSE library) by selection on solid-phase streptavidin, and elution with excess free biotin.

CLOSE libraries are reamplified where primer P1 bears a 5'-desthiobiotin modification, and primer P2 is unmodified (FIG. 6). The hemi-desthiobiotinylated amplified CLOSE library is denatured at 95° C./10 minutes, and then incubated with an excess of a solid-phase streptavidin matrix. The solid-phase streptavidin matrix is washed three times with Tris-buffered saline, and then the bound desthiobiotin strands are eluted with 5 mM free biotin (FIG. 6). The eluate is desalted and excess free biotin removed by gel size-exclusion chromatography.

The desthiobiotinyated strand corresponds to the same sense as the primary CLOSE library obtained from the original hybridization with aberrant RNA. Matched normal cells for the aberrant cells of interest are chosen. Whole RNA preparations are isolated from the normal cellular source.

Figure 7:
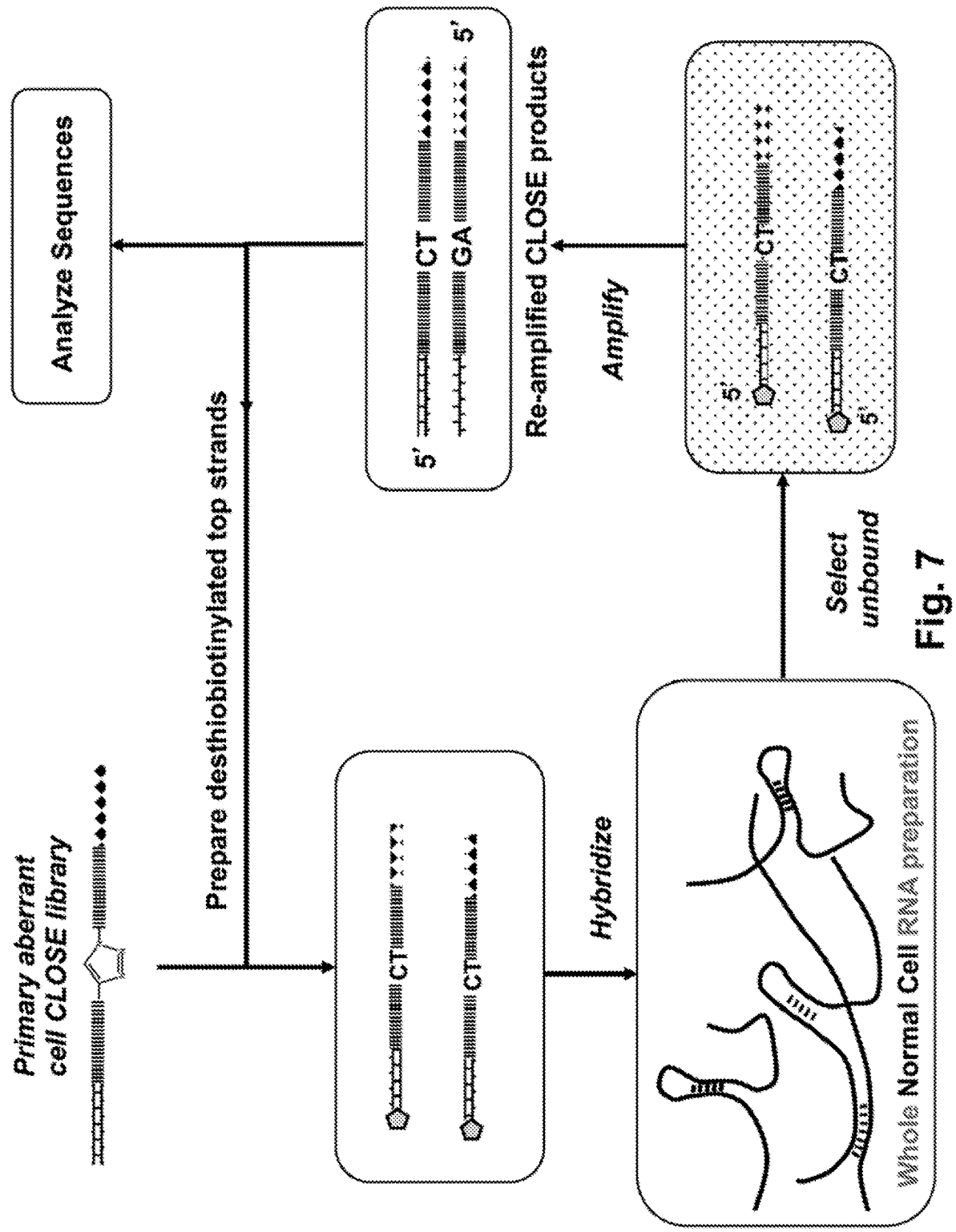
FIG. 7 shows representative selection of CLOSE clones on corresponding normal cell RNA sources, to enrich for CLOSE clones absent from the normal cellular background; desthiobiotinylated top strands are prepared as described herein.

Free desthiobiotinylated strands are denatured (80° C./5 minutes) and allowed to hybridize to the cellular RNA preparations for the same time period as used for the original CLOSE library hybridization itself with aberrant cell-derived RNA. RNA preparations are not heat-treated prior to addition of the denatured CLOSE library. RNA preparations are in a 2-fold molar excess over the desthiobiotinylated strands, calculated by assuming an average molecular weight of the cellular RNA of 1500 bases. This process is depicted in FIG. 7.

The hybridized RNA-CLOSE library members are separated from unbound CLOSE library members by gel size-exclusion chromatography. Samples of the unbound CLOSE library are re-amplified and processed under the same conditions as disclosed above, resulting in an amplified selected population of desthiobiotinylated strands (FIG. 7).

Free desthiobiotinylated strands are hybridized to the same normal RNA target, under the same conditions as disclosed above. The hybridized RNA-CLOSE library members are separated from unbound CLOSE library members by gel size-exclusion chromatography.

In some embodiments, the samples of the unbound CLOSE library are re-amplified with normal (non-biotinylated) primers, to form an amplified population of selected duplex strands. In some embodiments, the samples of the unbound CLOSE library are re-amplified and processed under the same conditions as disclosed above, resulting in an amplified secondarily selected population of desthiobiotinylated strands. Following hybridization to the same normal cell RNA targets, unbound desthiobiotinylated strands are selected, and then re-amplified with normal (non-biotinylated) primers, to form an amplified secondary population of selected duplex strands. The amplified unbound CLOSE libraries are subjected to sequence analyses.

Example 5: Evaluation of CLOSE-Derived Sequence or Structure Candidates by Pyrene Excimer Fluorescence: Confirmation of Molecular Proximity and Quantitation of Copy Number, and Optimization of Decamer Constituents (Prophetic Example)

CLOSE candidates identified through methods disclosed above (or any combination thereof), or any candidate pairs of sites derived independently, should be confirmed for their activity and efficacy in such a way as to permit focusing on the specific candidates with the greatest potential for driving high-level templated assembly. An independent measure of molecular proximity is the elicitation of excimer fluorescence between pyrene molecules.

Following application (or any combination thereof) of the methods disclosed above, each decamer constituent of a CLOSE pair candidate will have identified cellular template (s) upon which it can hybridize. Based on the known templates identified through application of the CLOSE technology, it may be useful in at least a subset of cases to extend either or both of the decamer pairs, as dictated by the complementary sequences of the templates to which they target for hybridization. Extension may assist in cyto templating through thermal duplex stabilization. Such extended and optimized candidates are also evaluated.

Figure 8A:
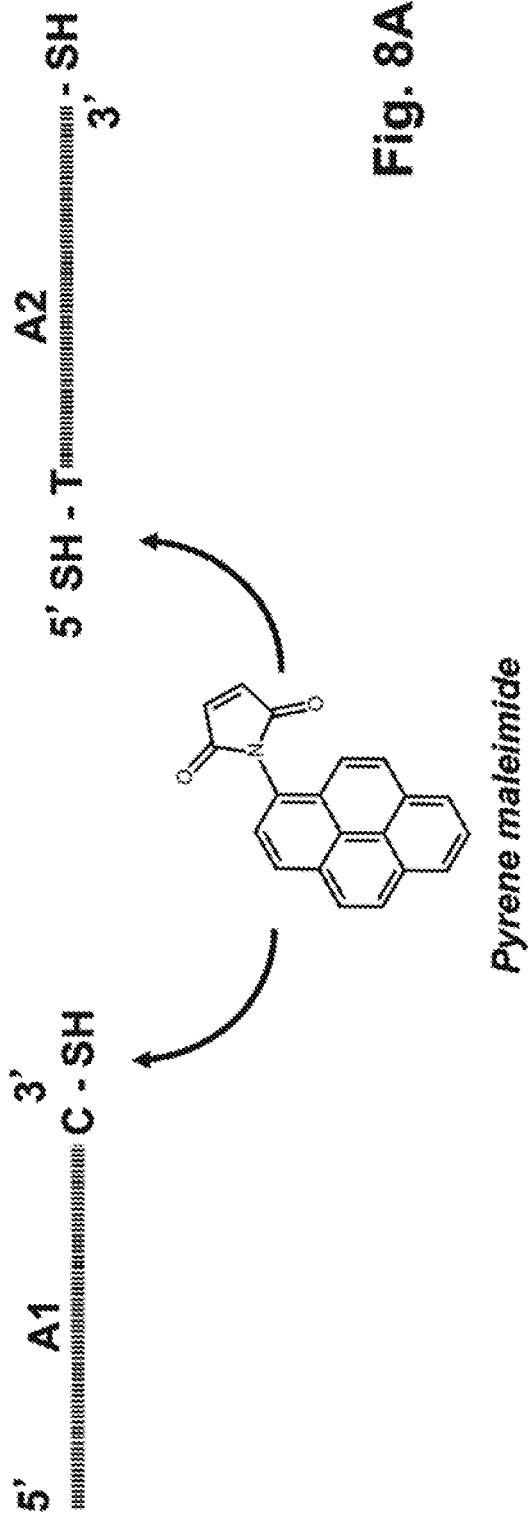
FIGS. 8A and 8B are representative illustrations of pyrene labeling of candidate specific CLOSE decamers (A1 and A2) and excitation-fluorescence generation; 7A) chemical conjugation of pyrene maleimide to 3'- or 5'-terminal-SH groups; and 7B) excimer fluorescence from hybridization-induced spatial proximity.
Figure 8B:
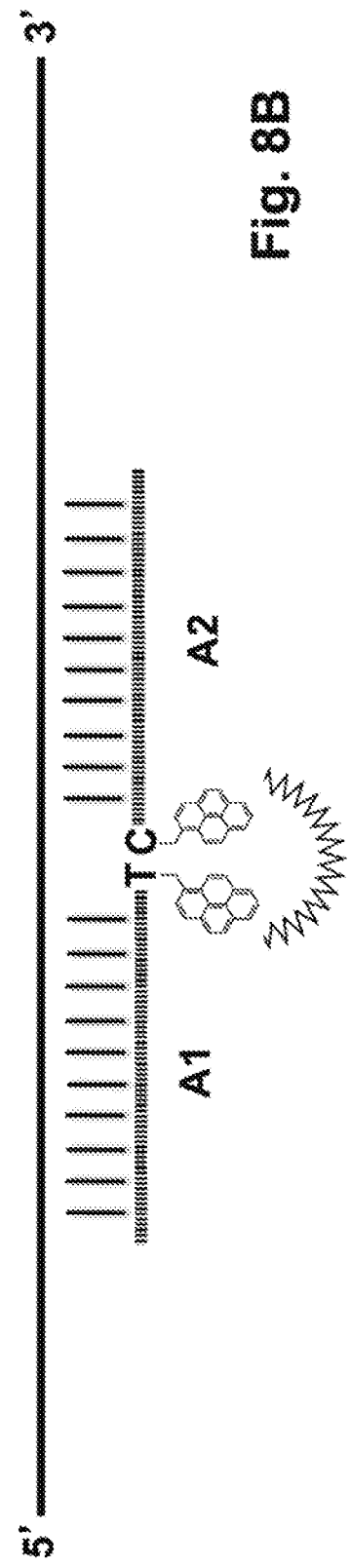

The individual decamer sequences which together constitute a CLOSE pair are separately re-synthesized and labeled with pyrene groups (FIGS. 8A and 8B). Pyrene labeling is effected by incorporating terminal thiol groups into synthesized DNAs (at either 5'- or 3'-ends as appropriate, as reducible disulfides in each case), and subsequently reacting the —SH groups with pyrene maleimide.

The pyrene group can be alternatively added by a pyrene maleimide with a spacer arm between the pyrene and maleimide moieties, including, but not limited to, pyrene-4-maleimide. The sites of pyrene additions are based on the type of CLOSE Method originally used. For CLOSE pairs identified with some of the methods above, pyrene modifications are appended at the same 5'- and 3'-ends as used for the original azide and alkyne modifications, respectively (FIGS. 1A-1D). Since CLOSE pairs identified with some of the methods above contain flanking sequences between the decamer tracts, these kinds of pairs are evaluated with pyrene groups appended to the exact original sequences, or the decamer tracts without the original flanking sequences.

Pyrene-modified CLOSE decamers are assessed for fluorescence changes upon hybridization in vitro to complementary DNA templates (FIGS. 8A and 8B). The ratio between excimer and monomer (e/m) emission spectra are measured with a spectrofluorometer, using control template sequences with varying degrees of sequence mismatch. Excitation wavelength is 335 nm, monomer peak emission wavelength is 375-410 nm, excimer emission peak is 480 nm.

For in cyto screening, pyrene modifications are performed on analogs of CLOSE decamers with nuclease-resistant phosphodiester backbones or sugar moieties. These include, but are not limited to, 2'-O-methyl-nucleotides and phosphothioate nucleotides.

Nuclease-modified and pyrene-labeled CLOSE decamers are transfected into target aberrant cells of interest, and also matched normal counterpart control cells lacking the exact target template. Fluorescence corresponding to excimer formation is assessed by fluorescence microscopy, and quantitated by spectrofluorometry.

Positive excimer signals both confirm the spatial proximity of the CLOSE oligonucleotide pairs, and also, by virtue of their relative signal strengths, provide relative transcript levels. Signal strength as a combination of both accessibility and template copy number thereby provides a metric for relative potential templated assembly levels between different CLOSE decamers equipped with effector partial structures.

Example 6: Evaluation of CLOSE-Derived Sequence or Structure Candidates by QPCR Amplification: Confirmation of Molecular Proximity and Quantitation of Copy Number, and Optimization of Decamer Constituents (Prophetic Example)

CLOSE candidates or any candidate pairs of sites derived independently, can be confirmed for their efficacy, and evaluated for the relative abundances of their target templates by click ligation and QPCR. In addition, the same approaches as described above can be applied towards optimization of each candidate pair. Where decamer pairs have been obtained from CLOSE libraries, extensions based on known target template sequences can also be evaluated in the same manner.

Individual specific CLOSE candidates are resynthesized with an alternative set of primer sites (P1 and P2, as in FIGS. 1A-1D). In some embodiments where multiplexing is initiated, a set of up to five separate candidate CLOSE decameric oligonucleotides are synthesized with distinct primer sites for each (P1.1/P2.1; P1.1/P2.2; P1.3/P2.3; P1.4/P2.4; and P1.5/P2.5).

Each pair of individual CLOSE candidates is separately incubated with an RNA preparation or a cytoplasmic lysate containing RNA and ribonucleoproteins, and excess oligonucleotides removed post-hybridization. Each preparation is subjected to click chemical ligation with Cu(I) catalysis under conditions of protection from RNases, and then desalted. After Cu(I) click-mediated ligations and desalting, preparations are treated with RNase A, RNase $1_f$, and RNase III.

Figure 9:
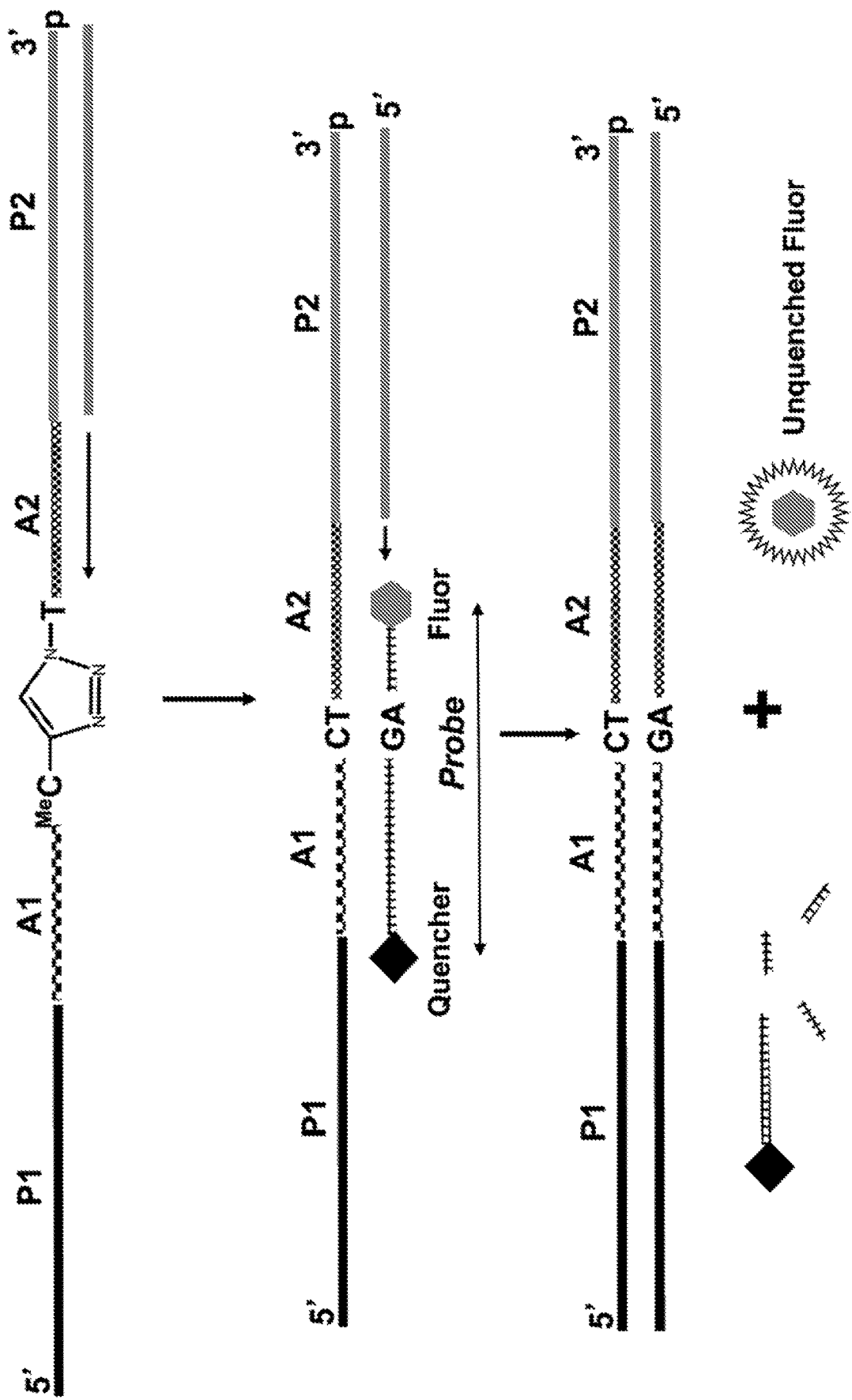
FIG. 9 illustrates representative QPCR for quantitation of relative levels of specific CLOSE clones as correlating with source RNA template levels; top: primary CLOSE clone chemically ligated population selected by hybridization proximity, depicting the Cu(I) catalyzed triazole linkage and two specific decamer regions A1 and A2; middle: the specific A1/A2 clone showing a second-cycle extension from the complement to P2, and an annealed QPCR probe with a 5'-fluor and 3' quencher; bottom: completion of the extension (as in the middle diagram), with strand displacement and digestion of the probe to unquench the fluor and allow fluorescence quantitation.

Samples of preparations are then subjected to quantitative PCR (QPCR) as depicted in FIG. 9, and described by Kono et al., Mol. Cancer Res., 2006, 4, 779-792. QPCR probes are 15-20 bases long, and complementary to a part of primer P1 region, all of one decamer, the bridging CT dinucleotide complementary to all CLOSE clones, and up to 5 bases of the second decamer (S2 of FIG. 9). Specific probe lengths are determined by the base composition of the selected decamer regions) which also confer probe specificity), such that the Tm of the probe-target duplex is at least 62 C under standard salt conditions. Each probe is equipped with a 5'-fluor and a 3'-quencher, such that fluorescence may be quantitated by standard TaqMan chemistry.

The appended 5'-fluor may be, but is not limited to, FAM™, TAMRA™, Cy5™ Cy3™, HEX™, JOE™ or ROX™. The appended 3'-quencher may be, but is not limited to, BHQ1™, BHQ2™, IowaBlack®-FQ, or IowaBlack® RQ. QPCR read-outs (threshold cycle numbers) are normalized to a corresponding signals from a composite panel of housekeeping genes (Vandesompele et al. 2002), or any subset or combination thereof. Relative normalized QPCR values are obtained for each candidate primer, where values are proportional to the original template copy number enabling proximity-promoted click-chemical ligation.

The initial hybridizing specific candidate CLOSE pairs are set up for multiplexing. In multiplex experiments, up to five separate pairs of specific CLOSE decamers are simultaneously added for hybridizing to the RNA or whole-cell lysate targets described above.

The multiplexed preparations are treated as described above. The multiplexed sets of chemically ligated specific CLOSE pairs are used for QPCR in single determinations, where each CLOSE pair itself is defined by a separate probe corresponding to the specific decamer regions in each case, and by use of ligated pair-specific probe-quencher combinations. The relative levels of each individual target within a multiplexed determination is derived from the specific fluorescent marker in each case, and related to corresponding levels of normal housekeeping gene controls.

Example 7: Evaluation of CLOSE-Derived Candidate Sequences or Structures by Digital PCR Amplification: Confirmation of Molecular Proximity and Quantitation of Copy Number, and Optimization of Decamer Constituents (Prophetic Example)

CLOSE candidates or any candidate pairs of sites derived independently, can be confirmed for their efficacy, and evaluated for the absolute abundances of their target templates by click ligation and digital PCR. It is desirable to gauge target transcript expression levels owing to the possibility of template titration, as noted above. In addition, the same approaches as described herein can be applied towards optimization of each candidate pair. Where decamer pairs have been obtained from CLOSE libraries, extensions based on known target template sequences (as described herein) can also be evaluated in the same manner.

Individual specific CLOSE candidates are resynthesized with an alternative set of primer sites (P1 and P2, as in FIGS. 1A-1D). In some embodiments where multiplexing is initiated, a set of up to five separate candidate CLOSE decameric oligonucleotides are synthesized with distinct primer sites for each (P1.1/P2.1; P1.1/P2.2; P1.3/P2.3; P1.4/P2.4; and P1.5/P2.5).

Figure 10:
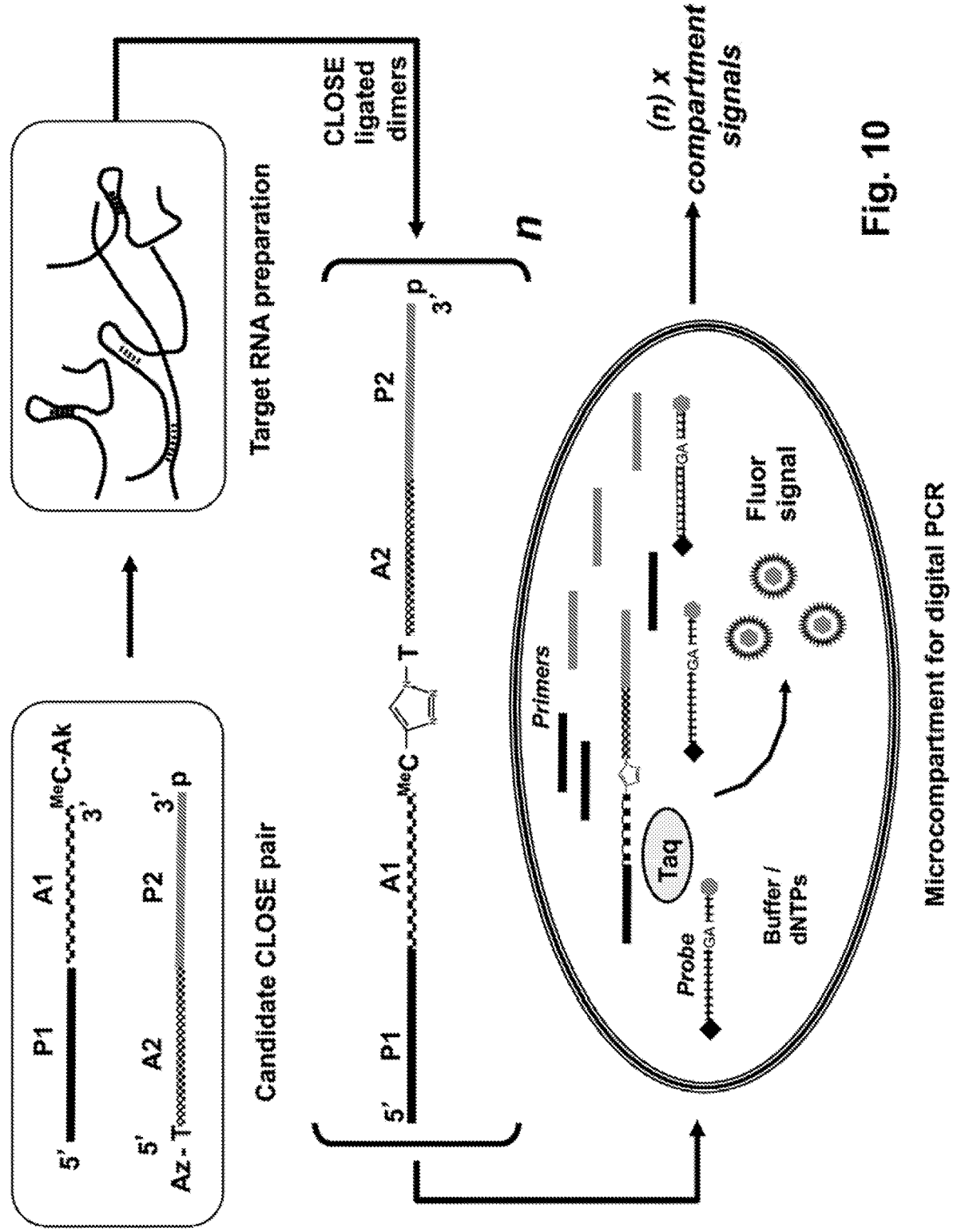
FIG. 10 depicts representative digital PCR for a single candidate CLOSE pair, with specific decamer regions A1 and A2; after hybridization with target RNA and Cu(I) catalyzed chemical ligation, the number of chemically ligated dimers approximates the number of template molecules in the target RNA; the ligated products are prepared for digital PCR by compartmentalization with molar excesses of primers and probes, and PCR-related buffer and enzyme requirements (Taq 1 DNA polymerase; other schematic symbols, and the process for fluorescence generation), upon amplification, compartments bearing ligated dimers and matching primers and probe with the target dimer generate a fluorescent signal; enumeration of (+) signal compartments thus equates with the original number of dimers present, and in turn approximates to the number of template molecules.

Each preparation is subjected to click chemical ligation with Cu(I) catalysis under conditions of protection from RNases, desalted, and treated with RNases. Samples of preparations separately derived in each specific case are then molecularly partitioned into distinct compartments for digital PCR, along with Taq DNA polymerase, dNTPs, standard PCR buffer with 1.5 mM magnesium chloride, cognate primers, and a specific dual-labeled probe for fluorescent quantitation of each targeted paired decamer (FIG. 10).

In some embodiments, molecular partitioning of components for digital PCR is achieved by means of microcompartments, effected through application of commercially available technologies, including, but not limited to, those marketed by Bio-Rad and RainDance Technologies as QX100 and RainDrop systems, respectively. In some embodiments, molecular partitioning of components for digital PCR is achieved by microfluidic chambers, effected through application of commercially available technologies, including, but not limited to, those marketed by Fluidigm (BioMark system).

Each preparation of partitioned targets, primers, probes, and other amplification components is subjected to thermal amplification, such that specific fluorescent signal is generated where amplification of target occurs, where signals provide a digital measure of active compartments, and in turn quantitation of their encompassed individual target molecules. Compartment processing, fluorescent measurements and subsequent enumeration of target numbers is performed according to the manufacturers' specifications and instructions.

The initial hybridizing specific CLOSE pairs are set up for multiplexing. In multiplex experiments, up to five separate pairs of specific CLOSE decamers are simultaneously added for hybridizing to the RNA or whole-cell lysate targets described above. The processing of the hybridizing sample and multiplexing CLOSE oligonucleotides proceeds as described above.

The combined sample containing multiplexed chemically ligated pairs of CLOSE decamers (selected by hybridization) is split into separate assays for each specific target determination by digital PCR amplification and analysis. Distinct targets are specified by unique primer combinations and unique fluor probe labels.

Multiplexing is performed at the hybridization level, but the digital PCR analysis is performed at a 1-plex level.

The combined sample containing multiplexed chemically ligated pairs of CLOSE decamers (selected by hybridization) is analysed by multiplexed digital PCR, where in addition to the components specified above, each specific primer pair (defined for each CLOSE target), and each fluorescently labeled probe is also present.

Each digital compartment contains multiple primers and probes, but where specificity within each compartment is generated by sequencing matching between primers and probes and the single CLOSE chemically ligated target molecule present in each case.

The digital PCR amplification and analysis is as specified described above, with the additional feature of simultaneous analysis of multiple fluorescent signals, distinguishable by virtue of their separate emission wavelengths, in accordance with the manufacturers' specifications and instructions for instruments specified above.

Multiplexing is performed both at the hybridization level, and the level of digital PCR analysis.

Example 8: DNase Treatment for Removal of Unhybridized CLOSE Oligos, and Follow-Up Cloning and Sequencing (Actual Example)

Azide and alkyne-modified CLOSE libraries were hybridized with a cellular RNA target (MU89) at 32 C for 16 hours. Incubations were performed in 20 µl with 200 pmol of each CLOSE library (previously annealed with 2'-O-Me complementary oligonucleotides to their priming site regions), with 20 µg MU89 RNA or no-template control. All components were mixed prior to the incubation without a pre-heating step.

Following the hybridization, each sample was treated +/−DNase I for 4 hours at 28 C, followed by phenol extraction, desalting (Bio-Rad P6 Spin columns in 10 mM Tris pH 7.4), and precipitation. After pelleting, washing, and drying, each sample was subjected to a standard THPTA-click reaction.

Briefly, a premix of the following components was prepared with additions in the following order: 20 µl 70 mM Tris (3hydroxypropyltriazolyl methyl) amine (THPTA) in 0.155 M NaCl, 4 µl 500 mM Na-ascorbate in 0.155 M NaCl, 2 µl 100 mM $CuSO_4$ in 0.155 M NaCl, and 2.6 µl of this premix was then added to each of the tubes for the click reaction, such that the final volume was 50 µl in ×1 phosphate-buffered saline. Tubes were incubated for 30 minutes/0 C (on ice), and then 2 hours/25 C. At the end of the incubation period, tube contents were desalted though Bio-Rad P6 columns as above, and 0.5 µl of each (1/100) was subjected to PCR amplification with primers matching the CLOSE oligonucleotide priming sites. The PCR cycle used the touchdown amplification strategy, with final temperature of 60 C, and 22 cycles at the final touchdown temperature.

Figure 11:
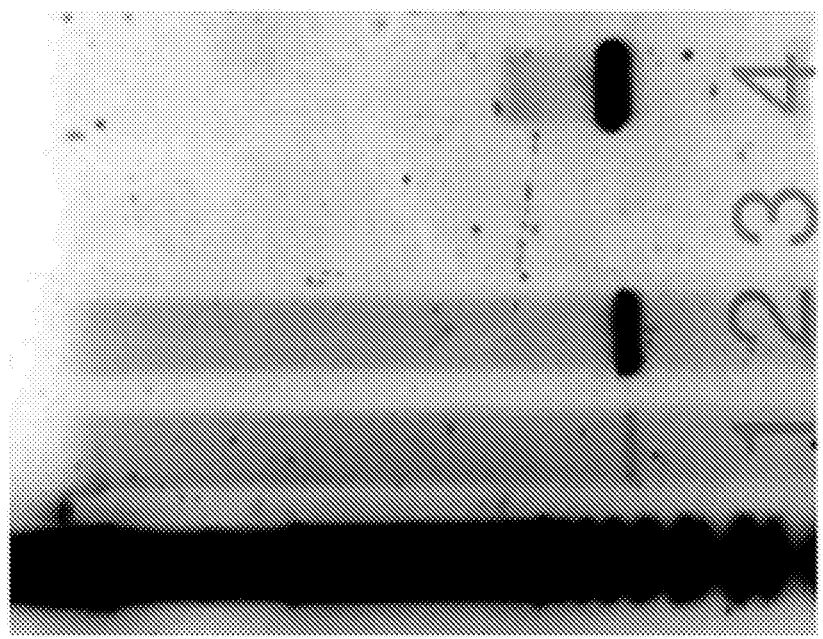
FIG. 11 depicts a representative gel evaluation of +/−DNase-treated CLOSE/RNA hybridization; lane 1, CLOSE oligonucleotides+RNA template+DNase; lane 2, CLOSE oligonucleotides+RNA template without DNase; lane 3, CLOSE oligonucleotides with no template+DNase; lane 4, CLOSE oligonucleotides with no template and without DNase); results showed presence of carry-over of CLOSE oligonucleotides irrespective of the presence of template (lanes 2 and 4), but only in the presence of RNA template was a band observed post-DNase treatment (lane 1 vs. lane 3); the band in lane 1 (amplified CLOSE oligonucleotides+RNA template+DNase) corresponding the expected size for a chemically ligated CLOSE dimer was excised and re-amplified with the original primers to increase the available yield.

Products were analyzed on a 15% acrylamide gel (FIG. 11; Lane 1, CLOSE oligonucleotides+RNA template+ DNase; Lane 2, CLOSE oligonucleotides+RNA template without DNase; Lane 3, CLOSE oligonucleotides with no template+DNase; Lane 4, CLOSE oligonucleotides with no template and without DNase). Results showed presence of carry-over of CLOSE oligonucleotides irrespective of the presence of template (Lanes 2 and 4), but only in the presence of RNA template was a band observed post-DNase treatment (Lane 1 vs. Lane 3). The band in Lane 1 (amplified CLOSE oligonucleotides+RNA template+DNase) corresponding the expected size for a chemically ligated CLOSE dimer was excised and re-amplified with the original primers to increase the available yield.

Products were cloned with the pGEM-Teasy vector system (Promega) and individual plasmid clones were sequenced with primers upstream and downstream of the insertion point of the cloned fragments. Sequences were compared with the human transcriptome via BLAST searches. Of 31 clones analyzed, a number showed matches to specific cellular RNAs for ≥16/20 bases within the regions corresponding to the two decameric random regions of each monomeric CLOSE oligonucleotide.

Expression of candidate cellular RNAs in the original MU89 melanoma cell source was tested by PCR with primers specific for each candidate RNA target. The following RNAs were expressed in MU89 and emerged as initial candidates for further CLOSE analysis: NOL9, OTUB1 (transcript variant 2), BRCA2, MAPKAPK2, and ALPK1 (transcript variants 1 and 2).

```
CLOSE oligos:
1) TRT-AK:
                                    (SEQ ID NO: 45)
CATCTCCACCTCCATAACCCANNNNNNNNNNC^Me-propargyl;

2) AZC-TRT-n2:
                                    (SEQ ID NO: 46)
azide-dT NNNNNNNNNNNAGGTGATAGGTGGAGGTGGTA-p;

Primers for amplification of the ligated CLOSE
oligos:
1) Trz.F:
                                    (SEQ ID NO: 47)
CATCTCCACCTCCATAAC;

2) Trz.R-n2:
                                    (SEQ ID NO: 48)
TACCACCTCCACCTATCACCT;

Protector oligonucleotides with 2'-O-methyl
backbones:
1) TrzEco-2OM:
                                    (SEQ ID NO: 49)
UGGGUUAUGGAGGUGGAGAUG;

2) TrzR-n2-2OM:
                                    (SEQ ID NO: 50)
UACCACCUCCACCUAUCACCU;
```

Example 9: Protocol for Removal of Unhybridized CLOSE Oligonucleotides by Sequential PEG Precipitations (Actual Example)

3.2% polyethylene glycol 8000 (PEG), in the presence of 2M NaCl, was useful for removal of almost all unhybridized CLOSE oligonucleotides. Briefly, melanoma cell line MU89 RNA (9.0 µg; prepared by Qiagen RNAeasy protocol) was mixed with 200 pmol of CLOSE oligonucleotides (200 pmol each of oligonucleotides TRT-AK and AZ-TRT-n2 (see Example 8) preannealed with equimolar amounts of 2'-O-Me primer site-protecting strands (see Example 8), or 200 pmol of the same CLOSE oligonucleotides without any protecting strand pre-annealing. Each preparation (50 µl final volume) was constituted with 50 mM Tris pH 8.3, 2.5 mM EDTA, 2 M NaCl, 40 units murine RNase inhibitor (Promega), with 3.2% PEG added (4 µl) as the final constituent from a 40% PEG stock. After 30 minutes on ice, tubes were centrifuged 10 minutes/maximal speed in a microfuge (≥14 k rpm). The resulting supernatants were carefully removed and retained, and pellets redissolved into a fresh solution (50 µl) containing the same buffer, salt, RNase inhibitor, and PEG concentrations. After an additional 30 minutes on ice, tubes were centrifuged as before, supernatants removed and retained, and the final pellets re-dissolved in 50 µl TE.

Figure 12:
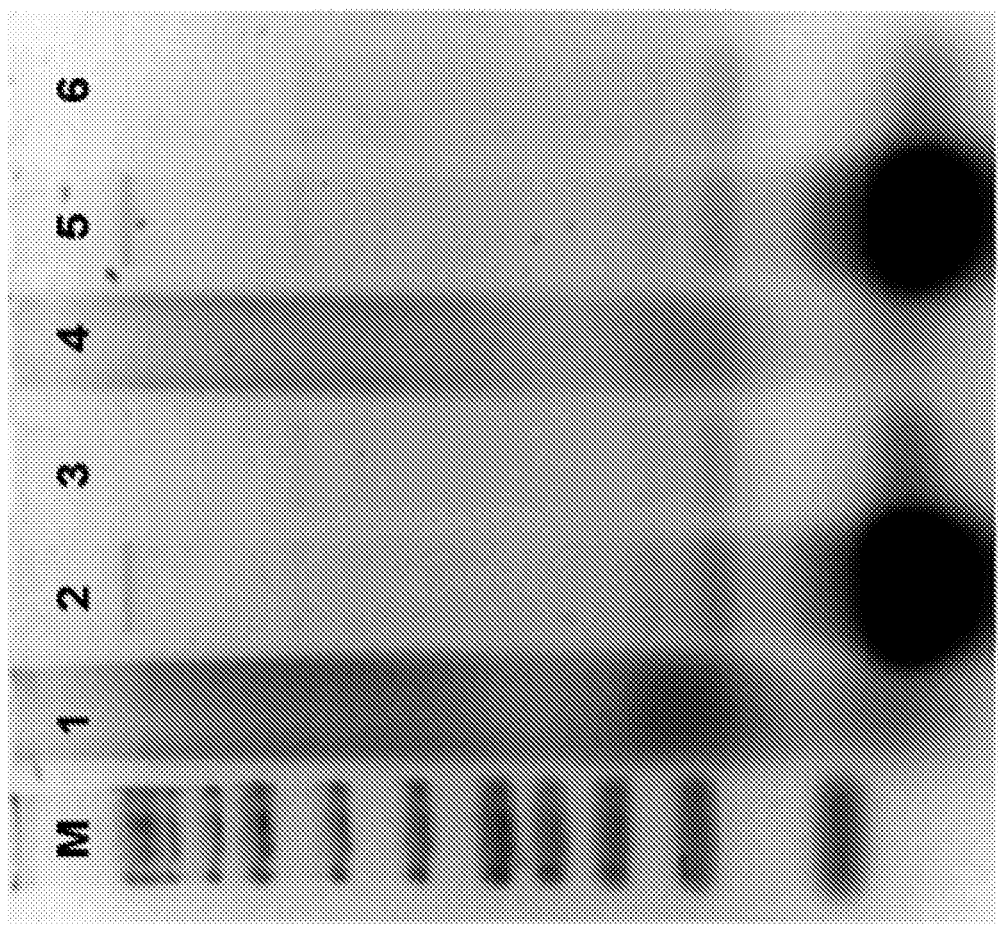
FIG. 12 depicts a representative gel analysis (2% agarose) of PEG test for RNA/unhybridized CLOSE oligonucleotide separations; lanes 1-3: MU89 RNA plus CLOSE oligonucleotides annealed with 2'-O-methyl protector strands; lanes 4-6; MU89 RNA plus CLOSE oligonucleotides without protector strands; lanes 1and 4: final PEG pellets (2× precipitations); lanes 2 and 5: first PEG supernatants; and lanes 3 and 6: second PEG supernatants.

Samples of the final pellets and the first and second supernatants (5 µl, ¹/₁₀ of each) were tested on a 2% agarose gel (FIG. 12). Results showed that the vast preponderance of (unhybridized) oligonucleotides were separated from the MU89 RNA and found in the first supernatants.

Example 10: Protocol for Removal of Unhybridized CLOSE Oligonucleotides by Single PEG Precipitation and DNase I Treatment (Actual Example)

Figure 13:
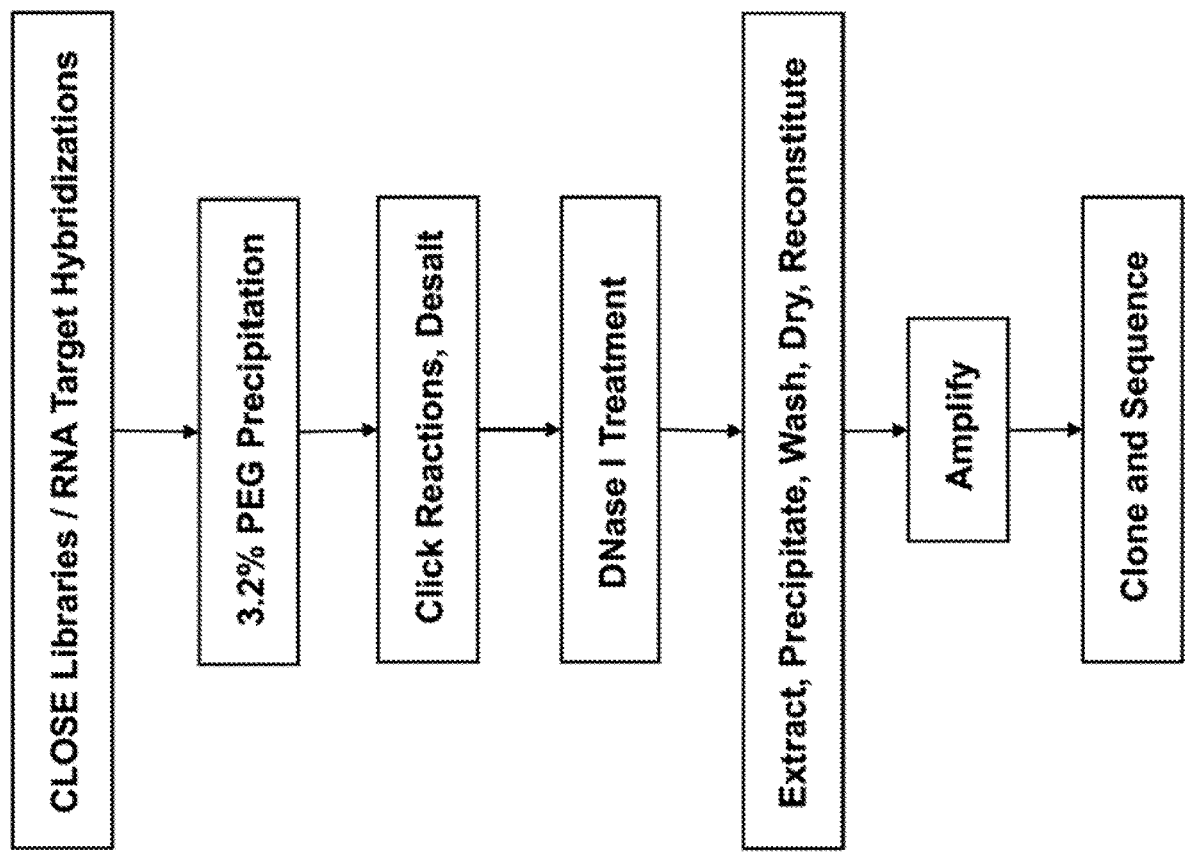
FIG. 13 depicts in a representative schematic form a CLOSE process with a single PEG precipitation and DNase step.

In another embodiment of CLOSE processing, a combination of a single PEG precipitation and DNase I treatment were effective for removal of the major portion of unhybridized CLOSE oligonucleotides. For this protocol, it is essential that the priming sites of the CLOSE oligonucleotides are protected from DNase I attack by hybridization with complementary 2'-O-methyl strands (as for Example 8). Hybridizations with target cellular RNAs (performed as detailed in Example 1; most commonly at 30 C) were subjected to precipitation with 3.2% PEG, using the same salt and buffer conditions as for Example 9. Following this, click reactions were performed (always with parallel controls of samples treated identically but without the click reagents) followed by desalting, using conditions as for Example 8. Then, DNase I treatments were performed at 28 C in ×1 RQ DNase I buffer (Promega) for 4 hours. Samples were then phenol extracted, precipitated with 20 µg glycogen/0.3 M sodium acetate/3 volumes ethanol, pelleted, washed with 1 ml 70% ethanol, dried, and reconstituted in 25 µl TE buffer, prior to PCR analysis (as for Example 8). All treatments were conducted in the presence of 0.6 units/ml murine ribonuclease inhibitor (New England Biolabs) until the end of the DNase I treatment. This process as whole is schematically depicted in FIG. 13. Results obtained were comparable to FIG. 11, whereby the combination of the PEG/DNase treatments were effective in removing unhybridized CLOSE oligonucleotides.

Example 11: Definition and Analysis of Different Forms of Discontinuous CLOSE Sites (Actual Example)

Application of the CLOSE process requires certain definitions of specific potential sites when these are discontinuous in terms of primary target RNA sequences. L- and R-CLOSE oligonucleotides (FIG. 1) form a 22-mer with an intervening CT sequence, either from contiguous hybridization sites, or sites which are proximally spatial but non-contiguous in target sequence (FIG. 14). With respect to the latter, the positioning of the hybridizing L- and R-CLOSE oligonucleotides along the template is significant for the kinds of secondary structures which can result in site spatial proximities. Herein, the arrangement where CLOSE L- and R-oligonucleotides bear effector 3' and 5' ends facing towards each other (the conventional orientation for contiguous sites) is termed an "Endo" configuration; the opposite orientation (effector 3' and 5' ends facing away from each other) is termed an "Exo" configuration (FIG. 14). In many cases Exo configurations will fail to promote reactivity, since functional effector groups are not directed towards each other. However, positioning of target sites in the context of certain secondary structures may favor Exo over Endo configurations. This is the case when hybridization sites exist within target template loops of sufficient size, (FIG. 15) where Endo rather than Exo orientations are spatially separated. This was initially tested with model effector partials (short oligonucleotides bearing alkyne and azide click groups) and longer oligonucleotides designed to assume loop structures through internal regions of self-complementarity. Within the resulting loop structures formed, these oligonucleotides possessed complementary sites to the click oligos, arranged in either Exo ("Loop-Exo1") or Endo ("Loop-Endo1") configurations. Click oligonucleotides (50 pmol each for 5'-azide and 3'-linear alkyne labeled strands) and Loop templates (50 pmol) were initially annealed in 25 µl×1 M buffer (10 mM Tris pH 7.5, 10 mM MgCl$_2$, 50 mM NaCl, 1 mM dithioerythritol) by heating 2 minutes at 80 C and cooling to room temperature.

Ten (10) µl from each annealing (20 pmol) were then subjected to Cu(I) click catalysis with THPTA, or in equivalent buffer lacking click catalyst. A premix of the following components was prepared with additions in the following order: 20 µl 70 mM Tris (3-hydroxypropyltriazolyl methyl) amine (THPTA) in 0.155 M NaCl; 4 µl 500 mM Na-ascorbate in 0.155 M NaCl; and 2 µl 100 mM CuSO$_4$ in 0.155 M NaCl. 2.6 µl of this premix was then added to each of the tubes for the click reaction, such that the final volume was 50 µl in ×1 phosphate-buffered saline.

Tubes were incubated for 30 minutes/0 C (on ice), and then 2 hours at 25 C. At the end of the incubation period, tube contents were desalted though Bio-Rad P6 columns as above, and precipitated with 20 µg glycogen (Sigma). After centrifugation, pellets were washed with 70% ethanol, dried, and re-dissolved in 5 µl TE. Samples of each (1 µl) were run on 15% urea denaturing gels and stained with SYBR-gold. Results showed the expected click chemical ligation product arising from templating on the linear template (FIG. 16; Lane 2, relative to the no-click control Lane 1). A corresponding click band was seen with the Loop-Exo1 (FIG. 16; Lane 4), but very little with Loop-Endo1 (FIG. 16; Lane 6), supporting the original prediction. An additional experiment showed that the Exo-configuration click activity was dependent on the loop secondary structure, by means of a control oligonucleotide where the self-complementary regions was replaced with minimally self-interactive sequence. Following annealing and click reactions carried out in the same manner as above, gel results showed a click product band from the Exo configuration with the self-complementary loop (Lane 4, FIG. 17) but no product when the self-complementarity was removed (Lane 6, FIG. 17). The Loop oligonucleotide in FIG. 17 (Loop-Exo2) differed from that used in FIG. 16 (Loop-Exo1) in terms of the positioning of the click-complementary sites relative to the self-complementary region: with Loop-Exo1, the click-complementary sites were 1 base from the self-complementary region; with Loop-Exo2, this was increased to 5 bases. Exo-click activity was nonetheless still observed.

Figure 16:
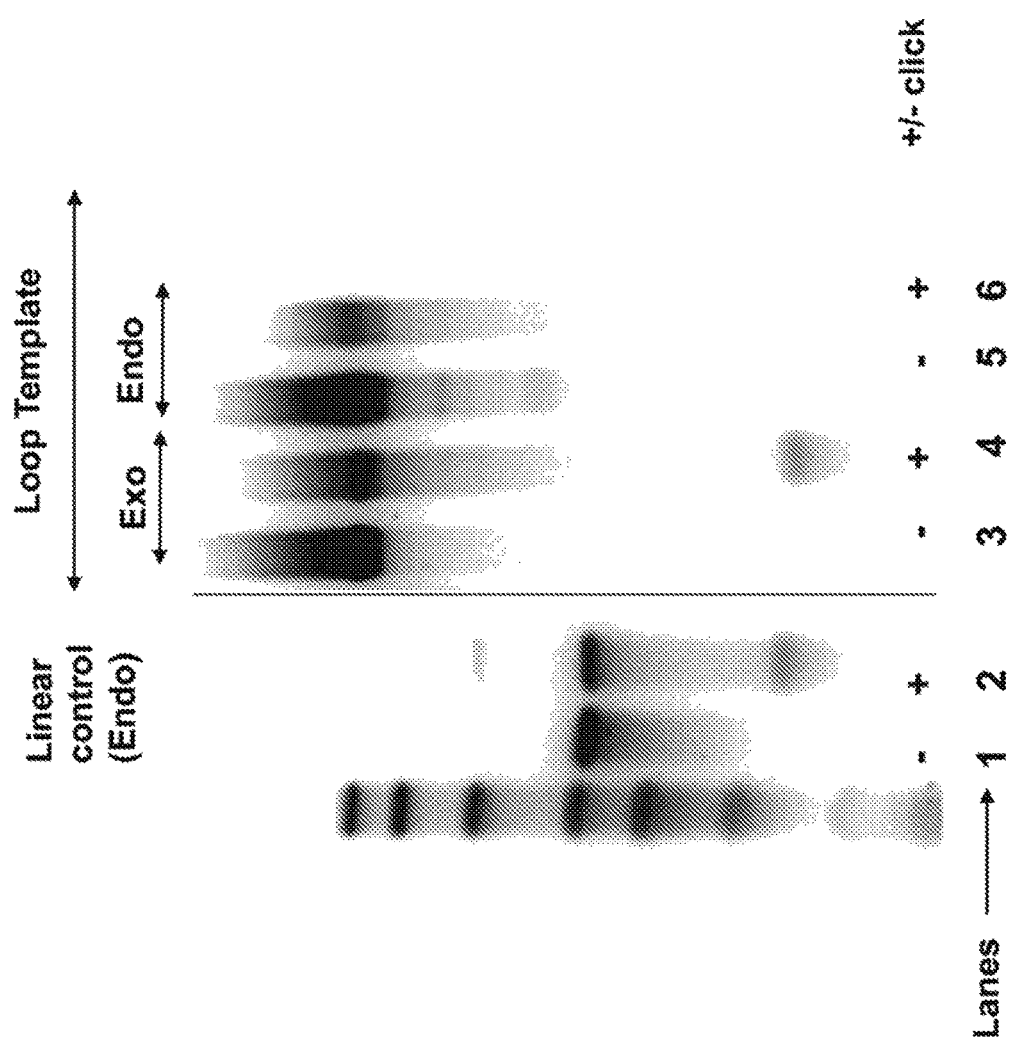
FIG. 16 depicts representative non-contiguous structures: testing "endo" vs. "exo" configurations; no significant click reactions were observed in the absence of template, under the conditions used.

Oligonucleotide Sequences for FIG. 16:

```
5'-azide oligo:
                                        (SEQ ID NO: 51)
azide-TGGACCATCT (click oligo-1);

3'- alkyne oligo:
                                        (SEQ ID NO: 52)
pCTTGTCCAGC^Me-propargyl (click oligo-2);

Linear template:
                                        (SEQ ID NO: 53)
GAAATAGATGGTCCA|GCTGGACAAGCAGAA;
```

Loop-forming template with complementary sites for click oligonucleotides 1 and 2, in Exo configuration ('Loop-Exo1'; 62-mer):

```
                                        (SEQ ID NO: 54)
GCGCGCGCGCTGCTGGACAAGTCCTTTTTTCCTTTTTTCCTAGATGGTCC

ATGCGCGCGCGC;
```

Loop-forming template with complementary sites for click oligonucleotides 1 and 2, in Endo configuration ('Loop Endo1'; 62-mer):

```
                                        (SEQ ID NO: 55)
GCGCGCGCGCTAGATGGTCCATCCTTTTTTCCTTTTTTCCTGCTGGACAA

GTGCGCGCGCGC;
```

Figure 17:
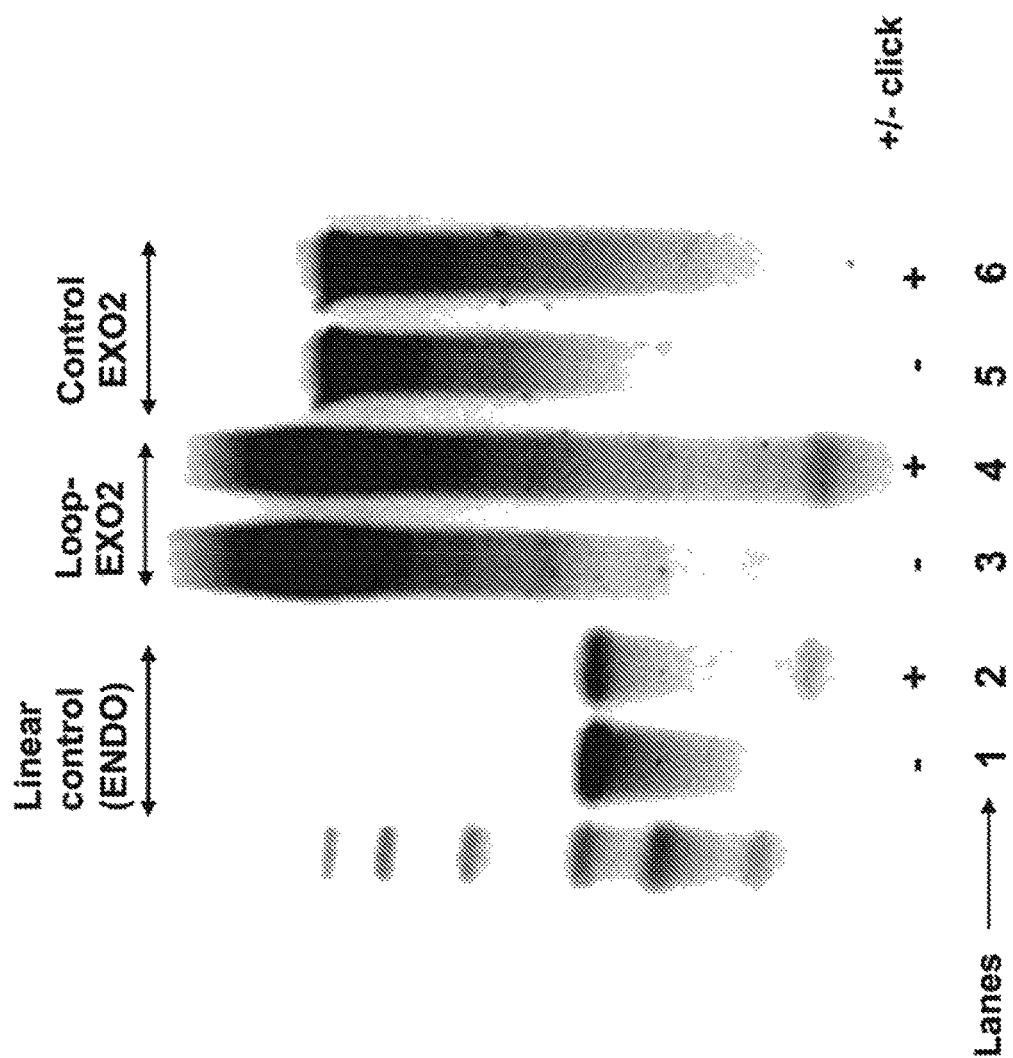
FIG. 17 depicts representative dependence of "exo" click on loop formation; the "control" sequences here have the G-C tracts which promote loop formation replaced with non-self-complementary sequences, such that no loops can form; no significant click reactions were observed in the absence of template, under the conditions used.

Oligonucleotide Sequences for FIG. 17:
5'-azide and 3'-alkyne oligos, and linear template: As for FIG. 16.
Loop-forming template with complementary sites for click oligonucleotides 1 and 2, in Exo configuration ('Loop-Exo2'; 60-mer):

```
                                        (SEQ ID NO: 56)
GCGCGCGCGCTCCTTGCTGGACAAGTTTTCCTTTTAGATGGTCCATTCCT

GCGCGCGCGC
```

Control oligonucleotide for Loop-Exo2, without self-complementary regions ('Ctrl-Exo2'; 60-mer):

```
                                        (SEQ ID NO: 57)
ACGGACTGCTTCCTTGCTGGACAAGTTTTCCTTTTAGATGGTCCATTCCT

TCATCAAACC
```

Underlined sequences show the GC regions whose self-complementarity enables loop formation. Bold sequences show sites complementary to the above click oligonucleotides 1 and 2. AGATGGTCCA: Complementary to click oligo-1 (SEQ ID NO:58); GCTGGACAAG: Complementary to click oligo-2 (SEQ ID NO:59).

Example 12: In Vitro Click Reactions with Spatially Proximal but Noncontiguous Hybridization Sites Through Stem Loops (Actual Example)

Figure 18:
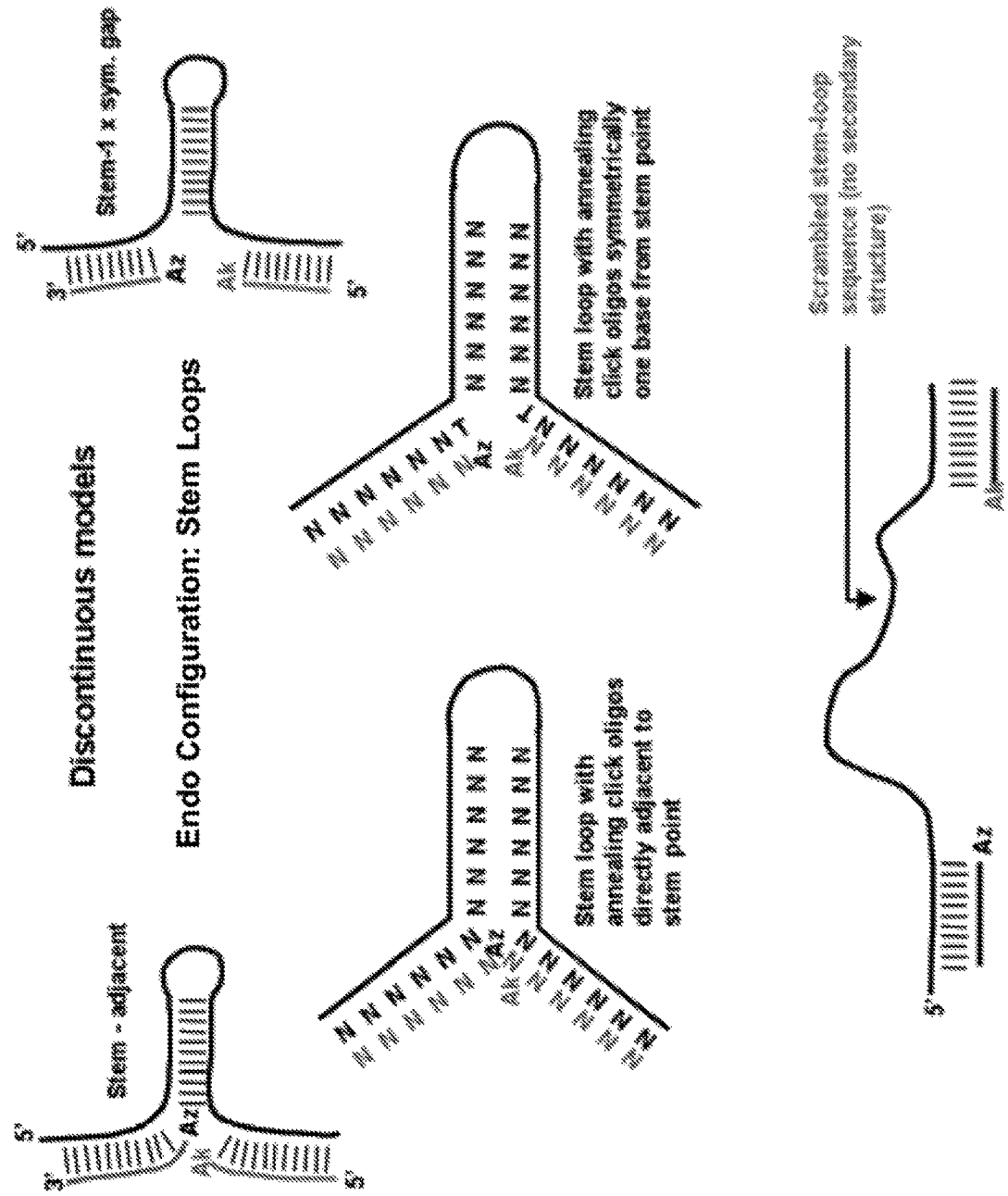
FIG. 18 depicts representative structures of stem loop templates used in FIG. 19.

Additional tests were performed where sites complementary to click-labeled oligonucleotides (model effector partials) were rendered spatially proximal through the formation of a stem loop in the target template, such that the hybridization sites were outside of the loop itself. Template sequences for in vitro click reactions were designed such that stem loop structures will form at room temperature, along with appropriate control sequences lacking such structures, where the click oligonucleotides hybridize in the Endo configuration (FIG. 18).

Click oligonucleotides (50 pmol each for 5'-azide and 3'-linear alkyne labeled strands) and various templates (50 pmol) were initially annealed in 25 μl×1 M buffer (10 mM Tris pH 7.5, 10 mM MgCl$_2$, 50 mM NaCl, 1 mM dithioerythritol) by heating 2 minutes at 80 C and cooling to room temperature.

Ten (10) μl from each annealing (20 pmol) were then subjected to Cu(I) click catalysis with THPTA, or in equivalent buffer lacking click catalyst. Click reactions were then performed in the same manner as for Example 11. Samples of each (1 μl) were run on 15% urea denaturing gels and stained with SYBR-gold (FIG. 19).

Chemically modified oligonucleotides were prepared by TriLink (5'-azide oligo) or University of Wisconsin Biotechnology Facility (3'-alkyne oligo).

Figure 19:
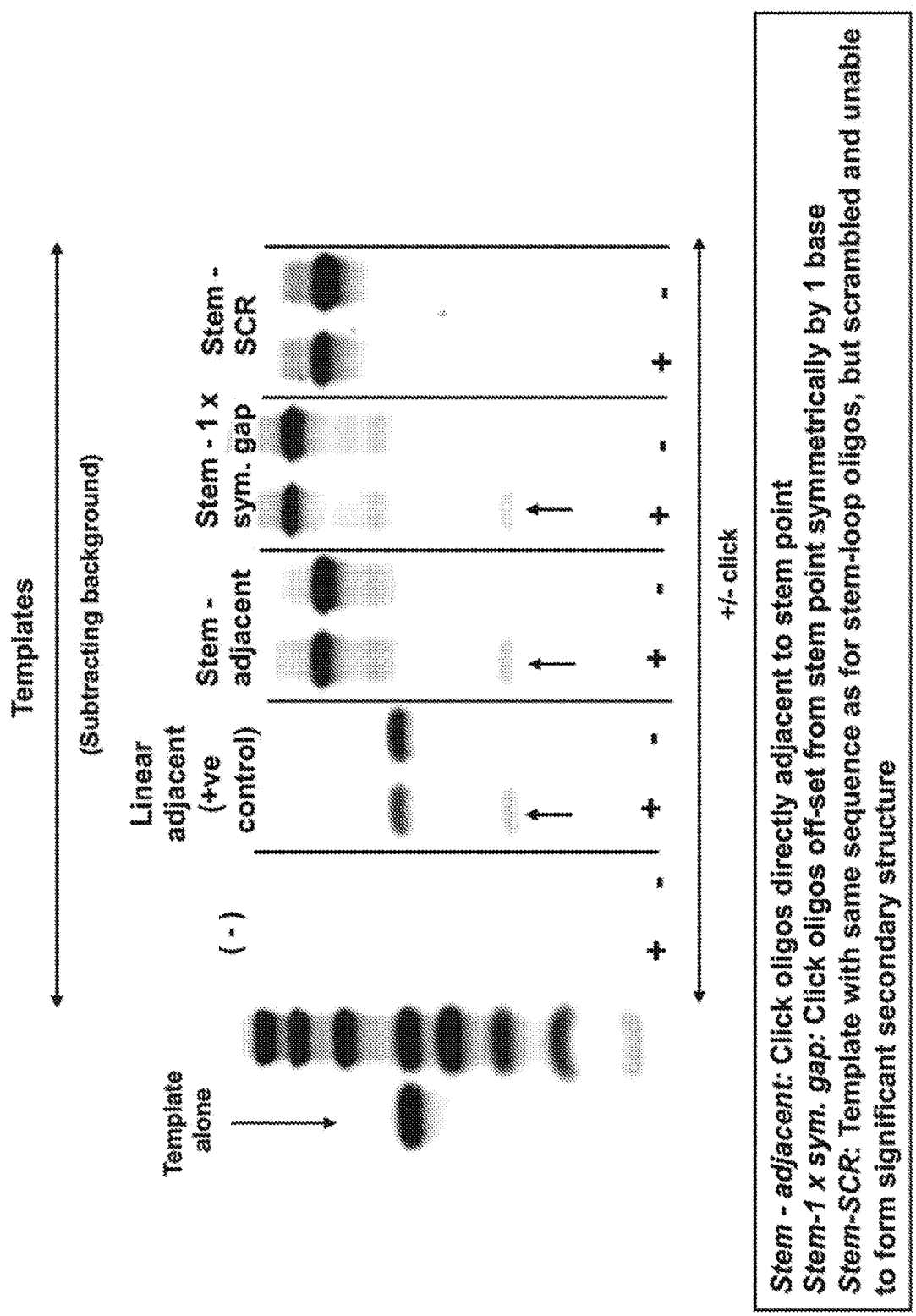
FIG. 19 shows a representative demonstration of click reaction following hybridization to discontinuous sites on a template strand; schematic depictions of stem-loop oligonucleotides shown in FIG. 18; bands show positions of click-ligated products (20-mers), distinguishable from the template strands (30-mers).

Oligonucleotide Sequences for FIG. 19:

```
5'-azide oligo:
                                       (SEQ ID NO: 51)
azide-TGGACCATCT (click oligo-1);

3'-alkyne click oligo:
                                       (SEQ ID NO: 52)
pCTTGTCCAGC^Me-propargyl (click oligo-2);

Linear template:
                                       (SEQ ID NO: 60)
GAAATAGATGGTCCA|GCTGGACAAGCAGAA;

Stem-adjacent:
                                       (SEQ ID NO: 61)
AGATGGTCCAGTCGGCGCGCCTCGAAAACGAGGCGCGCCGAC

GCTGGACAAG;

Stem-x1 sym gap:
                                       (SEQ ID NO: 62)
AGATGGTCCATGTCGGCGCGCCTCGAAAACGAGGCGCGCCGAC

TGCTGGACAAG;

Stem-scrambled:
                                       (SEQ ID NO: 63)
AGATGGTCCAGCCCCCAGGCCGCATACGACGGCTAGGGAGCG

GCTGGACAAG.
```

Underlined sequences show the regions whose self-complementarity enables stem loop formation. Bold sequences show sites complementary to the above click oligonucleotides 1 and 2. AGATGGTCCA: Complementary to click oligo-1 (SEQ ID NO:58); GCTGGACAAG: Complementary to click oligo-2 (SEQ ID NO:59).

Example 13: Pyrene Excimer Activity Produced by Specific Template-Directed Hybridization (Actual Example)

Pyrene excimer fluorescence can be used to demonstrate molecular proximity of CLOSE oligonucleotides on a target template, and thus serve as a means for validation of candidate targets. The following protocol for demonstration of specificity of pyrene-labeled oligonucleotides on DNA copies of Human Papillomavirus (HPV) RNA templates was used. Pyrene oligonucleotides with 2' O-methyl backbones:

```
                                       (SEQ ID NO: 64)
PyeTO.1: 5'-pyrene-(C6)-UUUCUUCAGGACACAG;

(SEQ ID NO: 65)
PyeTO.2: UCCAGAUGUCUUUGC-(C6)-pyrene-3';
```

Figure 20:
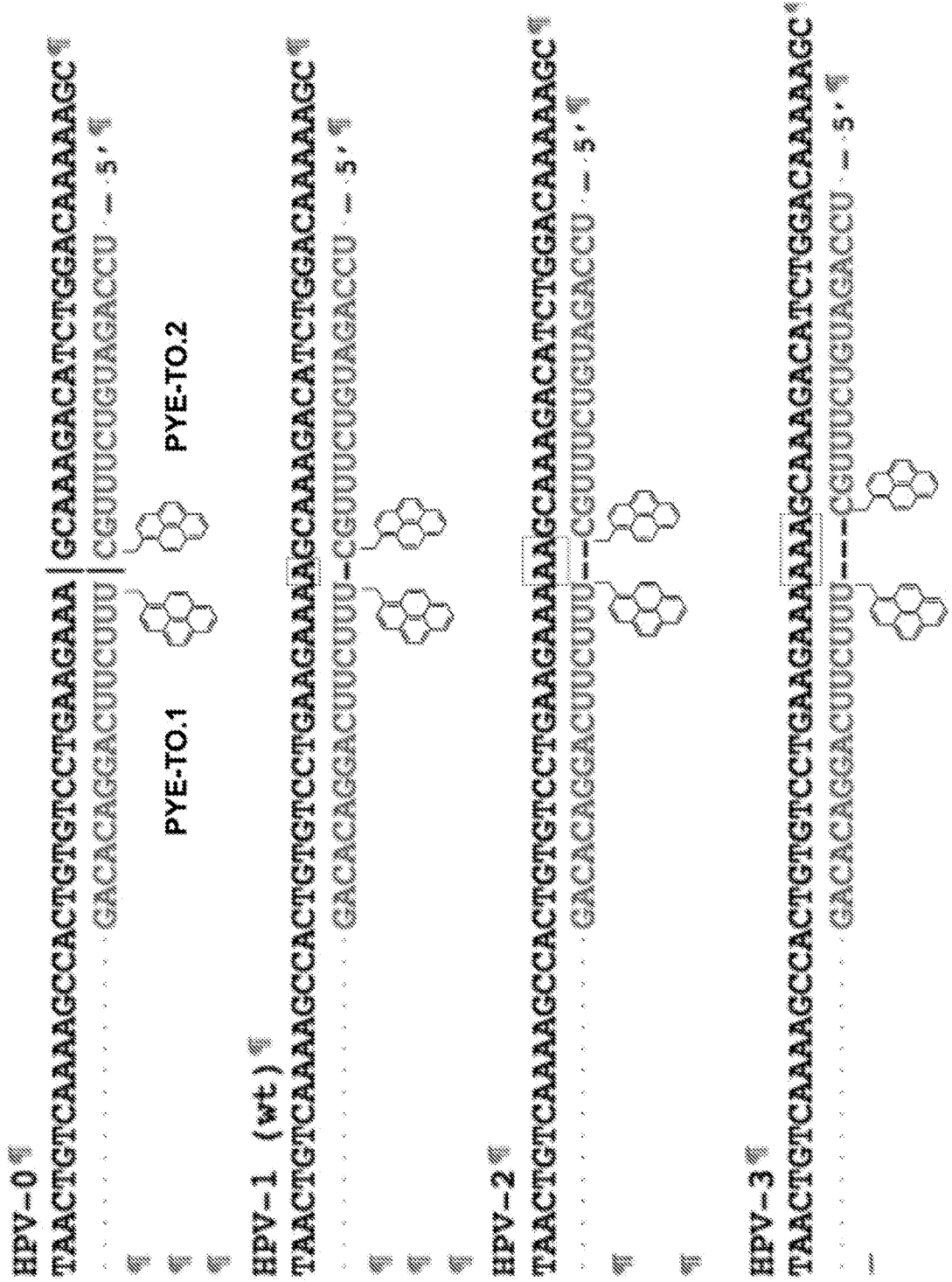
FIG. 20 shows representative pyrene-labeled oligonucleotides PyeTO.1 and Pye TO.2 annealed on wild-type and mutant HPV templates; for the wild-type sequence (HPV-1) the oligonucleotides are displaced from each other by one base (boxed dA residue), unlike the HPV-0 template where they are immediately juxtaposed; for the HPV-2 and HPV-3 templates, the displacement is two and three dA residues respectively (boxed); TAACTGTCAAAAGCCA CTGT-GTCCTGAAGAAAGCAAAGACATCTGGA-CAAAAAGC (SEQ ID NO:89); TAACTG TCAAAAGC-CACTGTGTCCTGAAGAAAAGCAAAGACATCTGGA-CAAAAAGC (SEQ ID NO:35); TAACTGTCAAAAGCCACTGTGTCCT-GAAGAAAAAGCAAAGACATCTGGACA AAAAGC (SEQ ID NO:90); TAACTGTCAAAAGCCACTGTGTC-CTGAAGAAAAAGCAA AGACATCTGGA-CAAAAAGC (SEQ ID NO:91); UCCAGAUGUC-UUUGC-pyrene (SEQ ID NO:36), pyrene-UUUCUUCAGGACACAG (SEQ ID NO:88).
Figure 21:
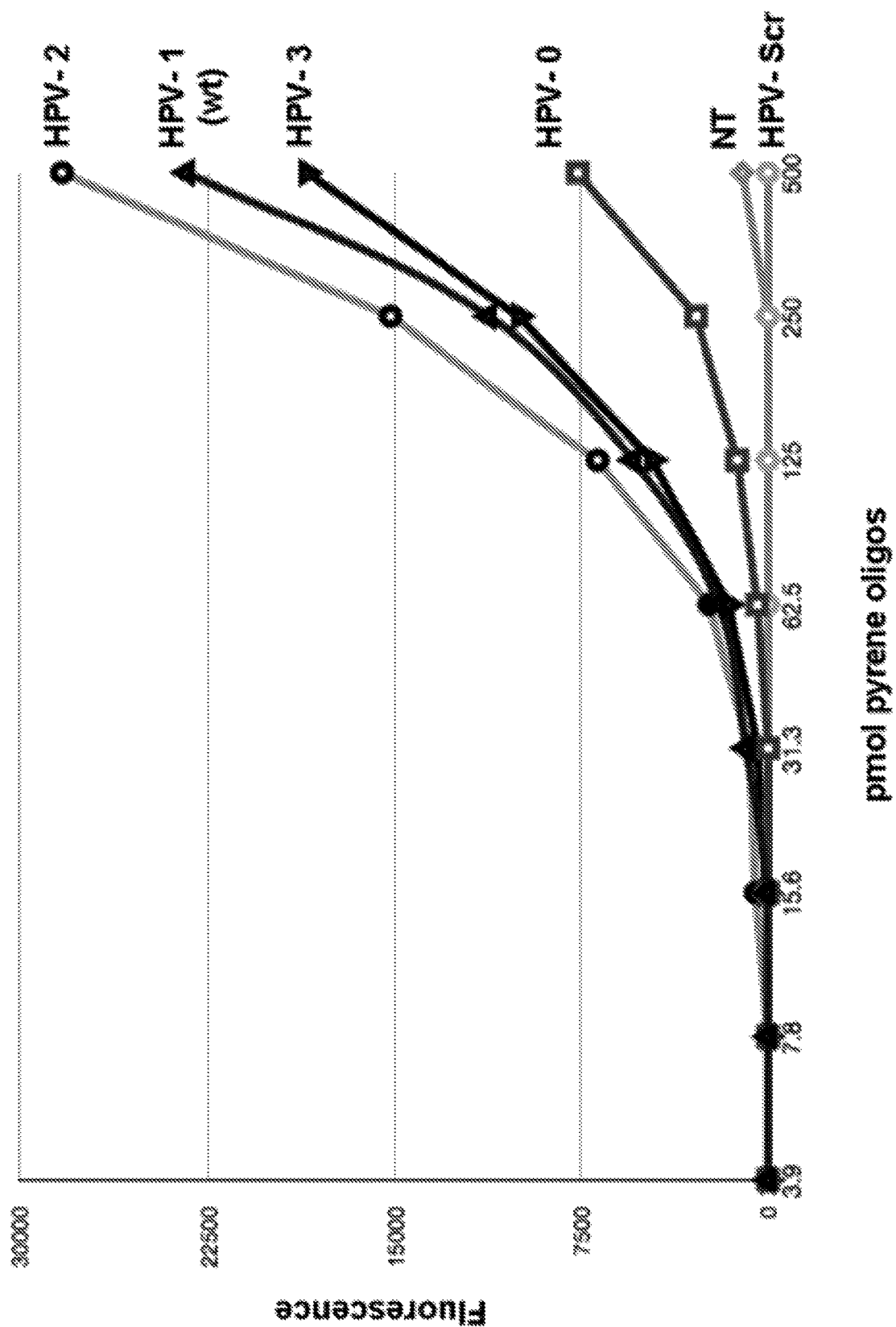
FIG. 21 shows induction of pyrene excimer fluorescence on specific templates in equimolar amounts; HPV-0, HPV-1, HPV-2, HPV-3; HPV-Scr=randomly scrambled template from HPV-0 sequences; NT=no template.

1 nmol HPV templates (10 μl) and 1 nmol each of PyeTO.1/PyeTO.2 (2 μl each) in 100 μl of ×1 "P-buffer" (used as 10 μl of ×10 stock: 200 mM Tris pH 7.4, 250 mM NaCl, and 50 mM MgCl$_2$) were mixed and made up to 100 μl final. Tubes were prepared with 100 μl mixes with PyeTO.1/PyeTO.2 oligonucleotides and following templates (FIG. 20): HPV-0, HPV-1, HPV-2, HPV-3, HPV-Scr (Randomly scrambled HPV template), and No Template. FIG. 21 shows PyeTO.1 and Pye TO.2 annealed on wild-type and mutant HPV templates.

Each were heated for 2 minutes at 80 C, and allowed to cool at room temperature. Tubes were centrifuged briefly and the contents added to each to 96 blackwell plates in 1:2 dilution series (50 μl each well final). Readings were taken with a Tecan spectrophotometer set for fluorescent measurement and for Becton-Dickinson 96-well black-sided plates. (Readings were set for 335 nm excitation/480 nm emission, with instrument-optimized fluorescent settings).

Fluorescence was observed for excimer-based excitation and emission wavelengths, and only for specific templates. (Signals absent in scrambled and no-template controls). Although all HPV templates elicited excimer fluorescence, best results were seen with a 2-base offset between the 5' and 3'-labeled oligonucleotides. See FIG. 21.

Example 14: Analysis of CLOSE Candidates by CLOSE Intersection Software (Actual Example)

Figure 22:
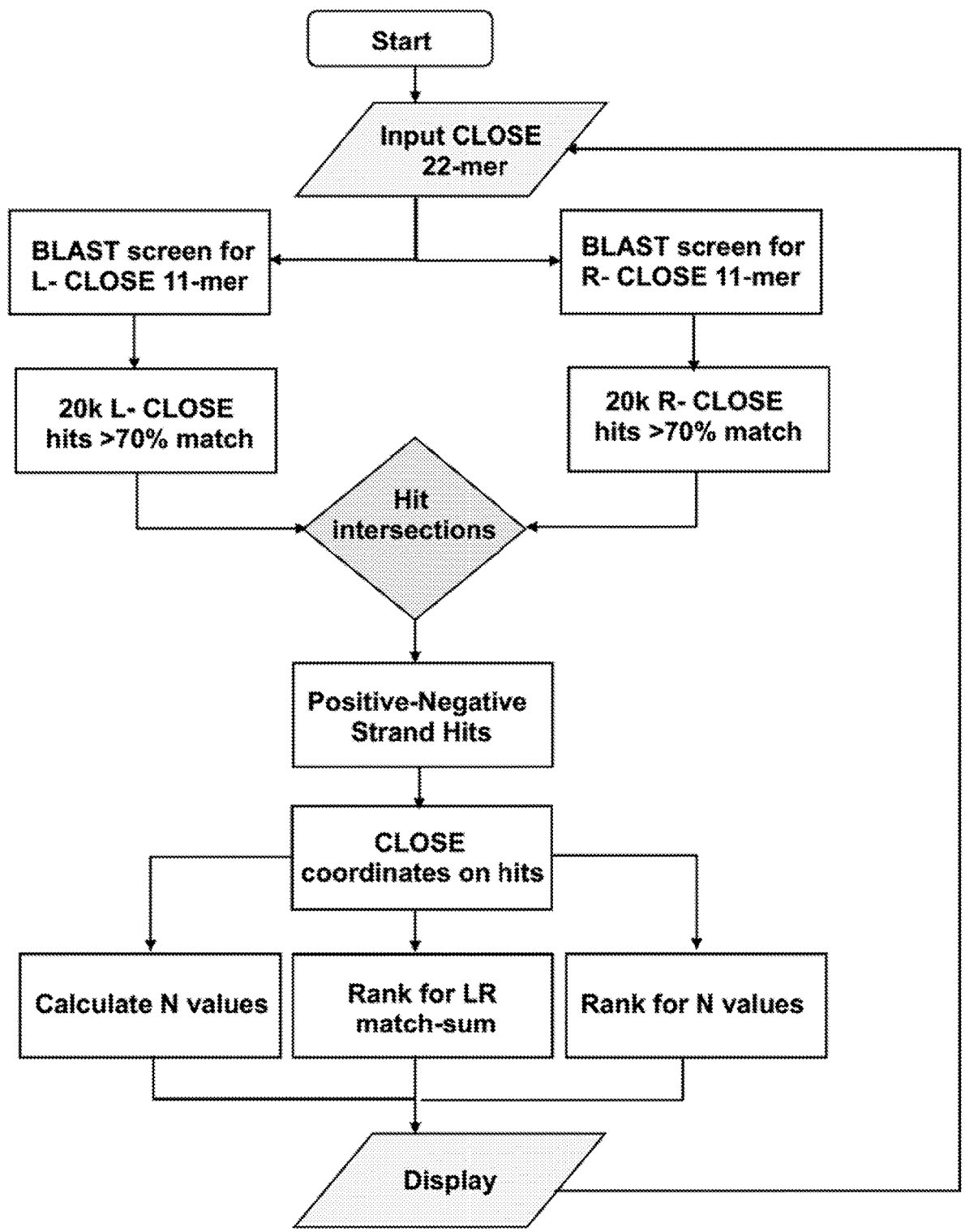
FIG. 22 depicts representative CLOSE Intersection software principle as a flow-chart, showing the processing pathway for each CLOSE clone sequence.
Figure 23:
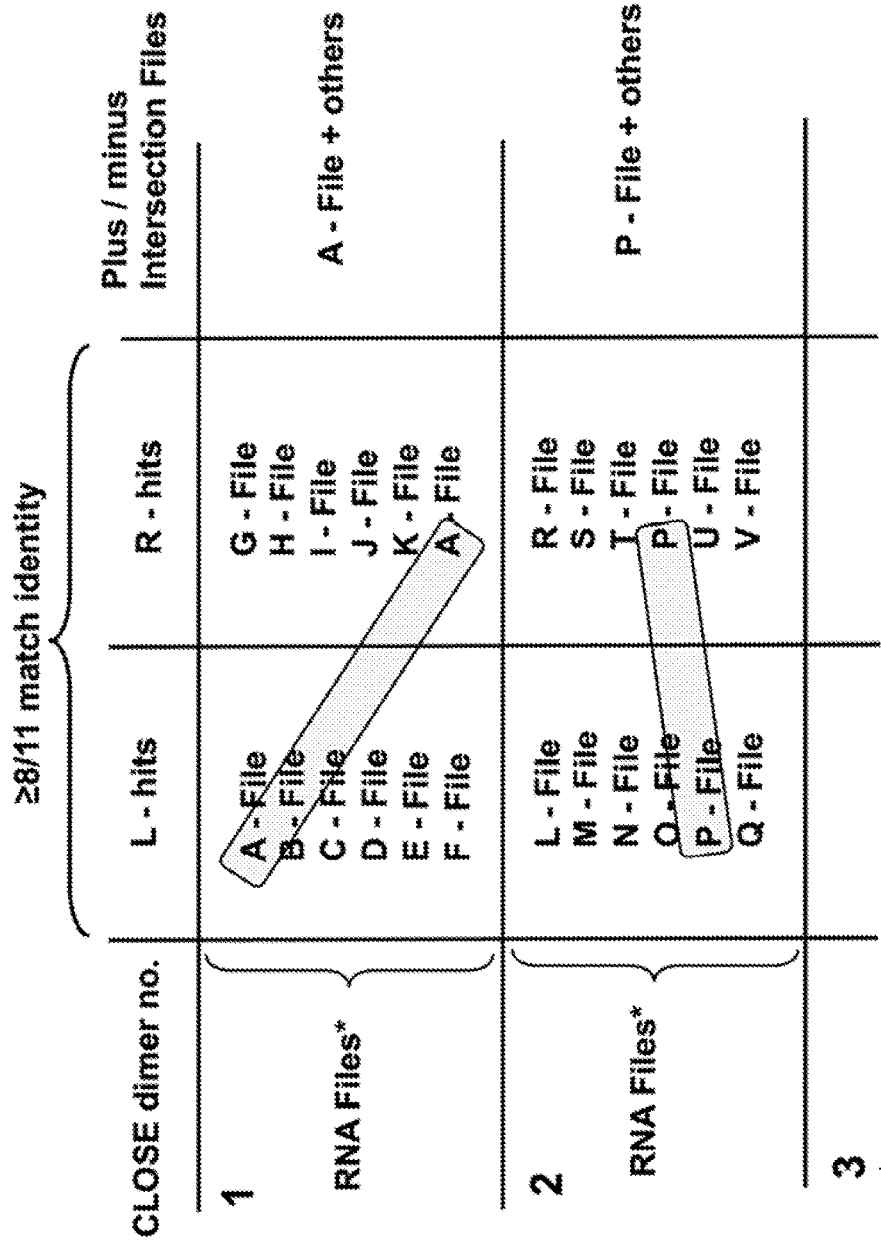
FIG. 23 depicts representative CLOSE intersection software principle.

In order to facilitate the identification of CLOSE clones, software was developed ("CLOSE intersection analysis") to work in conjunction with free online BLAST (Basic Local Alignment Search Tool) software, available through the National Center for Biotechnology Information. This novel software was particularly needed for identifying non-contiguous CLOSE hits on a single template, for which BLAST alone is not well-suited. The basic strategy involves treating each sequenced L- and R-11-mer of a CLOSE dimer separately for the purposes of BLAST searching of the human RNA-Seq database. (This parallels the actual situation with hybridization of each L- and R-CLOSE oligonucleotide, prior to RNA template-directed chemical ligation). It is obvious that when searching with an arbitrary 11-mer sequence among human transcriptomic sequences, a significant number of random complete matches will be expected (a random 11-mer will be found on average every $4 \cdot 10^6$ bases), and many more will result if the stringency is reduced to less than perfect matching. (In practice, CLOSE ligations may tolerate a number of mismatches per oligo). These first sequences are set to bring up a maximum of 20,000 hits, which encompasses in practice hits equal to or greater than 8/11 matches. These separate hit lists (as XML files) are then scanned for common RNA-Seq file entries; thus finding files which intersect for their hit matches for specific L- and R-CLOSE clone sequences. Following this, the program performs a winnowing on the basis of strandedness. Only "plus/minus" hits are relevant in this context, and therefore all others are rejected. (The input CLOSE sequences are by default in the "plus" orientation; since complementary hybridizing sequences in target RNAs are sought, "minus" orientation hits are mandated). Ranking of hits is then performed at two levels: a match score for combined L- and R-searches (maximum 22 for perfect matching), and in addition a rank based on "N values", where N=the distance between the 5' end of the CLOSE-match sequence nearest the 5' end of the target and the 3' end of the CLOSE-match sequence most distal to the 5' end of the target. While in principle RNA folding could bring sites into proximity that are very remote in terms of primary sequence, it was reasoned that low N values (closer in proximity) may be of greater frequency. (For fully contiguous sites, N=0). Representative software as a flow-chart is depicted in FIG. 22, and also illustrated in FIG. 23.

Figure 24:
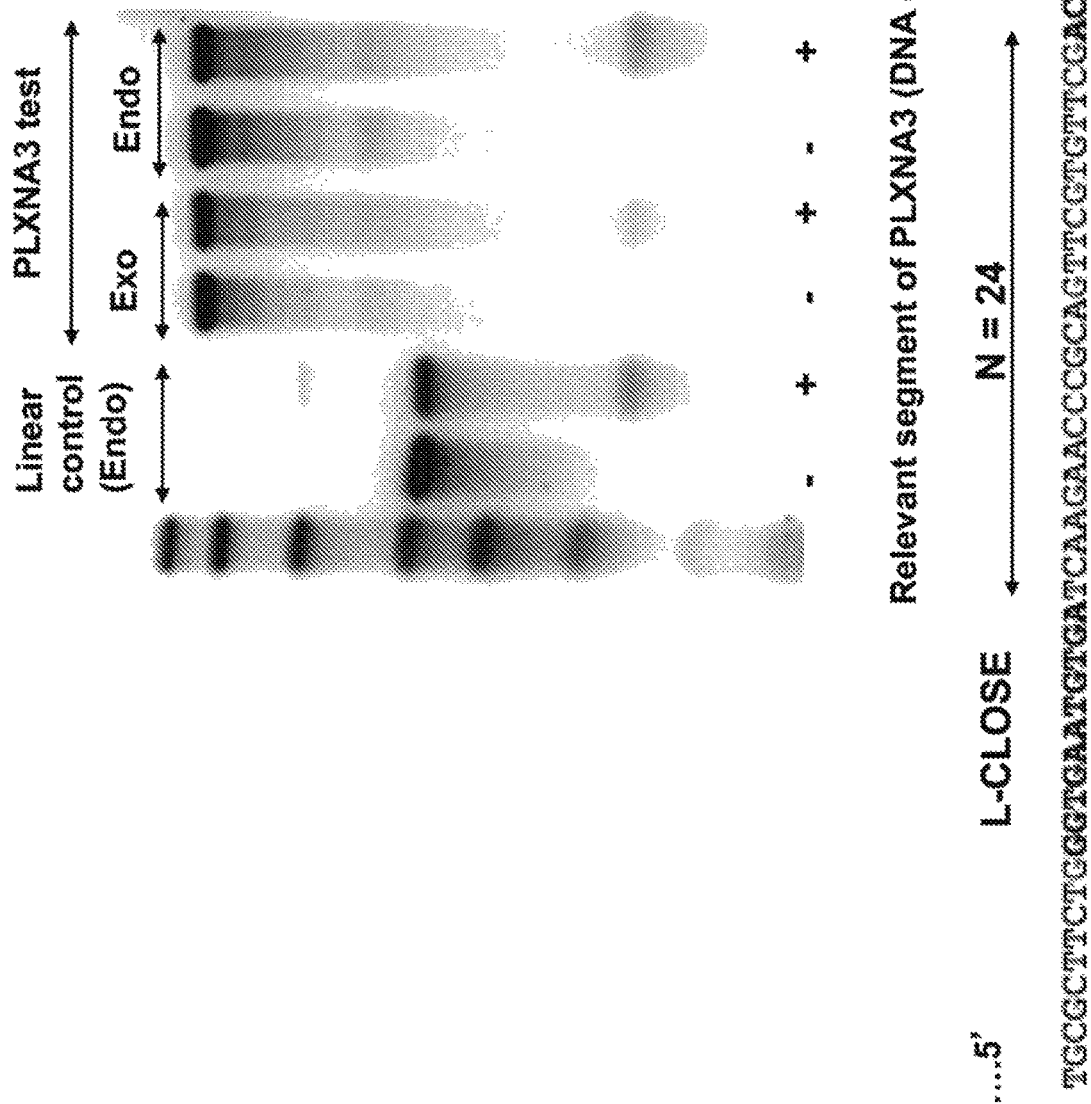
FIG. 24 depicts representative CLOSE intersection software principle: example of a hit; the PLXNA3 sequence was found from CLOSE intersection software with a specific CLOSE clone, where the CLOSE matches were in the EXO configuration (in such cases, the L-CLOSE match is closer to the 5' end of the target RNA sequence than the R-CLOSE match); the CLOSE sequences were replaced with the standard complements to the 10-mer click oligonucleotides used in these tests, in either EXO or ENDO configurations; no significant click reactions were 15 observed in the absence of template, under the conditions used; TGCGCTTCTGGGTG AATGTGATCAAGAACCCGCAGTTCGTGTTCGACATCCACAAGAACAGCATCACGG (SEQ ID NO: 126).

An example of a CLOSE software intersection file hit was examined further. From an amplified CLOSE dimeric library obtained from MU89 melanoma cell RNA, one candidate was a transcript from the gene PLXNA3. In this case, the CLOSE L- and R-sites were in an Exo configuration, and the N value was only 24 bases. To investigate further, the same PLXNA3 sequence (as single stranded DNA) was tested as a model template in vitro, except replacing the CLOSE sites within PLXNA3 with the same modified click oligonucleotide 10-mers as used for Examples 11 and 12. These were placed into the flanking sequences derived from PLXNA3 in both Exo and Endo configurations. Such templates were annealed with the 10-mer click oligos, and subsequently treated with and without click-catalyzing reagents as for Example 1 (FIG. 24). Results showed that click reactions occurred in either orientation. Thus, the observed CLOSE hybridizations in the Exo configuration were compatible with click reactivity in a model template.

Oligonucleotide Sequences for FIG. 24:

```
5'-azide oligo:
                                         (SEQ ID NO: 51)
azide-TGGACCATCT (click oligo-1);

3'-alkyne click oligo:
                                         (SEQ ID NO: 52)
pCTTGTCCAGC^Me-propargyl (click oligo-2);

Linear template:
                                         (SEQ ID NO: 60)
GAAATAGATGGTCCAGCTGGACAAGCAGAA;

PLXA3-Exo Model:
                                         (SEQ ID NO: 66)
TTCTGGCTGGACAAGTCAAGAACCCGCAGTTCGTGTTCGAGATGGTCCAG

AACA;

PLXA3-Endo Model:
                                         (SEQ ID NO: 67)
TTCTGAGATGGTCCATCAAGAACCCGCAGTTCGTGTTCGGCTGGACAAGG

AACA.
```

Bold sequences show sites complementary to the above click oligonucleotides 1 and 2. AGATGGTCCA: Complementary to click oligo-1 (SEQ ID NO:58); GCTGGACAAG: Complementary to click oligo-2 (SEQ ID NO:59). Underlined sequences corresponds to the N-region for the PLXNA3 CLOSE hit.

Example 15: Demonstrations of the Template Titration Effect with Model Effector Partials (Actual Example)

Figure 25:
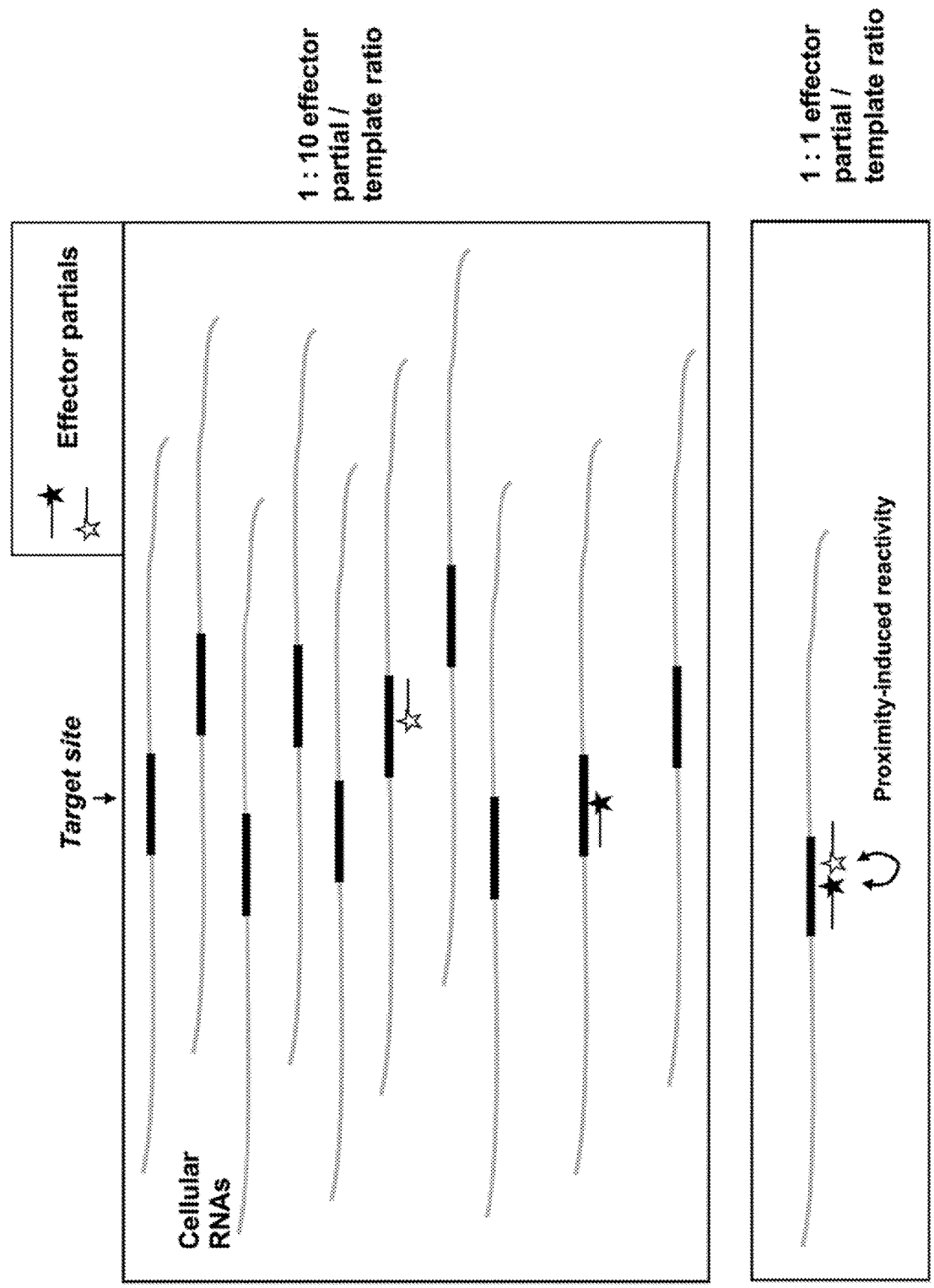
FIG. 25 depicts a representative schematic of template titration effect when target template is in molar excess of effector partials.
Figure 26:
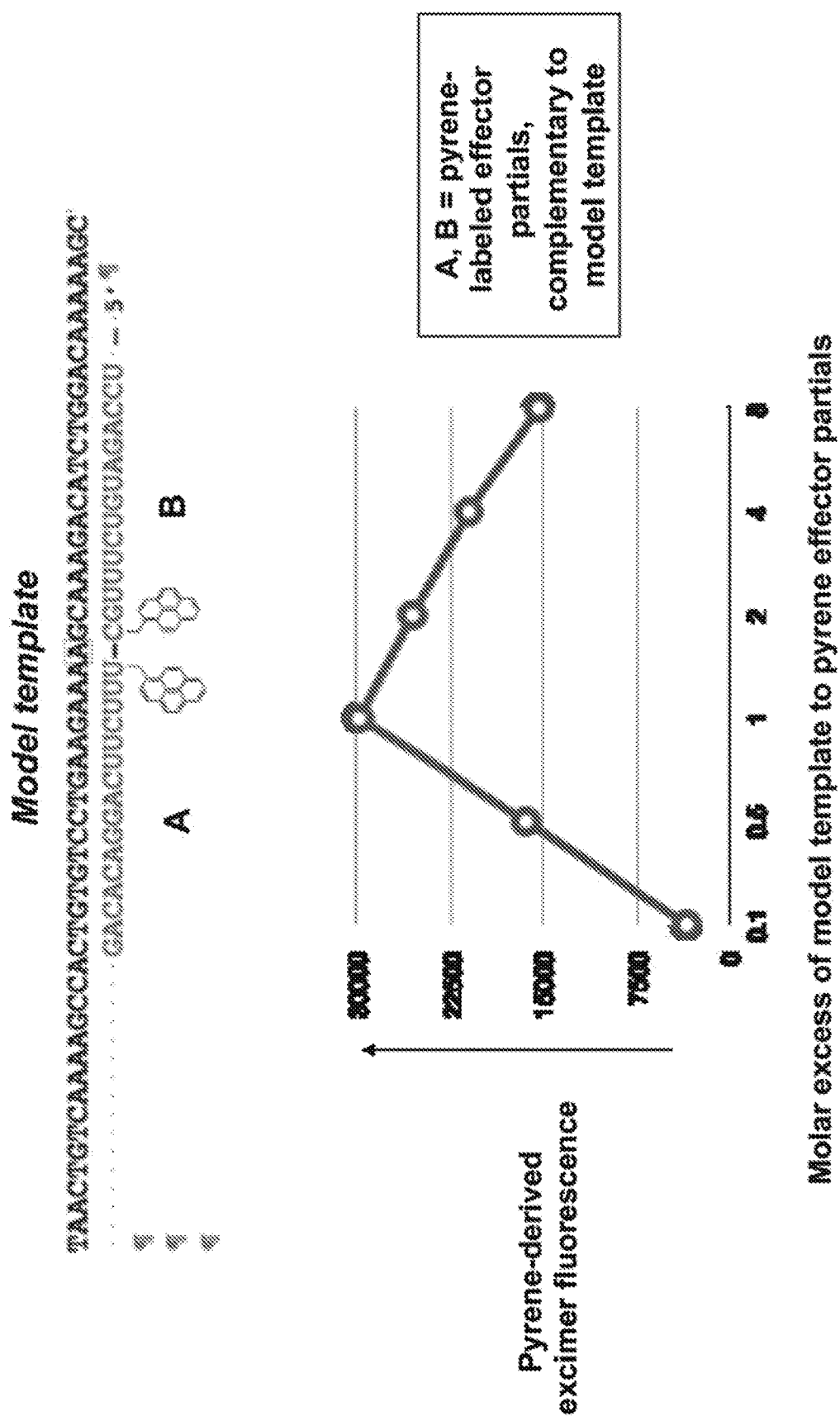
FIG. 26 depicts a representative demonstration of template titration effect with pyrene fluorescence; TAACTGTCAAAAGCCACTGTGTCCTGAAGAAAAGCAAAGACATCTG GACAAAAAGC (SEQ ID NO:35); UCCAGAUGUCUUUGC-pyrene (SEQ ID NO:36), pyrene-UUUCUUCAGGACACAG (SEQ ID NO:88).

The effect of excess target template on bimolecular effector partial assembly can be inferred from a priori reasoning (FIG. 25), stemming from the predicted sequestration and dilution of effector partials upon excess target templates, reducing the frequency whereby two effector partials pair on the same template with concomitant directed templated assembly. This was initially tested using pyrene fluorescence (Examples 5 and 13) as a read-out for spatial proximity between oligonucleotides hybridizing to sites closely linked on an oligonucleotide template. Varying amounts of the template HPV-1 (wild-type; FIG. 20) were mixed with a constant 1 nmol of each pyrene-labeled effector oligonucleotide (PYE-TO.1, PYE-TO.2; FIG. 14), subjected to a 5 min/80 C heating and cooling to room temperature, and then read for fluorescence with a Tecan spectrophotomer (as for Example 13). Results showed a fluorescence peak at 1:1 molar ratio, followed by a linear decline as far as monitored (FIG. 26; at an 8-fold effector molar excess).

Figure 27:
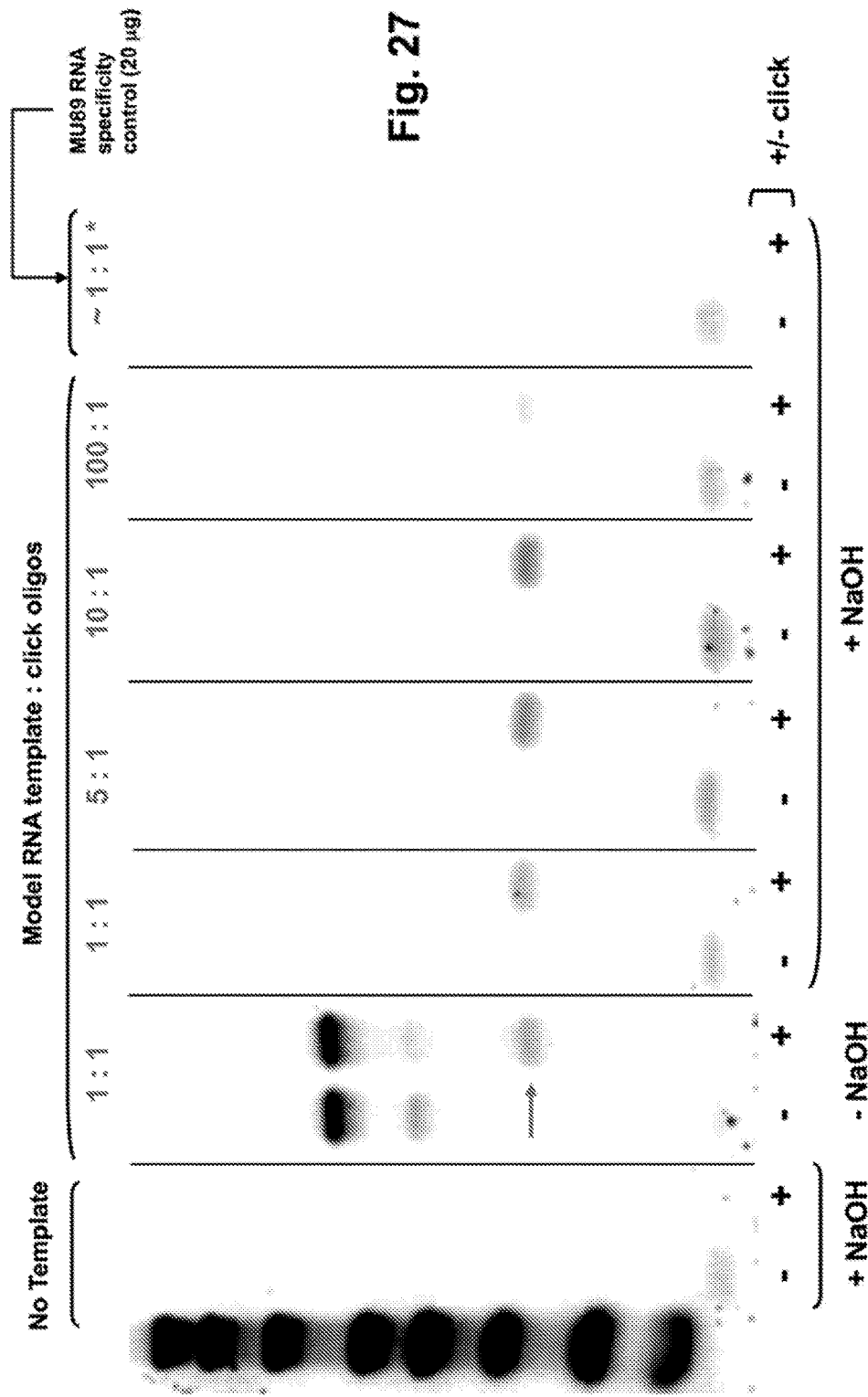
FIG. 27 depicts a representative demonstration of template titration effect with an RNA template in vitro; the assigned molar ratio of MU89 RNA:click oligonucleotides is based on assuming average RNA size of about 1500 bases; GAAAUAGAUGGUCCAGCUGGACAA GCAGAA (SEQ ID NO:37); CTTGTCCAGCTGGACCATCT (SEQ ID NO:38).

In an alternative test, templated in vitro reactivity between click-labeled oligonucleotides was used. In this case, an RNA oligonucleotide served as the template, since high concentrations of template would interfere with the gel-band assay read-out unless removed, and the RNA strands were readily removable by alkaline hydrolysis. The template oligonucleotide used in this case was an RNA version of the same linear DNA template as previously used (Examples 11 and 12). Click-labeled effectors as previously used (Examples 11 and 12) were used at 50 pmol each, and mixed with varying amounts of the RNA template bearing complementary sequences, in were initially annealed in 25 µl×1 M buffer (10 mM Tris pH 7.5, 10 mM MgCl$_2$, 50 mM NaCl, 1 mM dithioerythritol) Samples were heated 1 minutes at 70 C, cooled to room temperature, and treated with and without click-catalyzing reagents in the same manner as for Example 11, followed by desalting. Then all but a control sample were treated in 75 µl with 0.2 M NaOH for 20 minutes/70 C, neutralized with 1.2 M acetic acid (13.5 µl) and 1 M Tris (3.8 µl) to a final volume of 100 µl. Samples were then ethanol precipitated (3 volumes) with 20 µg glycogen and 0.3 M sodium acetate. Following pelleting and washing with 70% ethanol, samples were redissolved in 5 µl TE. 1 µl of each of these preparations was denatured at 98 C for 5 minutes in 98% formamide, 10 mM EDTA, and run on 15% denaturing urea gels. Gel analysis showed that in the absence of alkaline hydrolysis, the RNA template was visible and had been effective in promoting click reactivity between the labeled oligonucleotides (FIG. 27). In this experiment, MU89 RNA was included as a specificity control, and no templated effector assembly was found. A titration effect was also clearly demonstrable with the RNA oligonucleotide as template. Here optimal click product formation occurred at 10:1 template:effector ratio, but was almost absent at 100:1 template:effector ratio. This general trend was reproducible in subsequent tests.

It was notable that while the fluorescence-based assay gave peak activity at equimolar levels (FIG. 26), the RNA-templated assembly was improved at higher template levels, up to at least as much as a 10:1 molar ratio (FIG. 27). It is very likely that this apparent divergence can be ascribed to the nature of the respective templates. In the pyrene-based assay, the DNA template has little propensity for formation of secondary structures, whereas the RNA template can form a small stem loop (FIG. 27). Moreover, RNA duplexes have increased thermal stability over cognate DNA helices. Thus, the annealing of the DNA oligonucleotide effectors with the RNA template competed with internal annealing of the RNA strand itself, resulting in an increased requirement for template over equimolarity in order to give optimal results. Even so, when the RNA template levels were high enough, the titration effect is evident, severely limiting the amount of product. Overall, the theoretical titration effect (FIG. 25) is clearly demonstrable with real experimental systems, but other factors in addition to effector/template ratios per se can influence the point at which template levels become counterproductive.

In turn, these results confirm that measuring the expression levels of candidate CLOSE targets is an important adjunct experimental goal (Examples 6 and 7).
Oligonucleotide Sequences for FIG. 27:

```
5'-azide oligo:
                                          (SEQ ID NO: 51)
azide-TGGACCATCT (click oligo-1);

3'-alkyne click oligo:
                                          (SEQ ID NO: 52)
pCTTGTCCAGC^Me-propargyl (click oligo-2);

Linear RNA template:
                                          (SEQ ID NO: 68)
GAAAUAGAUGGUCCA|GCUGGACAAGCAGAA;
```

Bold sequences show sites complementary to the above click oligonucleotides 1 and 2. AGAUGGUCCA: Complementary to click oligo-1 (SEQ ID NO:69); GCUGGACAAG: Complementary to click oligo-2 (SEQ ID NO:70).

Example 16: Target-Directed CLOSE Analysis with BCR-ABL Target (Actual Example)

In contrast to the general CLOSE approach, Target-Directed CLOSE focuses on known tumor-specific transcripts. An expressed tumor-specific translocation is a good model for the this directed form of CLOSE technology, where both segments spanning the fusion junction correspond to normal transcripts. In such circumstances, a tumor-specific linear contiguous translocation is by definition restricted to the junction sequence itself. In contrast, folding of the transcripts (which are often very large) has the potential to produce multiple discontinuous sites that are unique to the translocation (shown schematically in FIG. 28). These sites in term may be found by CLOSE analysis, with application as templated assembly targets.

The BCR-ABL translocation transcript has long been known as a marker and driver (via the expression of the fusion BCR-ABL kinase) of chronic myelogeous leukemias, and certain other transformed states. It is strongly expressed in the leukemic cell line K562, which was used in the experimental work for this Example.

Figure 29:
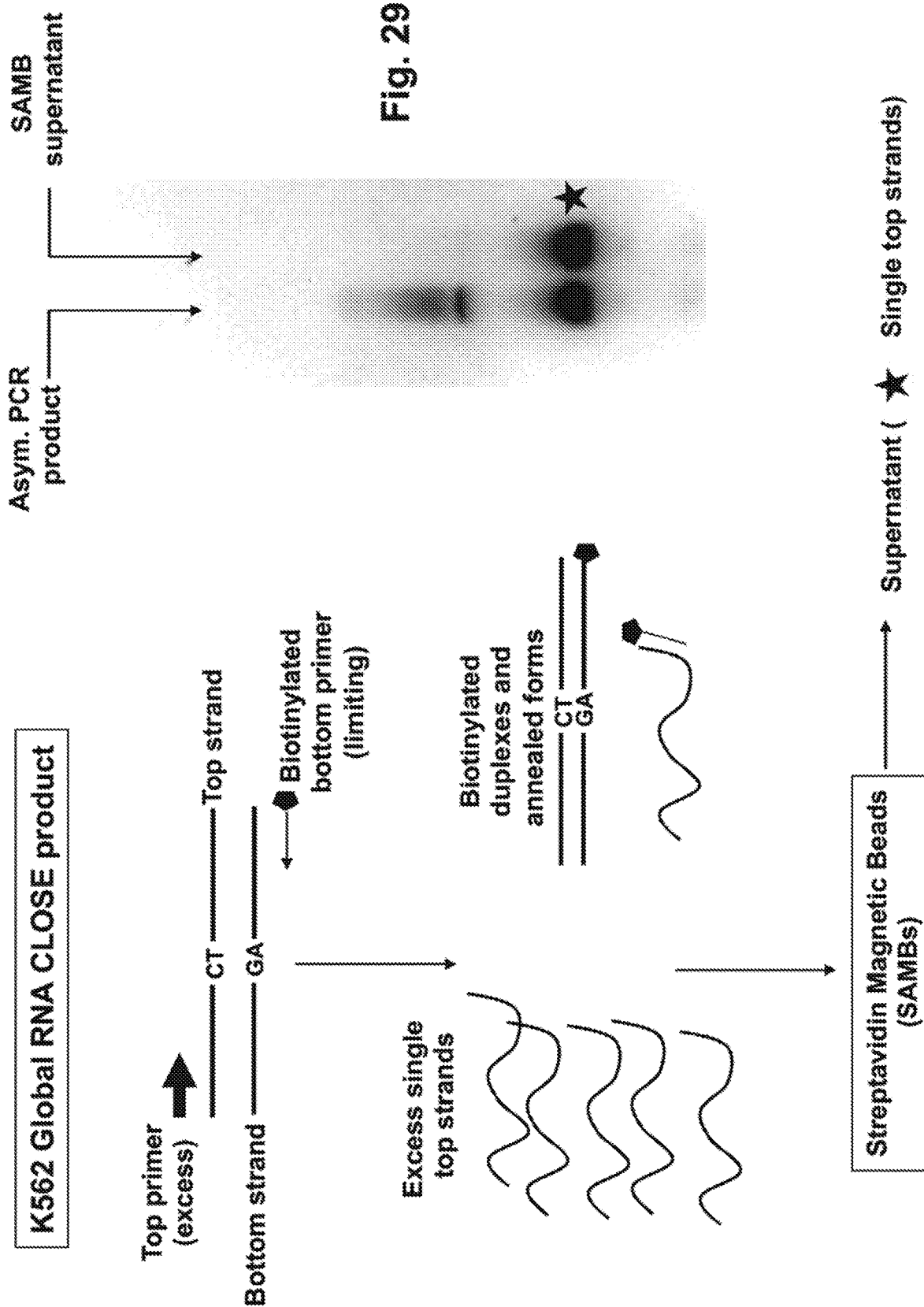
FIG. 29 depicts representative asymmetric PCR combined with biotinylated bottom-strand removal.

Whole cellular RNA from K562 cells was used to perform CLOSE analysis as for Example 1, and following the hybridization, unhybridized CLOSE oligonucleotides were removed according to the protocol described in Example 10. Amplified CLOSE chemically-ligated dimers (templated on global K562 RNA) were then used prepare single-strands corresponding to the same sense as the original CLOSE library oligonucleotides. To accomplish this, asymmetric PCR was performed with the top (desired) strand in a 10-fold excess over the bottom strand, which was also biotinylated. Following 35 cycles of amplification under these conditions, all products bearing the bottom strand (whether complete duplexes or single strands annealed with the bottom primer or partial extension products) were removed on streptavidin magnetic beads. This process and its utility is shown in FIG. 29.

Figure 30:
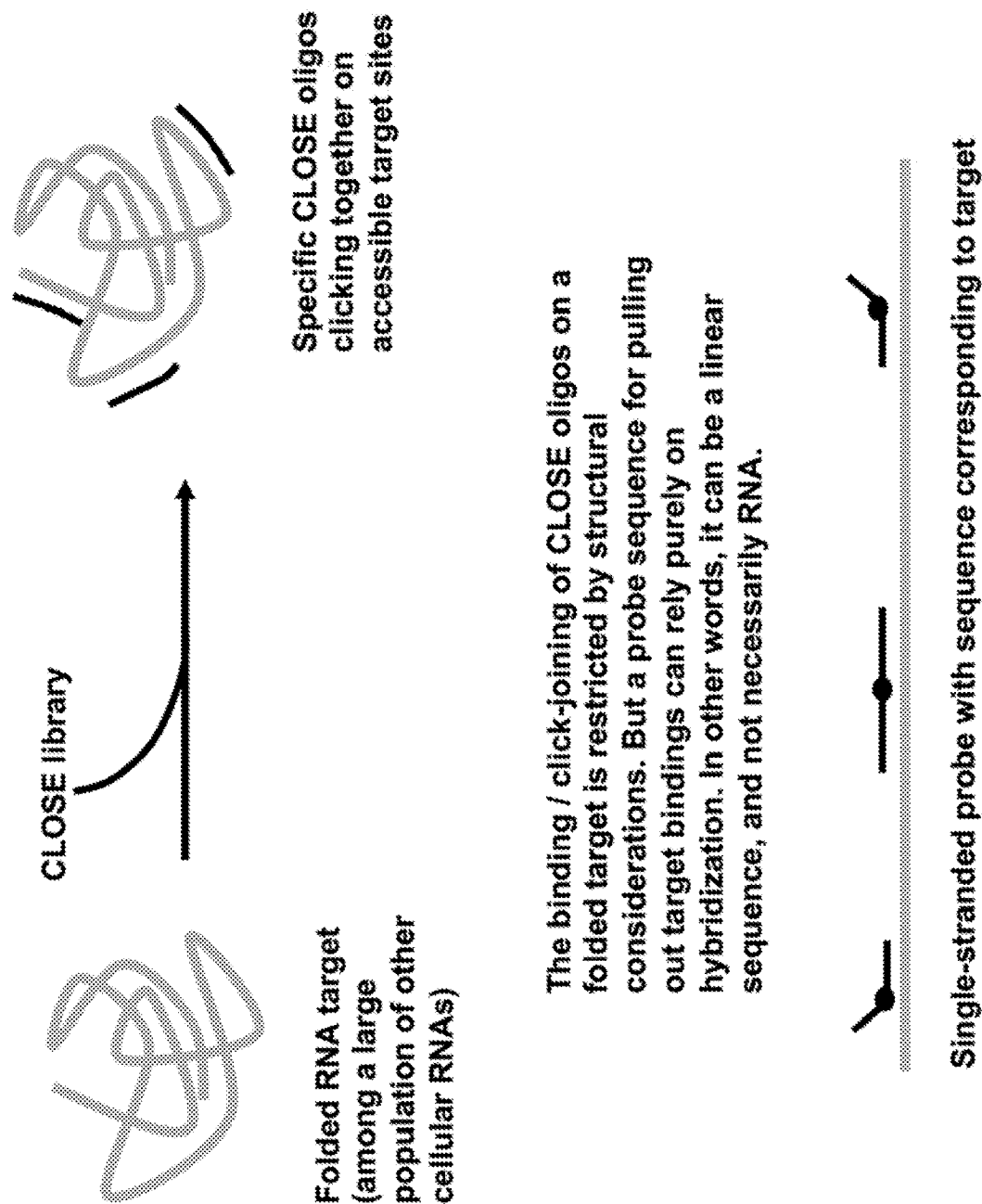
FIG. 30 depicts representative target-directed CLOSE principle; the probe "pulls out" CLOSE members with hybridizing sequences; these may, but not necessarily, include contiguous Left & Right CLOSE segments; discontinuous sites may thus be found by means of the linear hybridization probe.
Figure 31:
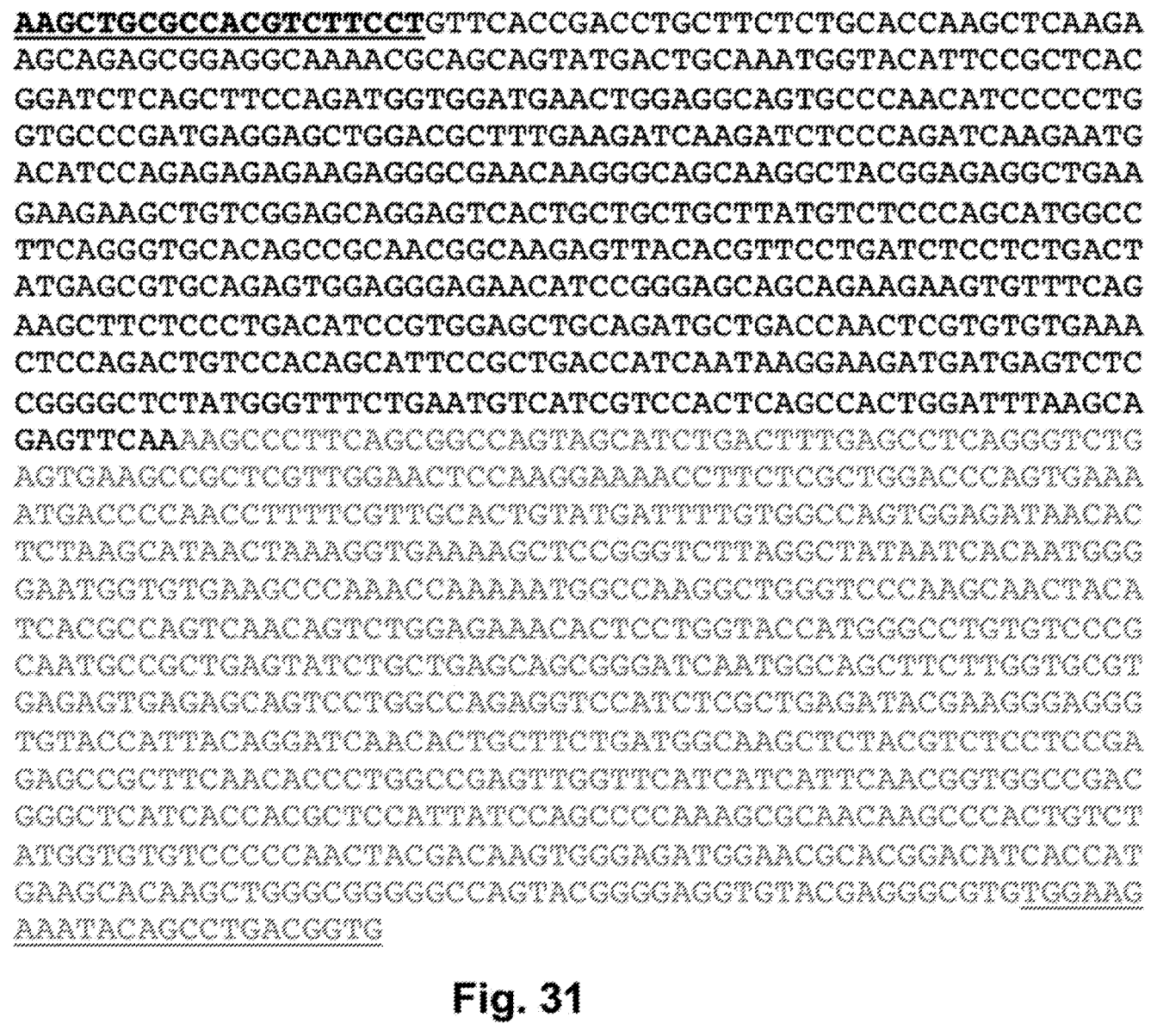

A single-stranded probe in the same sense as the original cellular defined RNA target is then necessary. Although the original CLOSE hybridizations are subject to RNA folding (thus enabling the juxtaposition of sites separated in terms of primary base sequence), it is not necessary that such structures be recapitulated for the Target-Directed CLOSE capture. While the L- and R-CLOSE sites may hybridize to discontinuous sites, all that is required is that either L- or R-regions bind to the capture probe (FIG. 30). It is also not essential that the entire natural transcript sequence be used. In the case of BCR-ABL, it is considered essential to span the transcript breakpoint region, since CLOSE clones binding to both BCR and ABL are necessary to establish full tumor specificity, and with very long probes (within various isoforms, some >8 kb) the probability of selecting BCR- or ABL-restricted CLOSE clones increases. A DNA probe of 1338 bases (1338-probe) spanning the breakpoint was accordingly used (FIG. 31).

To render single-stranded in the correct sense, the 1338-probe was amplified from reverse-transcribed K562 RNA, with the bottom strand biotinylated. After binding the product to streptavidin magnetic beads, the desired top strand was obtained by denaturation with 0.1 M sodium hydroxide/5 mM EDTA (20 seconds), followed by rapid ethanol precipitation with 20 µg glycogen/0.3 M sodium acetate. After pelleting and washing with 70% ethanol, the single-stranded probe was dried and reconstituted in TE buffer.

Figures 32A, 32B:
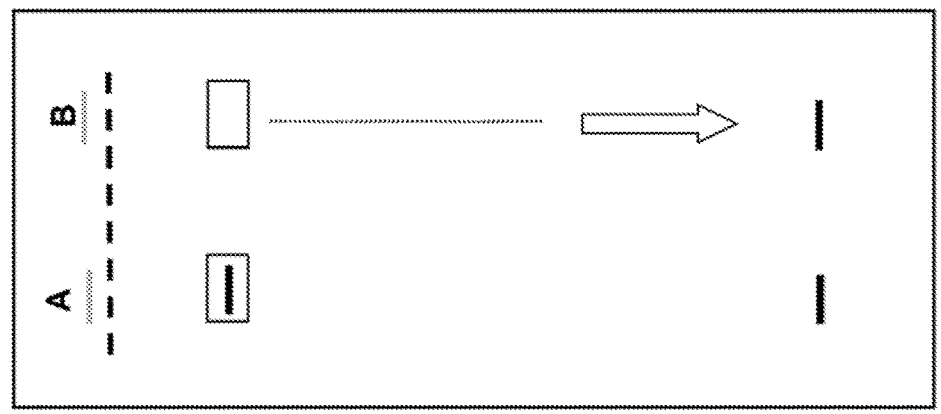
FIGS. 32A and 32B depict, respectively, a representative gel purification method for target-directed CLOSE, and examples of clones obtained with BCR-ABL probe, and examples of candidates for BCR-ABL (gel diagram: lane A: Boxed zone, long single-stranded probe after hybridization with single-stranded CLOSE dimers ligated on target cell whole RNA, thus bearing duplexed CLOSE clones with hybridizing sequences; lower molecular band, free excess CLOSE sequences; lane B: control lacking the long probe molecule; boxed zone, control region of gel of the same mobility as for the probe sequence; lower molecular band, free excess CLOSE sequences); and two examples of cloned CLOSE clones from K562 RNA obtained from 2 cycles of BCR-ABL selection; for each, the first sequence show the actual CLOSE 22-mers with the intervening CT dimers in gray (for dBBc2-01=ATAAGCACCTCTTCAAGGTCTG; SEQ ID NO:40; for dBBc2-08=TGACCTGCTCCTCACCCCTCCT; SEQ ID NO:41); the reverse complement (for dBBc2-01=CAGACCTTGAAGAGGTGCTTAT; SEQ ID NO:42; for dBBc2-08=AGGAGGGGTGAGGAGCAGGTCA; SEQ ID NO:43) to these strands corresponds to the (+) strand for the BCR-ABL probe, or the whole RNA transcript; underlined bold text shows BCR/ABL matches, with the coordinates below (from a compiled 8703-base BCR-ABL full-length transcript; the probe range spanned coordinates 2766-4103); the N value corresponds to the distance between the closest ends of the L- and R-matches.

Single strands for both the 1338-probe and primary K562 RNA-selected CLOSE products were hybridized for 6 hours at 30 C, after which it is necessary to separate the unbound CLOSE fraction. Several options exist in this case. One non-limiting approach is to use agarose gels, including the PippinPrep apparatus (Sage Science). This is shown schematically in FIG. 32A. Separation in such a gel system is facilitated by the large size differential between CLOSE dimeric oligonucleotides and probe sequence. The probe and hybridized CLOSE strands co-migrate; their mobilities may be identified by SYBR-gold staining following by band excision and nucleic acid elution. A mock band with the same mobility as the probe from CLOSE products lacking the hybridization probe may be included as a control (FIG. 32A).

CLOSE products co-migrating with the probe are re-amplified, and used to prepare single-stranded material as above. This enables the Target-Directed CLOSE cycle to proceed with hybridization of first-round CLOSE selected single-stranded product with the same probe, with progressive enrichment of specifically-hybridizing sequences achievable with each cycle run. After at least two cycles, CLOSE products may be cloned and subjected to sequence analysis as above.

Results after two such cycles showed that of 22 sequenced clones, 50% showed matches to both BCR and ABL sequences (the remainder showed matches to either BCR or ABL, but not both). Examples of clones with ≥8/11 matches for both L- and R-sequences are also shown in FIG. 32A. Note that since the probe is a subsection of the entire transcript, and L/R sites may have hybridized to discontinuous segments of the latter, it is not necessarily the case that both will match with the probe sequence. However, by the same token, a necessary validation requirement is that at least one matching CLOSE sequence falls within the boundaries of the probe. Cited examples (FIG. 32B) of candidates fulfilling this condition were discontinuous across the junction sequence, and exhibit the Exo-configurations, as defined above.

Example 17: Identification of Templated Assembly Target Sequences or Structures from a Sample, Via Processing of Unnatural 5'-5' Linkages to Allow Amplification of Chemically-Ligated Pairs (Prophetic Example)

Figure 34A:
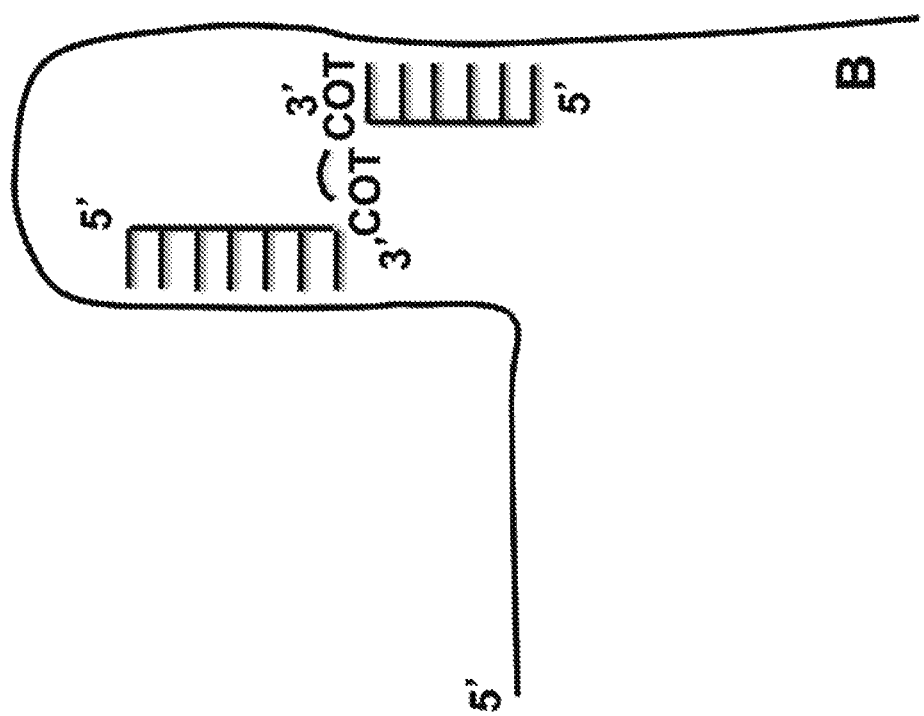
FIGS. 34A and 34B depict, respectively, representative "unnatural" 5'-5' (head-to-head, A) and 3'-3' (tail-to-tail, B) chemical ligation, driven by hybridization-mediated spatial proximity resulting from secondary structures of the target RNA strands; AZ, 5' azide; COT, 5' cyclooctyne.
Figure 34B:
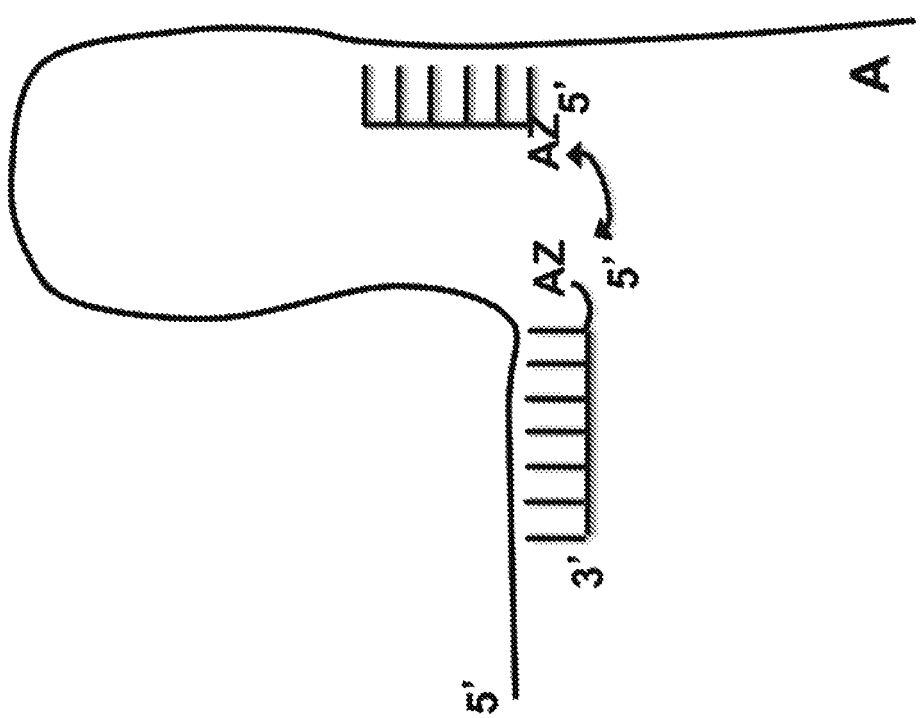
Figure 35:
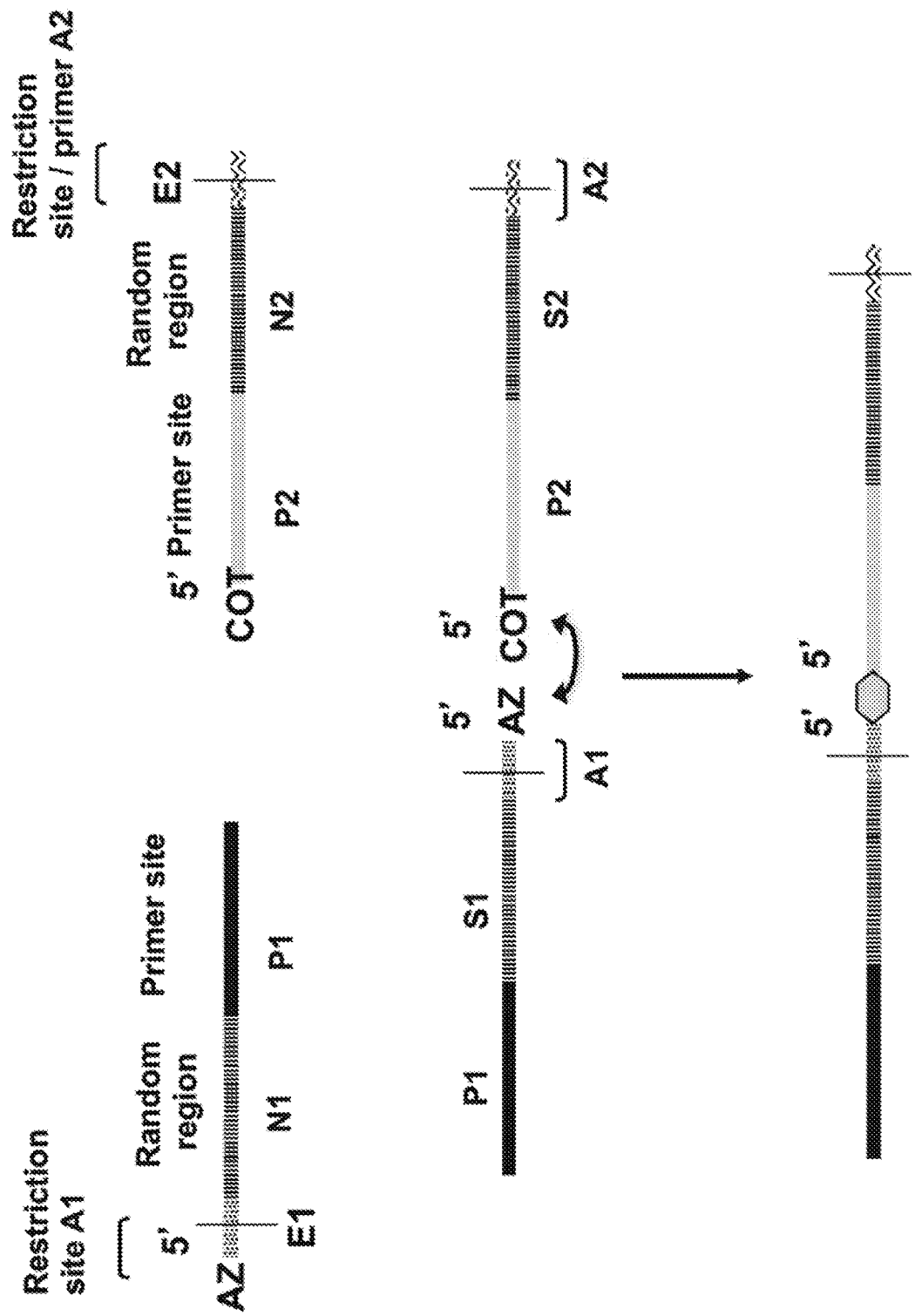
FIG. 35 depicts representative single-stranded oligonucleotides with 5' click groups (azide, AZ and cycloalkyne, COT), initial random regions (N1 and N2), PCR primer sites (P1 and P2), and restriction site/primer regions (A1 and A2); S1 and S2 denote selected subpopulations of decamers from the original random decamer total populations; also shown is a head-to-head chemically-ligated click product resulting through RNA secondary structural spatially proximal hybridization.

Separate populations of oligonucleotides with 5'-azide or 5'-cycloalkyne groups are synthesized, bearing random tracts with specific flanking sequences (depicted in FIGS. 33A and 33B). Folded RNA target structures may promote proximity between either 5'-5' or 3'-3' ends (FIGS. 34A and 34B), enabling click reactivity to produce unnatural strand linkages (shown for 5'-5'; FIG. 35). Flanking sequences constitute priming sites at one end of each oligonucleotide (P1 and P2), and at the other ends, shorter regions ("adapting sites"; A1 and A2; FIG. 35) for enabling enzymatic rearrangements and dimer amplifications. Each adapting site contains a recognition site for a separate restriction enzyme (E1 and E2 of FIG. 35), where the recognition site for each is distinct, but where the overhangs produced after duplex cleavage with each are mutually compatible for ligation. Upon ligation of DNA ends produced by E1 and E2 cleavage, the resulting ligated E1-E2 product is not cleavable by either enzyme. Primer sites are designed to exclude the recognition sequences chosen for E1 and E2.

Figure 36B:
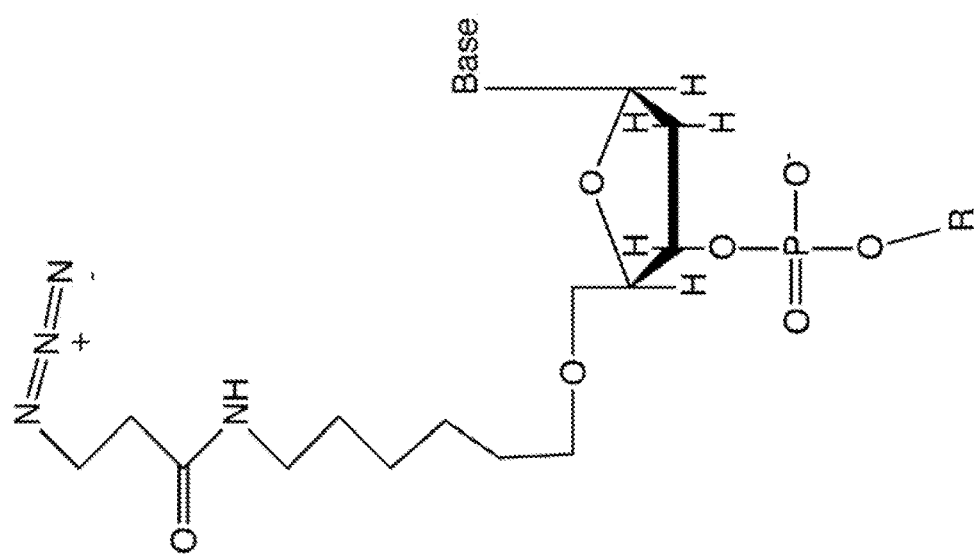
FIGS. 36A and 36B depict possible 5' structures for 5'-5' click reactivity; 36A, 5' hexynyl modification to supply an alkyne group; 36B, 5'-azide group, provided through reaction of a 5'-amino group (with a 6-carbon spacer from the 5'-hydroxyl) with N-hydroxylsuccinimide linked by a 3-carbon spacer to an azide moiety, with subsequent formation on an amide linkage.
Figure 36A:
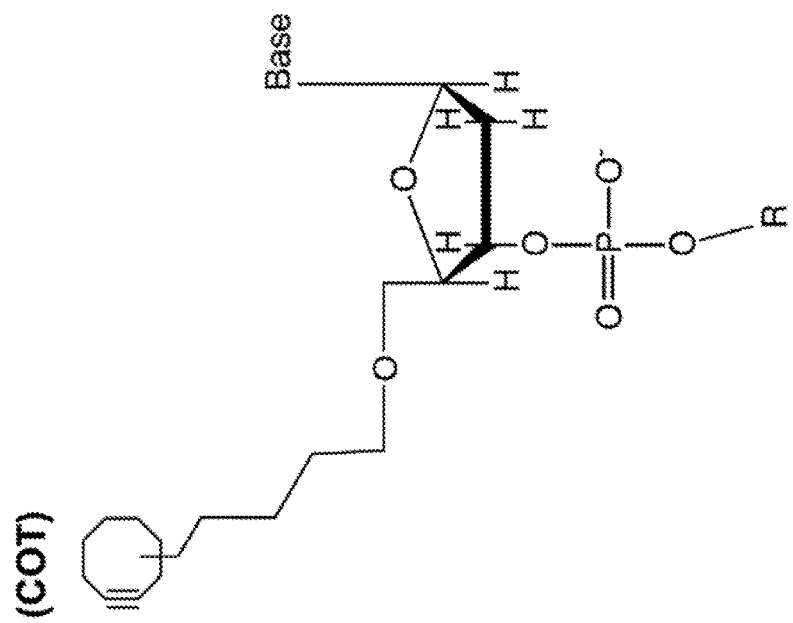

Since no form of 5'-5' chemical ligation is directly readable by any nucleic acid polymerase, the manner of chemical linkage of 5'-azide or 5'-cycloalkyne groups to the above oligonucleotides is not crucial, provided the site of stable chemical bonding between the active azide or alkyne groups to the terminal 5' nucleic acid moiety is bridged by a spacer arm or spacer group of at least 6 carbon atoms (FIGS. 36A and 36B). In some embodiments, the azide group is linked to the nucleic acid 5' end through reaction with N-hydroxysuccinimide, and the alkyne group through an appended hexanyl group.

Separate populations of 5'-azide and 5'-cycloalkyne-modified oligonucleotides of the above configurations are hybridized with whole RNA preparations from cells of interest, or alternatively whole cellular RNA-protein preparations. Hybridizations are performed with each oligonucleotide population in a 50:50 mixture with respect to each other by molarity, in a 10-100 fold excess over RNA quantities present, calculated by assuming an average molecular weight of the cellular RNA of 1500 bases, and with 1-10 micrograms of starting RNA. Hybridizations may be effected for periods of 2-16 hours.

Following hybridization, proximity-induced spontaneous reactions between 5'-azide and strained 5' cycloalkyne moieties, excess oligonucleotide removal, and desalting are performed. Preparations are then treated with RNase A and RNase 1. Resulting preparations include excess unchanged oligonucleotide strands, through inability to react via lack of spatial proximity, and minority desired 5'-5' reacted products.

All resulting oligonucleotide strands are rendered double-stranded. This can be effected by means of primers complementary to Priming Site 1 (P1) and Adapting Site 2 (A2), and extending each with all four deoxynucleotide triphosphates and Klenow fragment of DNA Polymerase I of E. coli, such that each new strand is extended as far as the 5'-5' junctional point (FIG. 37).

When directed cleavage of the extended duplex is effected, it is undesirable for sequences in the random regions to be cleaved through chance occurrence of restriction sites for the enzymes used for cleavage. In view of this, an alternative embodiment uses a deoxynucleotide triphosphate mixture consisting of 5-methyl-deoxycytidine triphosphate, deoxyadenosine triphosphate, deoxyguanosine triphosphate, and thymidine triphosphate, such that duplexes hemimethylated for 5-methylcytosine are generated in the complements to the random regions. Cleavage enzymes that are sensitive to 5-methylcytosine hemimethylation are accordingly used. Also, since hemimethylation should be prevented in adapting regions A1 and A2 where cleavage occurs, a 5'-phosphorylated strand complementary to region A1 is annealed with templates prior to extension reactions. (Adapting region A2 is kept unmethylated through priming from its non-methylated complementary strand; FIG. 38). Since the complementary strand to region A1 should not be displaced during primer extension, a non-strand-displacing polymerase is used, such as T4 DNA polymerase (FIG. 38). The resulting nick between the 5'-phosphorylated complement to region A1 and newly extended strand is sealed with T4 DNA ligase (FIG. 38).

Figure 37:
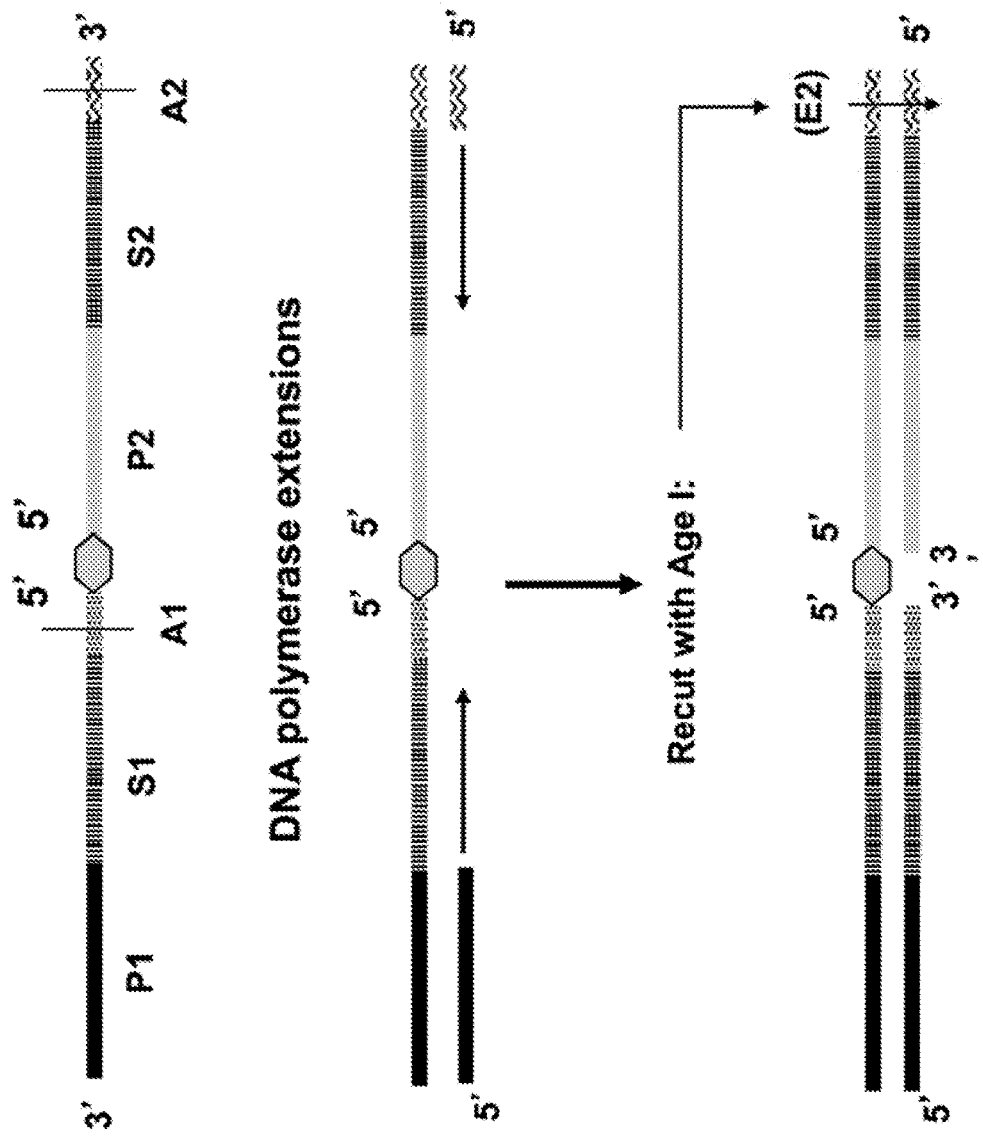
FIG. 37 shows representative production of double-stranded 5'-5' chemical ligation products by polymerase extensions, and subsequent recutting with restriction endonuclease Age I (S1 and S2 denote selected subpopulations of decamers from the original random decamer total populations).

The resulting extended duplexes are then cleaved with an enzyme recognizing restriction site E2 (FIG. 37). In some embodiments, the enzyme E2 specifically corresponds to Age I, recognizing the sequence ACCGGT to produce a four-base overhang 5'-CCGG.

In subsequent steps, the following conditions are imposed: a) Preserve the linkage information between proximally-hybridized sequences during the ligation-mediated rearrangement process that enables amplification; b) Maintain a microenvironment where cleaved sequences are in high concentration relative to each other, thus driving their religation; and c) Sequester unreacted strands into individually-isolated compartments, preventing their ligation-mediated reassortment that would give spurious amplification signals (signals which have not resulted from original click reactions driven by proximate templating). These conditions are achievable by means of in vitro compartmentalization.

Figure 39:
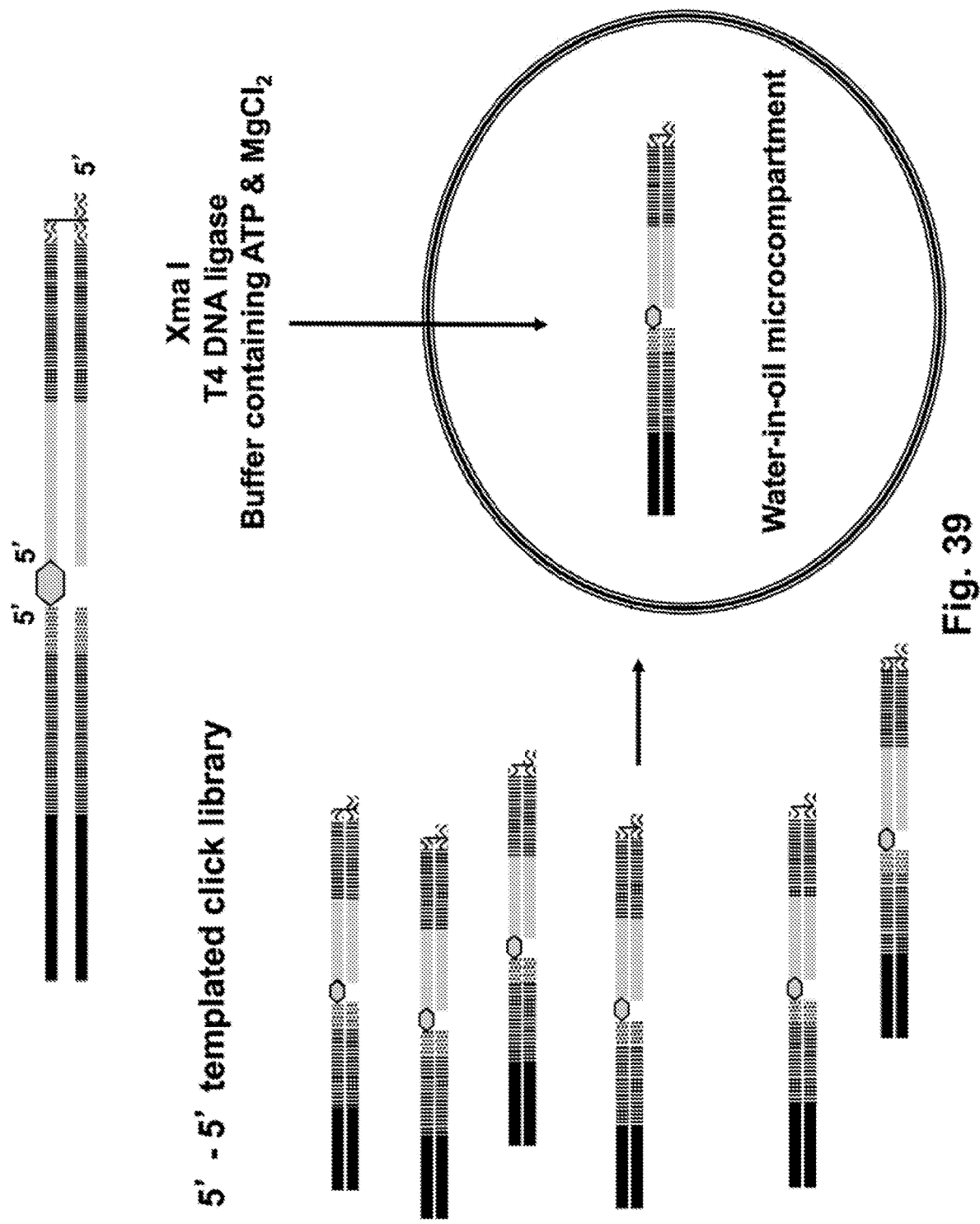
FIG. 39 is a representative diagram showing partitioning of 5'-5' chemically ligated duplex products into in vitro microcompartments; here each fragment has been initially cleaved with restriction enzyme E2 (Age I in the specified embodiment).
Figure 40:
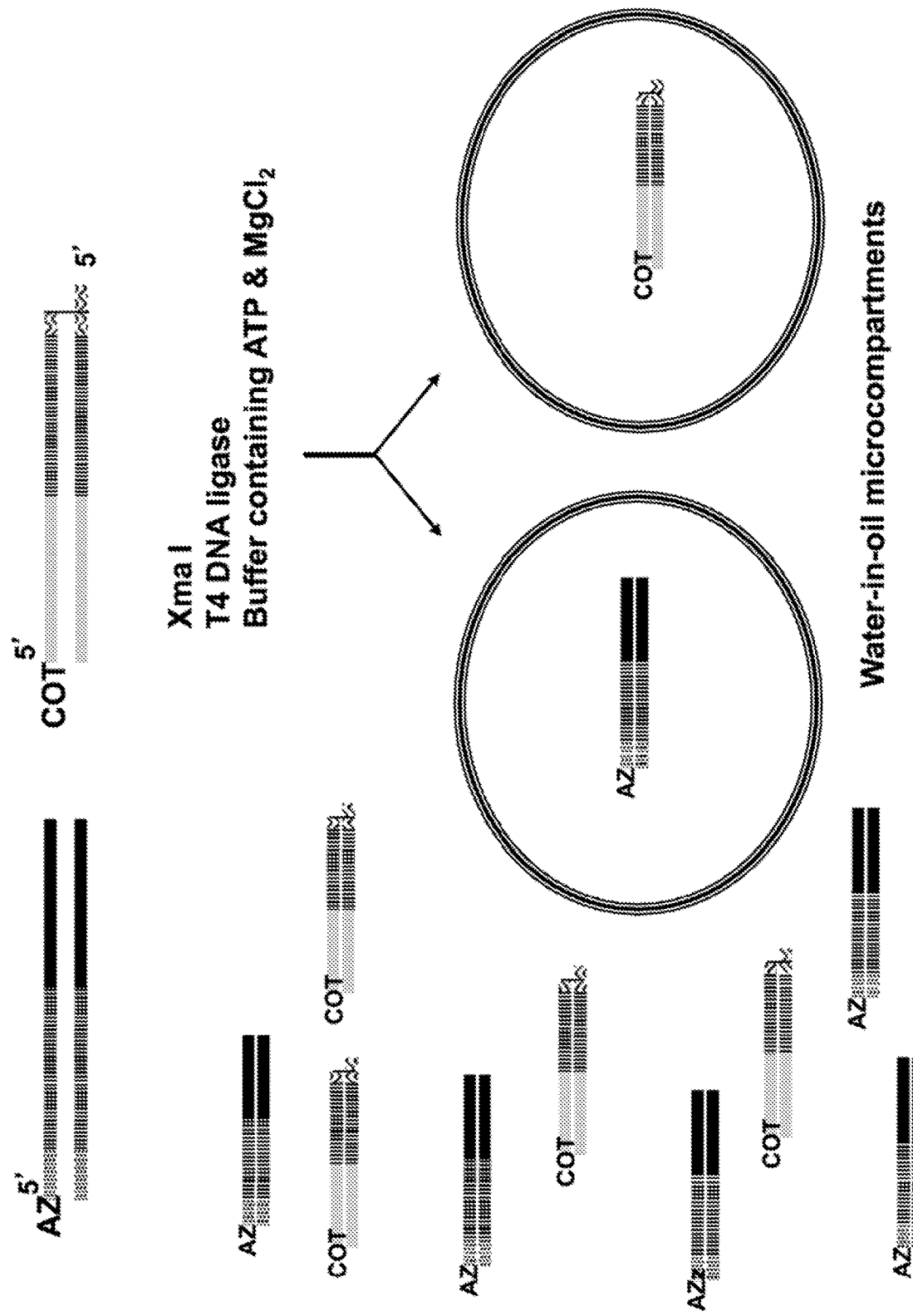
FIG. 40 depicts representative partitioning of unligated 5'-labeled duplex strands into microcompartments; here the 5'-cycloalkyne modified strand has been previously cleaved in the A2 region with restriction enzyme E2 (Age I in the specified embodiment).

In vitro compartmentalization is effected by making water-in-oil microcompartments to encompass individual molecules from the population of unreacted oligonucleotides and 5'-5' click ligated dimers, as rendered double-stranded, and cleaved with enzyme corresponding to site E2. Microcompartments are formed from reagent-grade mineral oil and detergents, with added desired internal components, under conditions of precisely controlled stirring as described by Davidson et al., 2009 (FIG. 39). During the formation of water-in-oil microcompartments, the following components are present in excess, such that each compartment will receive the same buffer composition (50 mM potassium acetate, 20 mM Tris-acetate, pH 7.9/25 C including 1 mM ATP and 10 mM magnesium acetate ions), and at least one copy of the protein T4 DNA ligase and a protein restriction enzyme recognizing site E1. Since the microcompartments are in large excess of the molecular species present, on average only one ligated molecule is incorporated into each compartment (FIG. 39). Likewise, unligated fragments are partitioned into microcompartments as well (FIG. 40). In some embodiments, the E1 restriction enzyme is Xma I, recognizing the sequence CCCGGG to produce a four-base overhang 5'-CCGG compatible with Age I. Upon ligation of overhangs from Age I and Xma I cleavage, the resulting sequence is ACCGGG, cleavable by neither enzyme.

Figure 42:
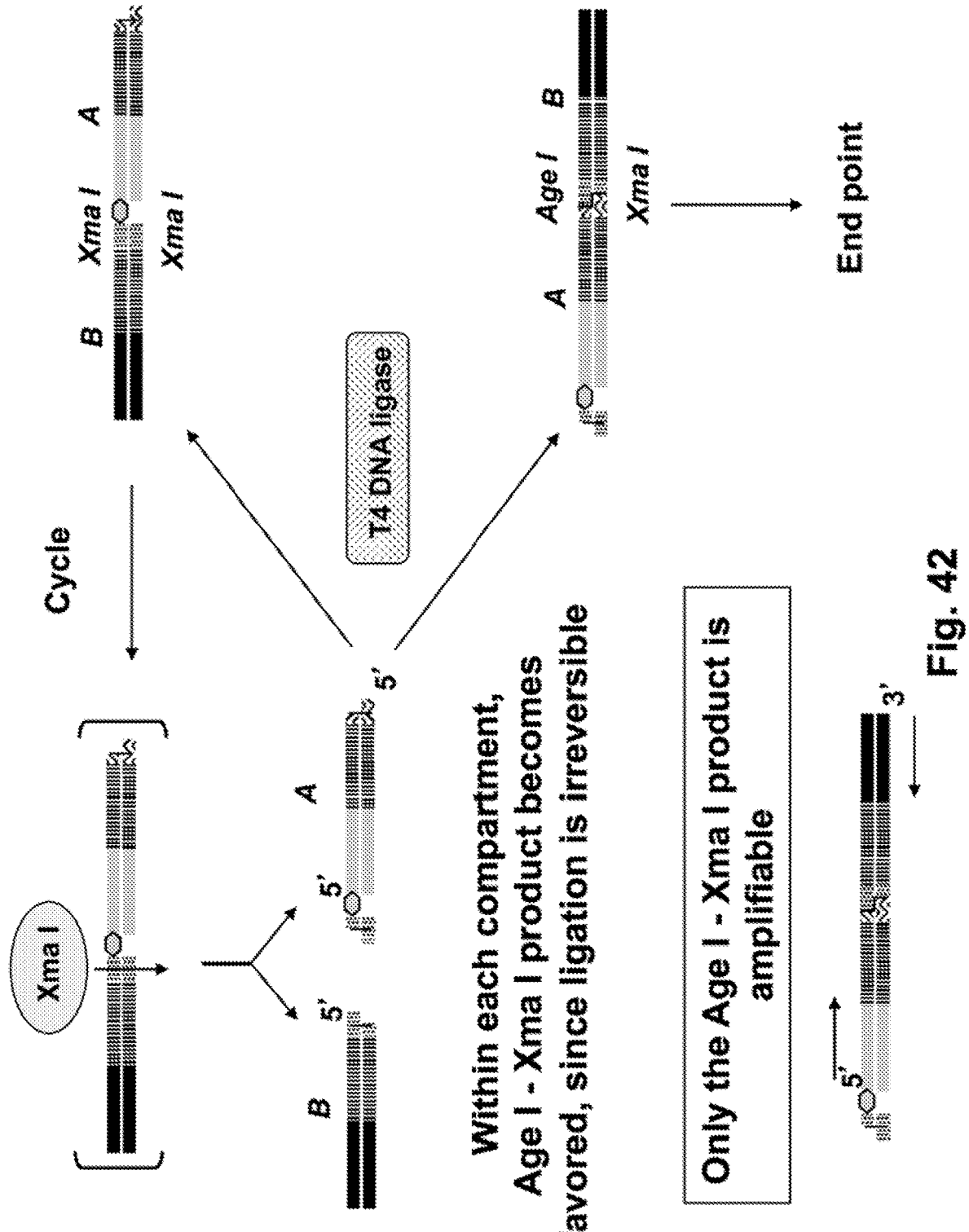
FIG. 42 is a representative illustration of cycling of Xma I cleaved 5'-5' ligation products (in the specified embodiment) in microcompartments, until irreversible and amplifiable rearrangement end-point is reached.

Microcompartments are incubated for 2 hours/37 C, and then 2 hours/20 C. Within each compartment bearing an individual 5'-5' chemically ligated dimer, cleavage with Xma I is followed by subsequent ligation with either another Xma I overhang (the reverse of the original cleavage) or ligation with the single Age I end present in the same compartment (FIG. 41). Xma I-Xma I religations are recleavable by Xma I, but Age I-Xma I ligations are not, and thus inevitably become the predominant species in each microcompartment (FIG. 42). Compartments whose oligonucleotides were not initially chemically ligated into dimers (FIG. 39) cannot participate in this re-ligation/re-cutting cycle.

Microcompartments are then disrupted by treatment with diethyl ether. Specific oligonucleotide pairs from the original random populations, selected by spatial proximity on RNA templates, are amplifiable by virtue of the rearrangement process described above.

Example 18: Identification of Templated Assembly Target Sequences or Structures from a Sample, Via Processing of Unnatural 3'-3' Linkages to Allow Amplification of Chemically-Ligated Pairs (Prophetic Example)

Figure 43:
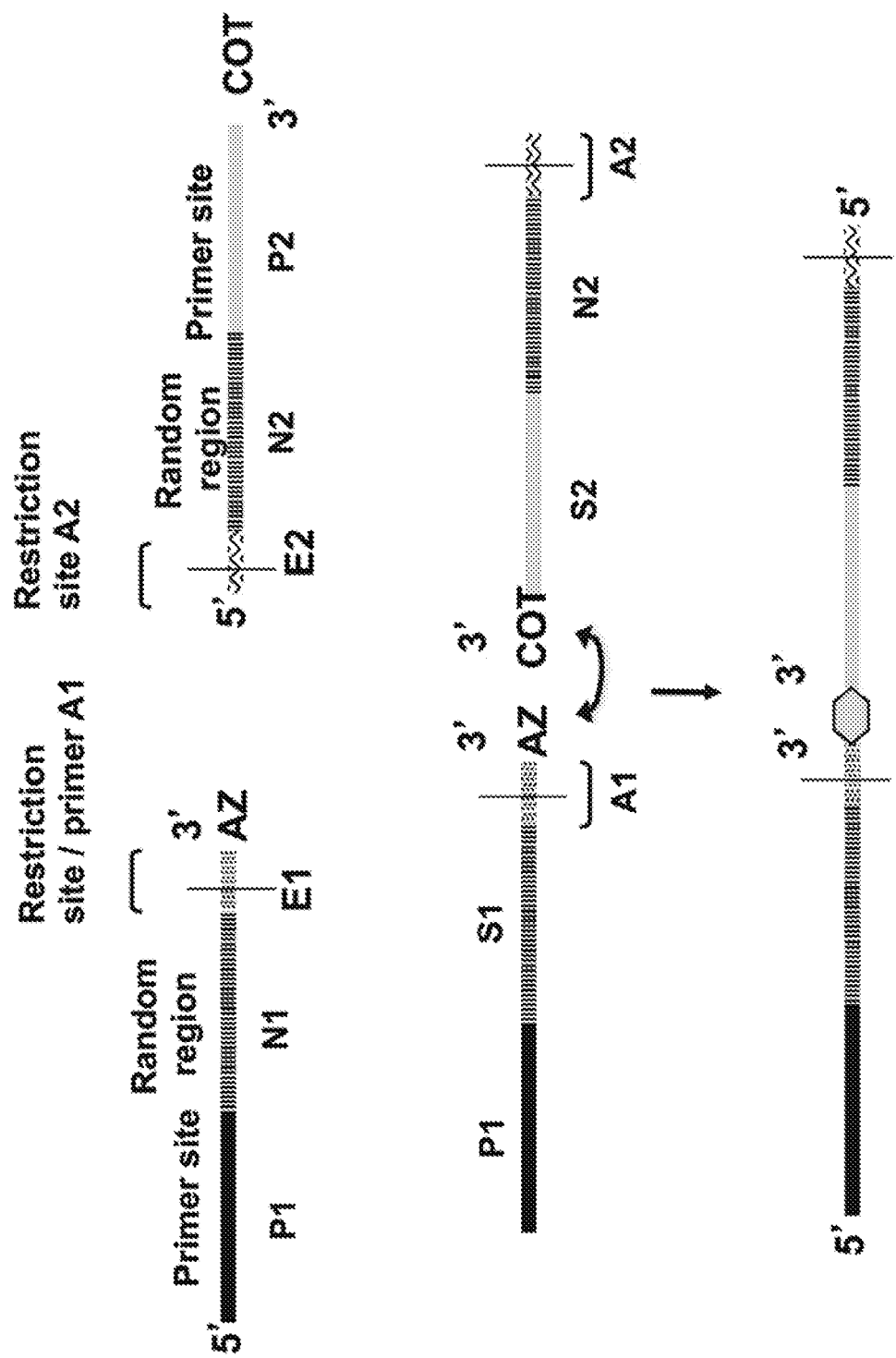
FIG. 43 is a representative diagram of single-stranded oligonucleotides with 3' click groups (azide and alkyne), initial random regions (N1 and N2), PCR primer sites (P1 and P2), and restriction site/primer regions (A1 and A2); S1 and S2 denote selected subpopulations of decamers from the original random decamer total populations; also shown is a tail-to-tail chemically-ligated click product resulting through RNA secondary structural spatially proximal hybridization.

Separate populations of oligonucleotides with 3'-azide or 3'-cycloalkyne groups are synthesized, bearing random tracts with specific flanking sequences (depicted in FIG. 43).

Figure 44B:
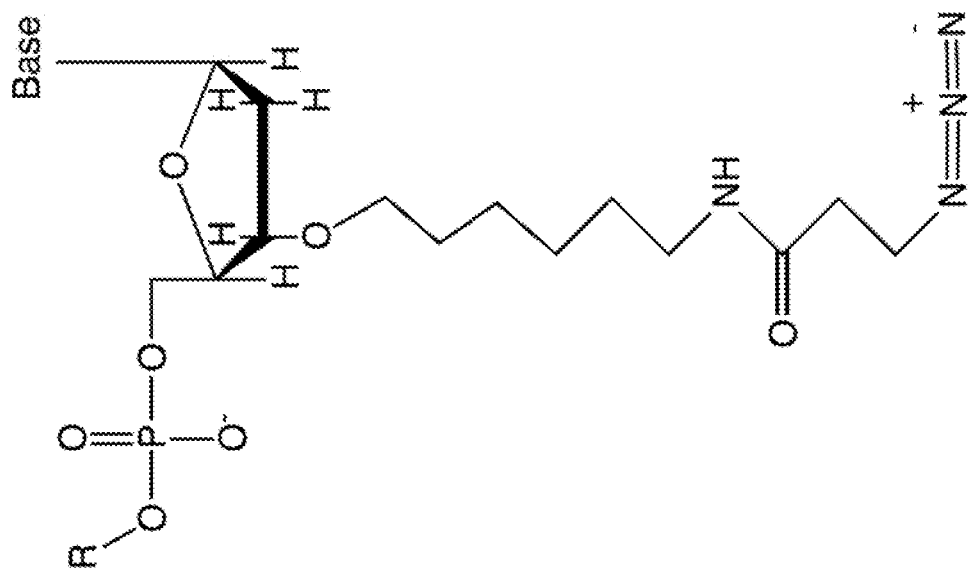
FIGS. 44A and 44B depict representative possible 3' structures for 3'-3' click reactivity; 44A) 3' modification to supply a cycloalkyne group; 44B) 3'-azide group, provided through reaction of a 3'-amino group (with a 6-carbon spacer from the 3'-hydroxyl) with N-hydroxylsuccinimide linked by a 3-carbon spacer to an azide moiety, with subsequent formation on an amide linkage.
Figure 44A:
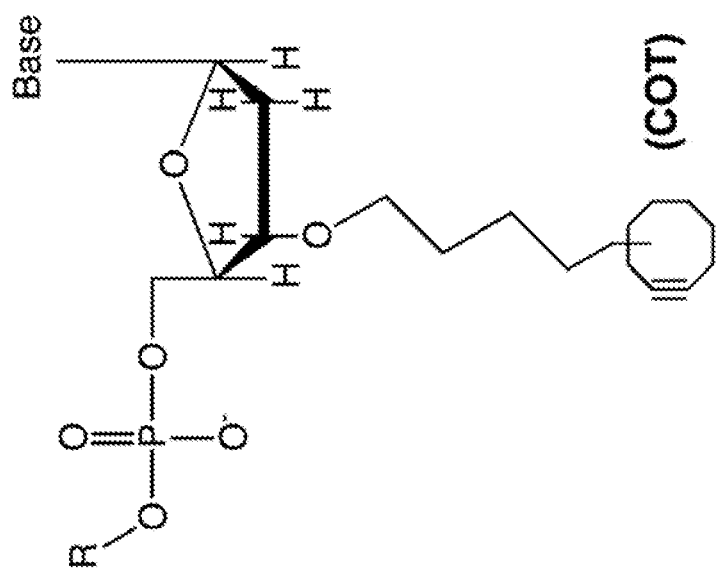

Since no form of 3'-3' chemical ligation is directly readable by any nucleic acid polymerase, the manner of chemical linkage of 3'-azide or 3'-cycloalkyne groups to the above oligonucleotides is not crucial, provided the site of stable chemical bonding between the active azide or cycloalkyne groups to the terminal 3' nucleic acid moiety is bridged by a spacer arm or spacer group of at least 6 carbon atoms (FIGS. 44A and 44B). In some embodiments, the azide group is linked to the nucleic acid 3' end through reaction with N-hydroxysuccinimide, and the cycloalkyne group through an appended hexanyl group.

Separate populations of 3'-azide and 3'-cycloalkyne-modified oligonucleotides of the above configurations are hybridized with whole RNA preparations from cells of interest, or alternatively whole cellular RNA-protein preparations. Hybridizations are performed with each oligonucleotide population in a 50:50 mixture with respect to each other by molarity, in a 10-100 fold excess over RNA quantities present, calculated by assuming an average molecular weight of the cellular RNA of 1500 bases, and with 1-10 micrograms of starting RNA. Hybridizations may be effected for periods of 2-16 hours.

Following hybridization, proximity-induced spontaneous reactions between 5'-azide and strained 5' cycloalkyne moieties, excess oligonucleotide removal, and desalting are performed. Resulting preparations include excess unchanged oligonucleotide strands, through inability to react via lack of spatial proximity, and minority desired 3'-3' reacted products.

Figure 45:
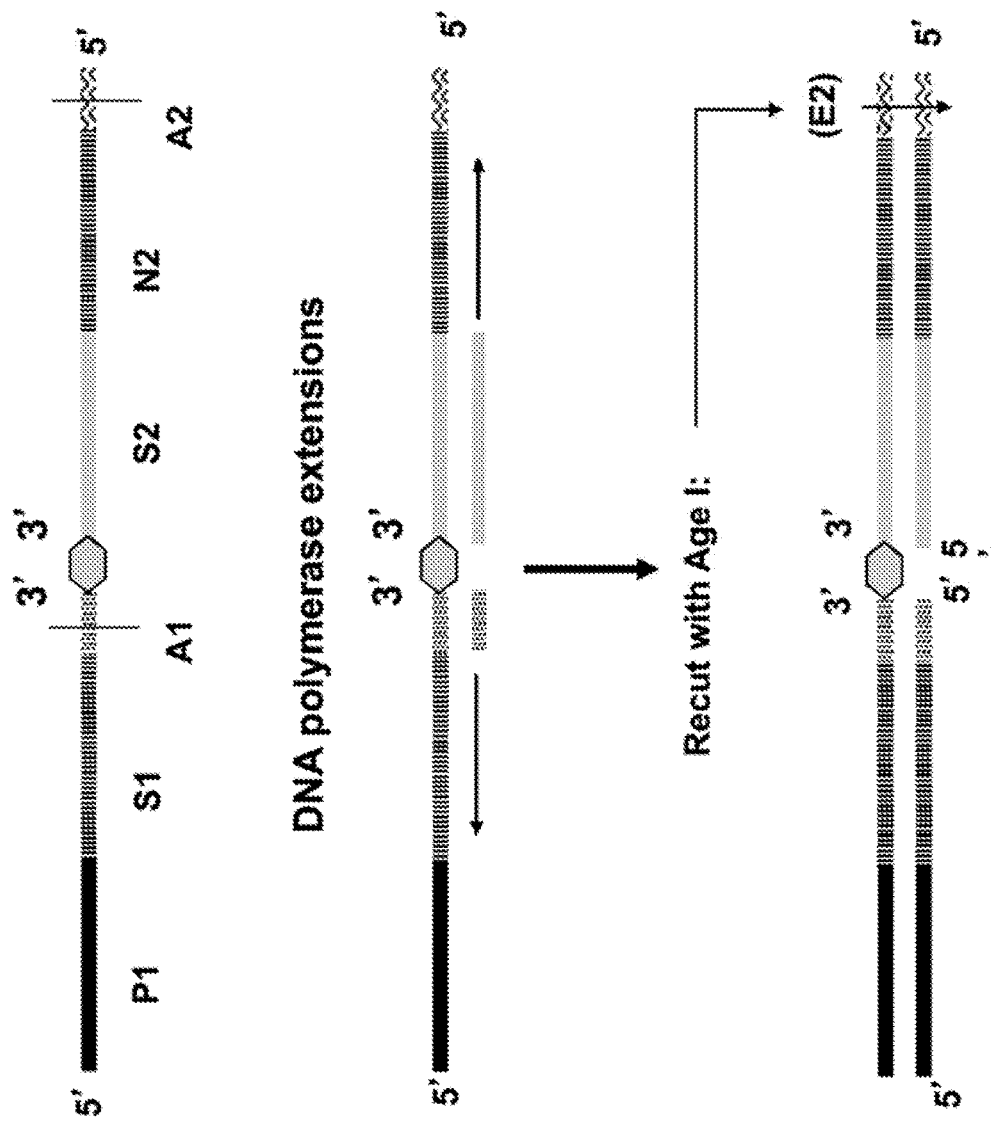
FIG. 45 illustrates representative production of double-stranded 3'-3' chemical ligation products by polymerase extensions, and subsequent recutting with restriction endonuclease Age I; S1 and S2 denote selected subpopulations of decamers from the original random decamer total populations.

All resulting oligonucleotide strands are rendered double stranded. This can be effected by means of primers complementary to Priming Site 2 (P2) and Adapting Site 1 (A1), and extending each with all four deoxynucleotide triphosphates and Klenow fragment of DNA Polymerase I of E. coli, such that each new strand is extended as far as the 3'-3' junctional point (FIG. 45).

When directed cleavage of the extended duplex is effected, it is undesirable for sequences in the random regions to be cleaved through chance occurrence of restriction sites for the enzymes used for cleavage. In view of this, an alternative embodiment uses a deoxynucleotide triphosphate mixture consisting of 5-methyl-deoxycytidine triphosphate, deoxyadenosine triphosphate, deoxyguanosine triphosphate, and thymidine triphosphate, such that duplexes hemimethylated for 5-methylcytosine are generated in the complements to the random regions. In some embodiments, cleavage enzymes that are sensitive to 5-methylcytosine hemimethylation are accordingly used. Also, since hemimethylation should be prevented in adapting regions A1 and A2 where cleavage occurs, a 5'-phosphorylated strand complementary to region A2 is annealed with templates prior to extension reactions. (Adapting region A1 is kept unmethylated through priming from its non-methylated complementary strand; FIG. 16). Since the complementary strand to region A1 should not be displaced during primer extension, a non-strand-displacing polymerase should be used, such as T4 DNA polymerase (FIG. 16). The resulting nick between the 5'-phosphorylated complement to region A1 and newly extended strand is sealed with T4 DNA ligase (FIG. 46).

The resulting extended duplexes are then cleaved with an enzyme recognizing restriction site E2. In some embodiments, the enzyme E2 specifically corresponds to Age I, recognizing the sequence ACCGGT to produce a four-base overhang 5'-CCGG.

In subsequent steps, the following conditions are imposed: a) Preserve the linkage information between proximally-hybridized sequences during the ligation-mediated rearrangement process that enables amplification; b) Maintain a microenvironment where cleaved sequences are in high concentration relative to each other, thus driving their religation; and c) Sequester unreacted strands into individually-isolated compartments, preventing their ligation-mediated reassortment that would give spurious amplification signals (signals which have not resulted from original click reactions driven by proximate templating). These conditions are achievable by means of in vitro compartmentalization.

Figure 47:
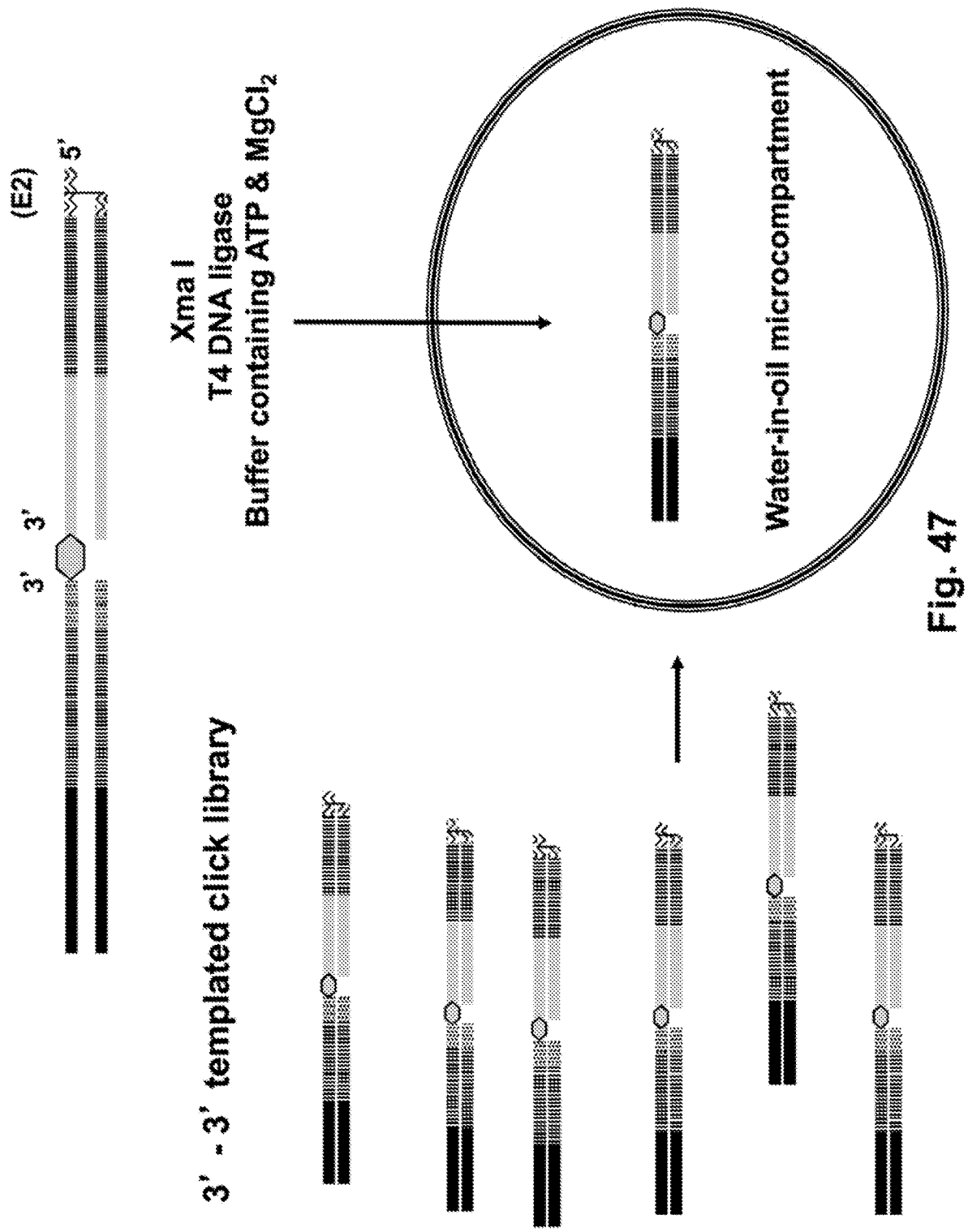
FIG. 47 is a representative illustration of partitioning of 3'-3' chemically ligated duplex products into in vitro microcompartments; here each fragment has been initially cleaved with restriction enzyme E2 (Age I in the specified embodiment).
Figure 48:
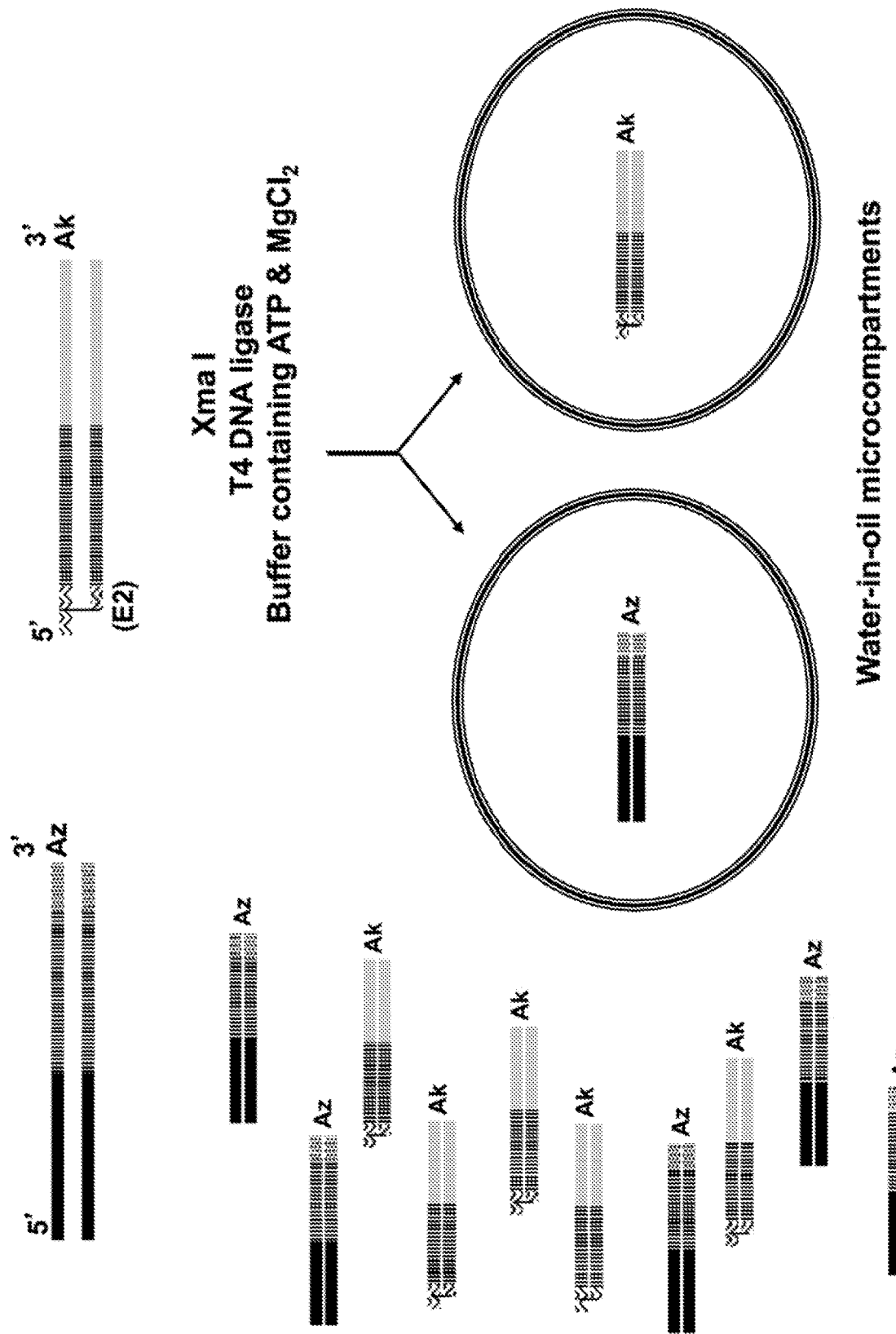
FIG. 48 diagrams representative partitioning of unligated 3'-click-labeled duplex strands into microcompartments; here the 3'-alkyne modified strand has been previously cleaved in the A2 region with restriction enzyme E2 (Age I in the specified embodiment).

In vitro compartmentalization is effected by making water-in-oil microcompartments to encompass individual molecules from the population of unreacted oligonucleotides and 3'-3' click ligated dimers, as rendered double-stranded, and cleaved with enzyme corresponding to site E2. Microcompartments are formed from reagent-grade mineral oil and detergents, with added desired internal components, under conditions of precisely controlled stirring as described by Davidson et al. 2009 (FIG. 47). During the formation of water-in-oil microcompartments, the following components are present in excess, such that each compartment will receive the same buffer composition (50 mM potassium acetate, 20 mM Tris-acetate, pH 7.9/25 C including 1 mM ATP and 10 mM magnesium acetate ions), and at least one copy of the protein T4 DNA ligase and a protein restriction enzyme recognizing site E1. Since the microcompartments are in large excess of the molecular species present, on average only one ligated molecule is incorporated into each compartment (FIG. 47). Likewise, unligated fragments are partitioned into microcompartments as well (FIG. 48). In this non-limiting example, the E1 restriction enzyme is Xma I, recognizing the sequence CCCGGG to produce a four-base overhang 5'-CCGG compatible with Age I. Upon ligation of overhangs from Age I and Xma I cleavage, the resulting sequence is ACCGGG, cleavable by neither enzyme.

Figure 49:
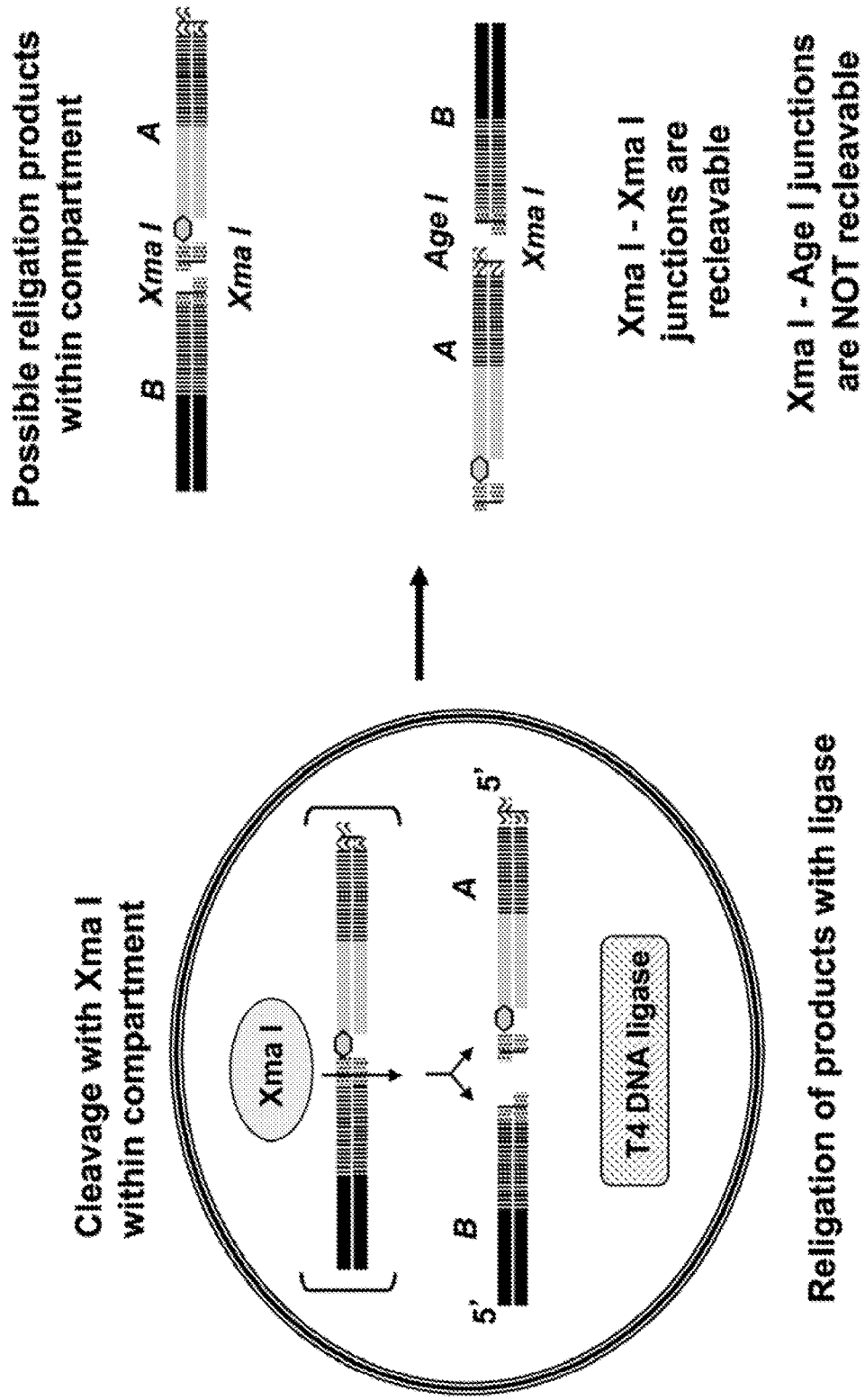
FIG. 49 is a representative diagram of Xma I cutting (in the specified embodiment) and re-ligation of 3'-3' linkages within microcompartments.
Figure 50:
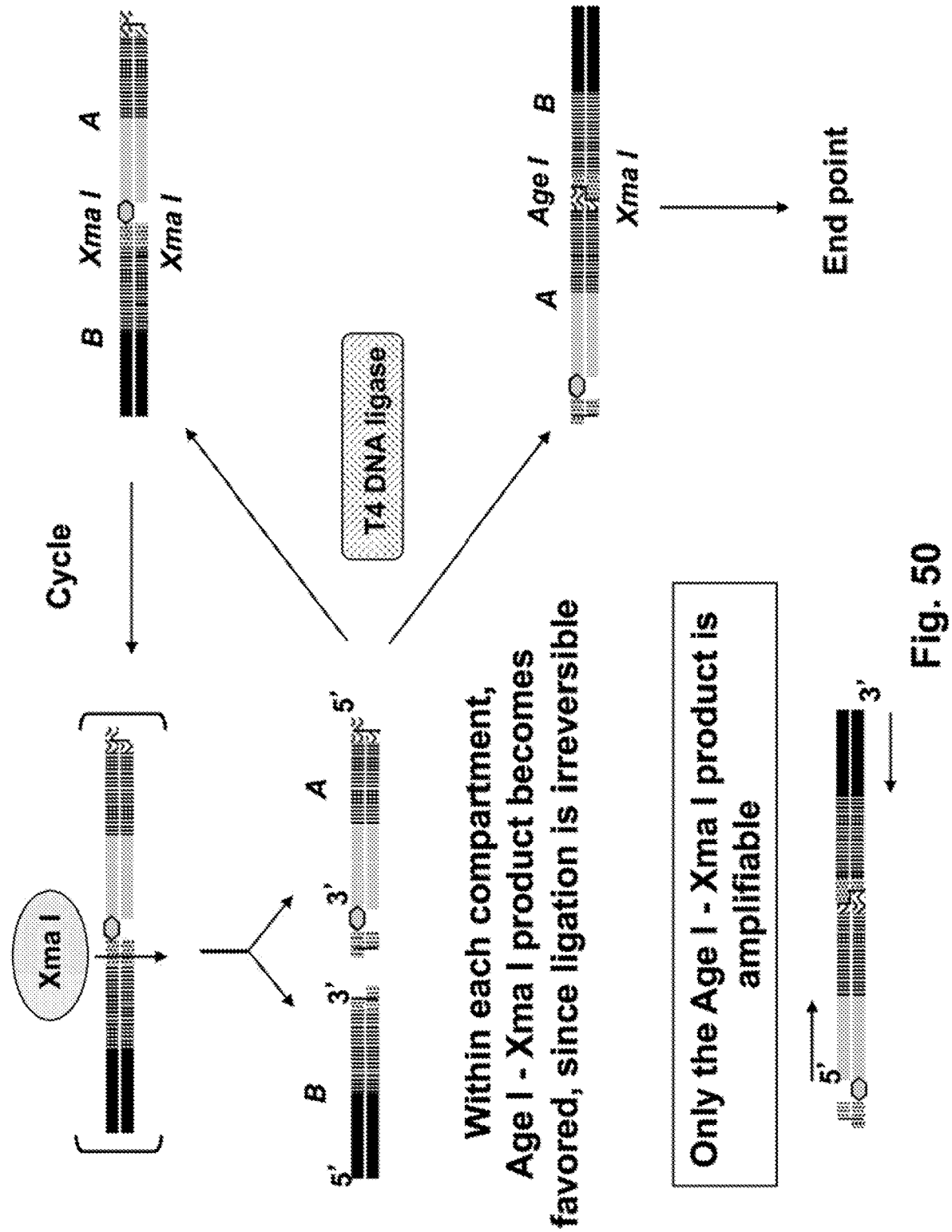
FIG. 50 shows representative cycling of Xma I cleaved (in the specified embodiment) 3'-3' ligation products in microcompartments, until irreversible and amplifiable rearrangement end-point is reached.

Microcompartments are incubated for 2 hours/37 C, and then 2 hours/20 C. Within each compartment bearing an individual 3'-3' chemically ligated dimer, cleavage with Xma I is followed by subsequent ligation with either another Xma I overhang (the reverse of the original cleavage) or ligation with the single Age I end present in the same compartment (FIG. 49). Xma I-Xma I religations are recleavable by Xma I, but Age I-Xma I ligations are not, and thus inevitably become the predominant species in each microcompartment (FIG. 50). Compartments whose oligonucleotides were not initially chemically ligated into dimers (FIG. 48) cannot participate in this religation/recutting cycle.

Microcompartments are then disrupted by treatment with diethyl ether. Specific oligonucleotide pairs from the original random populations, selected by spatial proximity on RNA templates, are amplifiable by virtue of the rearrangement process described above.

Example 19: Identification of Templated Assembly Target Sequences or Structures from a Sample, Via Processing of 5'-3' Linkages where the Chemical Ligation Between Pairs of Oligonucleotides is not Compatible with Direct Polymerase Read-Through (Prophetic Example)

In some cases, it may be useful or even essential to screen for 5'-3' proximal linkages with click groups that cannot be directly read-through by polymerases. At least two major factors are operative in this context: 1) If pre-activated click reactants (as with strained cyclo-octynes, for example) are used, the need for Cu(I) catalysis is circumvented; and 2) Pre-activated click reactants can be used for screening within living cells, which is difficult or impossible when the requirement for Cu(I) catalysis exists.

Figure 51:
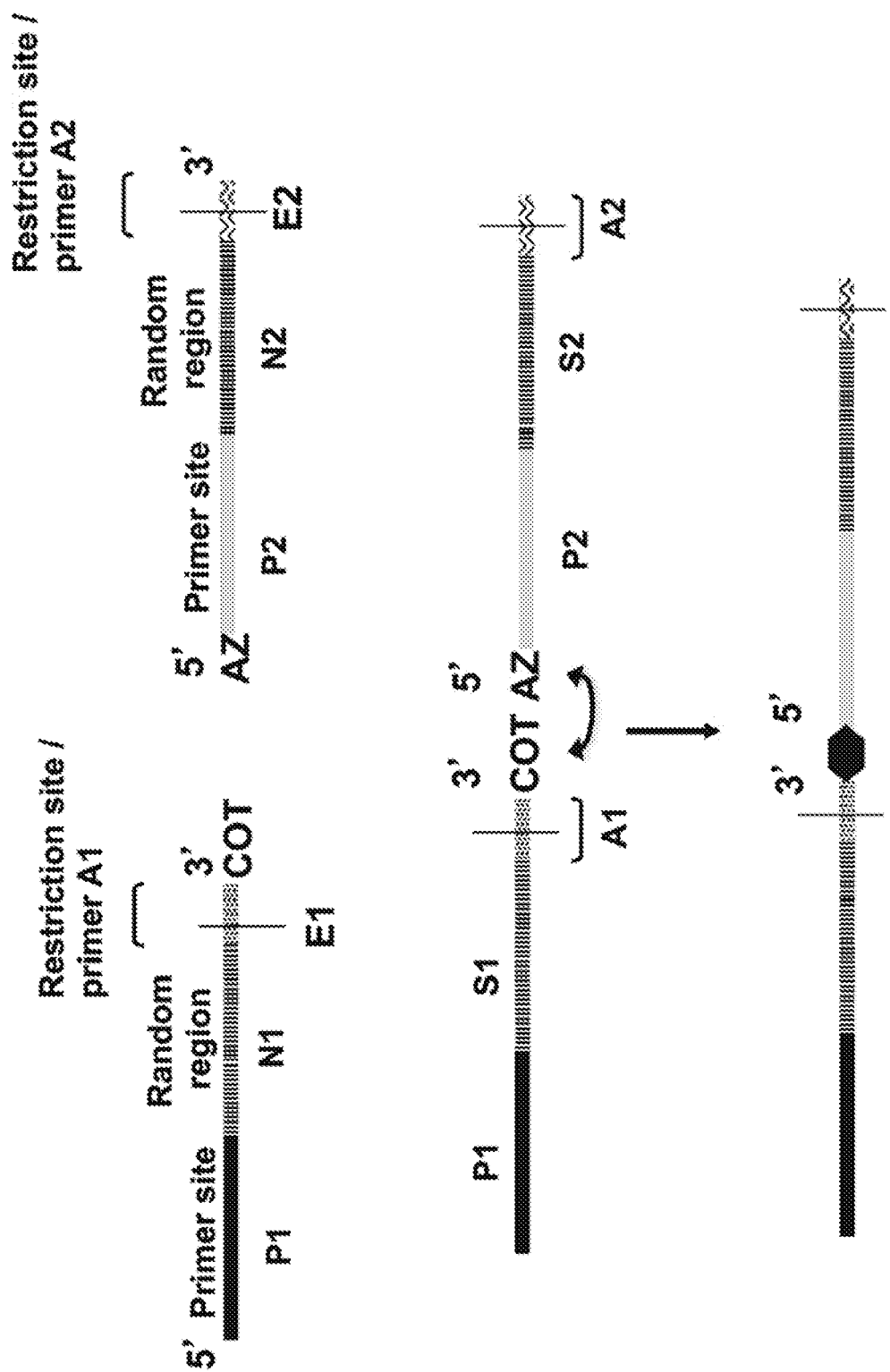
FIG. 51 illustrates representative single-stranded oligonucleotides with non-polymerase readable 5'- and 3'-click groups (cycloalkyne and azide respectively), initial random regions (N1 and N2), PCR primer sites (P1 and P2), and restriction site/primer regions (A1 and A2); S1 and S2 denote selected subpopulations of decamers from the original random decamer total populations; also shown is a head-to-tail chemically-ligated (non-amplifiable directly) click product resulting through RNA secondary structural spatially proximal hybridization.
Figure 52B:
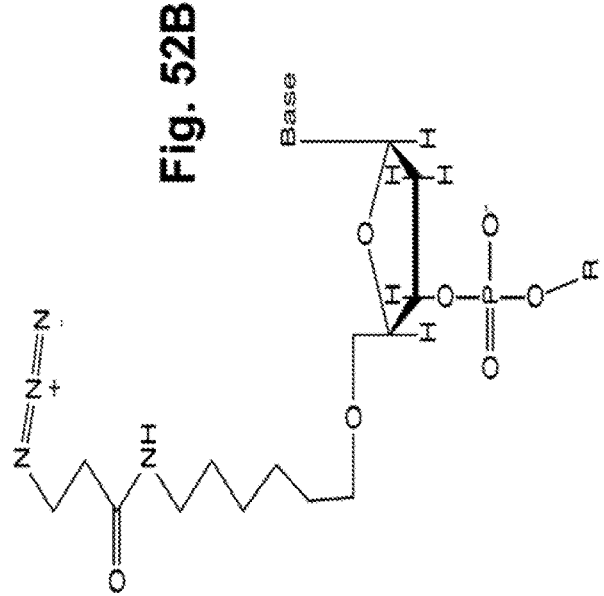
FIGS. 52A, 52B, 52C, and 52D are representative diagrams showing possible 5' and 3' structures for 5'-3' click reactivity, where no requirement exists for polymerase read-through; 52A) representative 5'-cycloalkyne and 5'-azide modifications; where polymerase read-through is not required, a pair of 5' and 3'-modified click-modified oligonucleotides can bear either cycloalkyne-azide combination of the above representative modifications: for example, a pair of oligonucleotides bearing the 5' and 3' structures represented by FIG. 52A/C; 52B) representative 5'-cycloalkyne and 5'-azide modifications; where polymerase read-through is not required, a pair of 5' and 3'-modified click-modified oligonucleotides can bear either cycloalkyne-azide combination of the above representative modifications: for example, a pair of oligonucleotides bearing the 5' and 3' structures represented by FIG. 52B/D; 52C) representative 3'-cycloalkyne and 3'-azide modifications; where polymerase read-through is not required, a pair of 5' and 3'-modified click-modified oligonucleotides can bear either cycloalkyne-azide combination of the above representative modifications: for example, a pair of oligonucleotides bearing the 5' and 3' structures represented by FIGS. 52A/C; and 52D) representative 3'-cycloalkyne and 3'-azide modifications; where polymerase read-through is not required, a pair of 5' and 3'-modified click-modified oligonucleotides can bear either cycloalkyne-azide combination of the above representative modifications: for example, a pair of oligonucleotides bearing the 5' and 3' structures represented by FIG. 52B/D.
Figure 52D:
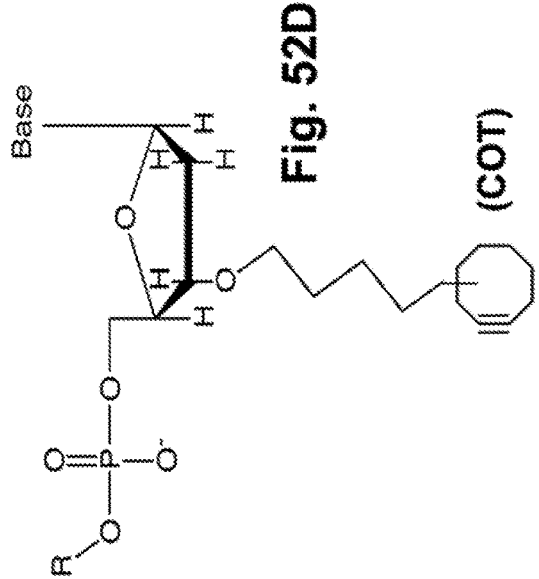
Figure 52A:
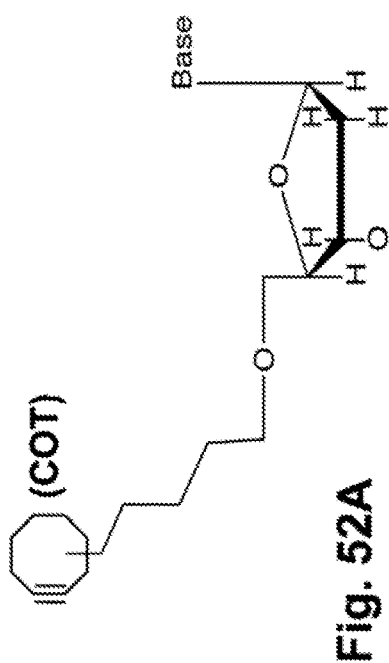
Figure 52C:
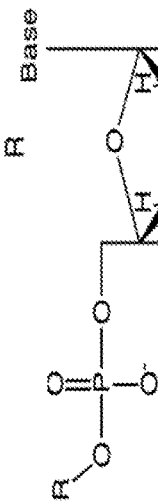

Separate populations of oligonucleotides with 5'- and 3'-click groups are synthesized. Either (5'-cycloalkyne plus 3'-azide), or (5'-azide plus 3'-cycloalkyne) sets of populations can be used, since there is no requirement for polymerase read-through. All oligonucleotides bear random tracts with specific flanking sequences (depicted in FIG. 51). Flanking sequences constitute priming sites at one end of each oligonucleotide (P1 and P2), and at the other ends, shorter regions ("adapting sites"; A1 and A2) for enabling enzymatic rearrangements and dimer amplifications. Each adapting site contains a recognition site for a separate restriction enzyme (E1 and E2 of FIG. 51), where the recognition site for each is distinct, but where the overhangs produced after duplex cleavage with each are mutually compatible for ligation. Upon ligation of DNA ends produced by E1 and E2 cleavage, the resulting ligated E1-E2 product is not cleavable by either enzyme. Primer sites are designed to exclude the recognition sequences chosen for E1 and E2.

Since in Example 4, there is no requirement for 5'-3' chemical ligations to be directly readable by any nucleic acid polymerase, the manner of chemical linkage of azide or cycloalkyne groups to the above oligonucleotides is not crucial, provided the site of stable chemical bonding between the active azide or alkyne groups to the terminal nucleic acid moiety is bridged by a spacer arm or spacer group of at least 6 carbon atoms (FIGS. 52A, 52B, 52C, and 52D). In some embodiments, the azide moiety is linked to either the nucleic acid 5' end or 3' end through reaction with N-hydroxysuccinimide, and the alkyne moiety to either the nucleic acid 5' end or 3' end in the form an appended cycooctyne group.

Separate populations of azide and alkyne-modified oligonucleotides of the above configurations are hybridized with whole RNA preparations from cells of interest, or alternatively whole cellular RNA-protein preparations. Hybridizations are performed with each oligonucleotide population in a 50:50 mixture with respect to each other by molarity, in a 10-100 fold excess over RNA quantities present, calculated by assuming an average molecular weight of the cellular RNA of 1500 bases, and with 1-10 micrograms of starting RNA. Hybridizations may be effected for periods of 2-16 hours.

Click reactivity occurs directly as a consequence of accelerated reactivity between strained alkyne groups in close proximity with azides, obviating the need for Cu(I) catalysis.

Figures 53A, 53B:
FIGS. 53A and 53B are representative diagrams of regions of single-stranded oligonucleotides with non-polymerase-readable 5'- and 3'-click groups where modified for nuclease-resistance; shown by stippled background; 53A) non-modified regions are retained with normal DNA backbones and bases for allowing restriction enzyme cleavage; the 3' sites are extended by three modified-bases with modified backbones; 53B) non-modified regions are retained with normal DNA backbones and bases for allowing restriction enzyme cleavage; the 3' sites are extended by three modified-bases with modified backbones.

Given the circumvention of the Cu(I) catalytic requirement, labeled oligonucleotide populations may be introduced into living cells, for in cyto hybridization. Hybrid oligonucleotides are synthesized with nuclease-resistant phosphodiester backbones or sugar moieties, except where there is a need for restriction enzyme cleavage in order to effect the desired rearrangements that permit amplification (FIGS. 53A and 53B). All oligonucleotide termini (including those capped with click groups) are composed of modified segments. Where these constitute the A1 and A2 regions containing restriction sites (FIG. 51), the A1 and A2 regions with normal bases and backbones are extended by 3 bases with modified backbones to deter exonucleolytic attack. Modified segments of these oligonucleotides, include, but are not limited to, 2'-O-methyl-nucleotides and phosphorothioate nucleotides.

In some embodiments, partially nuclease-resistant oligonucleotides are introduced into target cells of interest by commercially available transfection reagents, including, but not limited to Lipofectamine and Fugene.

Following hybridizations, the method proceeds as in Example 2 in terms of treatment with ribonucleases. In the embodiments where in cyto screening is used, cells are disrupted and subjected to treatments with both RNases and proteases. Protease treatments include, but are not limited to, Proteinase K. Following treatments, preparations are depleted of low-molecular weight products by gel size exclusion chromatography.

Figure 54:
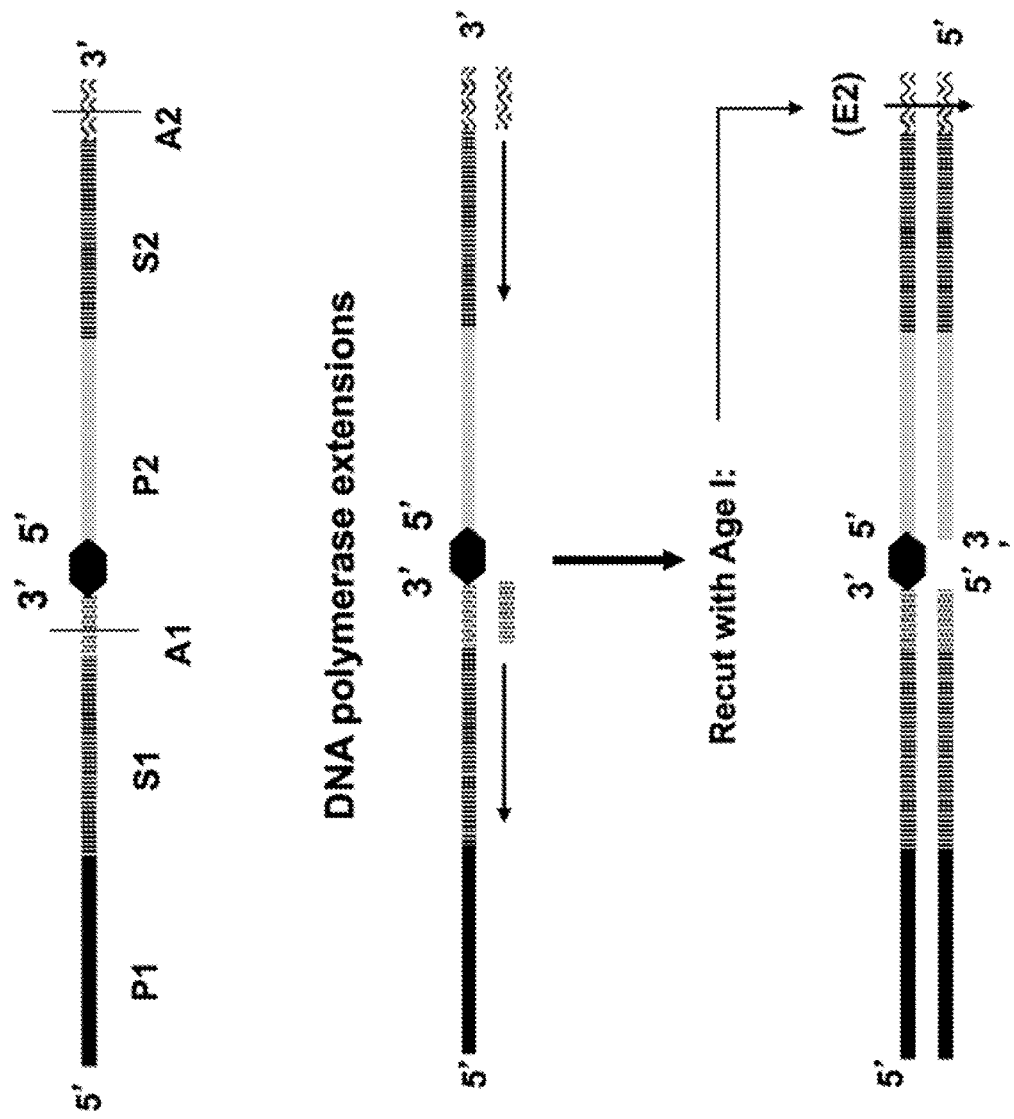
FIG. 54 illustrates representative production of double-stranded 5'-3' chemical ligation products by polymerase extensions, and subsequent recutting with restriction endonuclease Age I; S1 and S2 denote selected subpopulations of decamers from the original random decamer total populations.

Resulting preparations include excess unchanged oligonucleotide strands, through inability to react via lack of spatial proximity, and desired 5'-3' reacted products. All resulting oligonucleotide strands are rendered double stranded. This can be effected by means of primers complementary to Adapting Site 1 (A1) and Adapting Site 2 (A2), and extending each with all four deoxynucleotide triphosphates and Klenow fragment of DNA Polymerase I of $E.$ $coli$, such that each new strand is extended from, or as far as, the 5'-3' junctional point (FIG. 54).

In embodiments where modified nucleic acids are used for in cyto screening, the primer extension procedure is modified. Where ribose moieties are modified as 2'-O-methyl derivatives, reverse transcriptase enzymes may be used for extension purposes instead of Klenow fragment, using the same A1 and A2 primers as described above.

When directed cleavage of the extended duplex is effected, it is undesirable for sequences in the random regions to be cleaved through chance occurrence of restriction sites for the enzymes used for cleavage. In view of this, a deoxynucleotide triphosphate mixture consisting of 5-methyl-deoxycytidine triphosphate, deoxyadenosine triphosphate, deoxyguanosine triphosphate, and thymidine triphosphate is used, such that duplexes hemimethylated for 5-methylcytosine are generated in the complements to the random regions. In some embodiments, cleavage enzymes that are sensitive to 5-methylcytosine hemimethylation are accordingly used. (Adapting regions A1 and A2 are kept unmethylated through priming from non-methylated complementary strands; FIG. 54).

The resulting extended duplexes are then cleaved with an enzyme recognizing restriction site E2. In this non-limiting example, the enzyme E2 specifically corresponds to Age I, recognizing the sequence ACCGGT to produce a four-base overhang 5'-CCGG.

In subsequent steps, the following conditions are imposed: a) Preserve the linkage information between proximally-hybridized sequences during the ligation-mediated rearrangement process that enables amplification; b) Maintain a microenvironment where cleaved sequences are in high concentration relative to each other, thus driving their religation; and c) Sequester unreacted strands into individually-isolated compartments, preventing their ligation-mediated reassortment that would give spurious amplification signals (signals which have not resulted from original click reactions driven by proximate templating). These conditions are achievable by means of in vitro compartmentalization.

Figure 56:
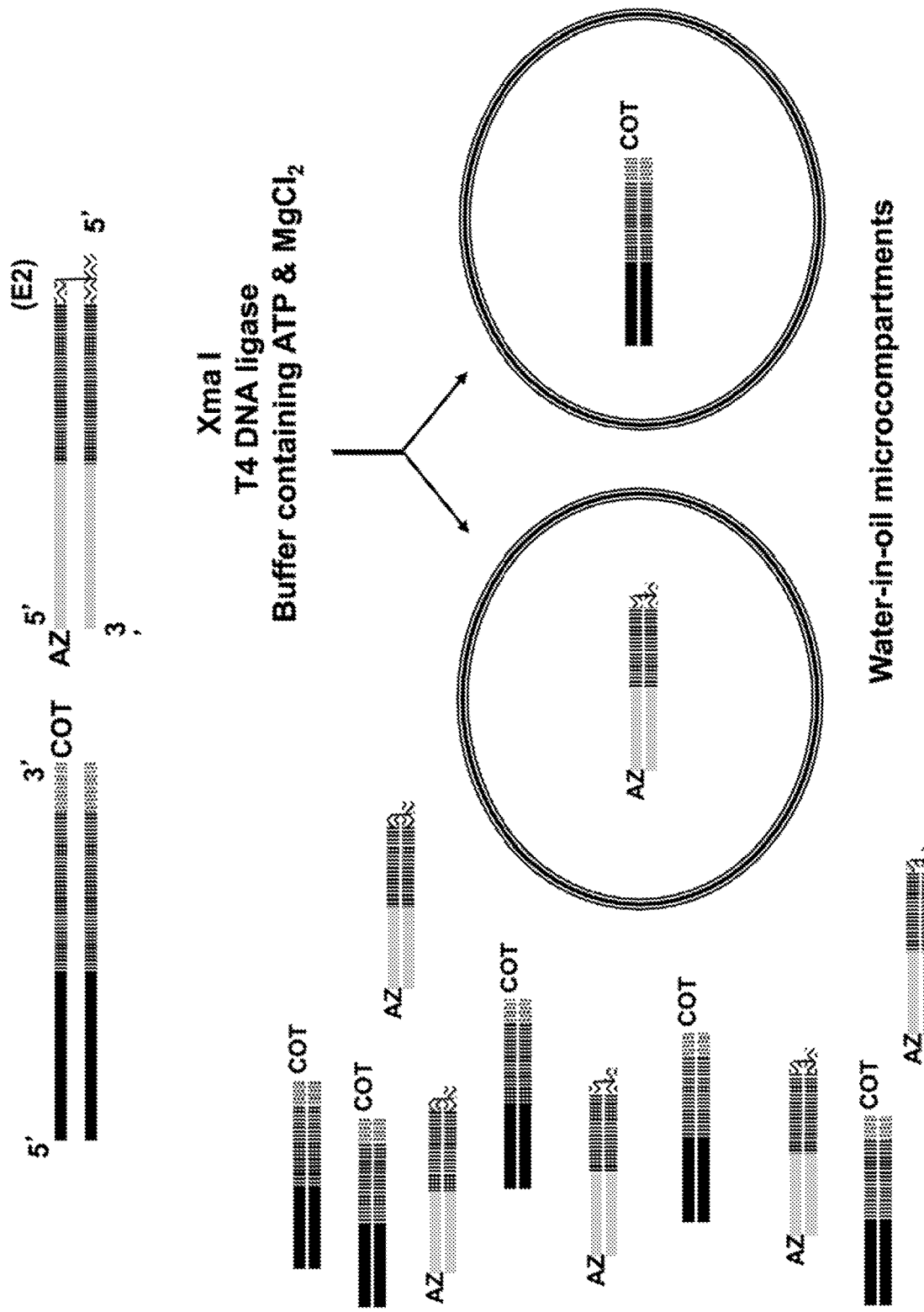
FIG. 56 is a representative illustration of partitioning of unligated 5'/3'-click-labeled duplex strands into microcompartments; here the 5'-azide modified strand has been previously cleaved in the A2 region with restriction enzyme E2 (Age I in the specified embodiment).
Figure 57:
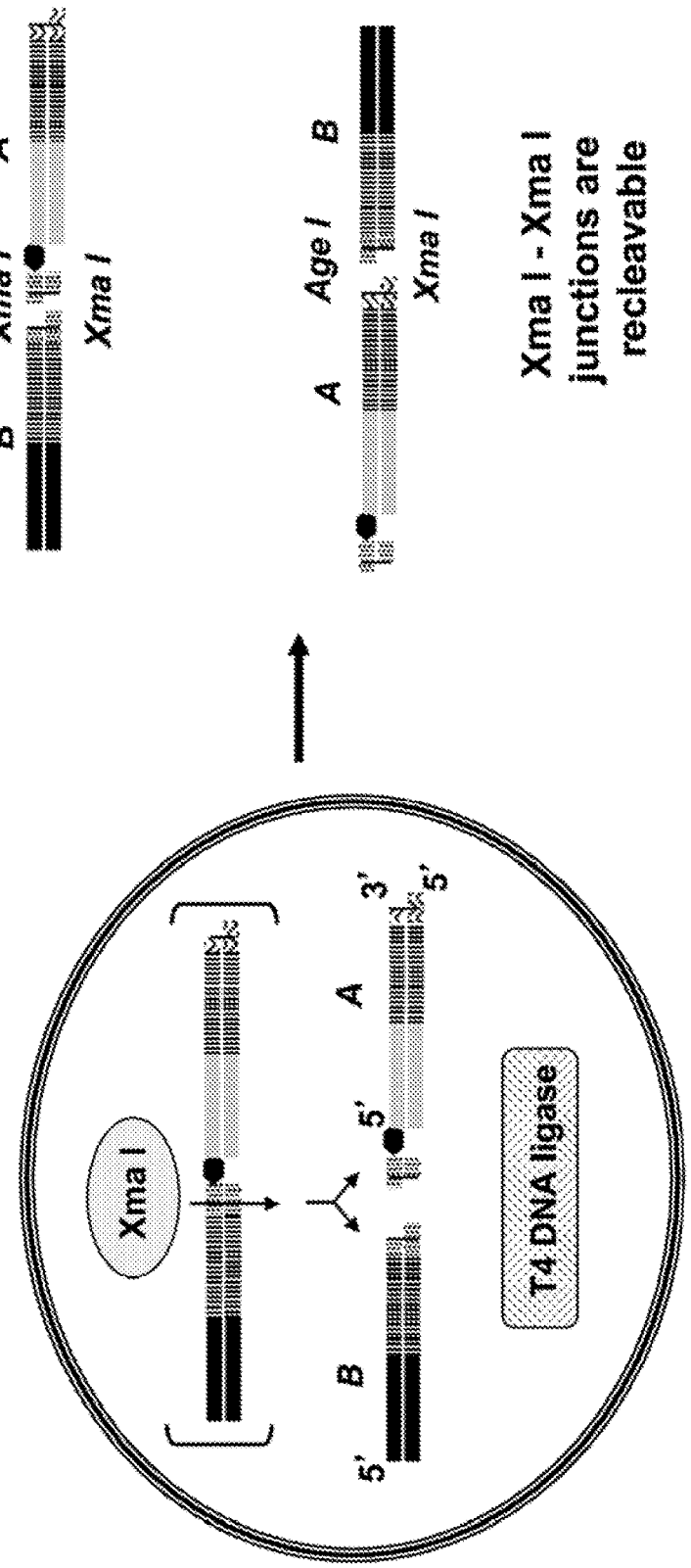
FIG. 57 is a representative diagram of Xma I cutting (in the specified embodiment) and re-ligation of 5'-3' linkages within microcompartments.

In vitro compartmentalization is effected by making water-in-oil microcompartments to encompass individual molecules from the population of unreacted oligonucleotides and 5'-3' click ligated dimers, as rendered double-stranded, and cleaved with enzyme corresponding to site E2. Microcompartments are formed from reagent-grade mineral oil and detergents, with added desired internal components, under conditions of precisely controlled stirring as described by Davidson et al. 2009 (FIG. 55). During the formation of water-in-oil microcompartments, the following components are present in excess, such that each compartment will receive the same buffer composition (50 mM potassium acetate, 20 mM Tris-acetate, pH 7.9/25 C including 1 mM ATP and 10 mM magnesium acetate ions), and at least one copy of the protein T4 DNA ligase and a protein restriction enzyme recognizing site E1. Since the microcompartments are in large excess of the molecular species present, on average only one ligated molecule is incorporated into each compartment (FIG. 55). Likewise, unligated fragments are partitioned into microcompartments as well (FIG. 56). In some embodiments, the E1 restriction enzyme is Xma I, recognizing the sequence CCCGGG to produce a four-base overhang 5'-CCGG compatible with Age I. Upon ligation of overhangs from Age I and Xma I cleavage, the resulting sequence is ACCGGG, cleavable by neither enzyme (FIG. 57).

Figure 58:
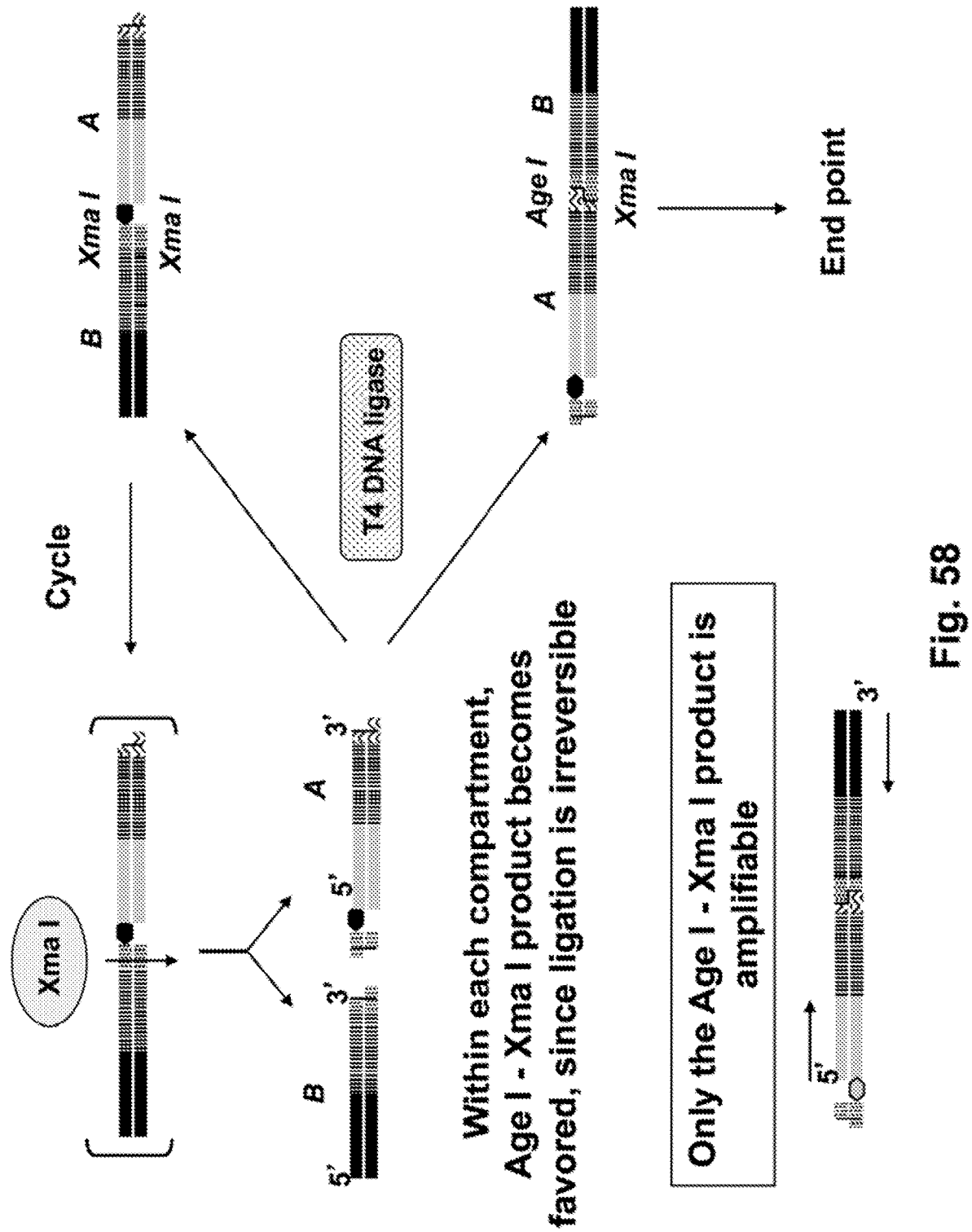
FIG. 58 shows representative cycling of Xma I cleaved (in the specified embodiment) 5'-3' ligation products in microcompartments, until irreversible and amplifiable rearrangement end-point is reached.

Microcompartments are incubated for 2 hours/37 C, and then 2 hours/20 C. Within each compartment bearing an individual 5'-3' chemically ligated dimer, cleavage with Xma I is followed by subsequent ligation with either another Xma I overhang (the reverse of the original cleavage) or ligation with the single Age I end present in the same compartment. Xma I-Xma I religations are recleavable by Xma I, but Age I-Xma I ligations are not, and thus inevitably become the predominant species in each microcompartment (FIG. 58). Compartments with unreacted oligonucleotides are partitioned from other potentially ligatable molecules (FIG. 56).

Microcompartments are then disrupted by treatment with diethyl ether. Specific oligonucleotide pairs from the original random populations, selected by spatial proximity on RNA templates, are amplifiable by virtue of the rearrangement process described above.

In another embodiment of Example 19, "communication" with microcompartments is effected by means of nanodroplets, as described by Miller et al., Nature Methods, 2006, 3, 561-570).

Example 20: Validation of In Vitro Compartmentalization for Containment of the CLOSE Rearrangement Process with a Model System (Actual Example)

It was desired to validate both the enzymatic rearrangement process and the ability of in vitro compartmentalization to contain a single molecular rearrangement, such that the information embodied in each CLOSE dimer is preserved. The most efficient way to approach this was with specific click-labeled oligonucleotides, whose sequences render them distinguishable from each other.

Oligonucleotide Sequences (A-D) for Example 20:

```
A. 5'Azide-
                                       (SEQ ID NO: 71)
   CTCCATAACCCATGGACATGTACCGGTGATCC B. 5' Hexynyl-
                                       (SEQ ID NO: 72)
   GATCCCCGGGCTATGTCTAGAGGAGAAGGAGA C. 5'Azide-
                                       (SEQ ID NO: 73)
   CTCCATAACCCAAGGATCCTCACCGGTGATCC D. 5'-Hexynyl-
                                       (SEQ ID NO: 74)
   GATCCCCGGGTACCGAGCATAGGAGAAGGAGA
``` where "Azide" indicates an azide group coupled via an N-hydroxysuccinimide intermediate, and "hexynyl" denotes an alkyne separated from the DNA carrier by means of a 6-carbon linear spacer. Underlined sequences indicate restriction sites: A, Nco I; B, Xba I; C, Bam HI; D, Asp718I. Bold sequences correspond to regions which are randomized in Examples 17, 18, and 19. Sequences CTCCATAACCCA (SEQ ID NO:75) and AGGAGAAGGAGA (SEQ ID NO:76): truncated forward (sense) and reverse (antisense) primer sites for amplification, respectively.

Model oligonucleotides A-D can be distinguished from each by restriction site digestion (as duplexes) or by PCR amplification with extended primers specific for each oligonucleotide.

In the first stage of the model, all four possible azide-alkyne combinations of oligonucleotides A-D were mixed in high concentrations (10 pmol/µl; 50 µl volumes) and subjected to untemplated catalyst-assisted click reactions as for Example 1, with the same post-reaction desalting. When reactions were tested on denaturing acrylamide gels, a biphasic click-specific band pattern was reproducibly observed: a "top" band at higher apparent molecular (roughly twice the monomeric molecular weight), and a "bottom" band with slightly slower mobility than the original bands (FIG. 59). Both top and bottom bands were purified by excision from preparative gels, with multiple lanes to avoid lane saturation (FIG. 59) were crushed and oligonucleotides allowed to diffuse out, followed by their precipitation and reconstitution.

At this point it was deemed necessary to test whether either or both bands could undergo the enzymatic rearrangement process which permits amplification (Examples 17, 18, and 19). Although performing this process in free solution does not preserve the information from each clicked molecule, the enzymatic requirements are constant, and success in this case also validates the rearrangement process itself. Samples of both Top and Bottom bands were initially rendered double-stranded with Klenow DNA Polymerase I fragment, dNTPs, and suitable primers:

Primers for rendering model or actual 5'-5' library oligonucleotides double-stranded:

```
                                       (SEQ ID NO: 77)
   E1-Ext:       GGATCACCGGT (SEQ ID NO: 78)
   Trz. R:       GCCTCTAAGTCTCCTTCTCCT
```

Figure 60:
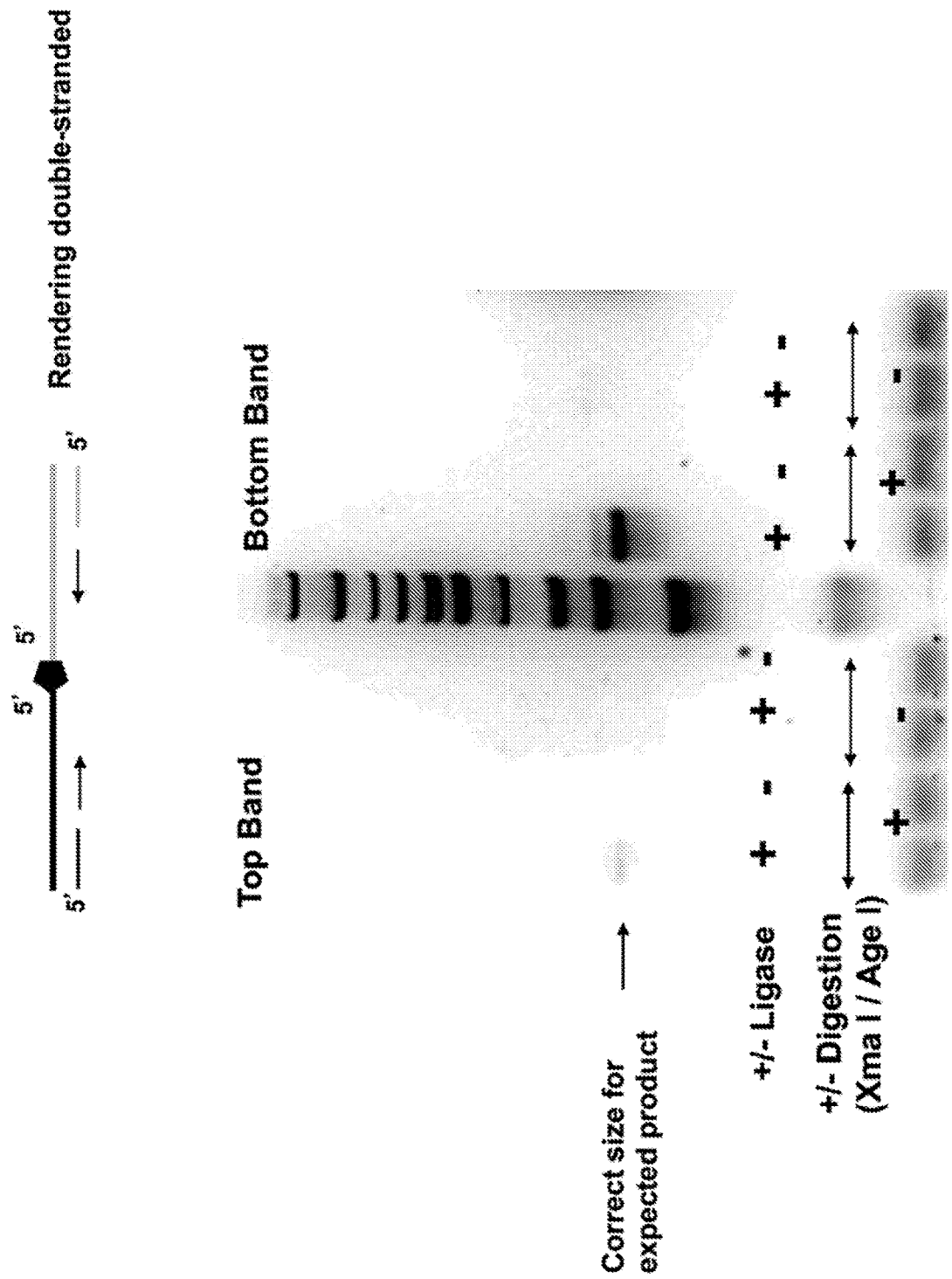
FIG. 60 depicts representative demonstration of enzymatic rearrangement process for 5'-5' oligonucleotide joins.

The double-stranded preparations were then treated with or without Xma I and Age I, and in turn with or without T4 DNA ligase. Following this, samples were amplified with the primers Trz.F (CATCTCCACCTCCATAACCCA) (SEQ ID NO:79) and Trz.R (as above), and run on non-denaturing acylamide gels. Bands of the expected size (68 bp) were observed from both Top and Bottom preparations, but only after both restriction enzyme digestion and religation, fully in support of the planned rearrangement process (FIG. 60). It was concluded that both Top and Bottom bands are rearrangeable 5'-5' adducts, where the faster-migrating Bottom band is most likely a self-folded denaturation-resistant form. For the continuation of the model process, the Top bands were used. Although in lower evident yields than the Bottom bands, the Top bands were much more easily resolved from unreacted monomers.

Accordingly, samples of the four possible 5'-5' adducts (FIG. 59) were shown to be essentially pure on denaturing gels (FIG. 61). Samples of these (1 pmol) were extended with Klenow enzyme as above, and then tested with Xma I/Age I and religation with T4 DNA ligase. In addition to each adduct separately, two mixes of adducts with heterologous constituent oligonucleotides were also included in the rearrangement tests. These were adducts $B_H+F_H$ (corresponding to 5'-5' joins of original oligonucleotides A/B and C/D respectively) and adducts $D_H+H_H$ (corresponding to 5'-5' joins of original oligonucleotides A/D and C/B respectively). After the enzymatic treatments, all adduct preparations showed amplifiable material (with the same process and primers as for FIG. 60), but nothing was observable without enzymes (FIG. 62).

At this point, it was possible to use the model oligonucleotide detection system for evaluating the success of IVC in enabling molecule-specific rearrangements without loss of CLOSE information from unnatural chemical ligations. The principle of this system is depicted schematically in FIG. 63. Where specific 5'-5' adducts are held in isolation, either in homogeneous solution or through successful microcompartmentalization, only one possible rearrangement product is possible. However, if different adducts of the same configuration are mixed (or if the IVC is inadequate), cross-overs between different adducts will occur during the ligation step, which will destroy the information contained in specific 5'-5' CLOSE oligonucleotides. If PCR primers specific for each original oligonucleotide sequence (A-D) can be designed, then the amplification patterns with various primer combinations will directly report the state of adduct rearrangements.

Primers with the desired specificity were designed for the original click-labeled oligonucleotides A-D. Here specific primer pairs were intended to amplify only a particular direct (single-molecule) rearrangement, or a particular cross-over product. For example, for the $B_H$ adduct, after rearrangement, the desired primers would amplify only B-A sequence, and likewise for the $B_H$ adduct, correct primers should specifically amplify only D-C sequence. When the $B_H$ and $F_H$ adducts are mixed, two possible cross-over products can be formed: B-C, and D-A, for which specific primer combinations are also desirable. Note that within such mixtures, the "direct" products will be able to form as well as the cross-over products.

Preparations of the $B_H$ and $F_H$ adducts were used after they had been rendered double-stranded, and subjected to the Age I/Xma I/DNA ligase treatment for rearrangement. These were performed as single adducts and as mixtures ($B_H+F_H$ adducts) at high sensitivity. It was found (FIG. 64) that the primer pairs designed to be specific for direct rearrangements of the $B_H$ and $F_H$ adducts were satisfactory (products seen only from homologous rearrangements, or from the $B_H+F_H$ mixtures). Of the two possible cross-over primer pairs, one (for B-C cross-over) showed low but detectable cross-specificity (showing product with ($B_H$ alone), but the other cross-over primer pair (D-A) appeared to be highly specific (FIG. 64). This primer pair was according used further, since either pair is sufficient to demonstrate the presence of absence of cross-overs.

Oligonucleotides sequences for rearrangement and cross-over testing: These were extensions of the 'general primers Trz.F and Trz.R (as above), which will amplify any combination of A-D rearrangements.

```
Primers specific for direct B_H rearrangement:
                                        (SEQ ID NO: 80)
   Trz.F + Te: CACCTCCATAACCCATGGACA (SEQ ID NO: 81)
   Trz.R + Ce: CTAAGTCTCCTTCTCCTCTAGACA Primers specific for direct F_H rearrangement:
                                        (SEQ ID NO: 82)
   Trz.F + Ae: CCACCTCCATAACCCAAGGAT (SEQ ID NO: 83)
   Trz.R + Ae: TCTAAGTCTCCTTCTCCTATGCT
```

Primers specific for $B_H$-$F_H$ cross-over rearrangement #1 (B-C):
Trz.F+Te/Trz.R+Ae (as above).
Primers specific for $B_H$-$F_H$ cross-over rearrangement #2 (D-A):
Trz.F+Ae/Trz.R+Ce (as above).

Bold sequences correspond to the extensions beyond the 3' ends of Trz.F and Trz.R.

It was also desired to perform an additional control, where samples of separately rearranged $B_H$ and $F_H$ adducts were separately mixed just prior to PCR (This is distinct from reactions where the $B_H$ and $F_H$ adducts were mixed prior to the rearrangement process itself, where cross-overs are promoted, as shown in FIG. 64). This second control set tests whether cross-overs can occur in this system through artefactual PCR effects. It was found (FIG. 65) that no such PCR-induced cross-over effects occurred.

With the primer specificity confirmed, the use of the model oligonucleotides for testing in vitro compartmentalization could proceed. Here, duplexed 5'-5' adducts precut with Age I (Example 17, FIG. 39) and Xma I/T4 DNA ligase/buffer/1 mM ATP were mixed with the necessary oil and surfactants for emulsion formation. (Precutting with Age I simplifies the enzymatic requirements for inclusion in the emulsion mixes). It was initially shown that both Xma I and T4 DNA ligase were active in 1× CutSmart buffer (New England Biolabs) in the presence of 1 mM ATP, which was thus used during in mixes for emulsion formation. If emulsions and compartmentalization are successful, no cross-over product should be detectable after rearrangements are allowed to proceed within the emulsions themselves, when both precut $B_H$ and $F_H$ adducts are present initially.

Emulsion mixes were prepared by the method of Davidson et al., Current Protocols in Molecular Biology, 2009, 24.6.1-24.6.12 with the exception that Triton-X100 was omitted. Emulsions themselves were generated in the following manner, always using positive-displacement pipettes (Gilson) for dispensing the viscous fluids: the emulsion mix corresponded to 950 μl mineral oil (molecular biology grade, Sigma), 45 μl Span-80 (Sigma) and 5 μl Tween-80 (Sigma). 50 μl mixes of Age I-precut adducts (in predefined quantities) or controls were prepared in ×1 CutSmart buffer with 1 mM ATP, containing Xma I and T4 DNA ligase. (Enzymes were only added immediately prior to emulsion formation, and all preparations were kept chilled at 0 C on ice.) The emulsion mix was placed in a 13 ml tube (17×95 mm; VWR Scientific) and chilled prior to addition of a 9.5×9.5 mm spinbar (Fisher Scientific) and mixed in the 13 ml tube contained with an ice-bearing flask, and centrifuged with a Corning PC-410D stirrer at 1150 rpm for 2 minutes. Following this, the chilled adduct/buffer/enzyme mix (50 µl) was added slowly (10×5 µl aliquots) to the top of the spinning emulsion, after which the centrifuging was continued for another 10 minutes. In some tests, this was followed by an additional sonication step to homogenize microdroplet size. Five rounds of three-second mid-strength sonication bursts were used, with chilling of tubes between bursts. Then the emulsions were carefully transferred to 2 ml tubes, and incubated for 1 hour at 30 C; 4 hours at 25 C. Control reactions were prepared in 50 µl volumes, as above, but were not subjected to the emulsification process. At the end of the incubation periods, the emulsions were broken with diethyl ether. Initially 500 µl Tris-buffered saline was added to each tube (including non-emulsified controls, which were then maintained on ice), and then the following extraction procedure was used: 1×0.5 ml ether; 2×1.0 ml ether; 1×0.5 ml ether, with centrifugations of 2 minutes/13,000 rpm each time to separate phases. Materials in all aqueous phases (including non-emulsified controls) were then precipitated with 40 µg glycogen/0.3 M sodium acetate/3 volumes ethanol, washed with 70% ethanol, dried, and reconstituted in 10 µl TE.

Tests were performed with inputs of 5·10$^9$ molecules each of B$_H$ and F$_H$ adducts (precut with Age I) as "high concentration", and 10$^8$ molecules each as "low concentration", each under enzymatic rearrangement conditions with and without emulsion-mediated compartmentalization.

To enhance the sensitivity of detection, a nested primer strategy was used for analysis of products post-emulsification. A set of first round primers each 5' to the above rearrangement-specific primers were used:

Trz.F + T:
(SEQ ID NO: 84)
CATCTCCACCTCCATAACCCAT (upstream of Trz.F + Te, sequence as above)

Trz.R + C:
(SEQ ID NO: 85)
GCCTCTAAGTCTCCTTCTCCTC (upstream of Trz.R + Ce, sequence as above)

Trz.F + A:
(SEQ ID NO: 86)
CATCTCCACCTCCATAACCCAA (upstream of Trz.F + Ae, sequence as above)

Trz.R + A:
(SEQ ID NO: 87)
GCCTCTAAGTCTCCTTCTCCTA (upstream of Trz.R + Ae, sequence as above)

Results of such an experiment are shown in FIG. 66. As expected, even with the low-concentration adducts, in the absence of compartmentalization, both B$_H$ and F$_H$ rearrangement products were observed, along with cross-over bands (Lanes L-Ct, FIG. 66.). High-concentration adducts subjected to both spinning and sonication for emulsification also showed clear-cut cross-over bands (Lanes H-Sc, FIG. 66). However, low-concentration adduct mixes, whether subjected to spin-only or spin plus sonication for emulsification, showed only direct B$_H$ and F$_H$ rearrangement product bands, with no evidence for cross-over.

It was concluded that:

1) the model system was a valid test for containment of the rearrangement process within in vitro microcompartments;

2) high amounts of adduct mixes can saturate the IVC process, allowing uncompartmented material to persist, and cross-over to occur; and 3) suitable amounts (10$^8$ molecules or less) of adduct mixes can be contained by the IVC and molecule-specific rearrangements can be detected.

Example 21: Amplification of CLOSE 5'-3' Linked Clones by Circularization and Inverse PCR (Prophetic Example)

In the case of non-amplifiable 5'-3' CLOSE joins (but not 5'-5' or 3'-3'), an alternative strategy exists in addition to microcompartmentalization. Here the 5'- and 3'-ends of joined CLOSE single strands are defined sequences, whereby complementary oligonucleotides to each can anneal and, thus, provide 5'-overhangs for self-ligation purposes. (CLOSE clones with the terminal defined sequences are sufficiently long for self-circularization to occur). Upon enzymatic circularization, primers P1 and P2 (FIG. 67) enable inverse amplification, including the information carried within the randomized regions (a specific sequence for each CLOSE clone).

The circularization must be performed at low concentration, to minimize the likelihood of inter-molecular ligations, as opposed to the desired intra-molecular circularization.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A method for identifying templated assembly targets comprising:
   synthesizing a first population of templated assembly reactants and a second population of corresponding templated assembly reactants, wherein the first and second populations of templated assembly reactants comprise oligonucleotide sequences;
   hybridizing both populations of templated assembly reactants to target nucleic acids, wherein the target nucleic acids maintain their native secondary structures and wherein the hybridization target sites are discontinuous;
   performing a templated assembly reaction, wherein the hybridized first population of templated assembly reactants and the hybridized second population of corresponding templated assembly reactants undergo templated assembly; and
   identifying the target nucleic acids that hybridized to either the first or second population of templated assembly reactants that underwent templated assembly, wherein the hybridized target nucleic acids are the templated assembly targets.

2. The method of claim 1, wherein the steps of synthesizing the first and second population of templated assembly reactants further comprises synthesizing random oligonucleotides sequences of about 7 to about 30 nucleotides long, or synthesizing gene specific sequences of about 7 to about 30 nucleotides long.

3. The method of claim 1, wherein the templated assembly reactants comprise a 5' or a 3' priming site adjacent to the oligonucleotide sequences.

4. The method of claim 1, further comprising obtaining the target nucleic acids prior to the step of hybridizing the populations of templated assembly reactants to the target nucleic acids.

5. The method of claim 1, wherein the target nucleic acids maintain their native secondary structures.

6. The method of claim 1, wherein the step of hybridizing both populations of templated assembly reactants to the target nucleic acids further comprises removing unbound templated assembly reactants.

7. The method of claim 1, wherein the step of performing the templated assembly reaction comprises at least one of a click chemical reaction, a Staudinger reduction, a non-traceless Staudinger ligation, a traceless Staudinger ligation, a traceless phosphinophenol Staudinger ligation, a traceless phosphinomethanethiol Staudinger ligation, a native chemical ligation, and a bio-orthogonal chemical reaction.

8. The method of claim 1, wherein the step of identifying the target nucleic acids further comprises removing the hybridized first population of templated assembly reactants and the hybridized second population of corresponding templated assembly reactants that failed to undergo templated assembly.

9. The method of claim 1, wherein the step of identifying the target nucleic acids further comprises amplifying the hybridized target nucleic acids.

10. The method of claim 1, wherein the step of identifying the target nucleic acids further comprises sequencing the hybridized target nucleic acids.

* * * * *